(12) United States Patent
Jang et al.

(10) Patent No.: US 10,516,113 B2
(45) Date of Patent: Dec. 24, 2019

(54) ORGANIC COMPOUND, ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Kipo Jang, Suwon-si (KR); Soohyun Min, Suwon-si (KR); Sangshin Lee, Suwon-si (KR); Sung-Hyun Jung, Suwon-si (KR); Ho Kuk Jung, Suwon-si (KR); Youngkwon Kim, Suwon-si (KR); Eun Sun Yu, Suwon-si (KR)

(73) Assignee: Samsung SDI Co., Ltd., Yongin-Si, Gyonggi-do (KR)

( * ) Notice: Subject to any disclaimer, the term of this patent is extended or adjusted under 35 U.S.C. 154(b) by 135 days.

(21) Appl. No.: 15/408,756

(22) Filed: Jan. 18, 2017

(65) Prior Publication Data

US 2017/0250349 A1   Aug. 31, 2017

(30) Foreign Application Priority Data

Feb. 26, 2016   (KR) .................. 10-2016-0023669

(51) Int. Cl.
*H01L 51/50* (2006.01)
*H01L 51/00* (2006.01)
*C07D 239/26* (2006.01)
*C07D 239/74* (2006.01)
*C07D 251/24* (2006.01)
*C09K 11/02* (2006.01)

(52) U.S. Cl.
CPC ........ *H01L 51/0067* (2013.01); *C07D 239/26* (2013.01); *C07D 239/74* (2013.01); *C07D 251/24* (2013.01); *C09K 11/025* (2013.01); *H01L 51/0052* (2013.01); *H01L 51/0072* (2013.01); *H01L 51/0081* (2013.01); *H01L 51/0085* (2013.01); *H01L 51/5012* (2013.01); *H01L 51/5016* (2013.01); *H01L 51/5072* (2013.01); *H01L 2251/5384* (2013.01)

(58) Field of Classification Search
None
See application file for complete search history.

(56) References Cited

U.S. PATENT DOCUMENTS

2004/0164292 A1*   8/2004   Tung ................. G02F 1/133603
                                                                              257/40
2007/0190355 A1*   8/2007   Ikeda .................. C07D 239/26
                                                                              428/690
2012/0228552 A1    9/2012   Parham et al.
(Continued)

FOREIGN PATENT DOCUMENTS

CN      102408407 A    4/2012
CN      104471021 A    3/2015
CN      105601612 A    5/2016
(Continued)

OTHER PUBLICATIONS

Chinese Office Action dated Mar. 27, 2019.

*Primary Examiner* — Gregory D Clark
(74) *Attorney, Agent, or Firm* — Lee & Morse, P.C.

(57) ABSTRACT

An organic compound represented by Chemical Formula 1, an organic optoelectric device including the organic compound, and a display device including the organic optoelectric device are disclosed.

9 Claims, 4 Drawing Sheets

(56) References Cited

U.S. PATENT DOCUMENTS

2012/0228554 A1* 9/2012 Franz .................. C07D 251/16
                                                                252/500

FOREIGN PATENT DOCUMENTS

| KR | 10-2010-0075079 A |   | 7/2010  |            |
|----|-------------------|---|---------|------------|
| KR | 10-2010-0077673 A |   | 7/2010  |            |
| KR | 10-2011-0048838 A |   | 5/2011  |            |
| KR | 10-1084287 B1     |   | 11/2011 |            |
| KR | 10-1093122 B1     |   | 12/2011 |            |
| KR | 10-2012-0122812 A |   | 11/2012 |            |
| KR | 10-2014-0004549   |   | 1/2014  |            |
| KR | 10-2014-0014959   |   | 2/2014  |            |
| KR | 10-2014-0046209   |   | 4/2014  |            |
| KR | 10-2015-0074603   | * | 7/2015  | ...... C09K 11/06 |
| KR | 10-2015-0083786 A |   | 7/2015  |            |
| KR | 10-2017-0086211 A |   | 7/2017  |            |
| WO | WO 2015/105316 A1 |   | 7/2015  |            |
| WO | WO 2015/178731 A1 |   | 11/2015 |            |

\* cited by examiner

ORGANIC COMPOUND, ORGANIC OPTOELECTRIC DEVICE AND DISPLAY DEVICE

CROSS-REFERENCE TO RELATED APPLICATION

This application claims priority to and the benefit of Korean Patent Application No. 10-2016-0023669 filed in the Korean Intellectual Property Office on Feb. 26, 2016, the entire contents of which are incorporated herein by reference.

BACKGROUND OF THE INVENTION

1. Field

An organic compound, an organic optoelectric device, and a display device are disclosed.

2. Description of the Related Art

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode.

Performance of an organic light emitting diode may be affected by characteristics of the organic layer, and among them, may be mainly affected by characteristics of an organic material of the organic layer. Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides an organic compound capable of realizing an organic optoelectric device having high efficiency, a long life-span, and a low driving voltage.

Another embodiment provides an organic optoelectric device including the organic compound.

Yet another embodiment provides a display device including the organic optoelectric device.

According to one embodiment, an organic compound represented by the following Chemical Formula 1 is provided.

[Chemical Formula 1]

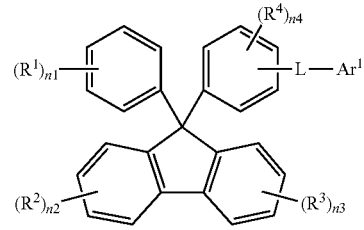

In Chemical Formula 1,
$R^1$ to $R^4$ are independently hydrogen or deuterium,
L is represented by $*-L^1-L^2-L^3-L^4-*$,
$L^1$ to $L^4$ are independently a single bond, a substituted or unsubstituted C6 to C20 arylene group, or a substituted or unsubstituted C2 to C20 heteroarylene group, provided that at least one of $L^1$ to $L^4$ is a substituted or unsubstituted C6 to C20 arylene group,
$Ar^1$ is a substituted C2 to C20 heteroaryl group,
n1 is an integer of 5, and
n2 to n4 are independently integers of 4.

Another embodiment provides an organic optoelectric device including an anode and a cathode facing each other and at least one organic layer between the anode and the cathode, wherein the organic layer includes the organic compound.

Yet another embodiment provides a display device including the organic optoelectric device.

An organic optoelectric device having high efficiency, a long life-span, and a low driving voltage may be realized.

DETAILED DESCRIPTION

Figure 1:
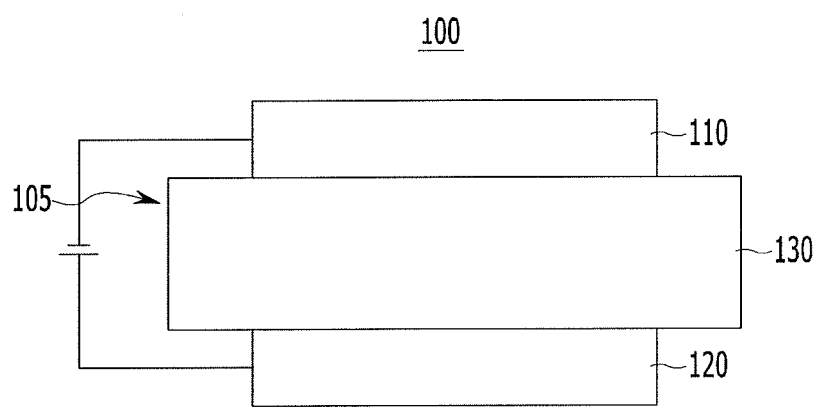
FIGS. 1 to 4 are cross-sectional views showing organic light emitting diodes according to embodiments.

Hereinafter, embodiments of the present invention are described in detail.

However, these embodiments are exemplary, the present invention is not limited thereto and the present invention is defined by the scope of claims.

In the present specification, when a definition is not otherwise provided, "substituted" refers to one substituted with deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heterocyclic group, a C1 to C20 alkoxy group, a fluoro group, a C1 to C10 trifluoroalkyl group such as a trifluoromethyl group, or a cyano group, instead of at least one hydrogen of a substituent or a compound. In one examples of the present invention, "substituted" refers to one substituted with deuterium, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heterocyclic group, instead of at least one hydrogen of a substituent or a compound. In one examples of the present invention, "substituted" refers to one substituted with deuterium, a C1 to C 10 alkyl group, a C6 to C30 aryl group, a C6 to C30 heterocyclic group, instead of at least one hydrogen of a substituent or a compound.

In addition. two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heterocyclic group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one heteroatom selected from the group consisting of N, O, S, P and Si, and remaining carbons in one functional group.

In the present specification, "an aryl group" refers to a group having at least one hydrocarbon ring aromatic moiety, and broadly hydrocarbon ring aromatic moieties linked by a single bond and a non-aromatic fused ring including hydrocarbon ring aromatic moieties fused directly or indirectly. An aryl group may be monocyclic, polycyclic, or fused polycyclic (i.e., rings sharing adjacent pairs of carbon atoms) functional group.

In the present specification, "a heterocyclic group" includes a heteroaryl group, and a cyclic group including at least one heteroatom selected from N. O. S, P. and Si instead of carbon (C) of a cyclic compound such as an aryl group, a cycloalkyl group, a fused ring or a combination thereof. When the heterocyclic group is a fused ring, each or entire ring of the heterocyclic group may include at least one heteroatom.

More specifically, a substituted or unsubstituted C6 to C30 aryl group and/or a substituted or unsubstituted C2 to C30 heterocyclic group refer to a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p- terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group. a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, a combination thereof, or a combined fused ring of the foregoing groups, but is not limited thereto.

In the present specification, a substituted or unsubstituted arylene group or a substituted or unsubstituted heteroarylene group refer to a substituted or unsubstituted aryl group or a substituted or unsubstituted heteroaryl group which is defined above and has two linking points, for example, a substituted or unsubstituted phenylene group, a substituted or unsubstituted naphthylene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quaterphenylene group, a substituted or unsubstituted chrysenylene group. a substituted or unsubstituted triphenylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyrrolylene group, a substituted or unsubstituted pyrazolylene group, a substituted or unsubstituted iimidazolylene group, a substituted or unsubstituted triazolylene group, a substituted or unsubstituted oxazolylene group, a substituted or unsubstituted thiazolylene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolylene group, a combination thereof, or a combined fused ring of the foregoing groups, but is not limited thereto.

In the specification, hole characteristics refer to an ability to donate an electron to form a hole when an electric field is applied and that a hole formed in the anode may be easily injected into the light-emitting layer, and a hole formed in a light-emitting layer may be easily transported into an anode and transported in the light-emitting layer due to conductive characteristics according to a highest occupied molecular orbital (HOMO) level.

In addition, electron characteristics refer to an ability to accept an electron when an electric field is applied and that an electron formed in a cathode may be easily injected into the light-emitting layer, and an electron formed in a light-emitting layer may be easily transported into a cathode and transported in the light-emitting layer due to conductive characteristics according to a lowest unoccupied molecular orbital (LUMO) level.

Hereinafter, an organic compound according to an embodiment is described.

An organic compound according to an embodiment is represented by Chemical Formula 1.

[Chemical Formula 1]

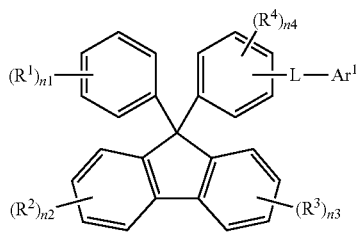

In Chemical Formula 1,
$R^1$ to $R^4$ are independently hydrogen or deuterium,
L is represented by *-$L^1$-$L^2$-$L^3$-$L^4$-*,
the $L^1$ to $L^4$ are independently a single bond, a substituted or unsubstituted C6 to C20 arylene group, or a substituted or unsubstituted C2 to C20 heteroarylene group, provided that at least one of $L^1$ to $L^4$ is a substituted or unsubstituted C6 to C20 arylene group,
$Ar^1$ is a substituted C2 to C20 heteroaryl group,
n1 is an integer of 5, and
n2 to n4 are independently integers of 4.

The organic compound represented by Chemical Formula 1 includes a 9,9-diphenylfluorene structure, a substituent having electron characteristics, and a linking group (including an arylene group or an arylene group) between the 9,9-diphenylfluorene structure and the substituent having electron characteristics. The linking group may increase flexibility of the compound and further apply excellent morphology characteristics thereto and thus play a significant role of realizing high efficiency, a long life-span, and a low driving voltage in an organic optoelectric device.

Furthermore, the substituent having electron characteristics necessarily includes another substituent and thus may protect the weakest part of a heteroring compared with a substituent having electron characteristics but being not substituted and resultantly, improve heat resistance.

In addition, as for the 9,9-diphenylfluorene structure in the organic compound according to one embodiment, a carbon atom consisting of a ring other than the ring including the linking group forms a bond with hydrogen or deuterium except for other carbon atoms but has no other substituents. This structure may facilitate a design of a molecule to have a low molecular weight and high energy T1 compared with one additionally substituted with fluorine and ultimately, secure characteristic improvement and thermal resistance stability of a material.

The $Ar^1$ may be a substituted C2 to C20 heteroaryl group, and the heteroaryl group includes at least two nitrogen atoms.

In an example of the present invention, the $Ar^1$ may be a substituted pyrimidinyl group, a substituted triazinyl group, a substituted quinolzolinyl group, or a substituted isoquinazolinyl group. In an example of the present invention, the $Ar^1$ may be specifically a substituted triazinyl group, a substituted quinolzolinyl group, or a substituted isoquinazolinyl, and a substituted or unsubstituted triazinyl group. The "substituted" described in definition of a substituent of the $Ar^1$ may be performed by one selected from deuterium, a C1 to C10 alkyl group, a substituted or unsubstituted C6 to C30 allyl group, a substituted or unsubstituted C2 to C30 heteroaryl group, or a combination thereof, and in an example of the present invention, a substituted or unsubstituted C6 to C30 aryl group may be used.

For example, the $Ar^1$ may be represented by one selected from Chemical Formula 2 to Chemical Formula 6.

[Chemical Formula 2]

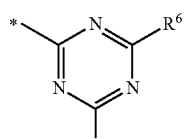

[Chemical Formula 3]

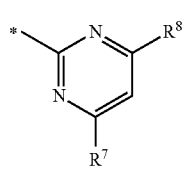

[Chemical Formula 4]

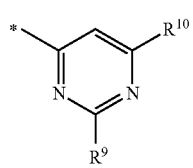

[Chemical Formula 5]

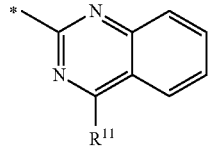

[Chemical Formula 6]

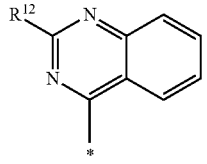

In Chemical Formulae 2 to 6,
$R^5$ to $R^{12}$ are independently a substituted or unsubstituted C1 to C20 alkyl group, a substituted or unsubstituted C6 to C20 aryl group, or a substituted or unsubstituted C2 to C20 heteroaryl group.

The organic compound according to one embodiment may have excellent heat resistance due to these structural characteristics.

When a substituent represented by Chemical Formulae 2 to 6 is included as the substituent having electron characteristics, the organic compound may have LUMO in a range of −2.0 eV to −1.7 eV and show excellent electronic characteristics compared with a compound including no pyridine or nitrogen atom.

The $R^5$ to $R^{12}$ may independently be a substituted or unsubstituted C6 to C20 aryl group.

For example, when the $R^5$ to $R^{12}$ are independently a substituted or unsubstituted C6 to C20 aryl group, the ring or unsubstituted C6 to C20 aryl group may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, or a substituted or unsubstituted pyrenyl group, but is not limited thereto.

The L may be represented by one selected from Chemical Formula L-1 to Chemical Formula L-7.

[Chemical Formula L-1]

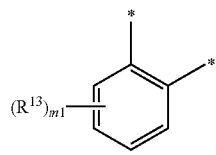

[Chemical Formula L-2]

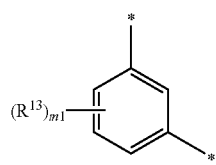

[Chemical Formula L-3]

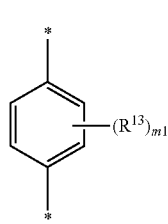

[Chemical Formula L-4]

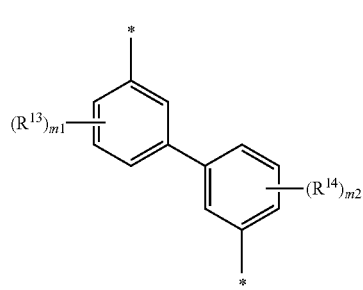

[Chemical Formula L-5]

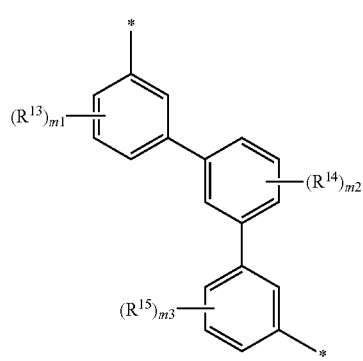

[Chemical Formula L-6]

[Chemical Formula L-7]

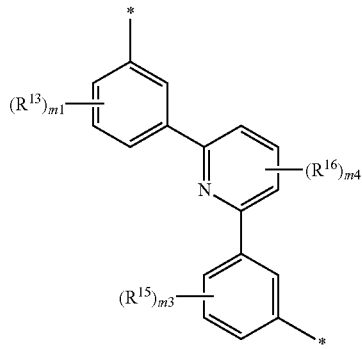

In Chemical Formula L-1 to Chemical Formula L-7, $R^{13}$ to $R^{17}$ are independently a substituted or unsubstituted C1 to C20 alkyl group or a substituted or unsubstituted C6 to C20 aryl group, m1 to m3 and m5 are independently an integer of 0 to 4, m4 is an integer of 0 to 3.

The organic compound represented by Chemical Formula 1 includes a 9,9-diphenylfluorene structure, a substituent having electron characteristics, and a linking group (including an arylene group or an arylene group) between the 9,9-diphenylfluorene structure and the substituent having electron characteristics.

Particularly, when the organic compound according to one embodiment has a linking group represented by Chemical Formulae L-1 to L-7 as the linking group, the linking group may increase flexibility of the compound or finely tune its corresponding characteristics and thus apply more appropriate morphology characteristics thereto and resultantly, play a significant role of realizing high efficiency, a long lifespan, and a low driving voltage in an organic optoelectric device. In one example of the present invention, the L may be L-2, L-4, or L-5, and desirably L-2 or L-4. An organic compound according to an embodiment may be represented by one selected from Chemical Formula 2-1 to Chemical Formula 2-24 of, Chemical Formula 3-1 to Chemical Formula 3-24, Chemical Formula 4-1 to Chemical Formula 4-24, Chemical Formula 5-1 to Chemical Formula 5-23, Chemical Formula 6-1 to Chemical Formula 6-23 of [Group 1], but is not limited thereto. (the heteroatoms of specific compounds of [Group 1] are all "N")

[Group 1]
[Chemical Formula 2-1]
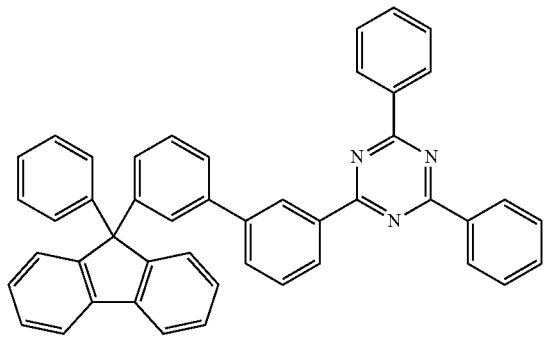
[Chemical Formula 2-2]
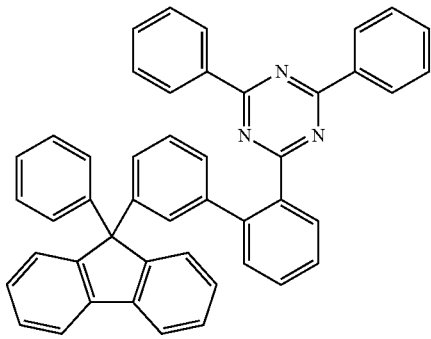
[Chemical Formula 2-3]
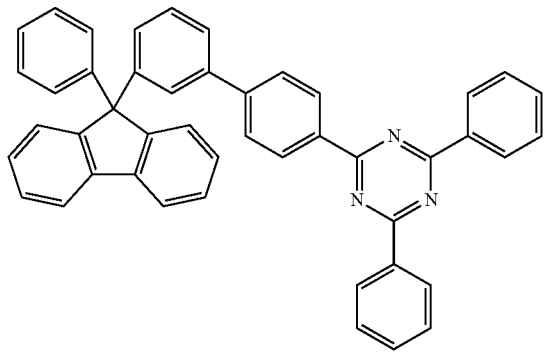
[Chemical Formula 2-4]
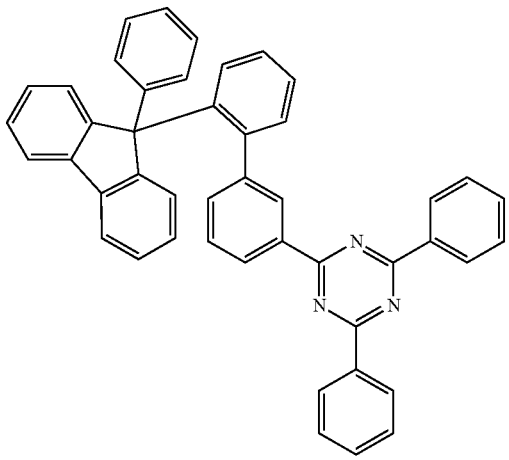
[Chemical Formula 2-5]
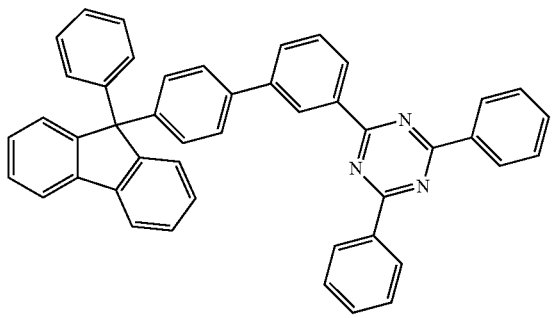
[Chemical Formula 2-6]
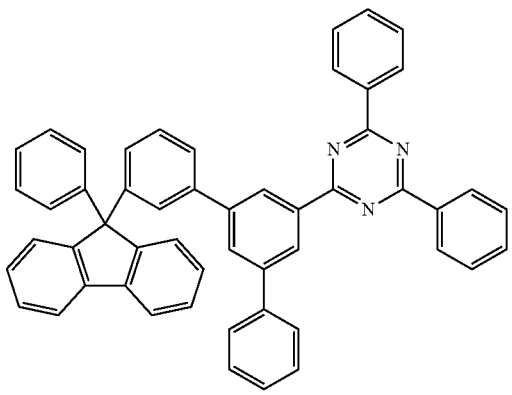

[Chemical Formula 2-7]
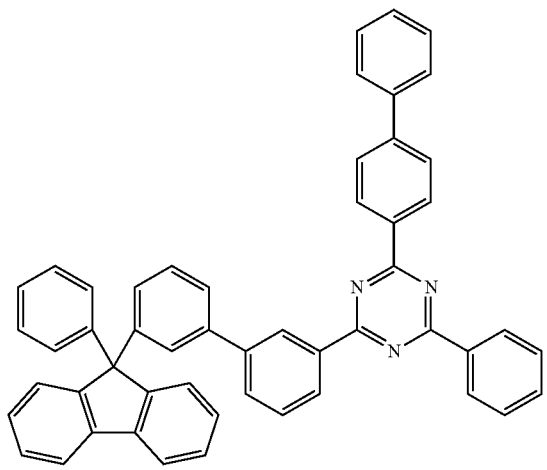
[Chemical Formula 2-8]
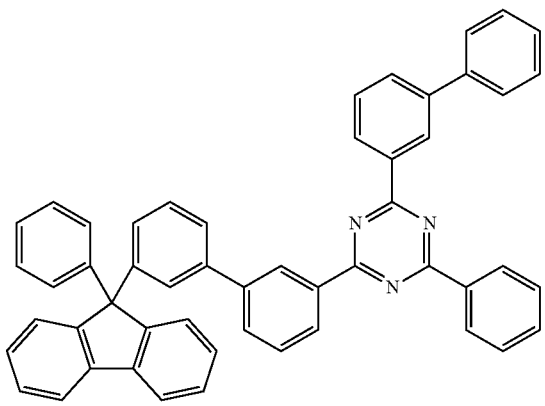
[Chemical Formula 2-9]
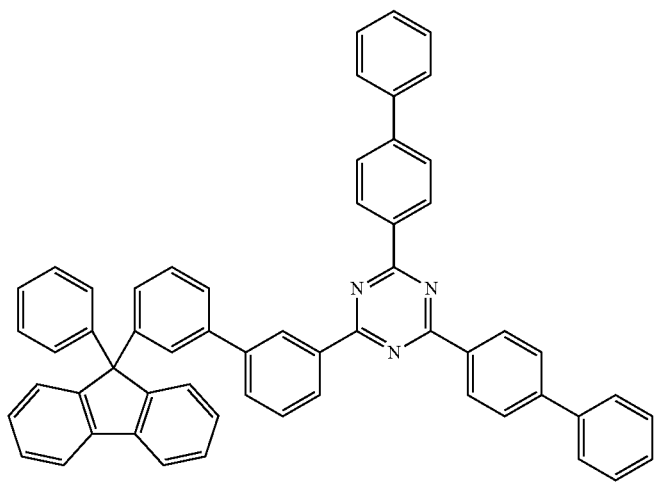
[Chemical Formula 2-10]
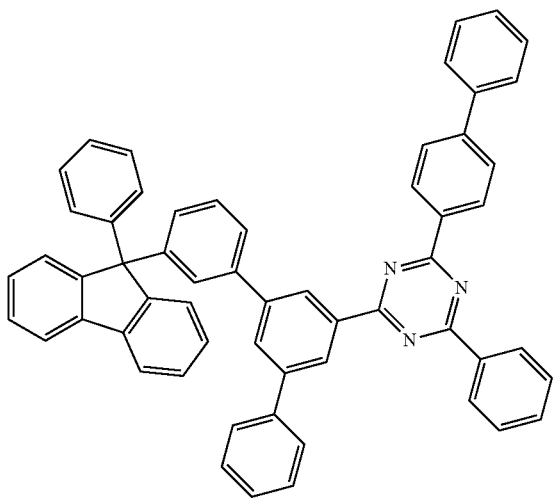

[Chemical Formula 2-11]
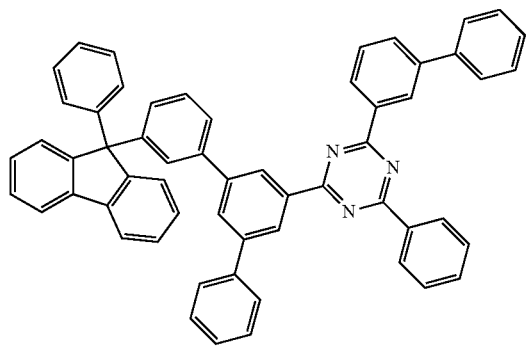
[Chemical Formula 2-12]
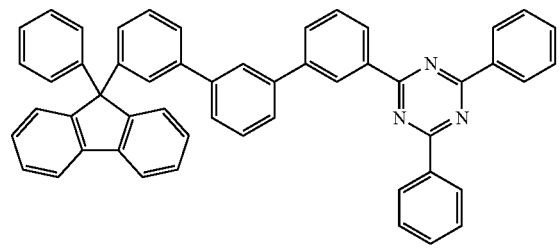
[Chemical Formula 2-13]
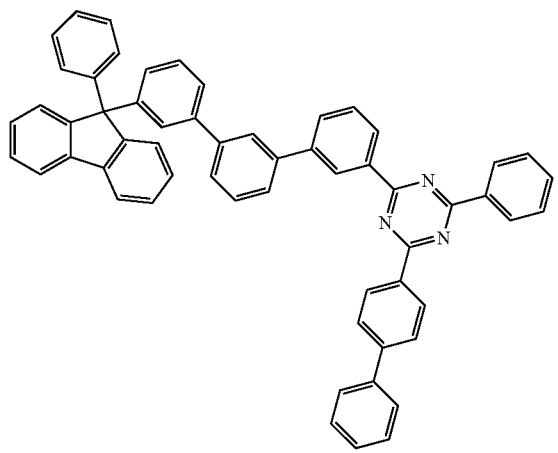
[Chemical Formula 2-14]
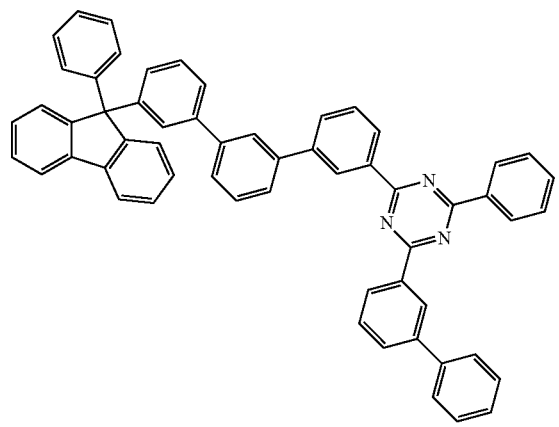
[Chemical Formula 2-15]
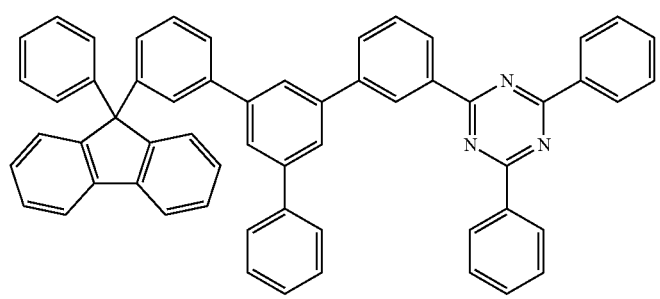
[Chemical Formula 2-16]
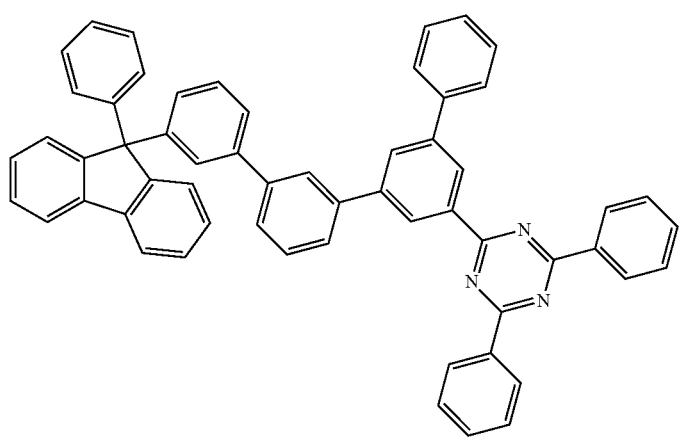

-continued
[Chemical Formula 2-17]
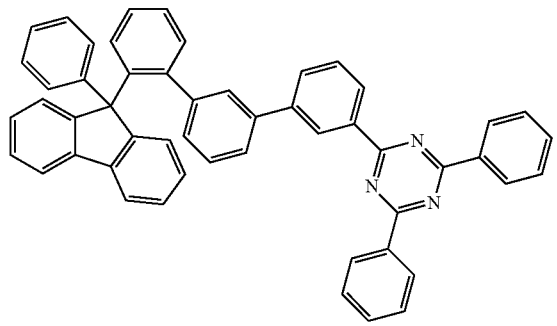
[Chemical Formula 2-18]
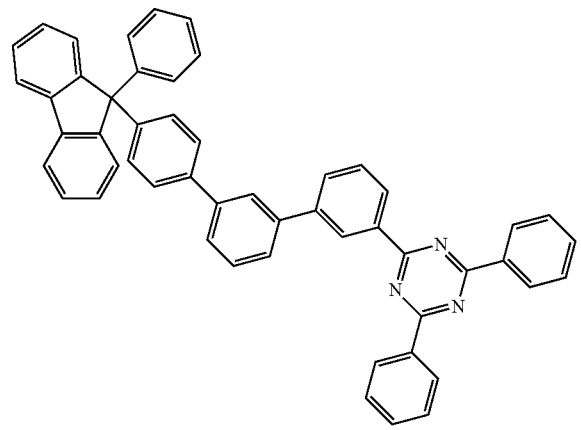
[Chemical Formula 2-19]
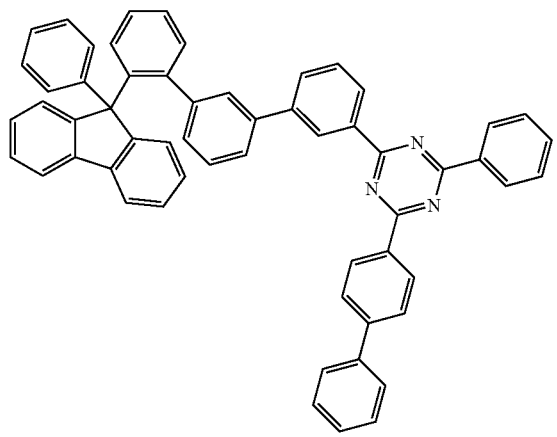
[Chemical Formula 2-20]
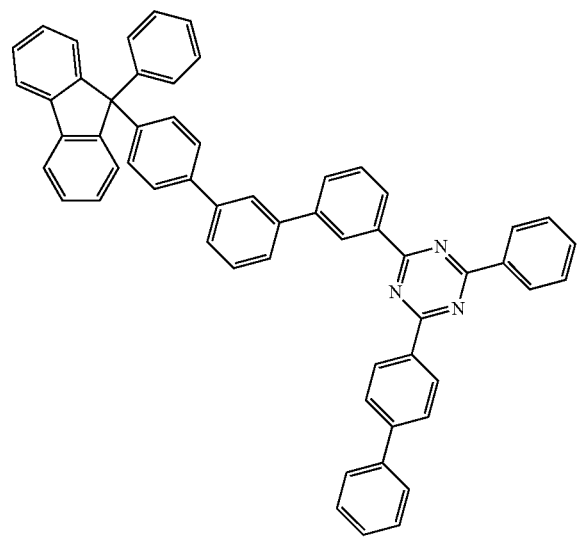
[Chemical Formula 2-21]
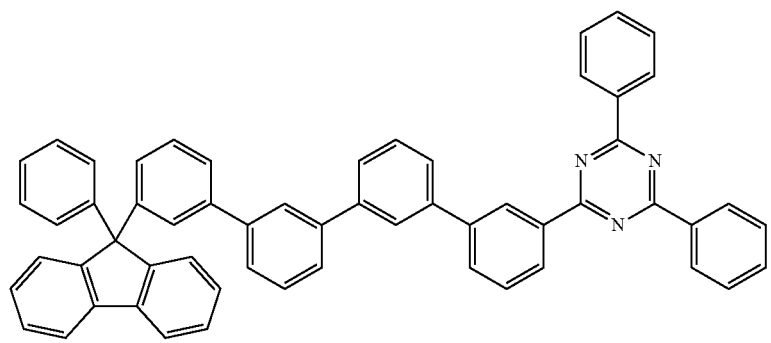

-continued
[Chemical Formula 2-22]
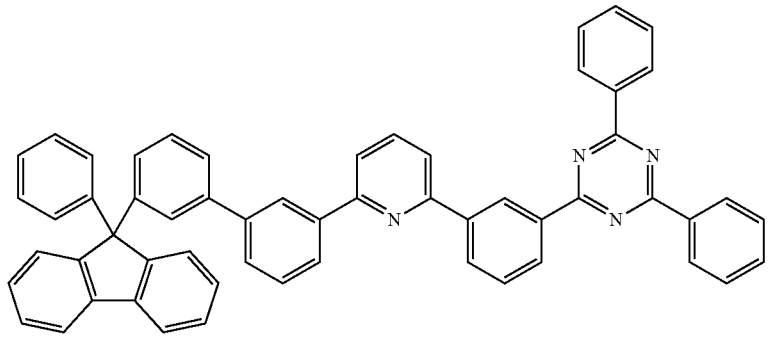
[Chemical Formula 2-23]
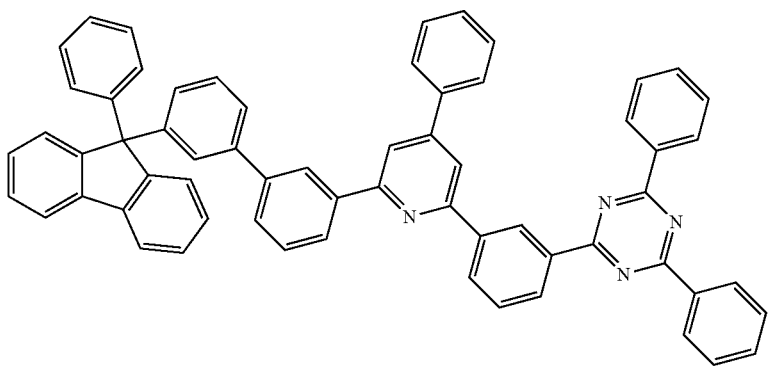
[Chemical Formula 2-24]
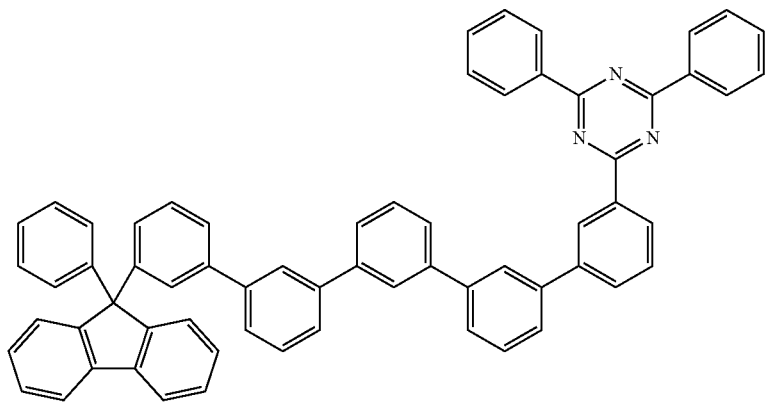
[Chemical Formula 3-1]     [Chemical Formula 3-2]
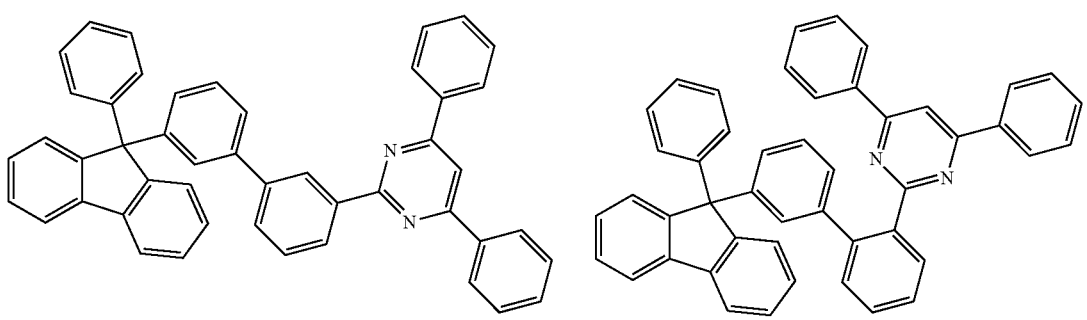

-continued
[Chemical Formula 3-3]
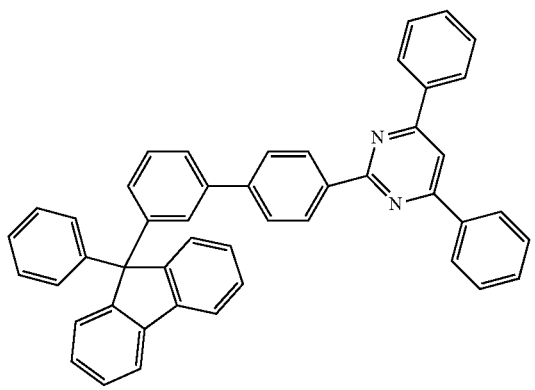
[Chemical Formula 3-4]
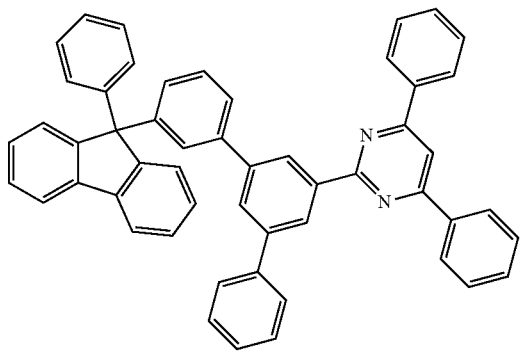
[Chemical Formula 3-5]
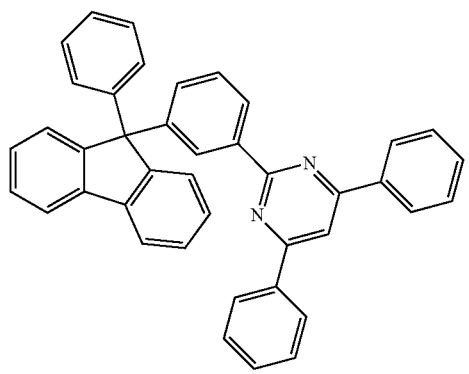
[Chemical Formula 3-6]
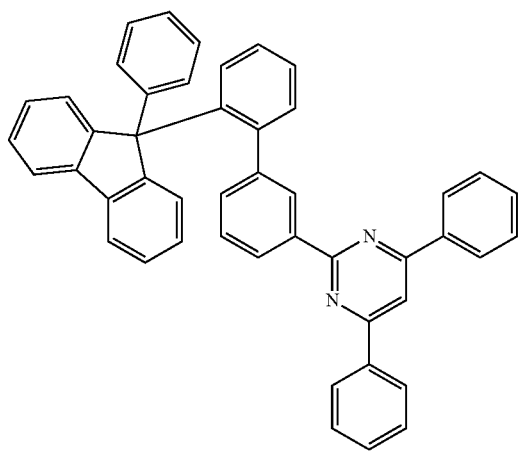
[Chemical Formula 3-7]
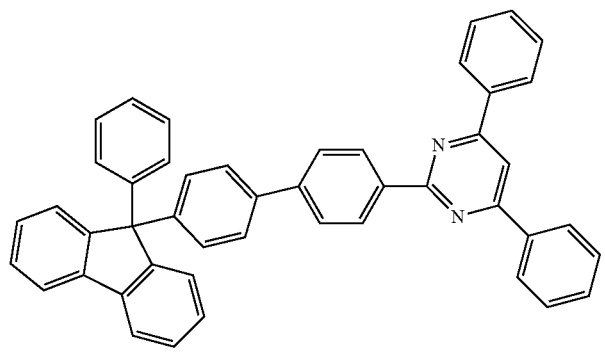

[Chemical Formula 3-8]
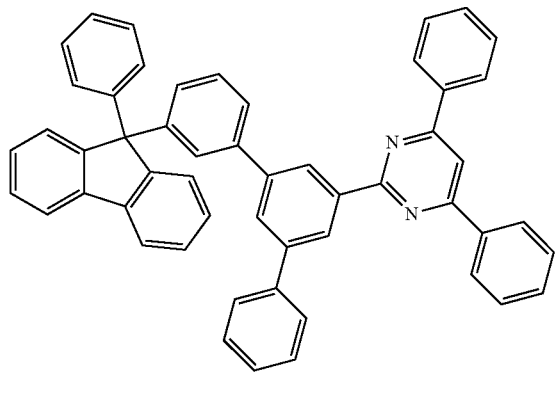
[Chemical Formula 3-9]
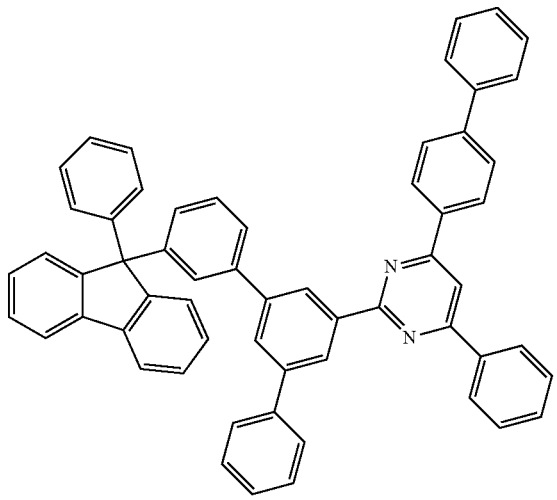
[Chemical Formula 3-10]
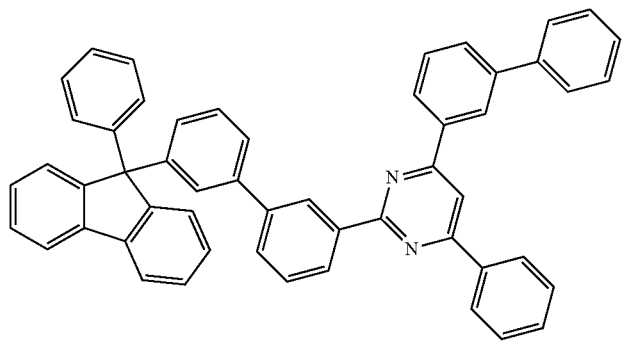
[Chemical Formula 3-11]
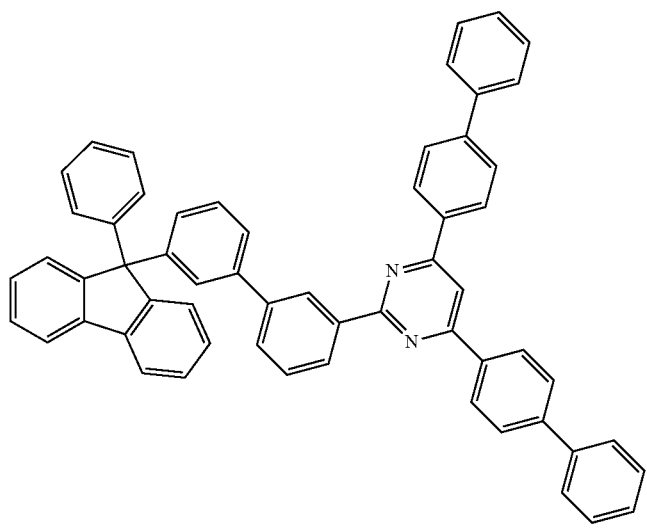

[Chemical Formula 3-12]
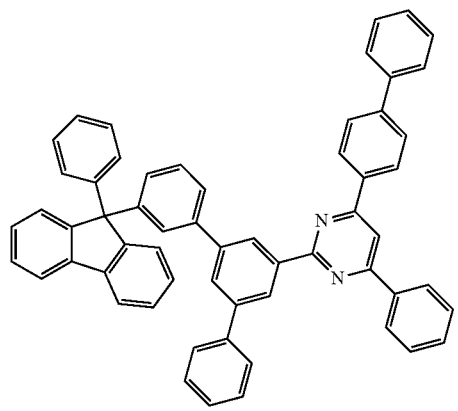
[Chemical Formula 3-13]
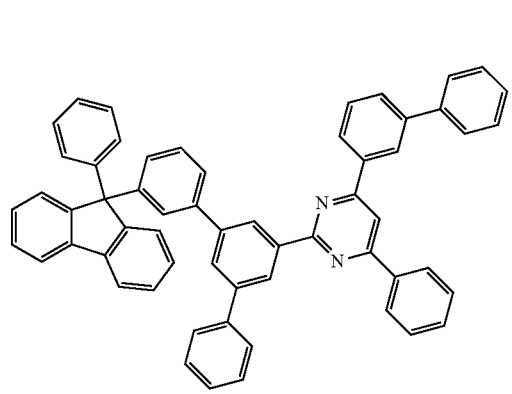
[Chemical Formula 3-14]
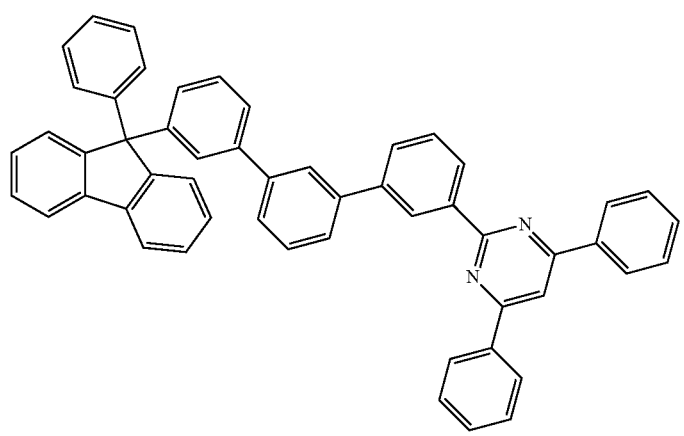
[Chemical Formula 3-15]
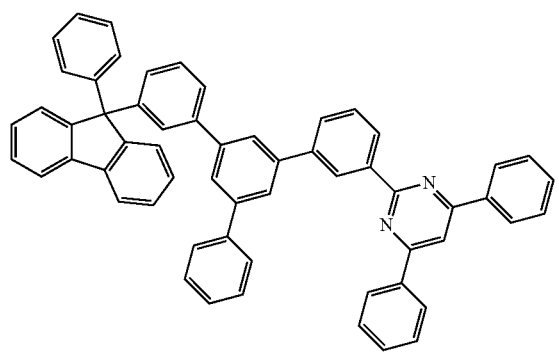
[Chemical Formula 3-16]
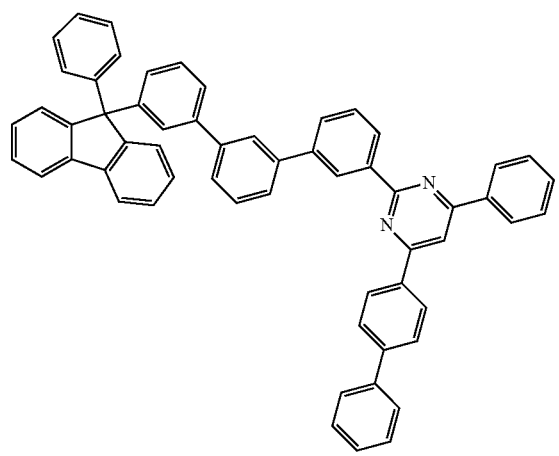

[Chemical Formula 3-17]
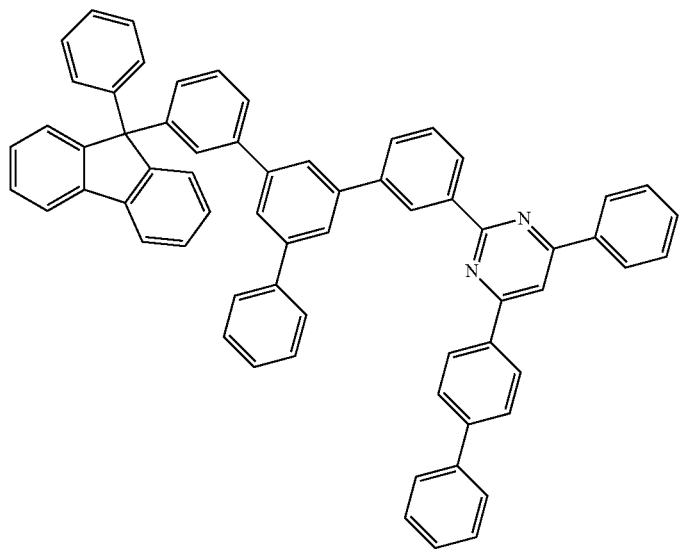
[Chemical Formula 3-18]
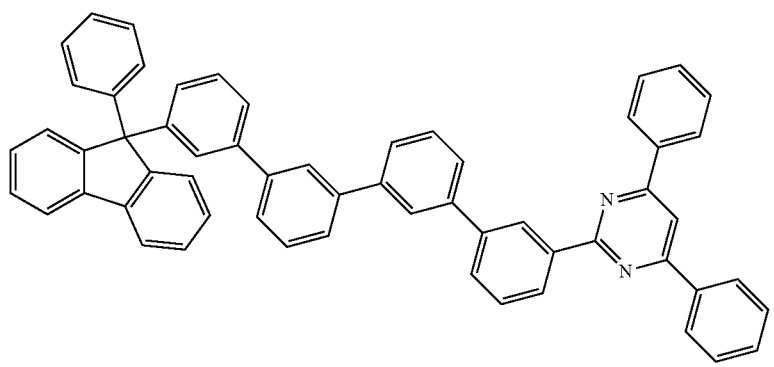
[Chemical Formula 3-19]
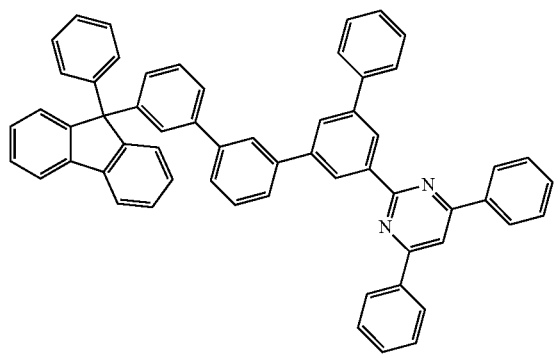
[Chemical Formula 3-20]
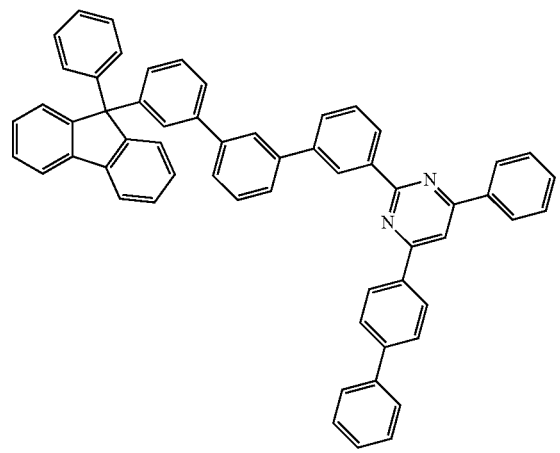

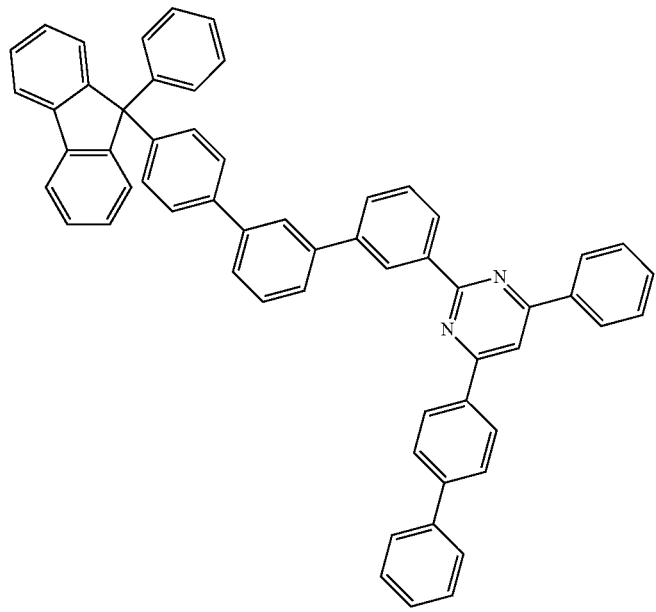
[Chemical Formula 3-21]
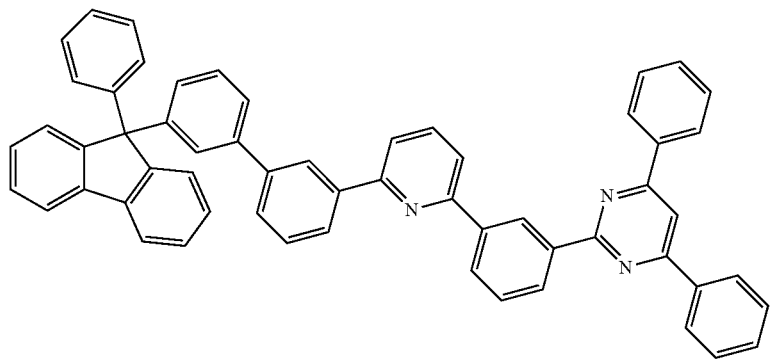
[Chemical Formula 3-22]
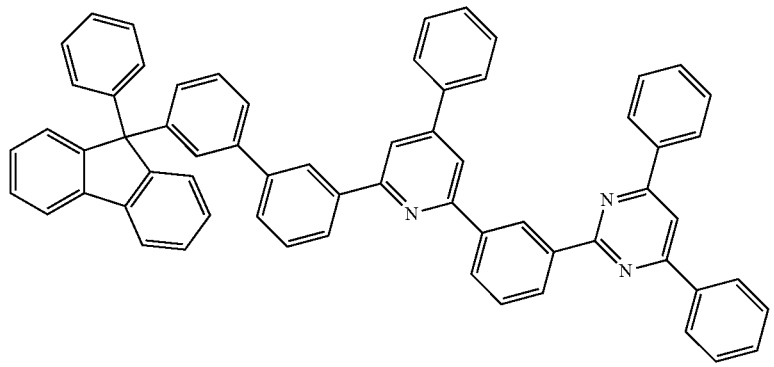
[Chemical Formula 3-23]

[Chemical Formula 3-24]
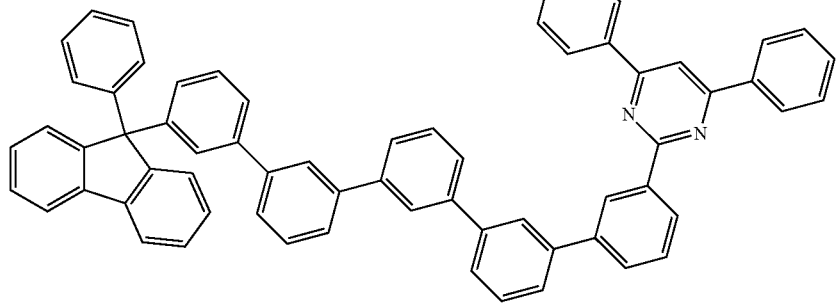
[Chemical Formula 4-1]
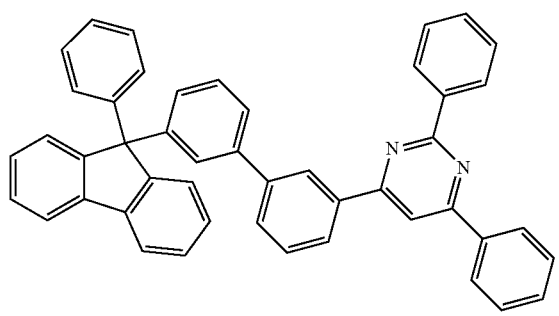
[Chemical Formula 4-2]
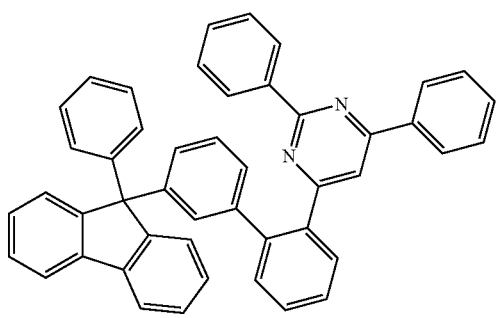
[Chemical Formula 4-3]
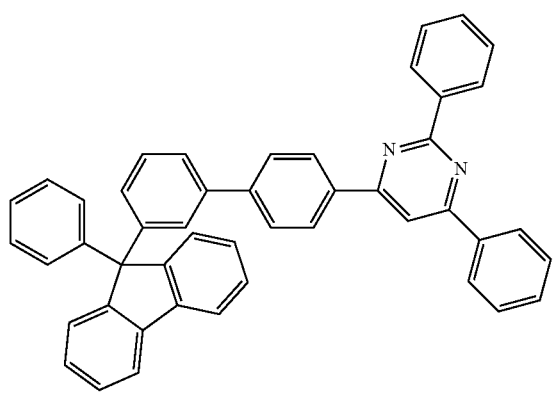
[Chemical Formula 4-4]
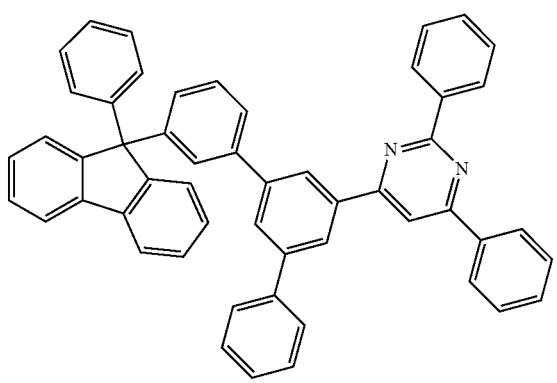
[Chemical Formula 4-5]
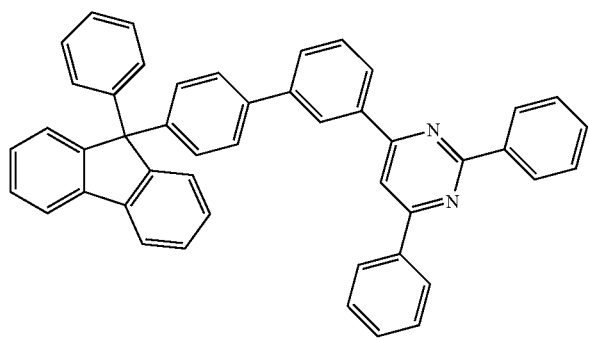

[Chemical Formula 4-6]
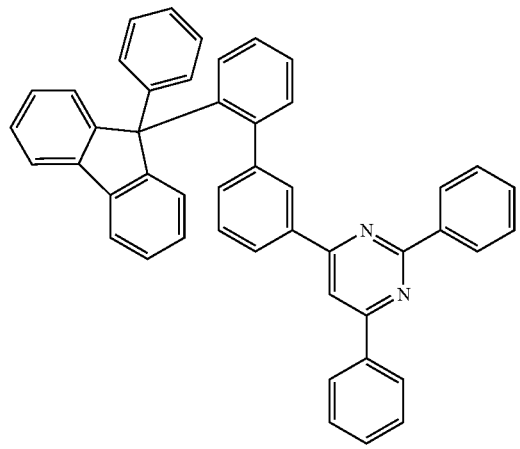
[Chemical Formula 4-7]
[Chemical Formula 4-8]
[Chemical Formula 4-9]
[Chemical Formula 4-10]

[Chemical Formula 4-11]
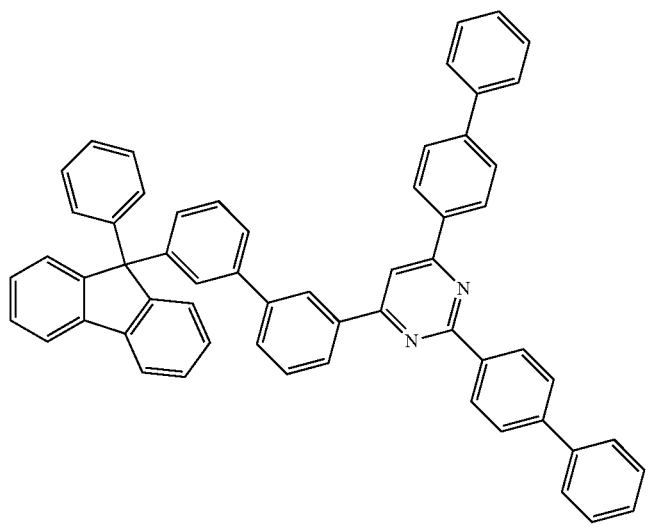
[Chemical Formula 4-12]
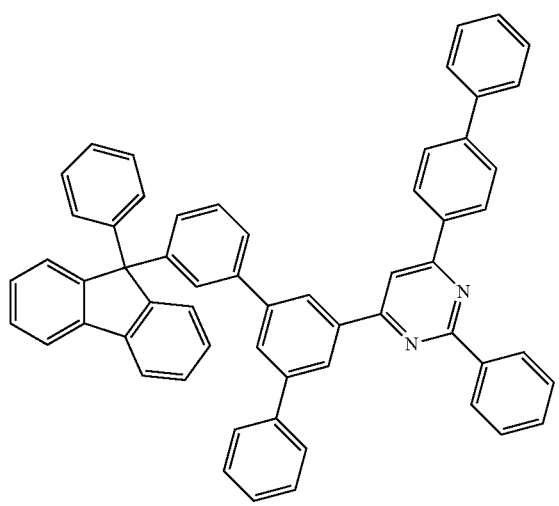
[Chemical Formula 4-13]
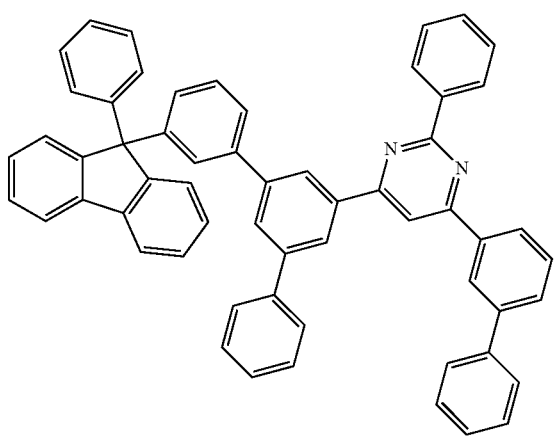
[Chemical Formula 4-14]
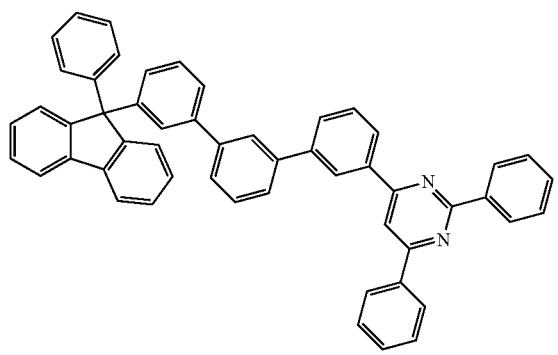
[Chemical Formula 4-15]
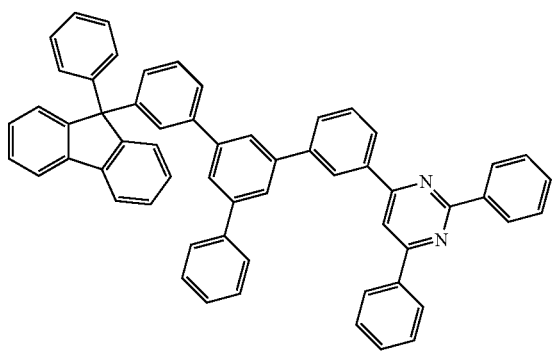

[Chemical Formula 4-16]
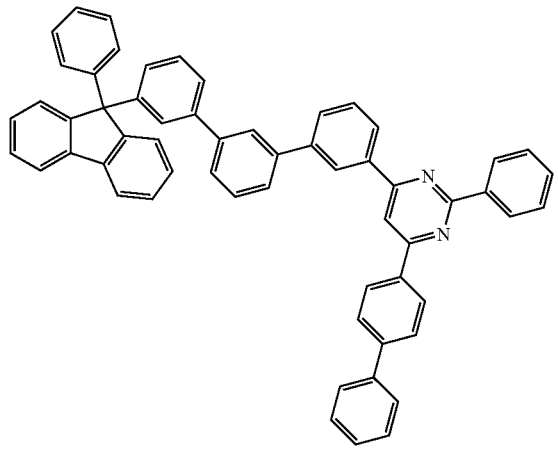
[Chemical Formula 4-17]
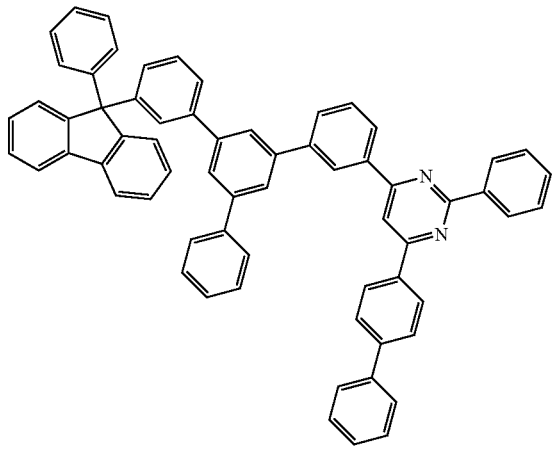
[Chemical Formula 4-18]
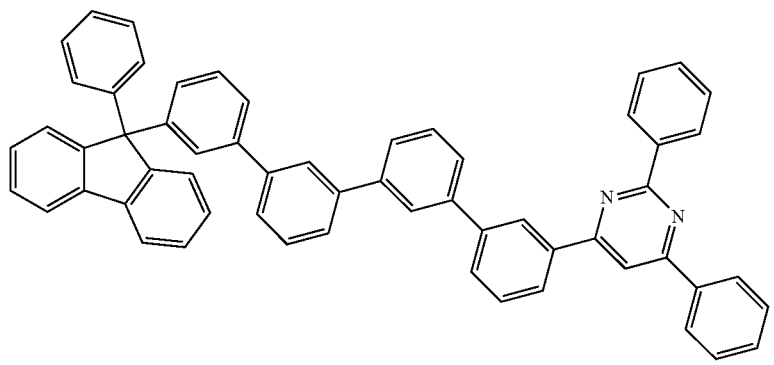
[Chemical Formula 4-19]
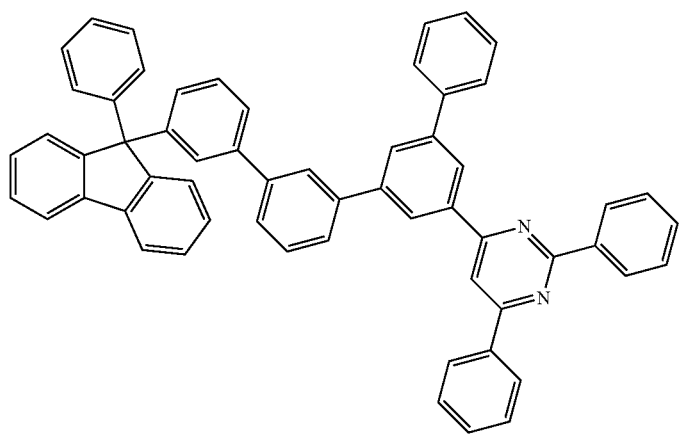

[Chemical Formula 4-20]
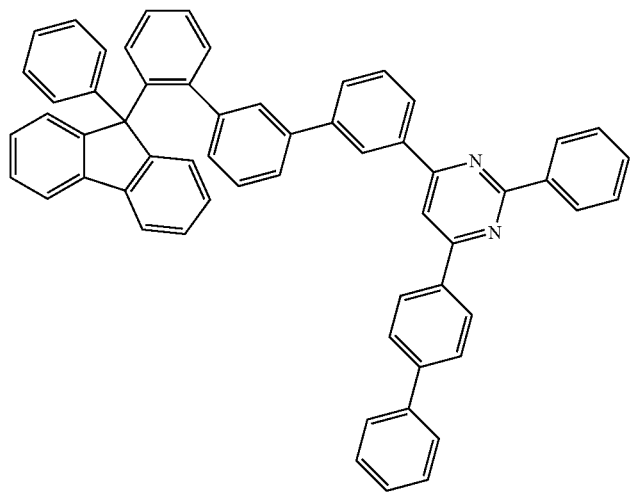
[Chemical Formula 4-21]
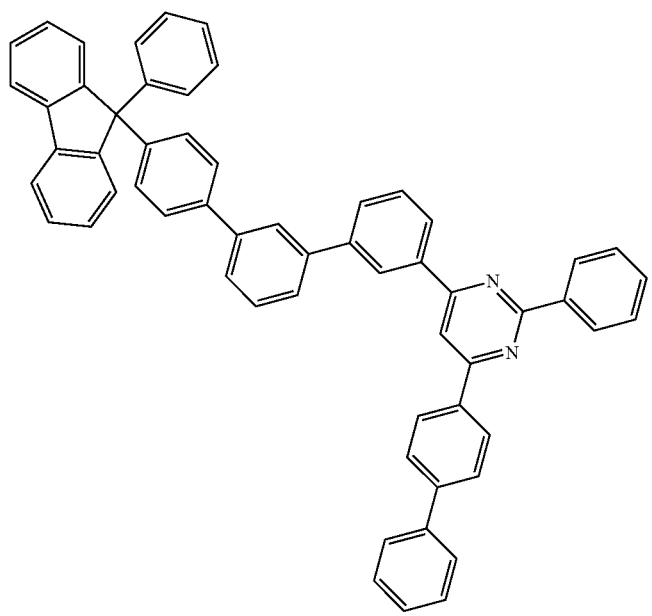
[Chemical Formula 4-22]
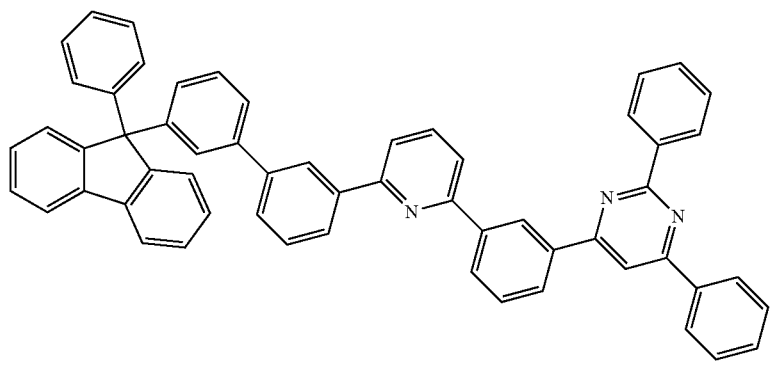

[Chemical Formula 4-23]
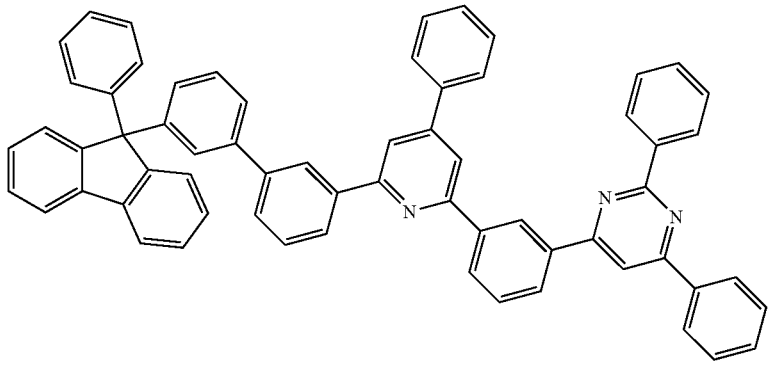
[Chemical Formula 4-24]
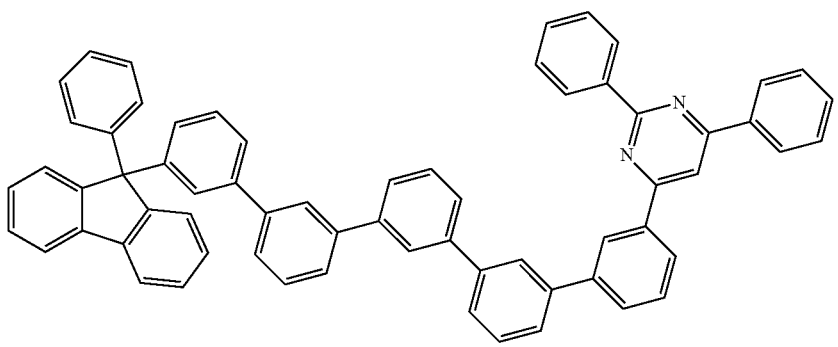
[Chemical Formula 5-1]
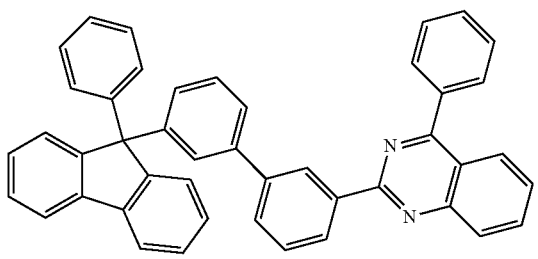
[Chemical Formula 5-2]
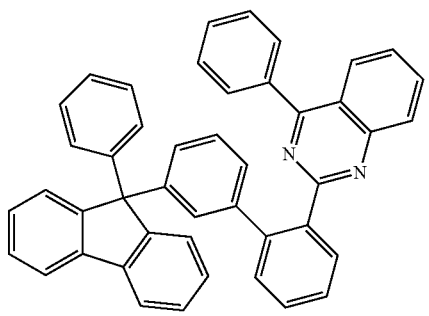
[Chemical Formula 5-3]
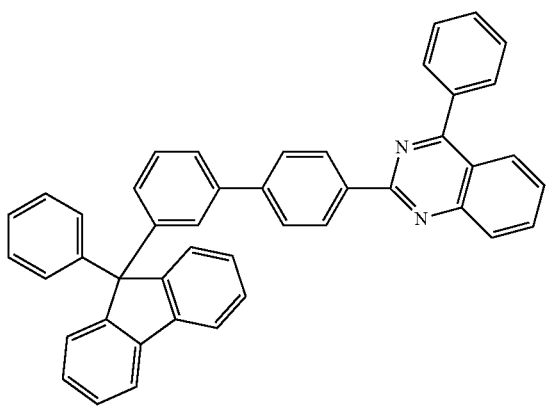
[Chemical Formula 5-4]
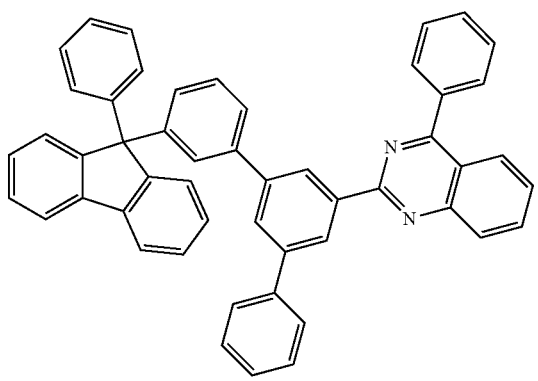

[Chemical Formula 5-5]
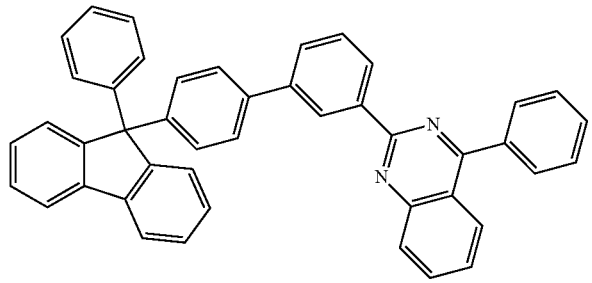
[Chemical Formula 5-6]
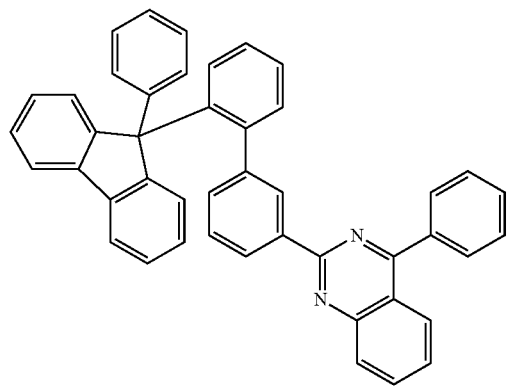
[Chemical Formula 5-7]
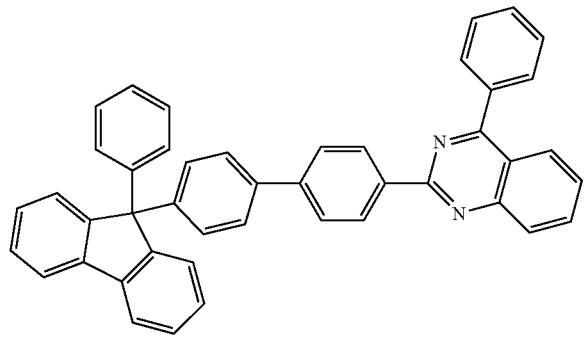
[Chemical Formula 5-8]
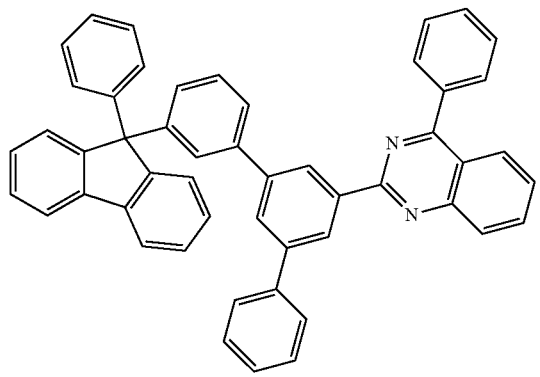
[Chemical Formula 5-9]
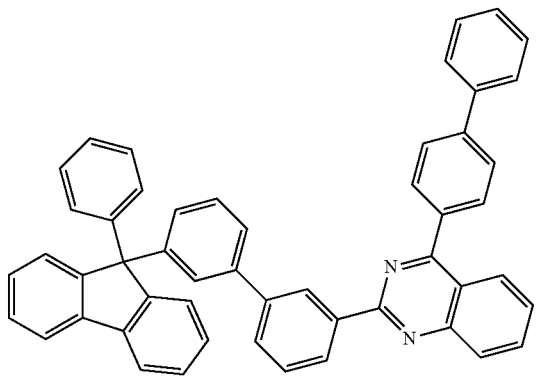

-continued
[Chemical Formula 5-10]
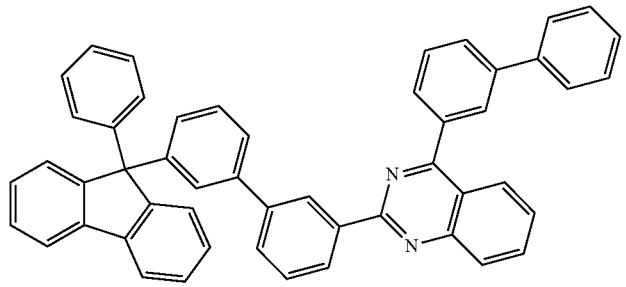
[Chemical Formula 5-11] [Chemical Formula 5-12]
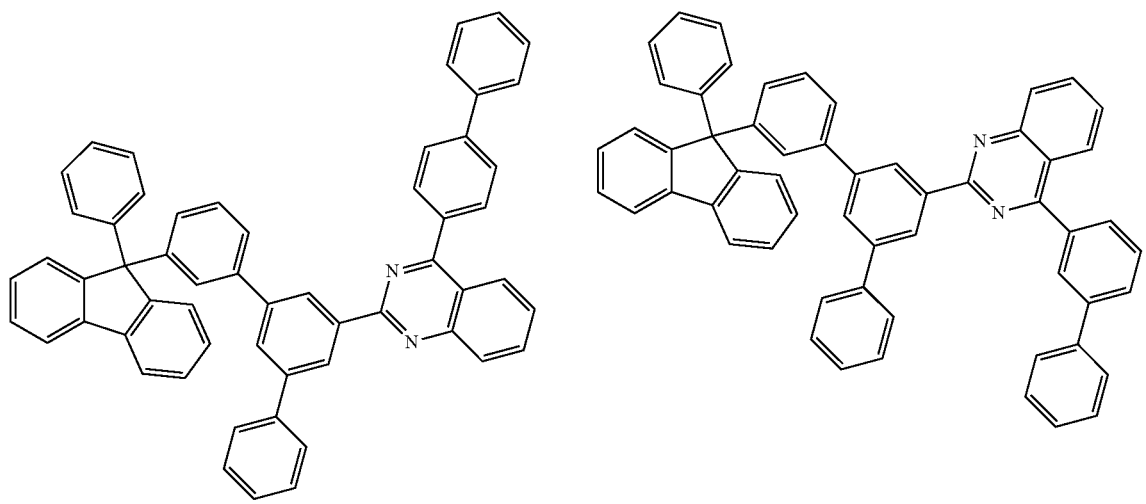
[Chemical Formula 5-13] [Chemical Formula 5-14]
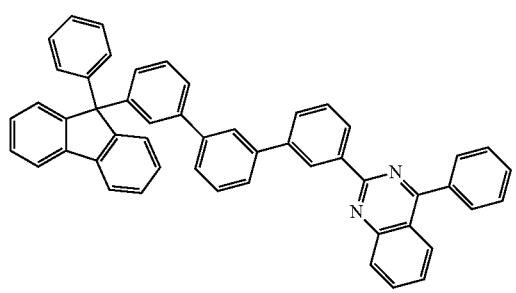

[Chemical Formula 5-15]
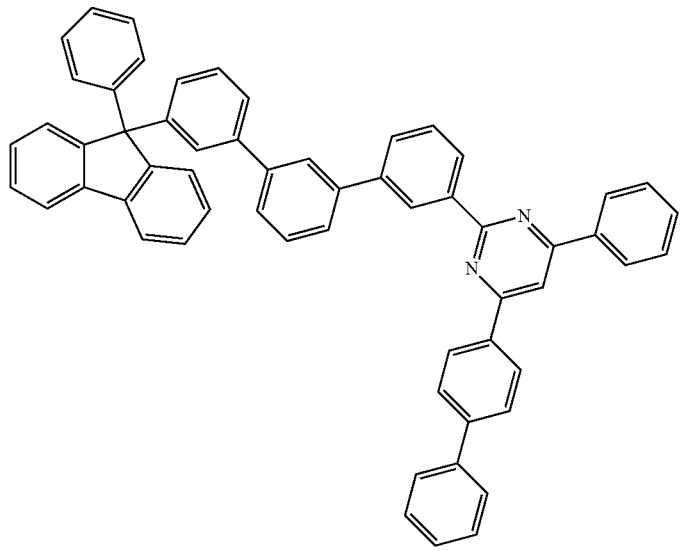
[Chemical Formula 5-16]
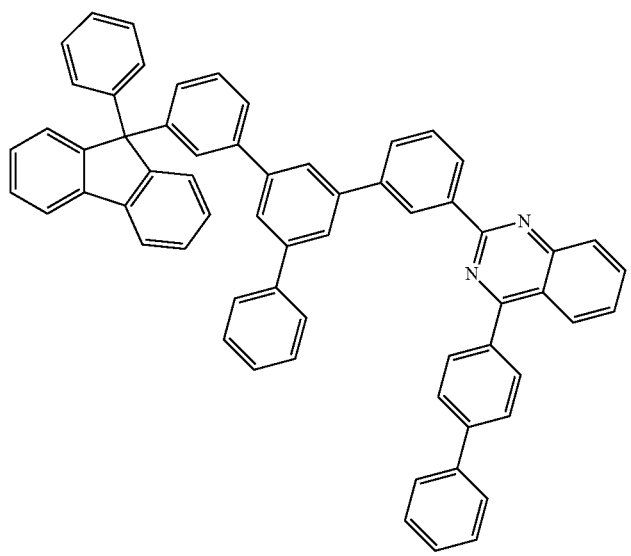
[Chemical Formula 5-17]
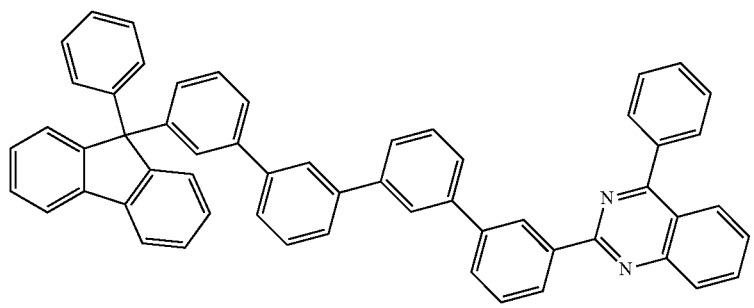

[Chemical Formula 5-18]
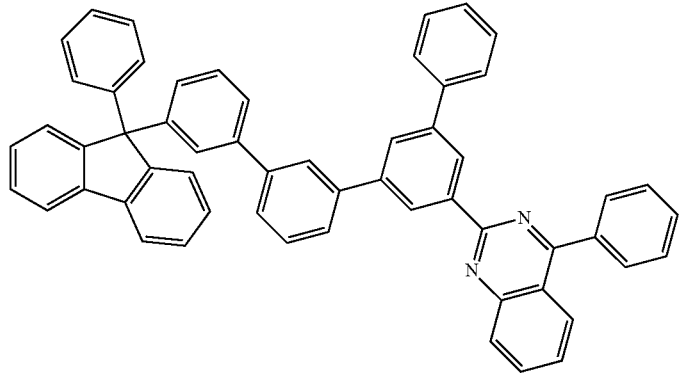
[Chemical Formula 5-19]
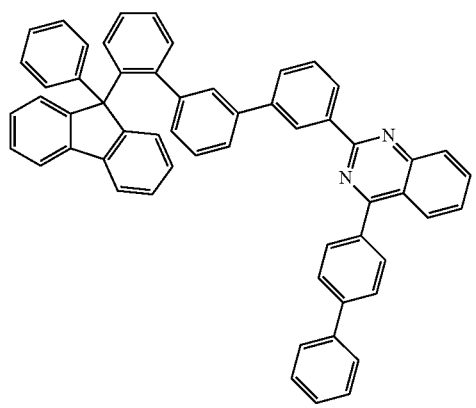
[Chemical Formula 5-20]
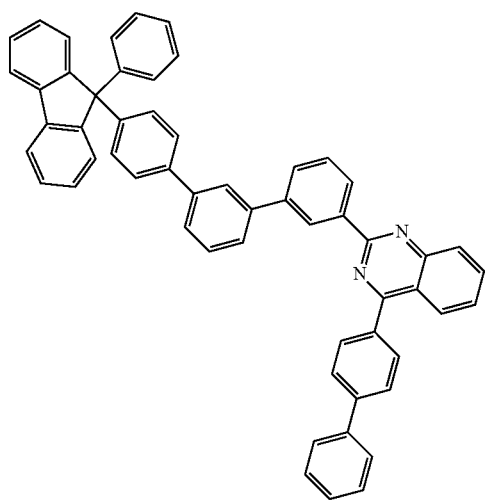
[Chemical Formula 5-21]
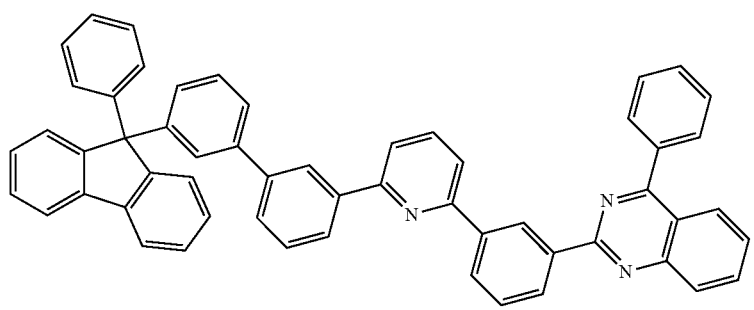
[Chemical Formula 5-22]
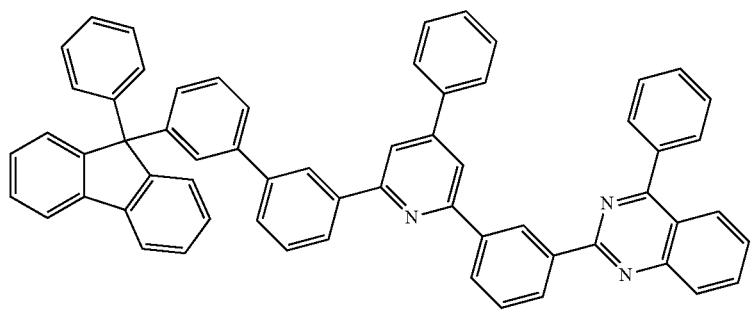

[Chemical Formula 5-23]
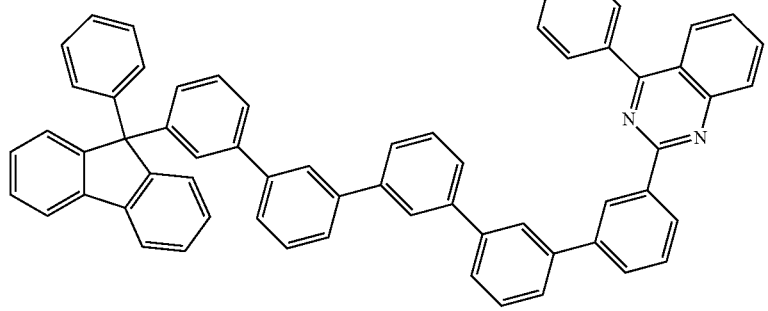
[Chemical Formula 6-1]
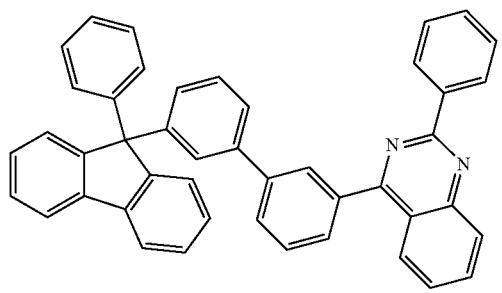
[Chemical Formula 6-2]
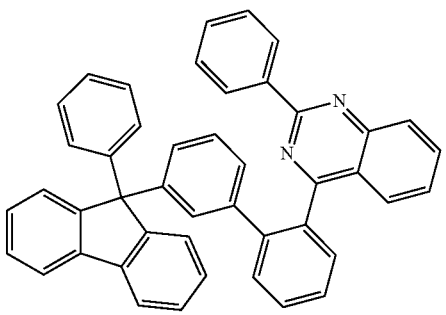
[Chemical Formula 6-3]
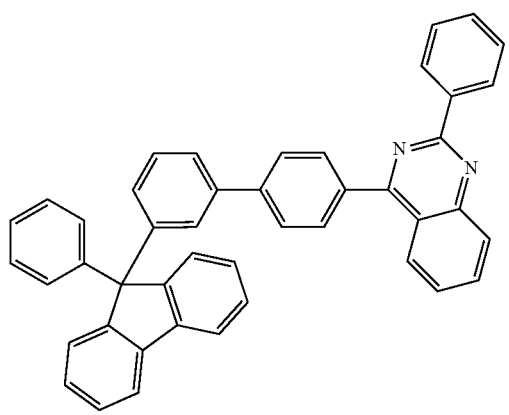
[Chemical Formula 6-4]
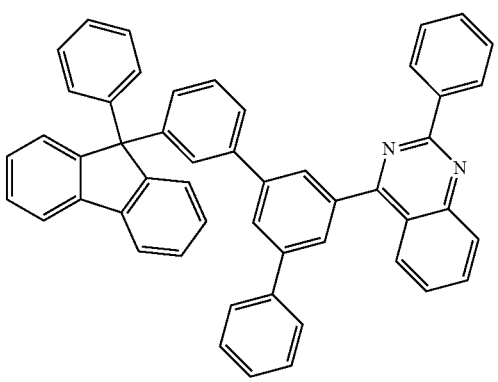
[Chemical Formula 6-5]
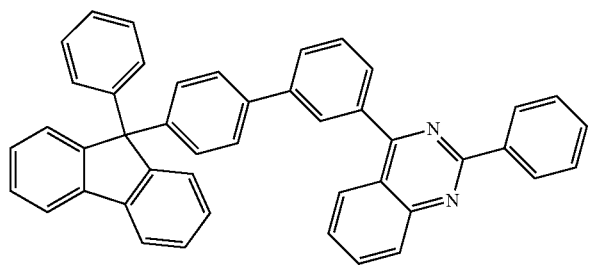

[Chemical Formula 6-6]
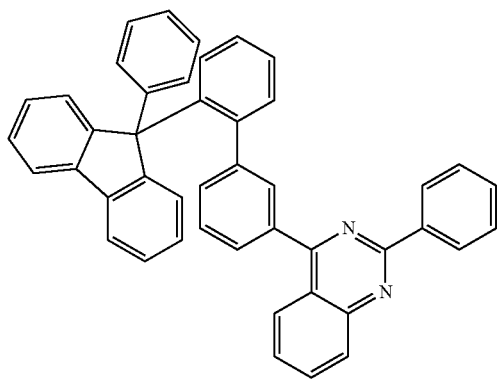
[Chemical Formula 6-7]
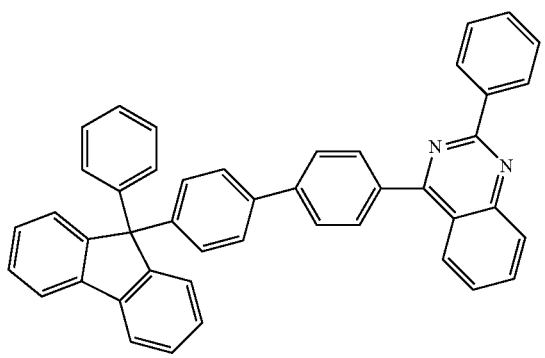
[Chemical Formula 6-8]
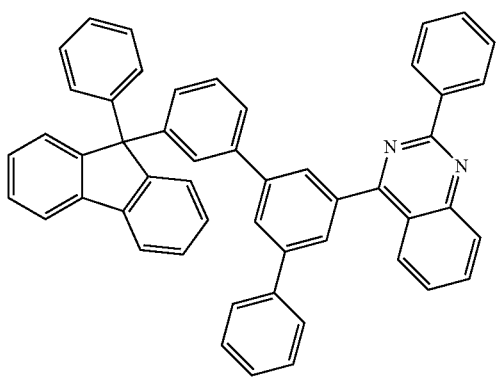
[Chemical Formula 6-9]
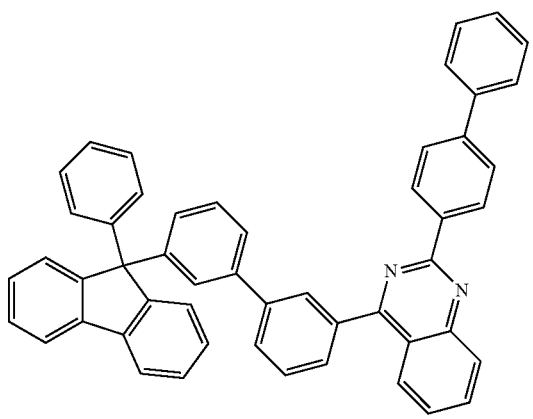
[Chemical Formula 6-10]
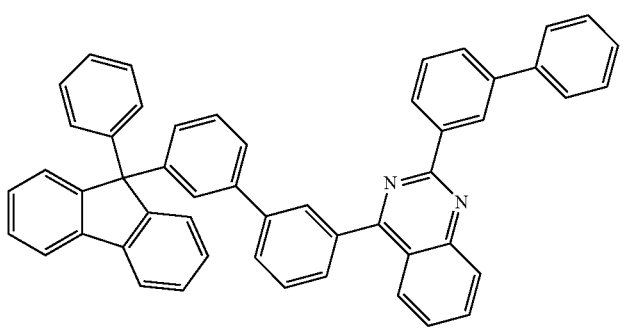

[Chemical Formula 6-11]
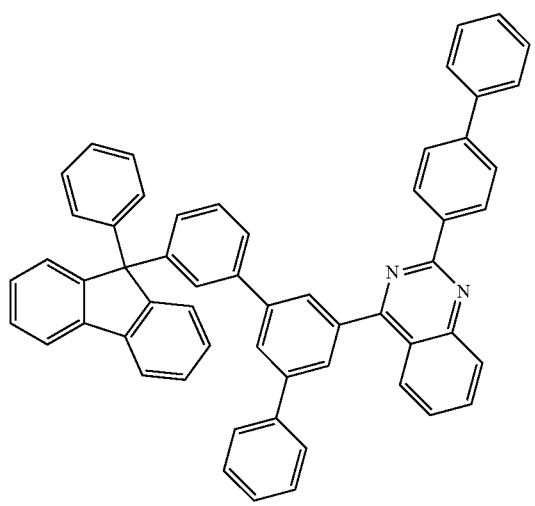
[Chemical Formula 6-12]
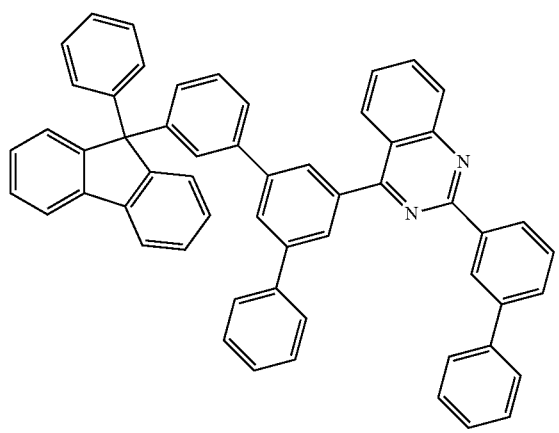
[Chemical Formula 6-13]
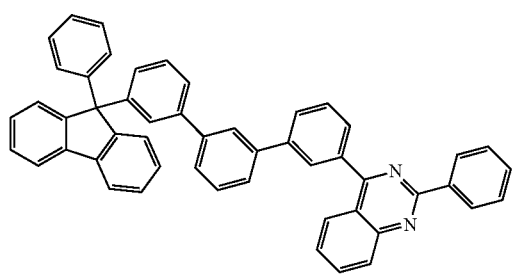
[Chemical Formula 6-14]
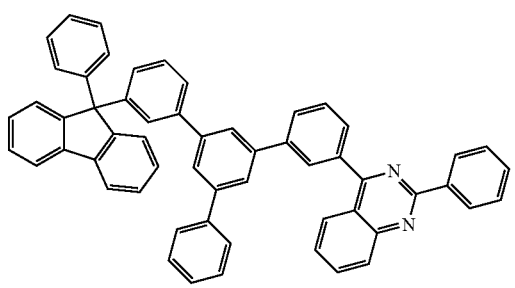

[Chemical Formula 6-15]
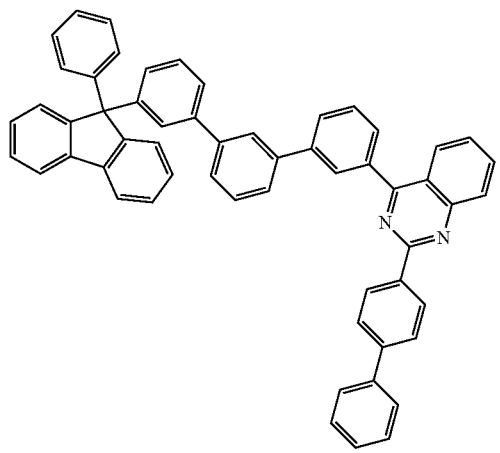
[Chemical Formula 6-16]
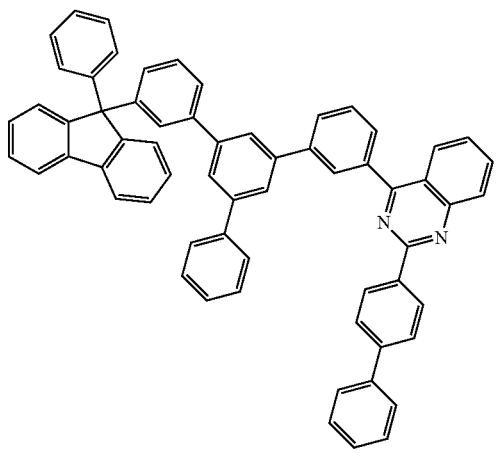
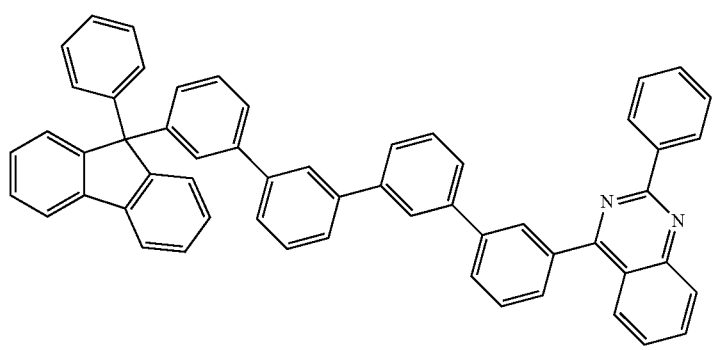
[Chemical Formula 6-17]
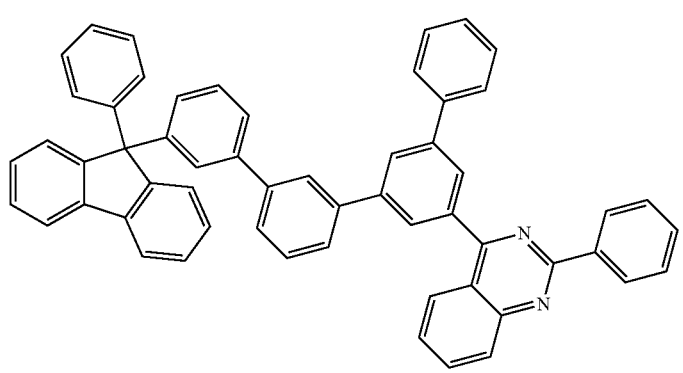
[Chemical Formula 6-18]

-continued
[Chemical Formula 6-19]
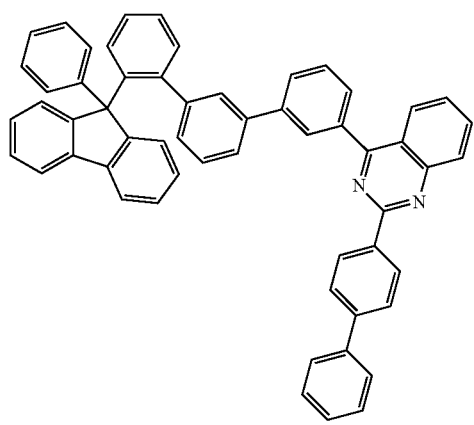
[Chemical Formula 6-20]
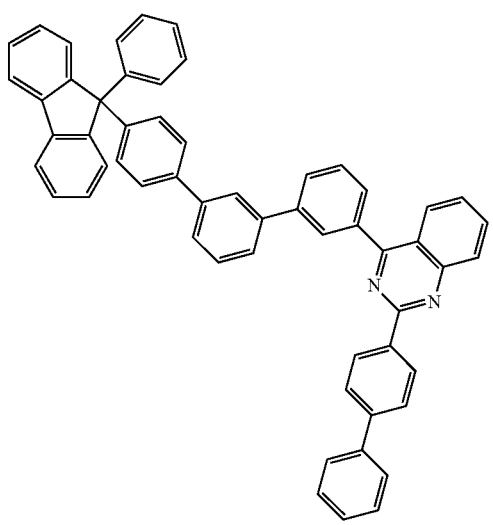
[Chemical Formula 6-21]
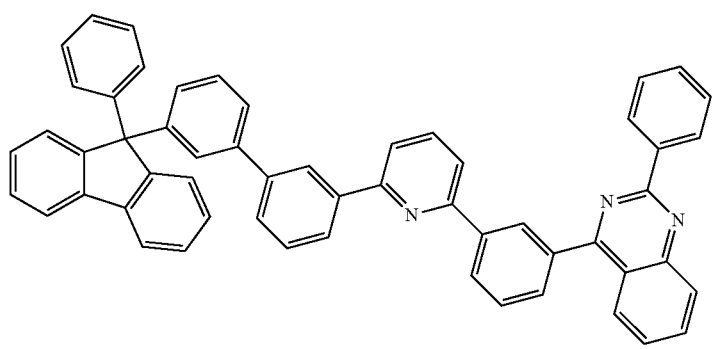
[Chemical Formula 6-22]
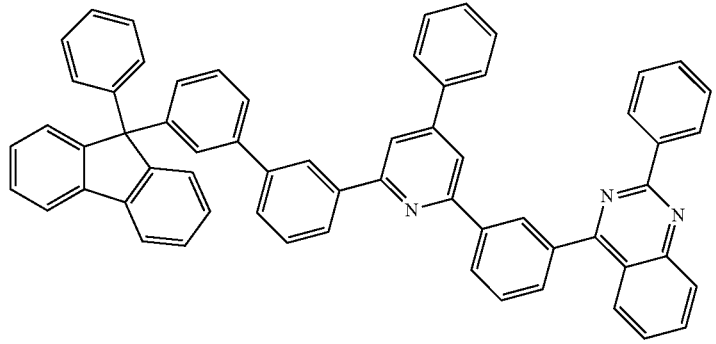
[Chemical Formula 6-23]
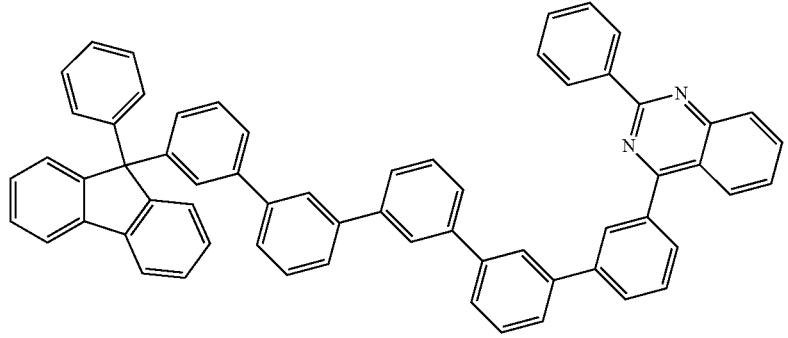

The organic compound may be applied to an organic optoelectric device.

The organic compound alone or as a mixture with other organic compounds may be applied to an organic optoelectric device. The organic compound is used with other organic compounds as a composition.

Hereinafter, an organic optoelectric device including the organic compound is described.

The organic optoelectric device may be any device to convert electrical energy into photoenergy and vice versa without particular limitation, and may be, for example an organic photoelectric diode, an organic light emitting diode, an organic solar cell, and an organic photo conductor drum.

The organic optoelectric device may include an anode and a cathode facing each other, at least one organic layer between the anode and the cathode, and the organic layer includes the organic compound.

For example, the organic layer includes a hole transport layer, an electron transport layer, and an emission layer between the hole transport layer and the electron transport layer, and the organic compound may be included in the electron transport layer.

For example, the organic layer includes a hole transport layer, an electron transport layer, and an emission layer between the hole transport layer and the electron transport layer, and the organic compound may be included in the emission layer.

For example, the organic compound may be used as a host material in the emission layer.

For example, the organic layer further includes a hole transport layer, an electron transport layer, an emission layer between the hole transport layer and the electron transport layer, and an electron transport auxiliary layer (hole blocking layer) between the emission layer and the electron transport layer, and the organic compound may be included in the electron transport auxiliary layer.

Herein, an organic light emitting diode as one example of an organic optoelectric device is described referring to drawings.

FIGS. 1 to 4 are cross-sectional views showing organic light emitting diodes according to each embodiment.

Referring to FIG. 1, an organic light emitting diode 100 according to an embodiment includes an anode 120 and a cathode 110 and an organic layer 105 between the anode 120 and the cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like of an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/A1, $LiO_2$/Al, LiF/Ca, LiF/Al and $BaF_2$/Ca, but is not limited thereto.

The organic layer 105 includes the organic compound.

Figure 2:
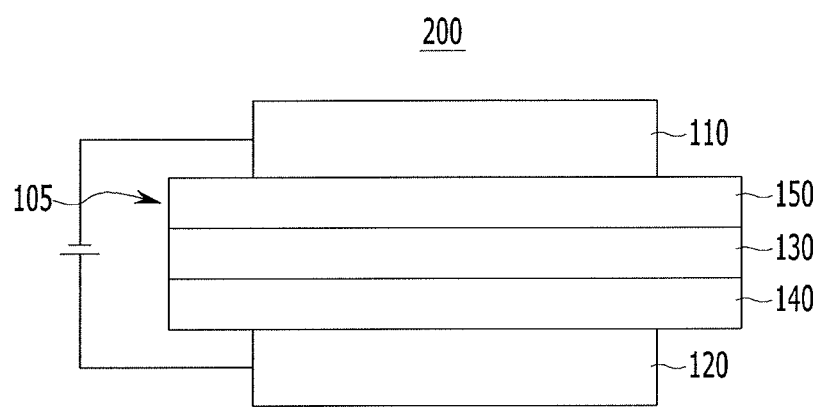

Referring to FIG. 2, an organic light emitting diode 200 according to an embodiment includes an anode 120 and a cathode 110 facing each other, and an organic layer 105 between the anode 120 and the cathode 110, and the organic layer 105 includes an emission layer 130, a hole transport layer 140, and an electron transport layer 150.

The emission layer 130 is disposed between the hole transport layer 140 and the electron transport layer 150 and may include the organic compound.

The emission layer 130 may include the organic compound as a host, and may include the organic compound alone, at least two of the organic compounds, or a mixture of the organic compound and other organic compounds.

The emission layer 130 may further include a dopant. The dopant may be a red, green, or blue dopant, for example a phosphorescent dopant.

The dopant is mixed with the first host compound and the second host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The phosphorescent dopant may be an organometal compound including Ir, Pt,

Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

[Chemical Formula Z] $L_2MX$

In Chemical Formula Z, M is a metal, and L and X are the same or different, and are a ligand to form a complex compound with M.

The M may be, for example, Ir, Pt, Os, Ti, Zr, Hf, Eu, Tb, Tm, Fe, Co, Ni, Ru,

Rh, Pd, or a combination thereof, and the L and X may be. for example a bidendate ligand.

The emission layer 130 may be formed using a dry film formation method or a solution process. The dry film formation method may be, for example a chemical vapor deposition (CVD) method, sputtering, plasma plating, and ion plating, and two or more compounds may be simultaneously formed into a film or compound having the same deposition temperature may be mixed and formed into a film. The solution process may be, for example inkjet printing, spin coating, slit coating, bar coating and/or dip coating.

Figure 3:
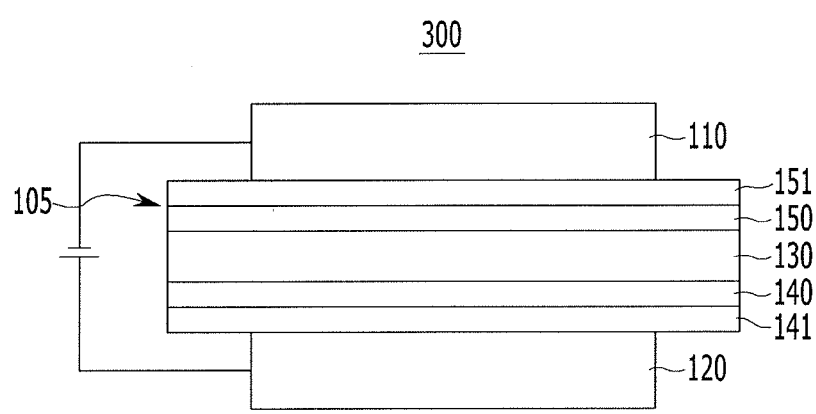

Referring to FIG. 3, an organic light emitting diode 300 according to an embodiment includes a anode 120 and a cathode 110 facing each other, and an organic layer 105 between the anode 120 and the cathode 110, the organic layer 105 includes an emission layer 130, a hole transport layer 140, and an electron transport layer 150, a hole injection layer 141 between the anode 120 and the hole transport layer 140, and an electron injection layer 151 between the cathode 110 and the electron transport layer 150, and the emission layer 130 or the electron transport layer 150 includes the organic compound.

Figure 4:
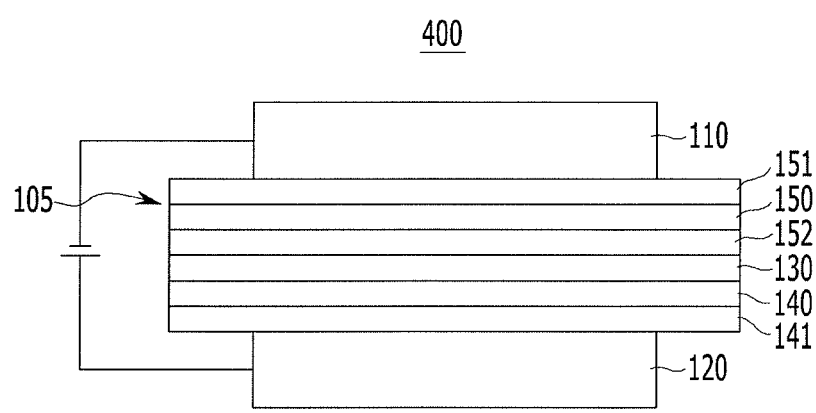

Referring to FIG. 4, an organic light emitting diode 400 according to an embodiment includes an anode 120 and a cathode 110, and an organic layer 105 between the anode 120 and the cathode 110, the organic layer 105 includes an emission layer 130, a hole transport layer 140, and an electron transport layer 150, a hole injection layer 141 between the anode 120 and the hole transport layer 140, and an electron injection layer 151 between the cathode 110 and the electron transport layer 150, and an electron transport auxiliary layer (holeblocking layer) 152 between the emission layer 130 and the electron transport layer 150, and the emission layer 130, the electron transport layer 150, or the electron transport auxiliary layer (hole blocking layer) 152 includes the organic compound.

The hole injection layer may improve interface properties between ITO as an anode and an organic material used for the hole transport layer, and is applied on a non-planarized ITO and thus planarizes the surface of the ITO. For example, the hole injection layer may include a material having a median value, particularly desirable conductivity between a work function of ITO and HOMO of the hole transport layer, in order to adjust a difference a work function of ITO as an anode and HOMO of the hole transport layer. In connection with the present invention, the hole injection layer may include N4,N4'-diphenyl-N4,N4'-bis(9-phenyl-9H-carbazol-3-yl)biphenyl-4,4'-diamine), but is not limited thereto. In addition, the hole injection layer may further include a conventional material, for example, copper phthlalocyanine (CuPc), aromatic amines such as N,N'-dinaphthyl-N,N'-phenyl-(1,1'-biphenyl)-4,4'-diamine (NPD), 4,4',4"- tris[methylphenyl(phenyl)amino] triphenyl amine (m-MTDATA), 4,4',4"-tris[1- naphthyl(phenyl)amino] triphenyl amine (1-TNATA), 4,4',4"-tris[2- naphthyl(phenyl)amino]triphenyl amine (2-TNATA), 1,3,5-tris[N-(4- diphenylaminophenyl)phenylamino]benzene (p-DPA-TDAB), and the like, compounds such as 4,4'-bis[N-[4-{N,N-bis(3-methylphenypamino}phenyl]-N- phenylamino]biphenyl (DNTPD), hexaazatriphenylene-hexacarbonitirile (HAT-CN), and the like, a polythiophene derivative such as poly(3,4-ethyleneclioxythiophene)- poly(styrnesulfonate) (PEDOT) as a conductive polymer. The hole injection layer may be, for example coated on ITO as, an anode in a thickness of about 10 Å to about 300 Å.

When a hole transport region includes a hole injection layer, the hole injection layer may be formed on the anode 120 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ ton to about $10^{-3}$ torr, and a deposition rate of about 0.01 to about 100° C./sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in a driving voltage.

The hole transport region may further include a charge-generating material to improve conductivity, in addition to the materials as described above. The charge- generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited theieto. For example, non-limiting examples of the p- dopant are quinone derivatives such as tetracyanoquinonedimethane (TCNQ), 2,3,5,6- tetralluoro-tetracyano-1,4-benzoquinonedimethane (F4-TCNQ), and the like; metal oxides such as tungsten oxide, molybdenum oxide, and the like; and cyano-containing compounds such as compound HT-D1 below, but is not limited thereto.

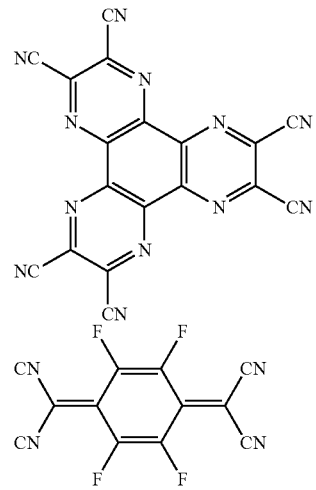

<Compound HT-D1>

<F4-TCNQ>

The hole transport region may further include a buffer layer.

The buffer layer may compensate for an optical resonance distance of light according to a wavelength of the light emitted from the emission layer, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer.

The emission layer may include a host and a dopant.

An organic optoelectric device according to an embodiment of the present invention includes the compound for an organic optoelectric device represented by Chemical Formula 1 alone, or the compound for an organic optoelectric device represented by Chemical Formula 1 as a first host and a carbazole-based compound as a second host.

The carbazole-based compound may specifically be represented by Chemical Formula A or may consist of a combination of a moiety represented by Chemical Formula B and a moiety represented by Chemical Formula C.

[Chemical Formula A]

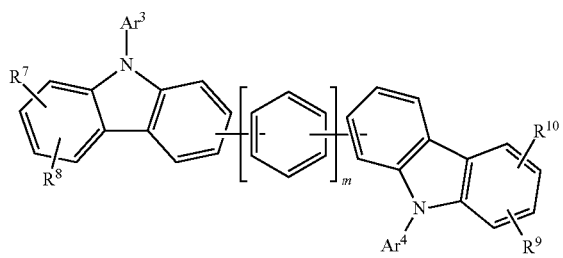

[Chemical Formula B]

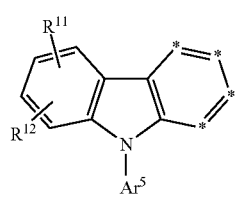

[Chemical Formula C]

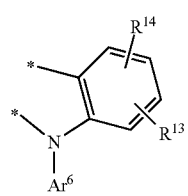

In Chemical Formula A to Chemical Formula C, $Ar^3$ to $Ar^6$ are independently a substituted or unsubstituted C6 to C30 aryl group, or a substituted or unsubstituted C2 to C30 heteroaryl group, p m is an integer of 0 or 1, adjacent two *'s of Chemical Formula B are combined with two *'s of Chemical Formula C to form a fused ring and * that does not form the fused ring of Chemical Formula B is independently $CR^b$, and $R^b$ and $R^7$ to $R^{14}$ are independently hydrogen, deuterium, a substituted or unsubstituted C1 to C10 alkyl group, a substituted or unsubstituted C6 to C30 aryl group or a substituted or unsubstituted C2 to C30 heteroaryl group.

The bicarbazole represented by Chemical Formula A may be, for example selected from compounds of [Group B], and the indolocarbazole consisting of the combination of the moiety represented by Chemical Formula B and the moiety represented by Chemical Formula C may be for example selected from compounds of [Group C].

[Group B]

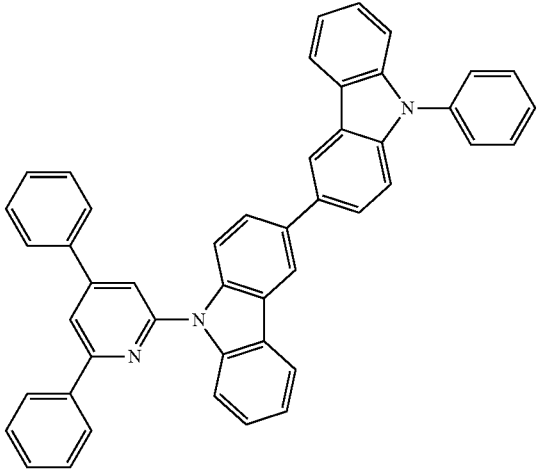
[B-1]

[B-2]

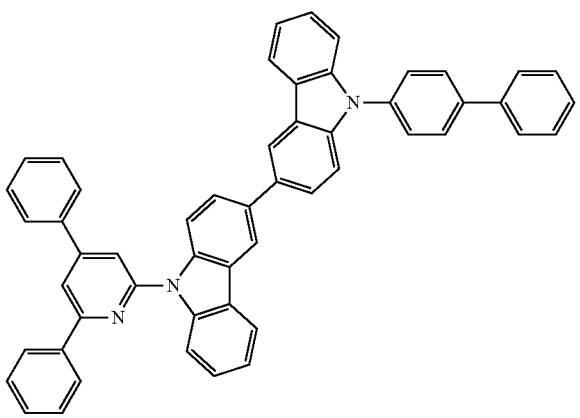
[B-3]

[B-4]
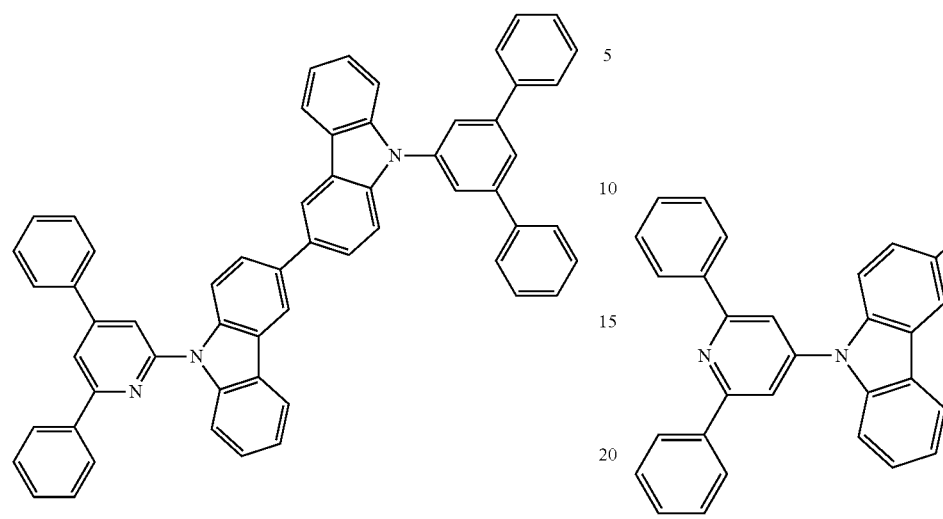
[B-7]
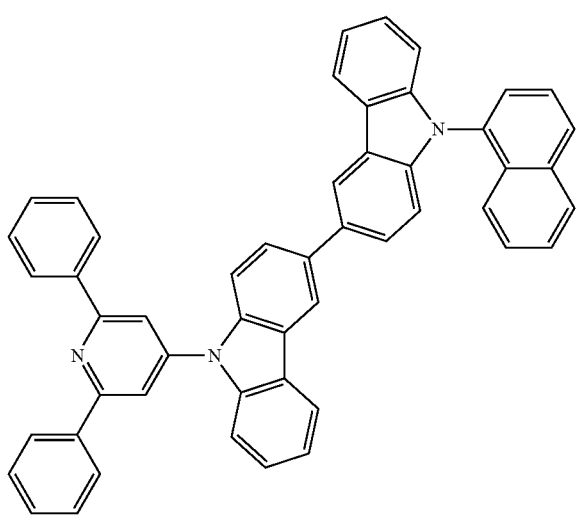
[B-5]
[B-8]
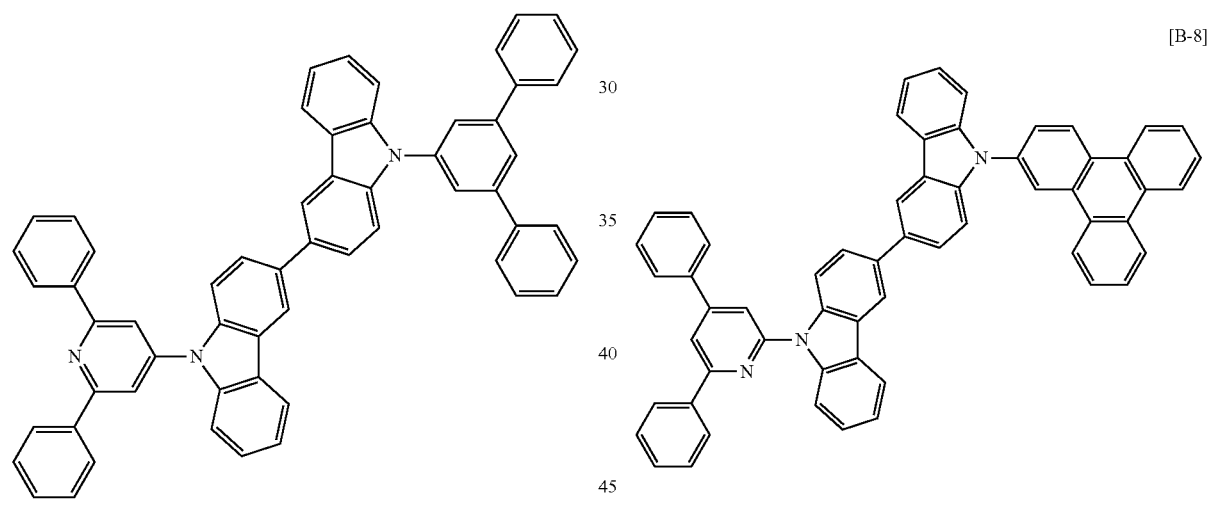
[B-6]
[B-9]
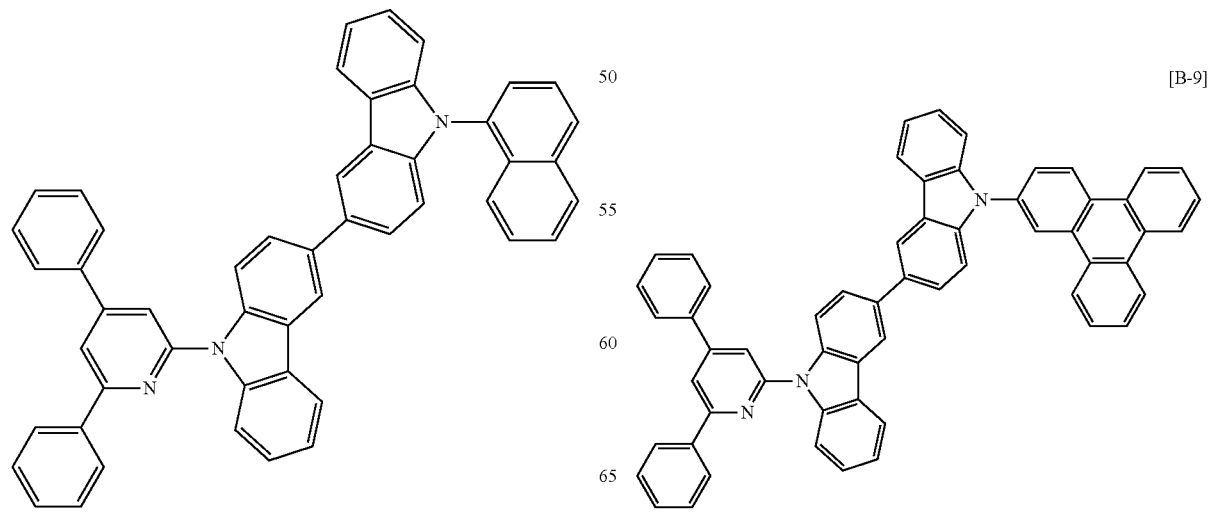

-continued
[B-10]
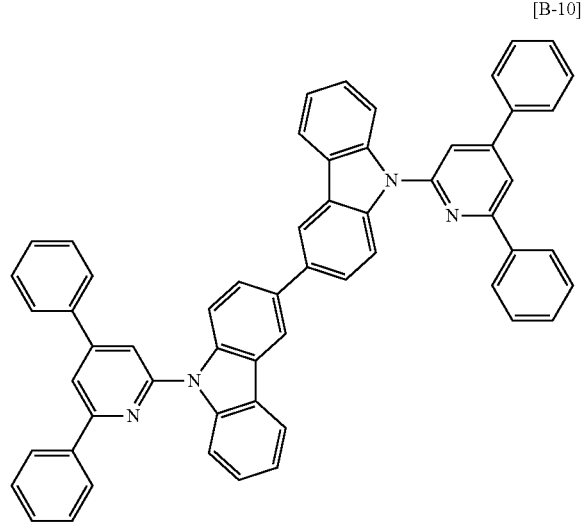
[B-11]
[B-12]
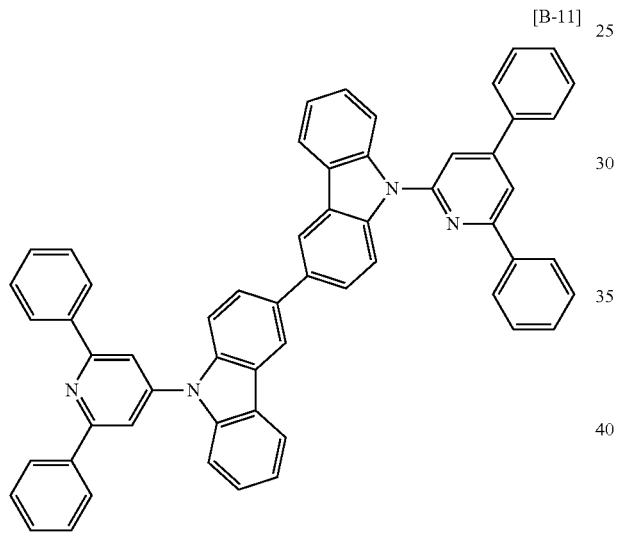
-continued
[B-13]
[B-14]
[B-15]
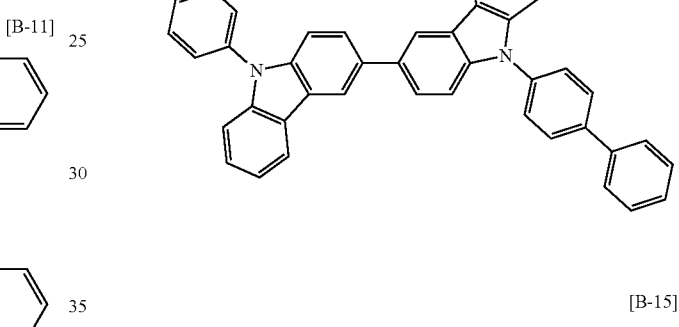
[B-16]
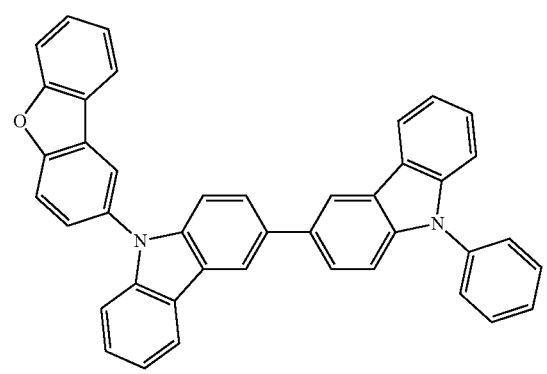

[B-17]
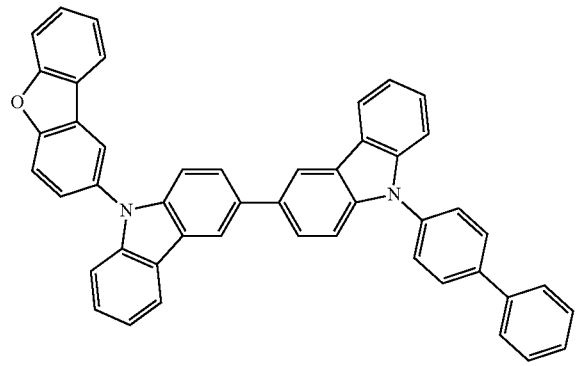
[B-18]
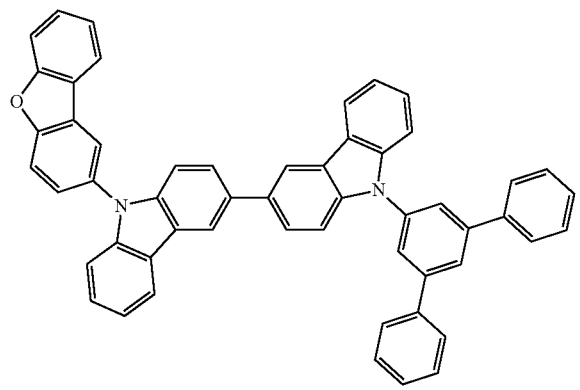
[B-19]
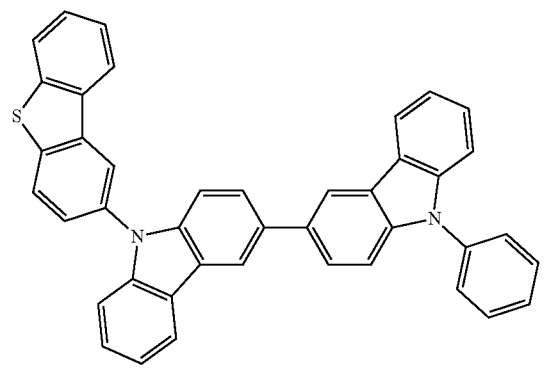
[B-20]
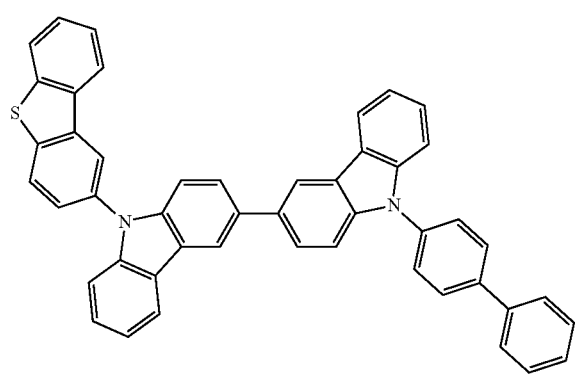
[B-21]
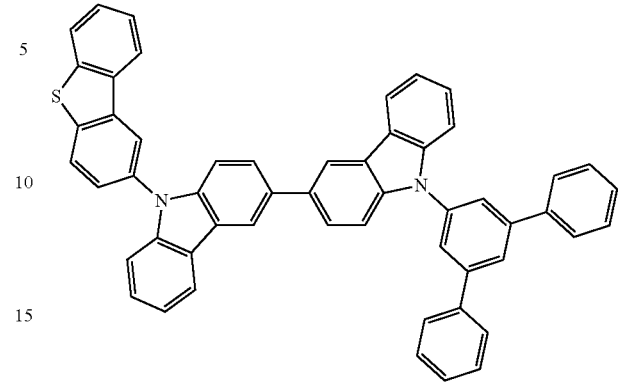
[B-22]
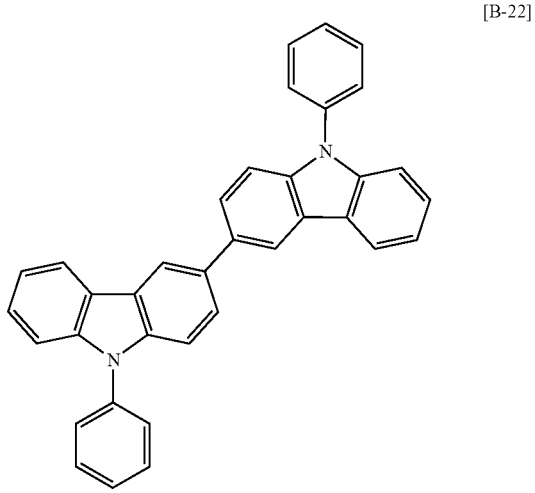
[B-23]
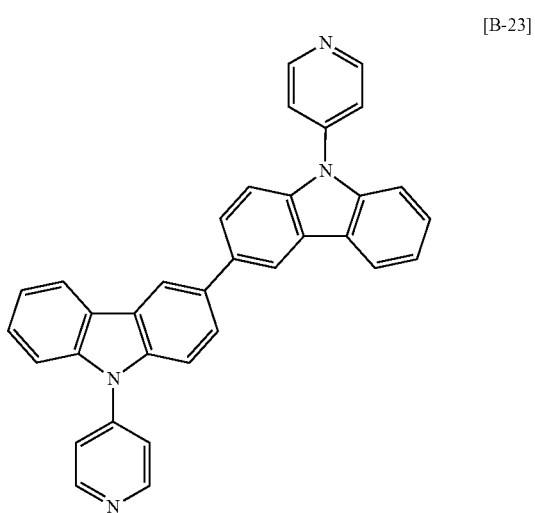

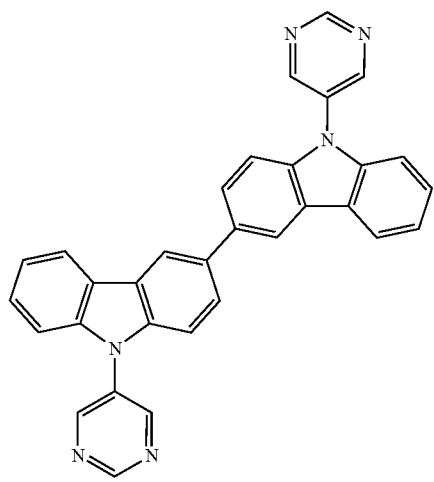
[B-24]
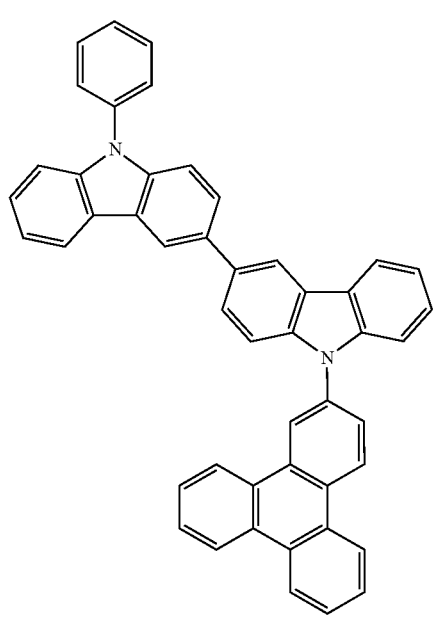
[B-25]
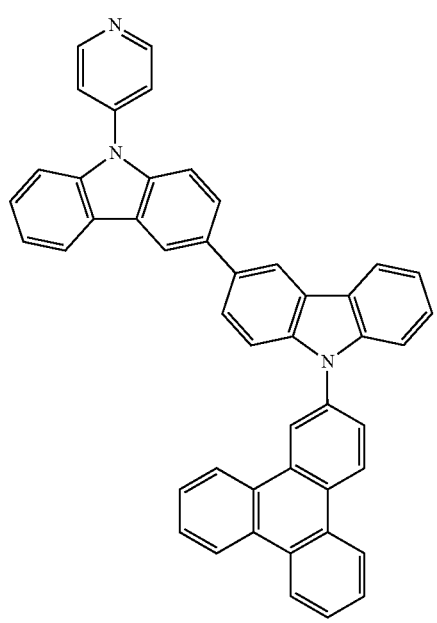
[B-26]
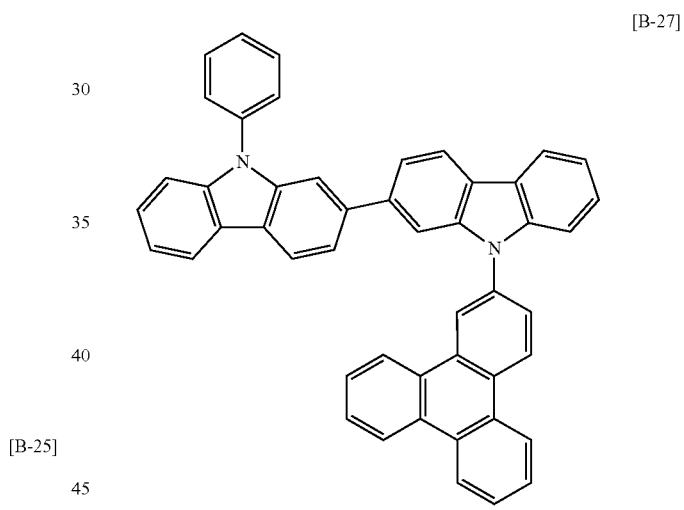
[B-27]
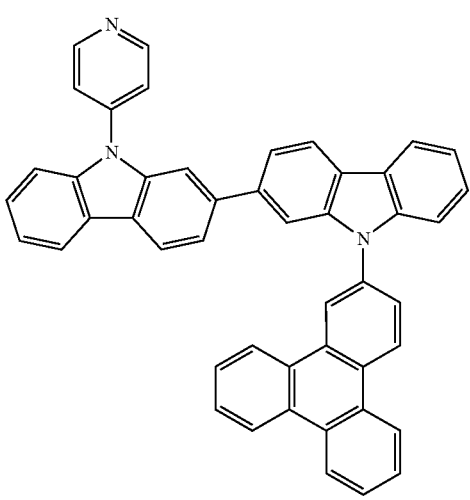
[B-28]

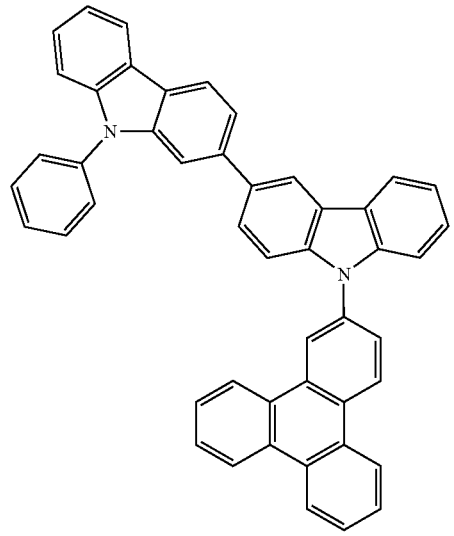
[B-29]
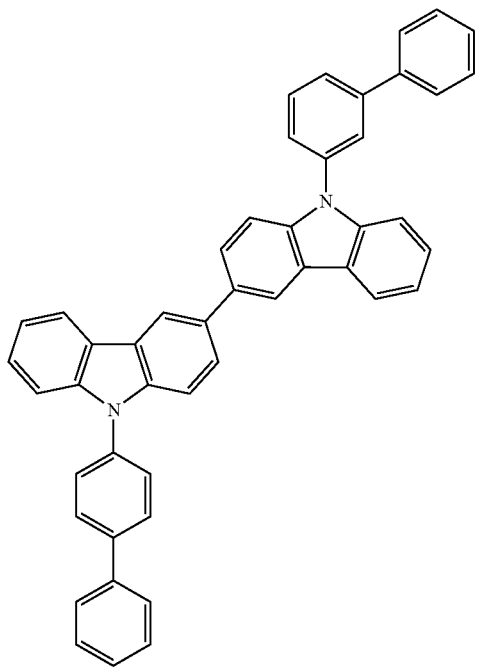
[B-31]
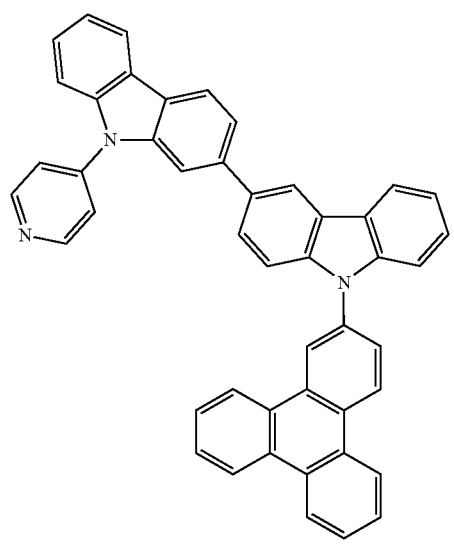
[B-30]
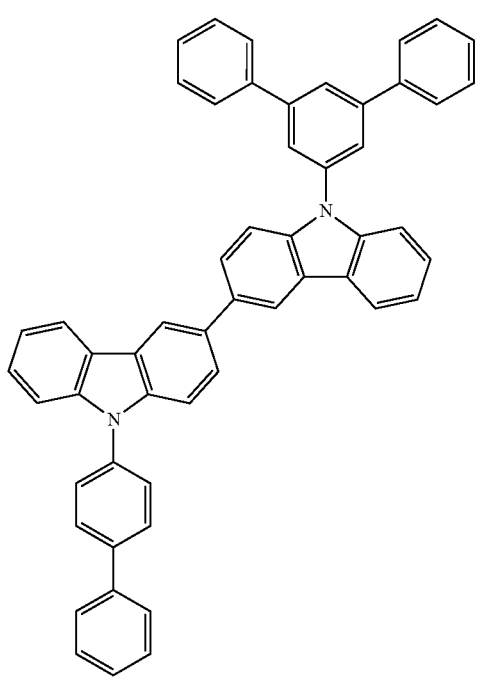
[B-32]

[B-33]
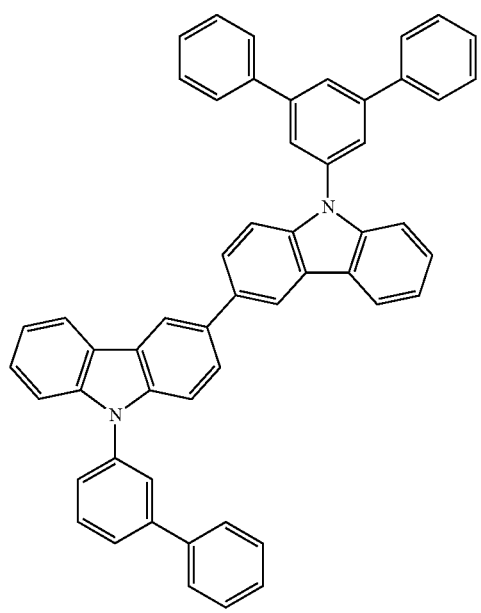
[B-34]
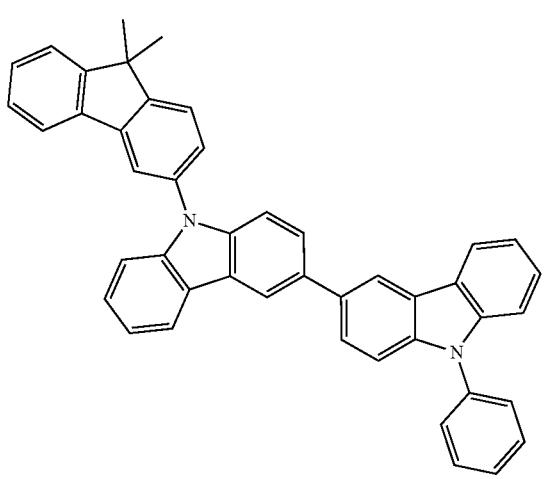
[B-35]
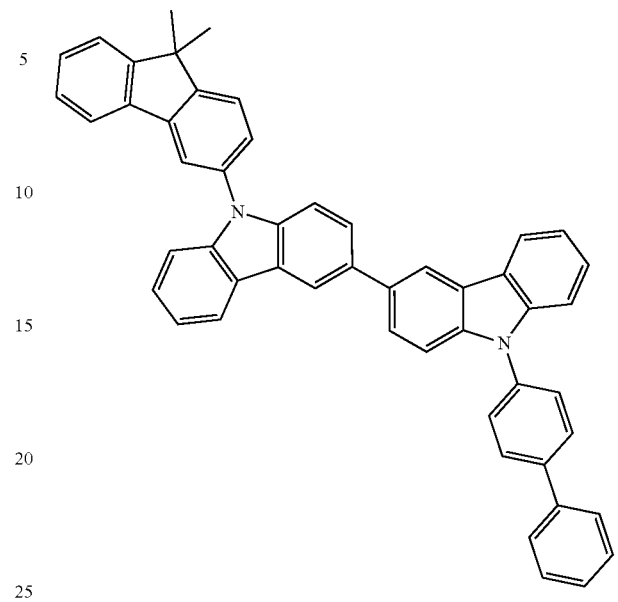
[B-36]
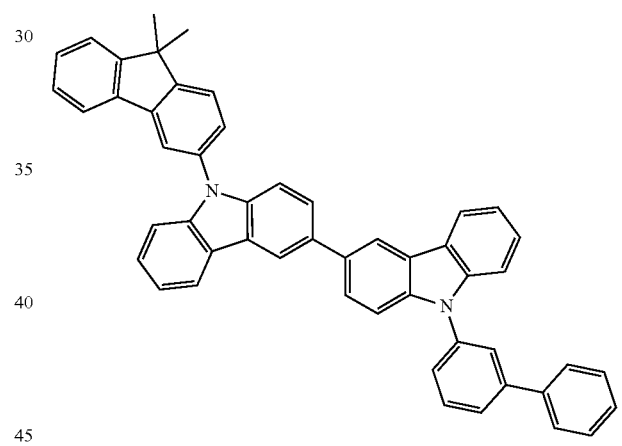
[B-37]

[B-38]
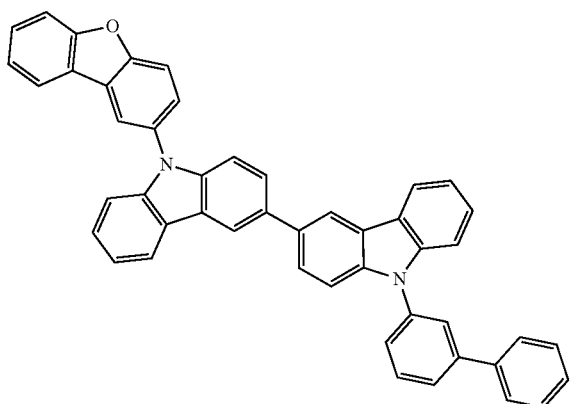
[B-39]
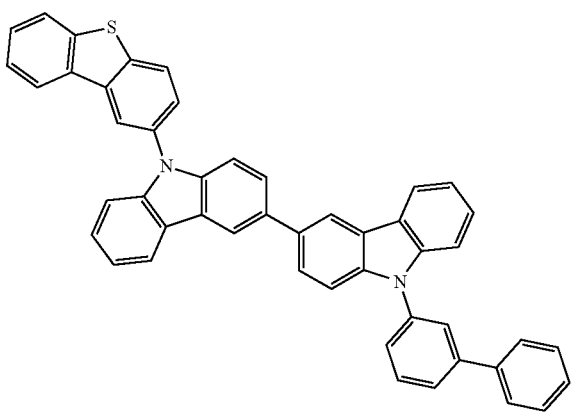
[B-40]
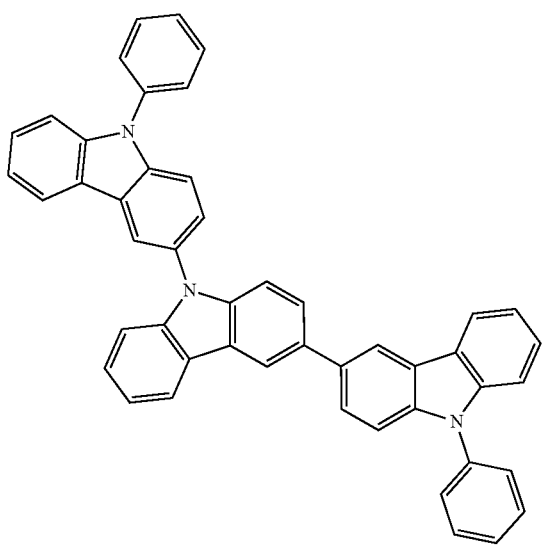
[B-41]
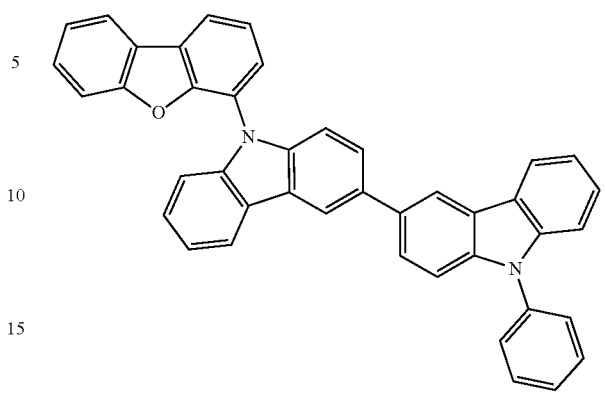
[B-42]
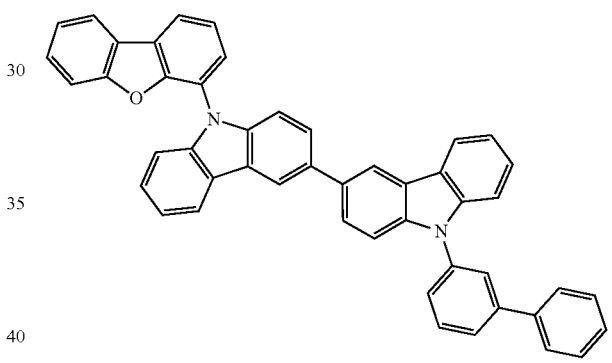
[B-43]
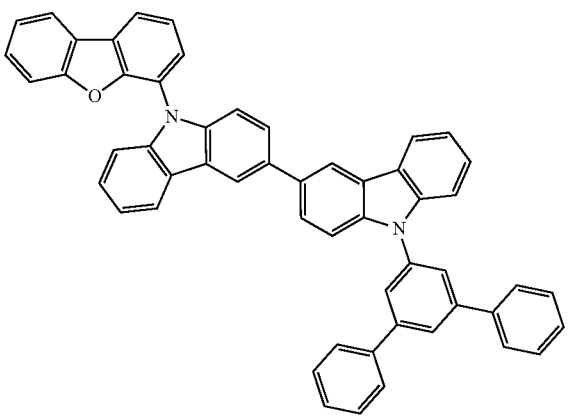

[B-44]
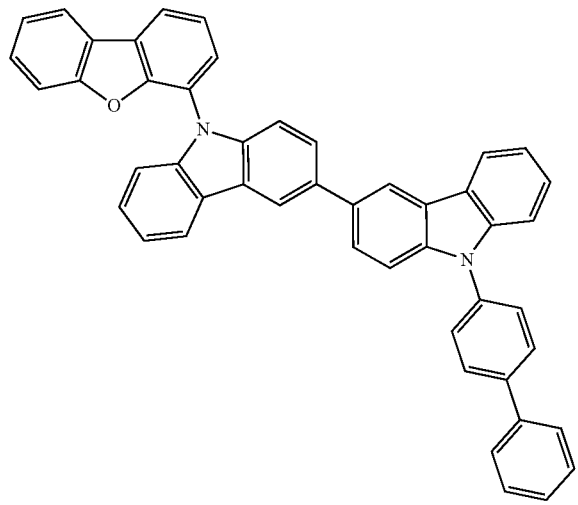
[B-45]
[B-46]
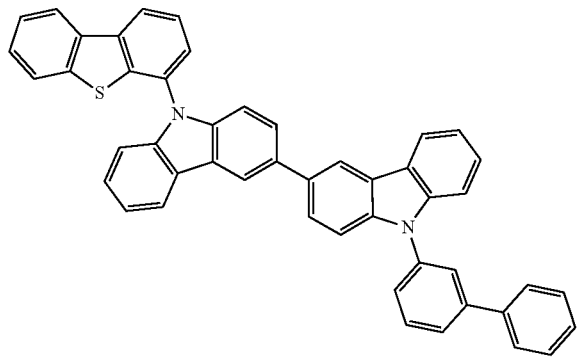
[B-47]
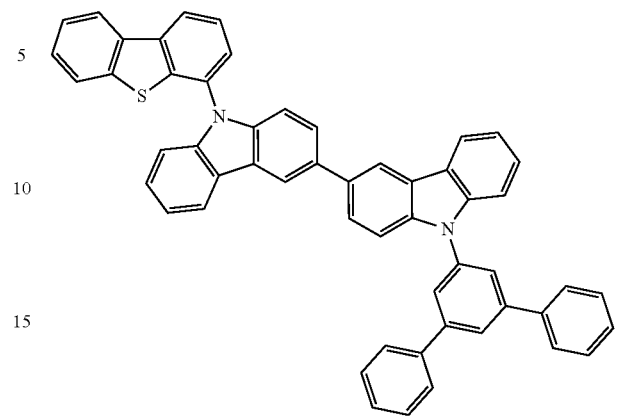
[B-48]
[B-49]
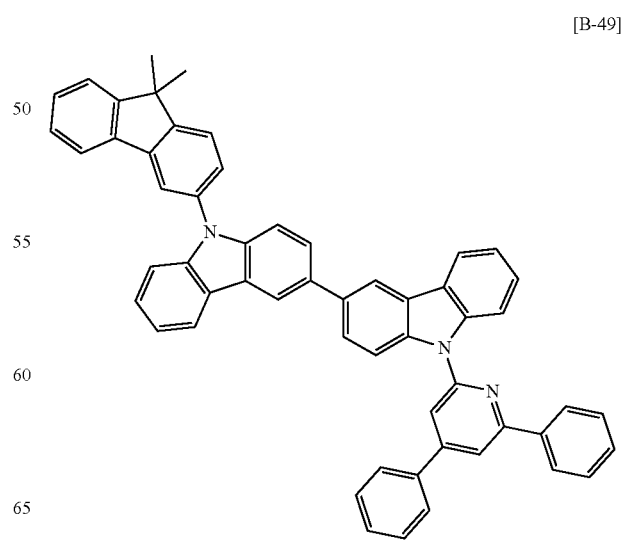

[B-50]
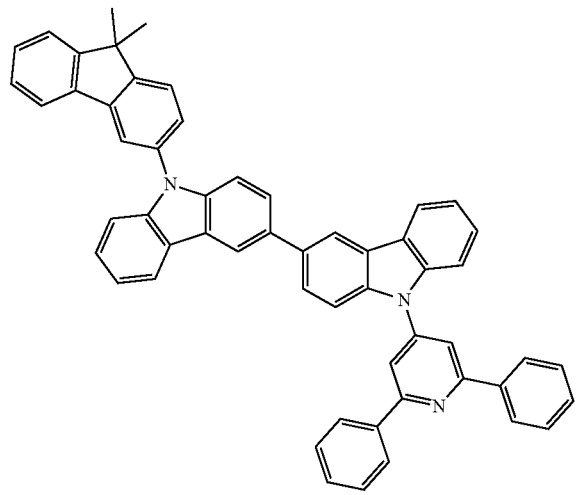
[B-51]
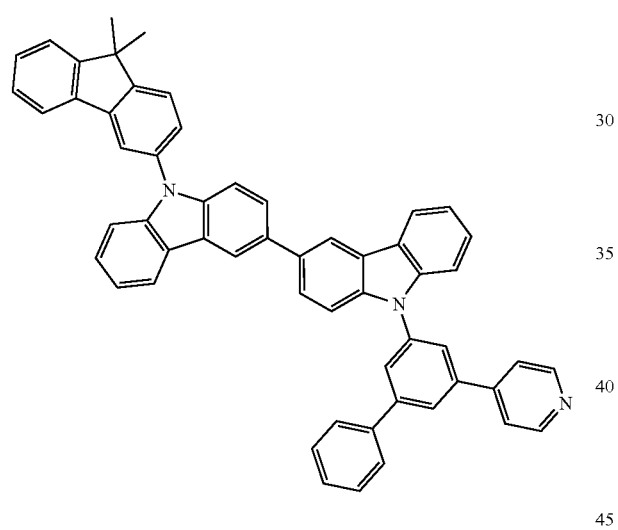
[B-52]
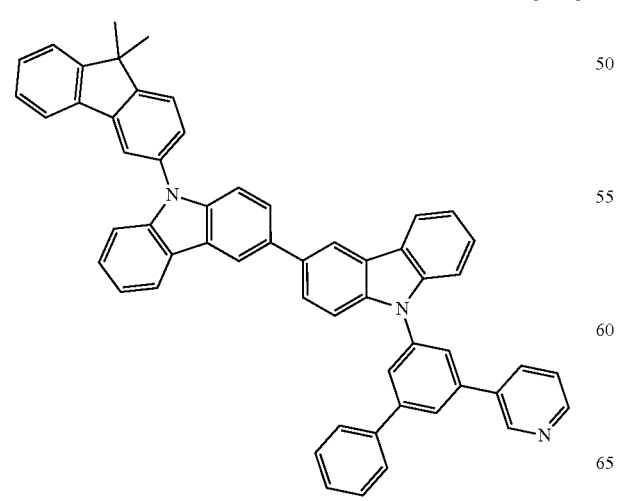
[B-53]
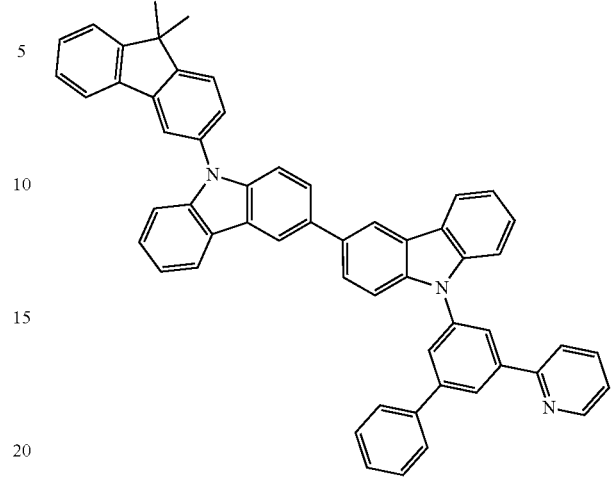
[B-54]
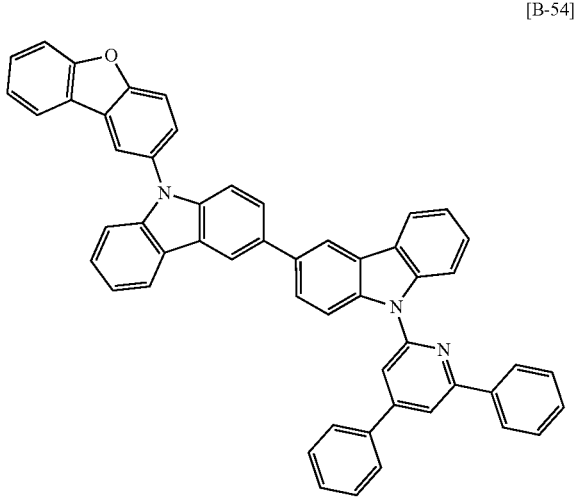
[B-55]
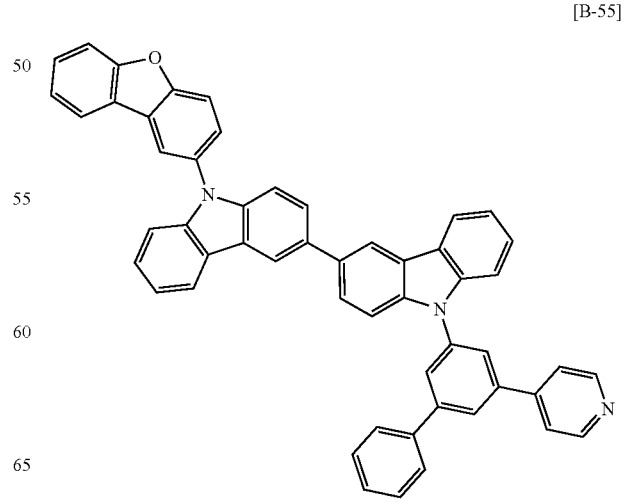

[B-56]
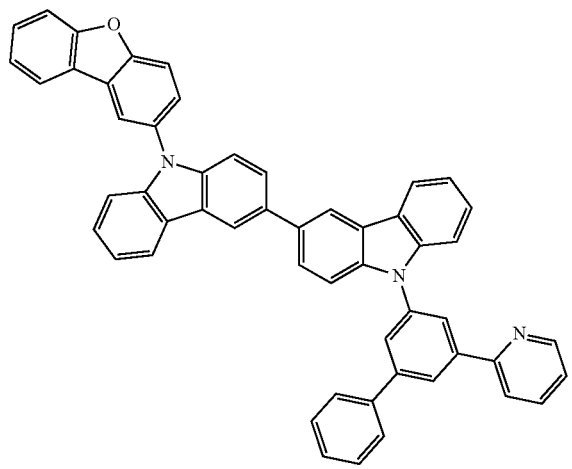
[B-57]
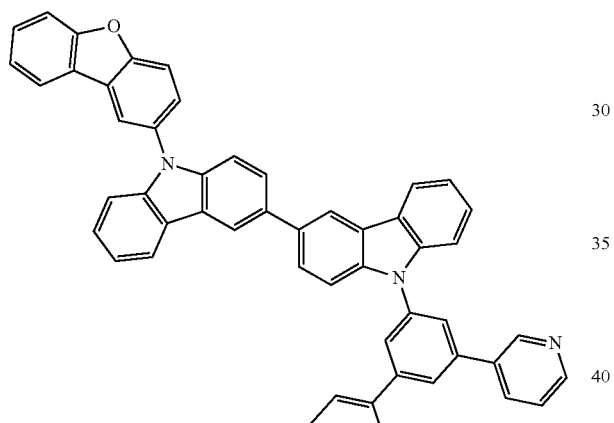
[B-58]
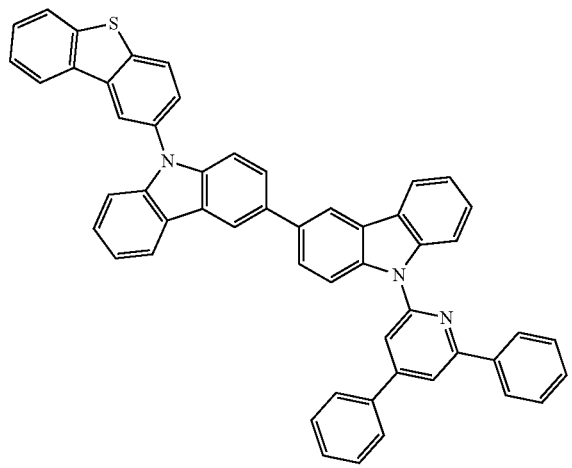
[B-59]
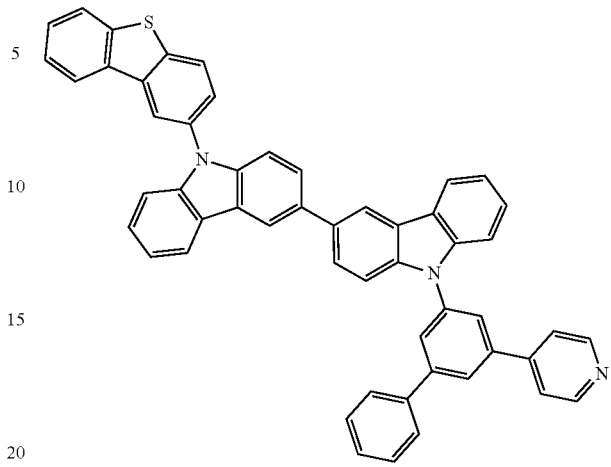
[B-60]
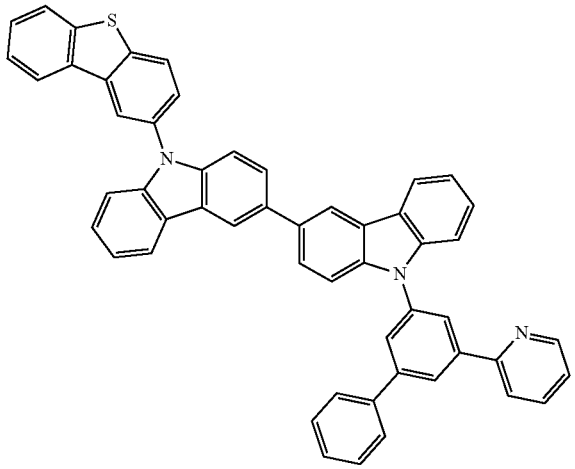
[B-61]
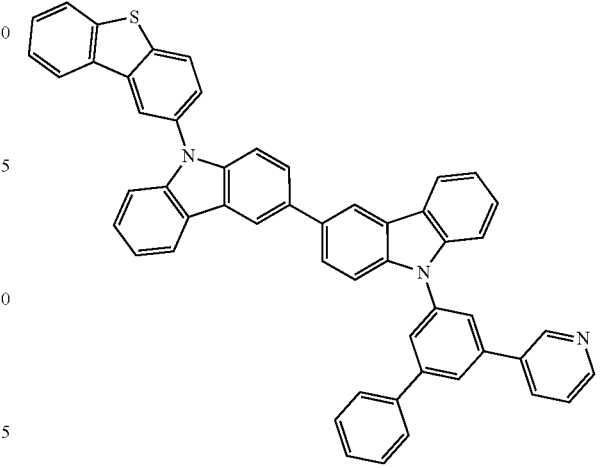

[B-62]
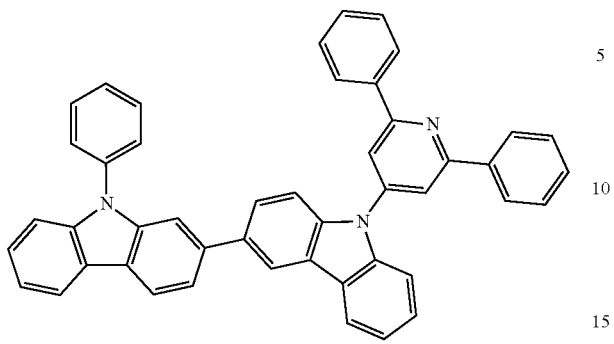
[B-66]
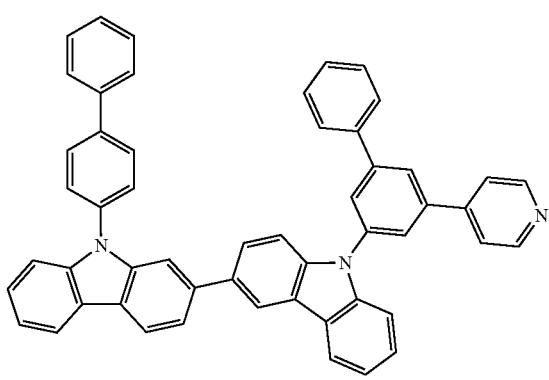
[B-63]
[B-67]
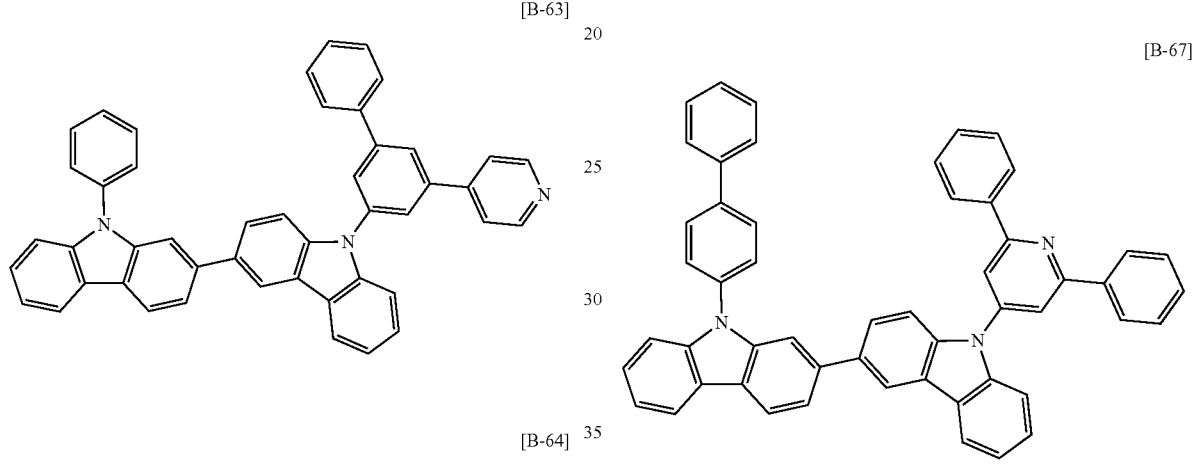
[B-64]
[B-68]
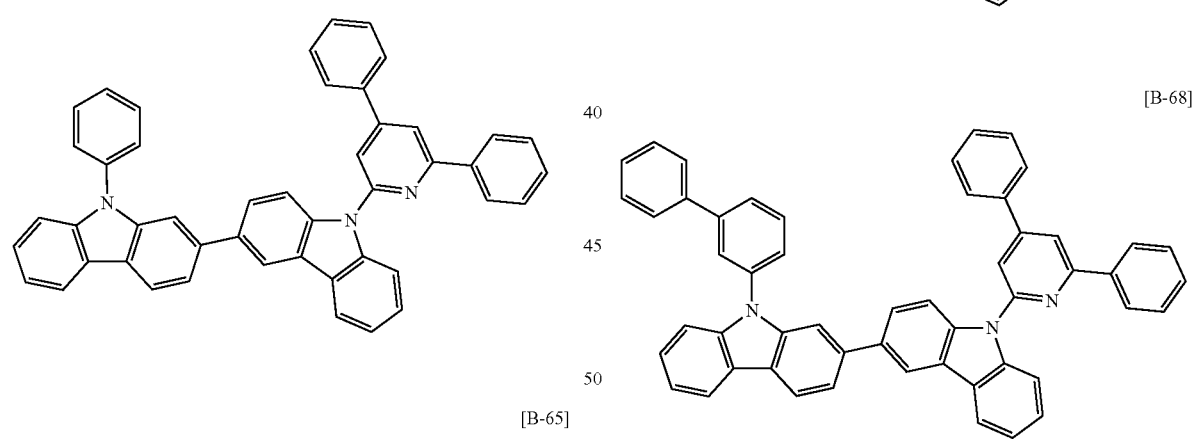
[B-65]
[B-69]
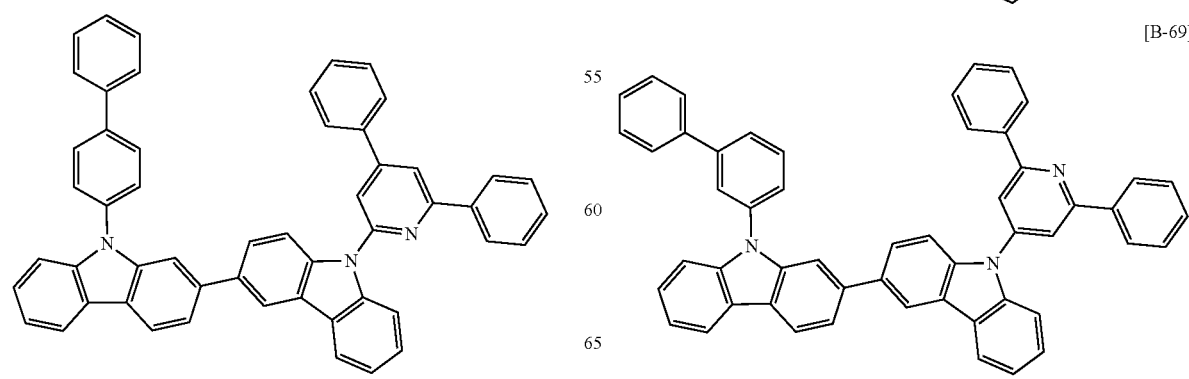

[B-70]
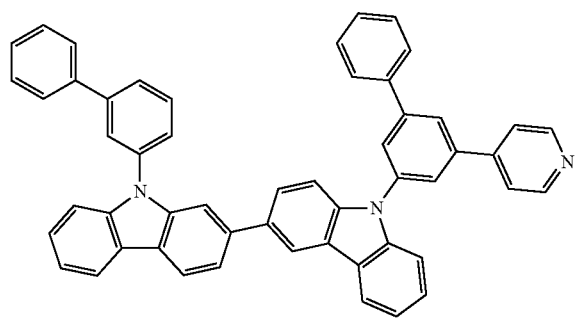
[B-74]
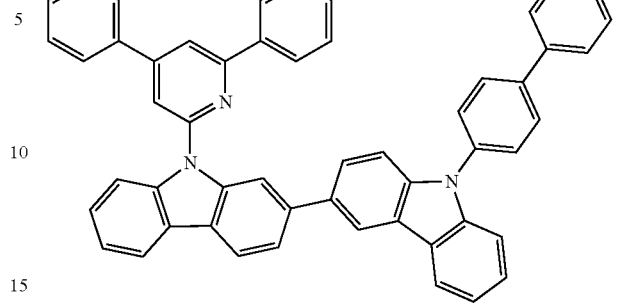
[B-71]
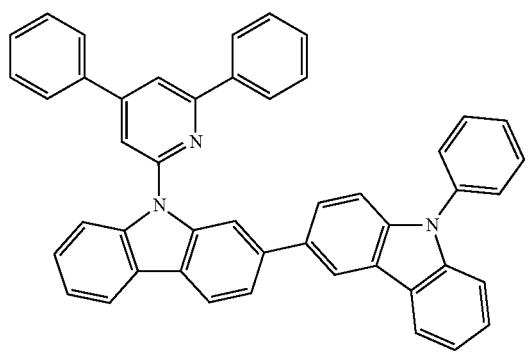
[B-75]
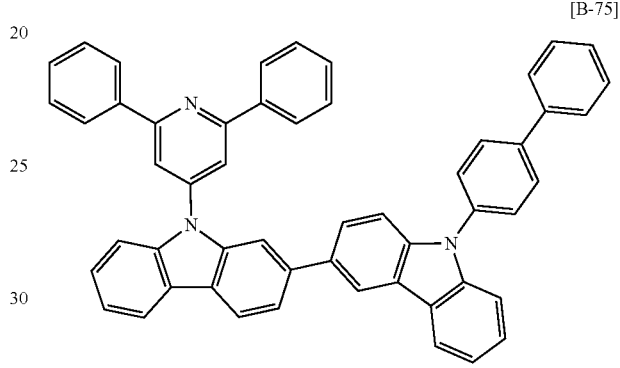
[B-72]
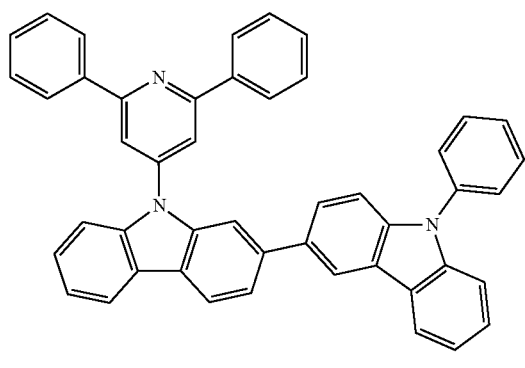
[B-76]
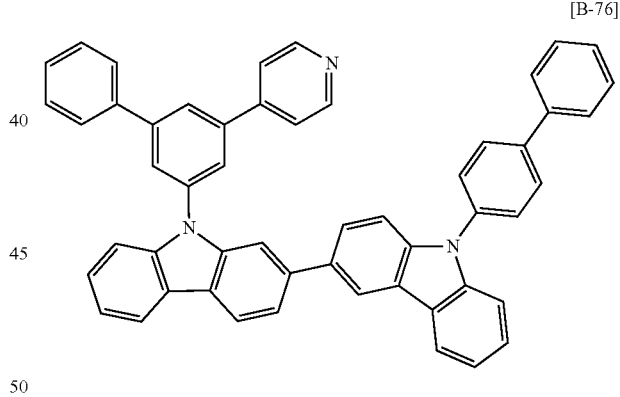
[B-73]
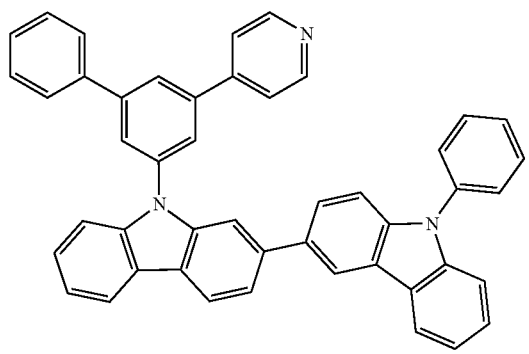
[B-77]
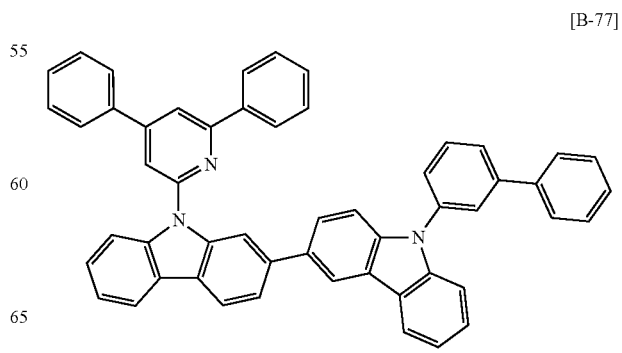

[B-78]
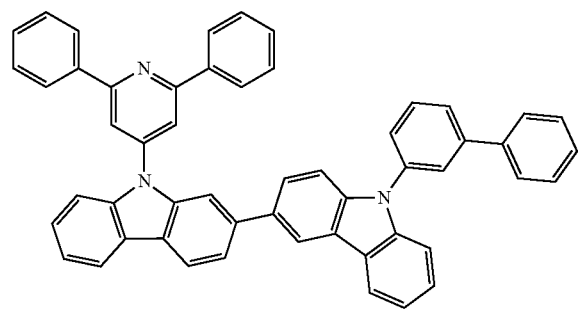
[B-82]
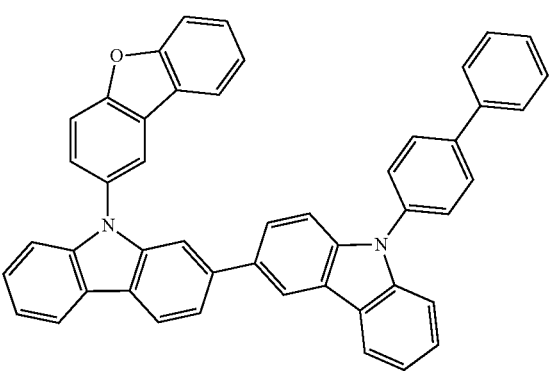
[B-79]
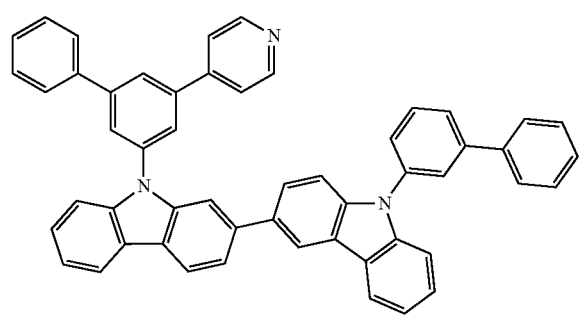
[B-83]
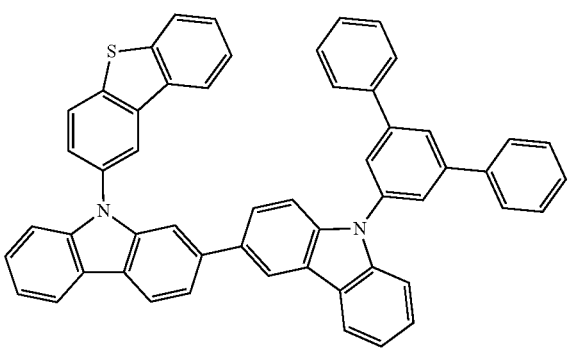
[B-80]
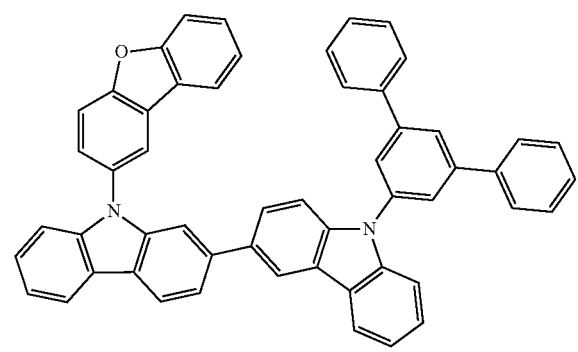
[B-84]
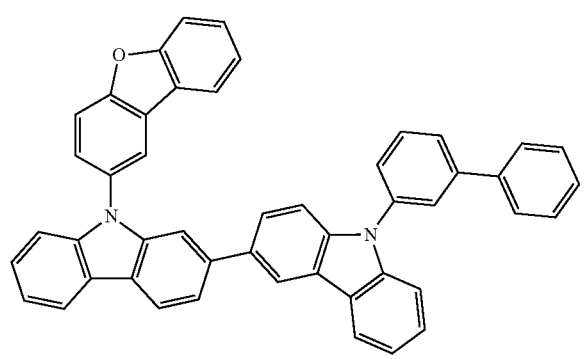
[B-81]
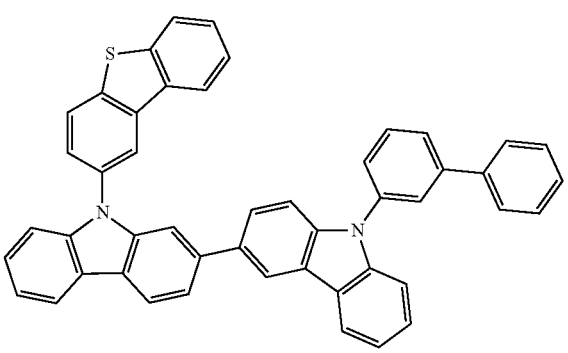
[B-85]

-continued
[B-86]
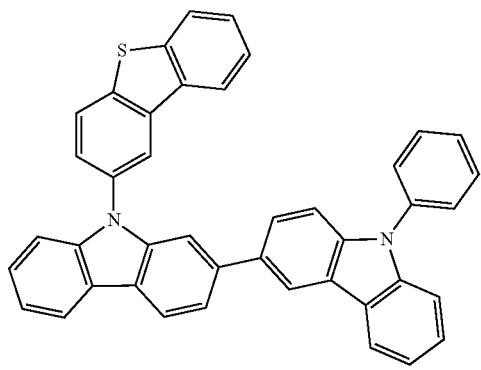
[B-87]
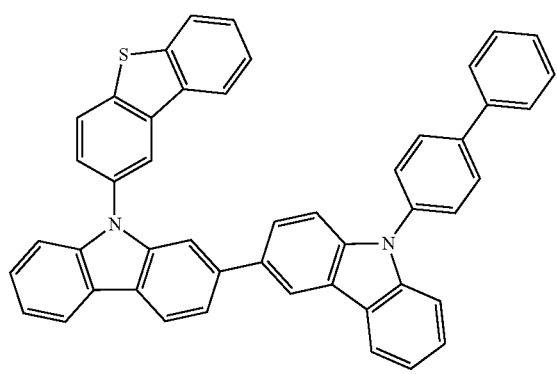
[B-88]
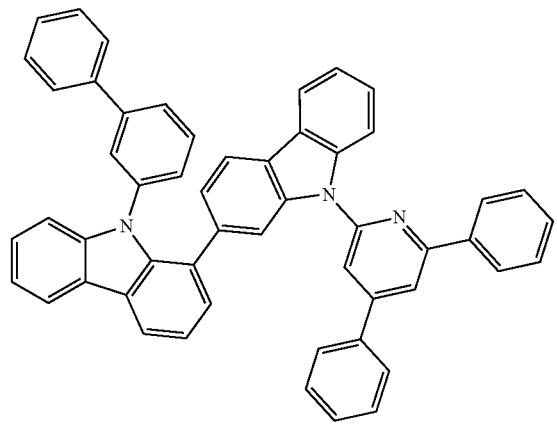
[B-89]
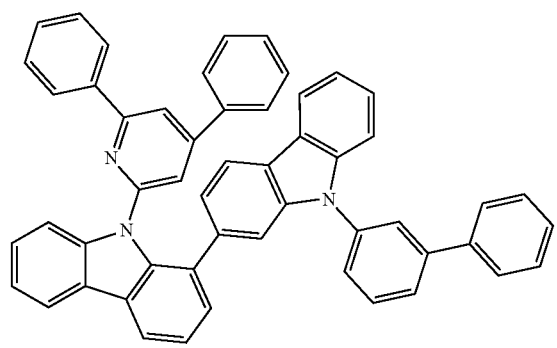
-continued
[B-90]
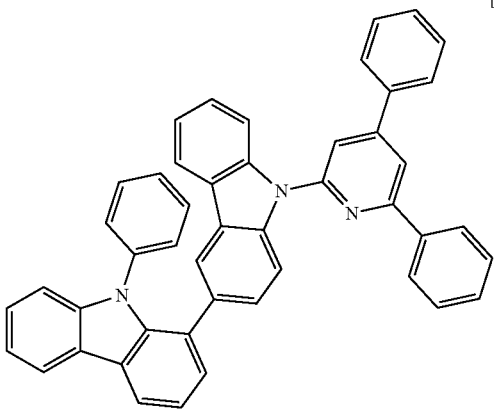
[B-91]
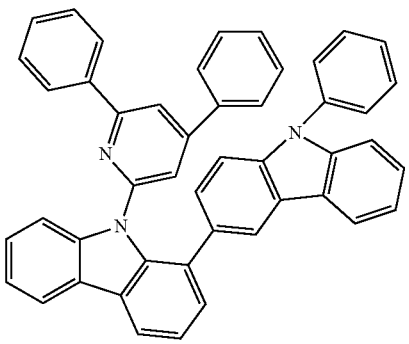
[B-92]
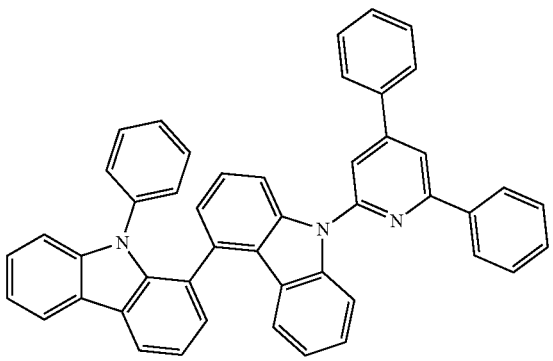
[B-93]
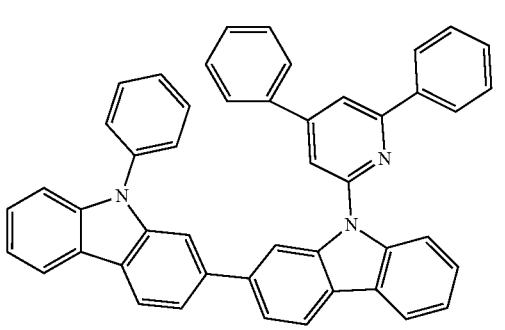

[B-94]
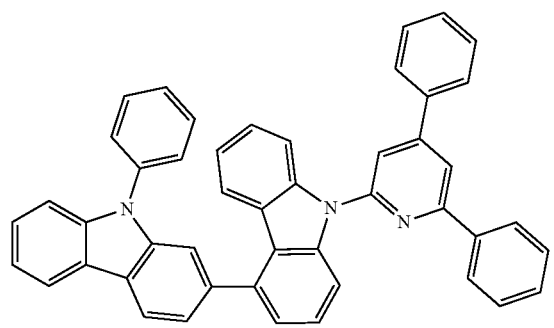
[B-98]
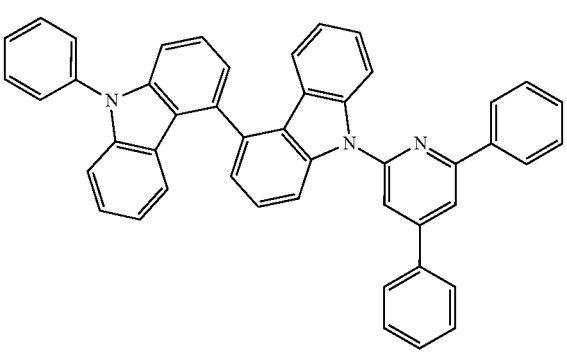
[B-95]
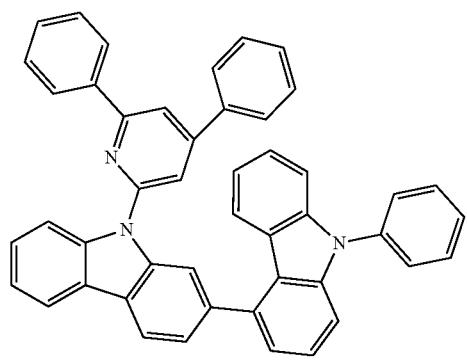
[B-96]
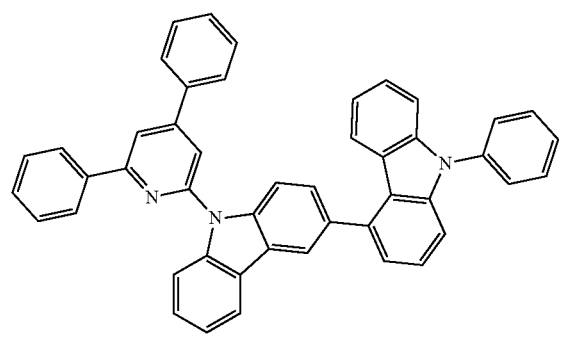
[B-99]
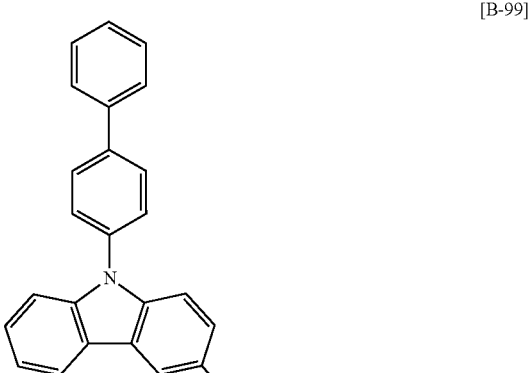
[B-97]
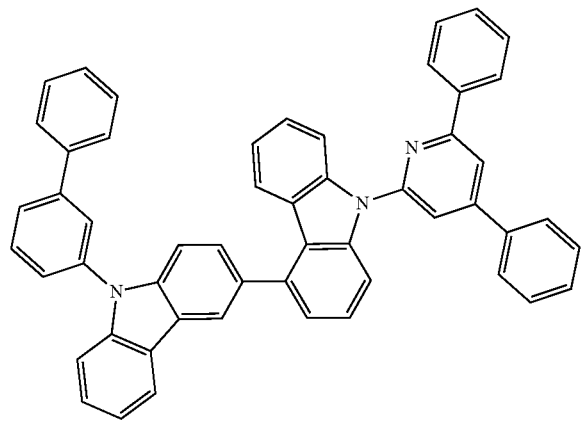

[B-100]
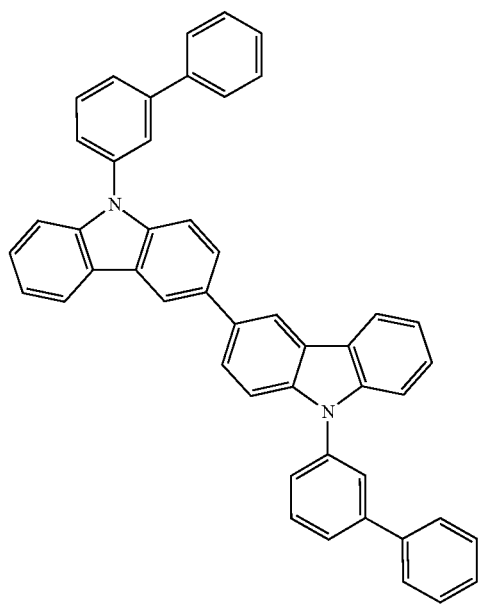
[B-101]
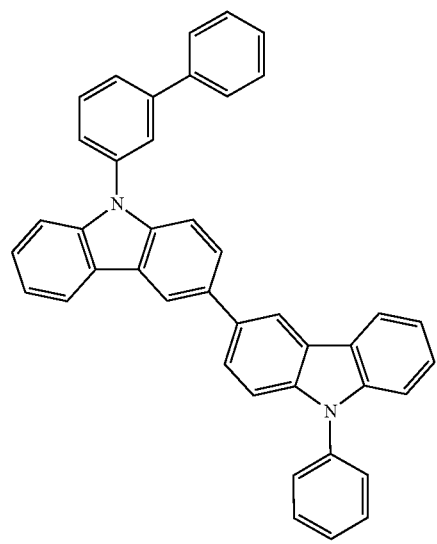
[B-102]
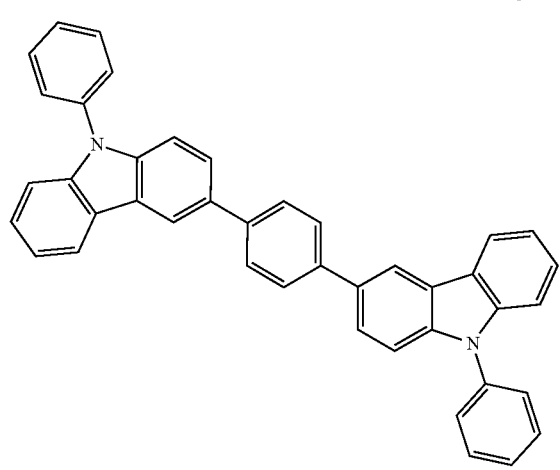
[B-103]
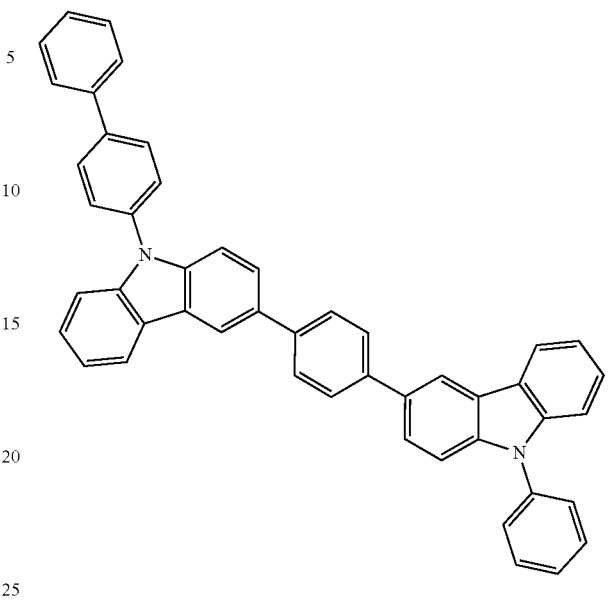
[B-104]
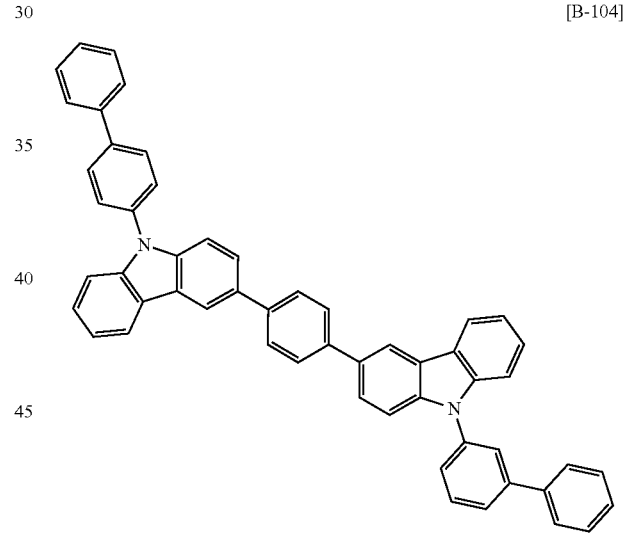
[B-105]
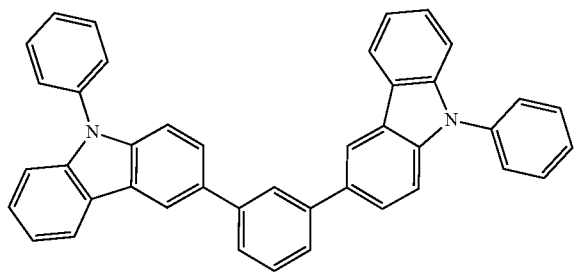

-continued
[B-106]
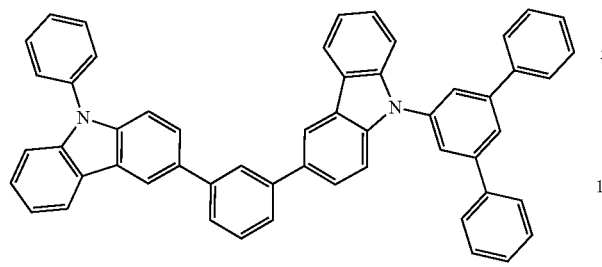
[B-107]
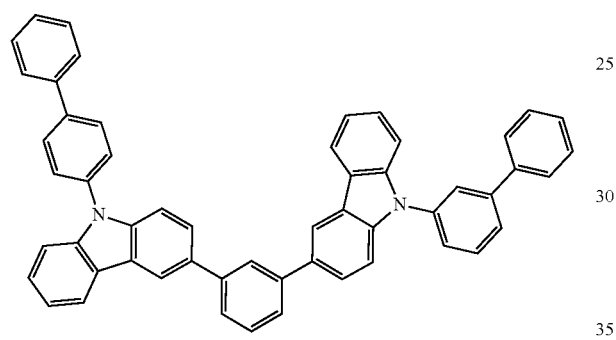
[B-109]
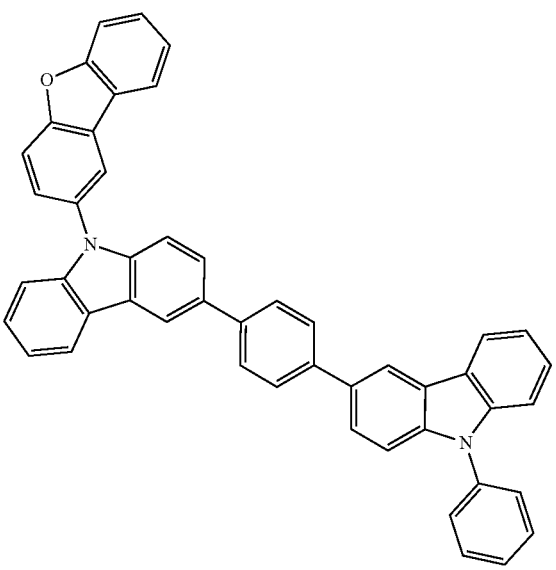
[B-108]
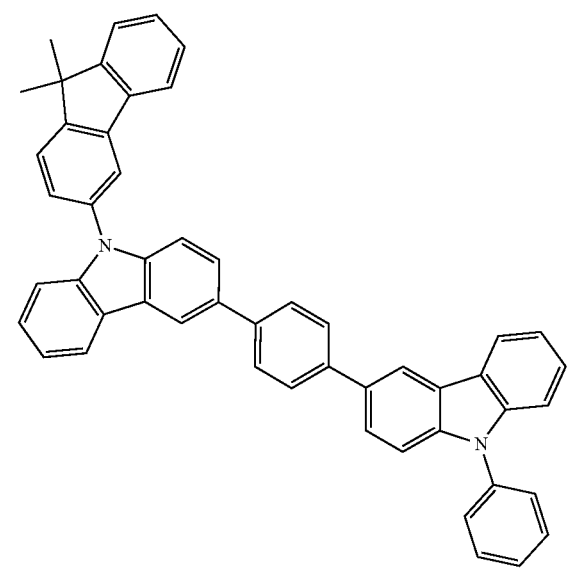
[B-110]
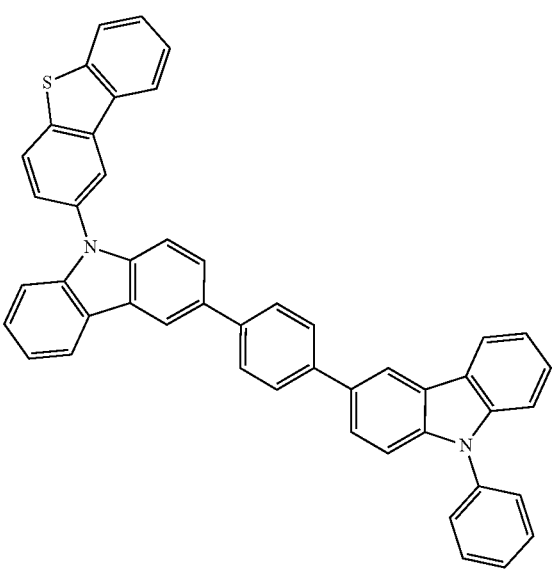

[B-111]
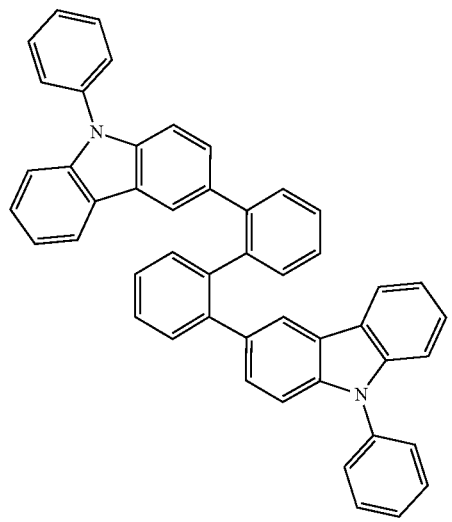
[B-112]
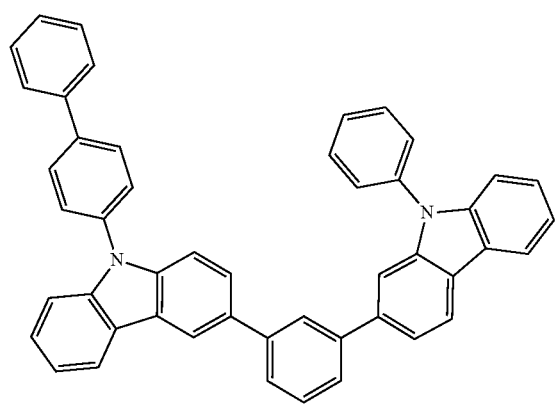
[B-113]
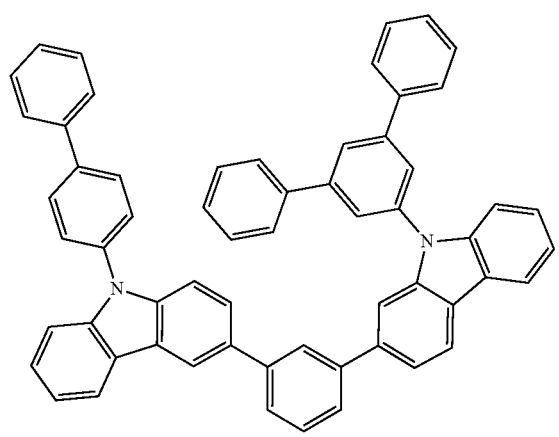
[B-114]
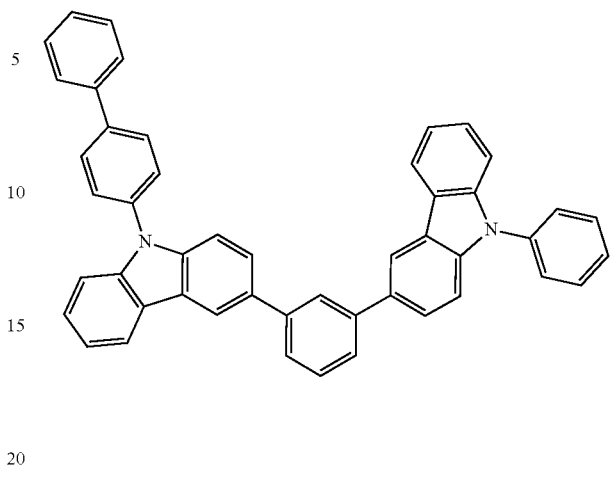
[B-115]
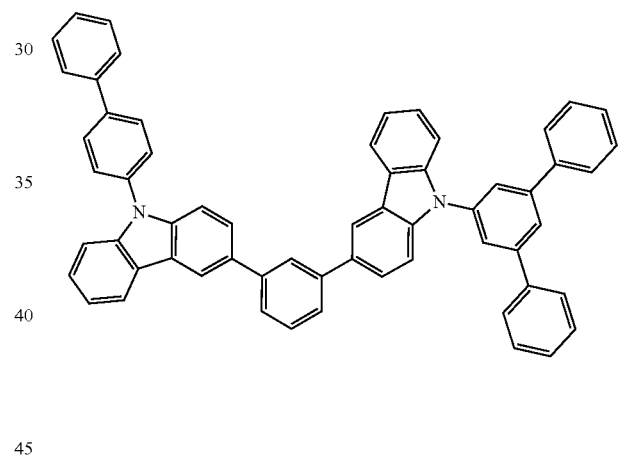
[B-116]
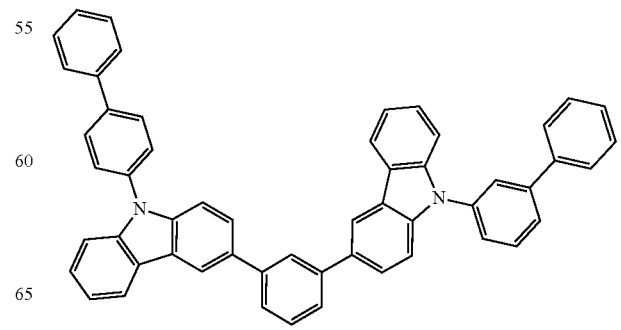

[B-117]
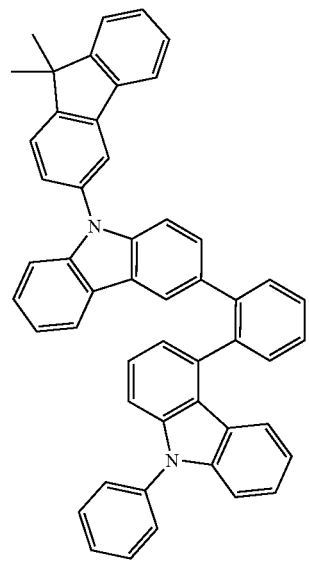
[B-119]
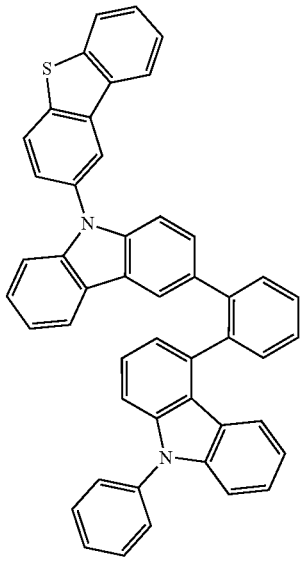
[B-120]
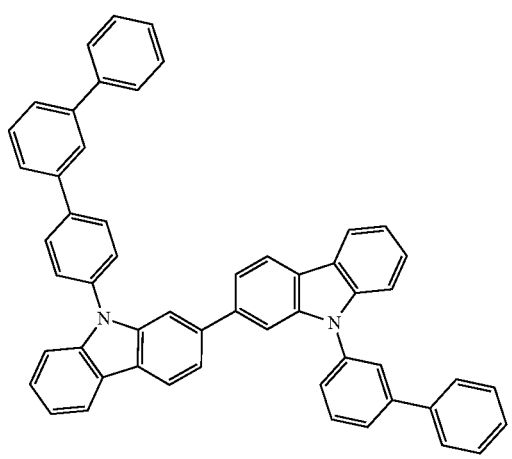
[B-118]
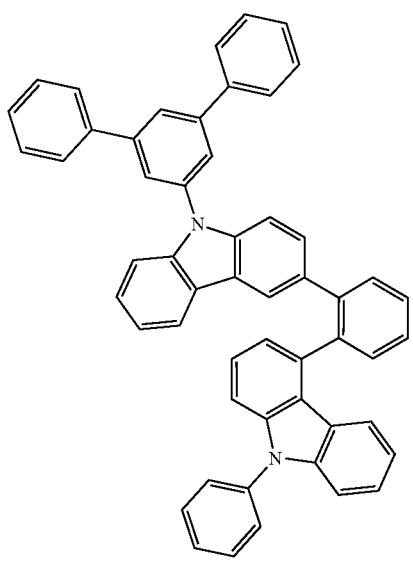
[B-121]
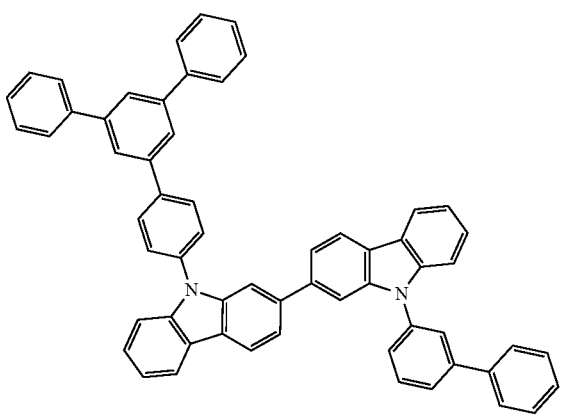

[B-122]
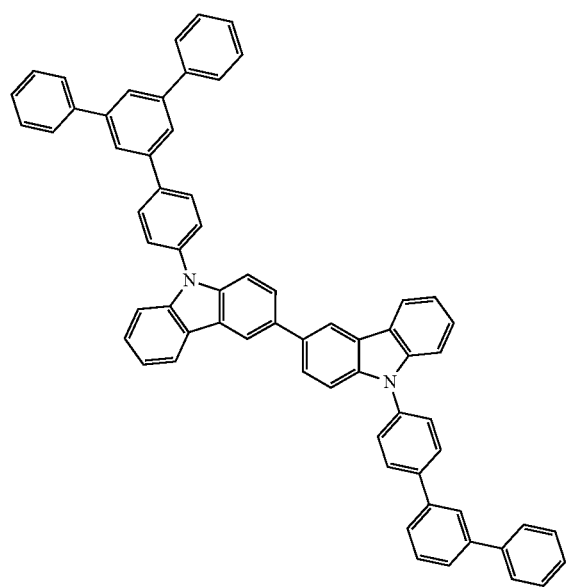
[B-124]
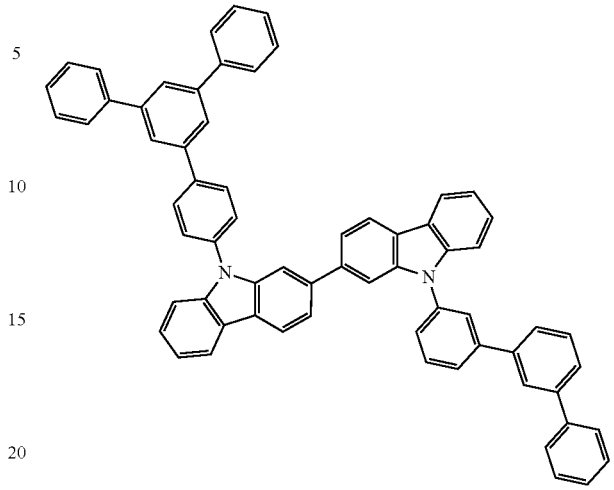
[B-123]
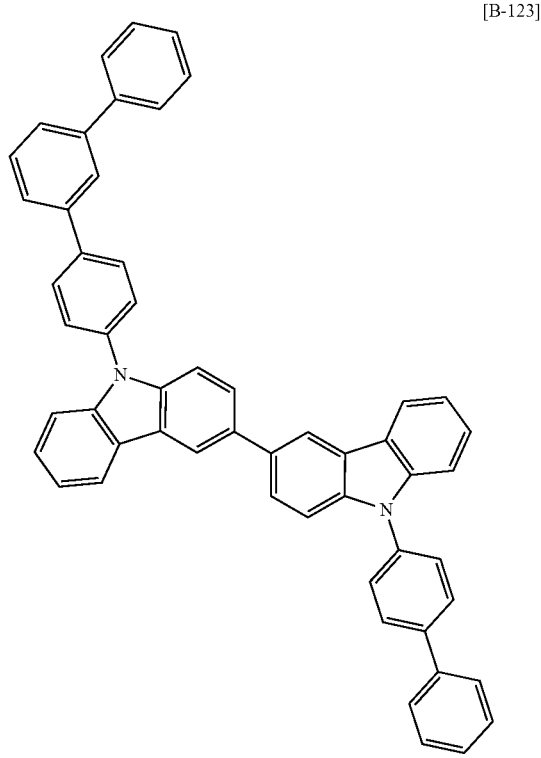
[B-125]
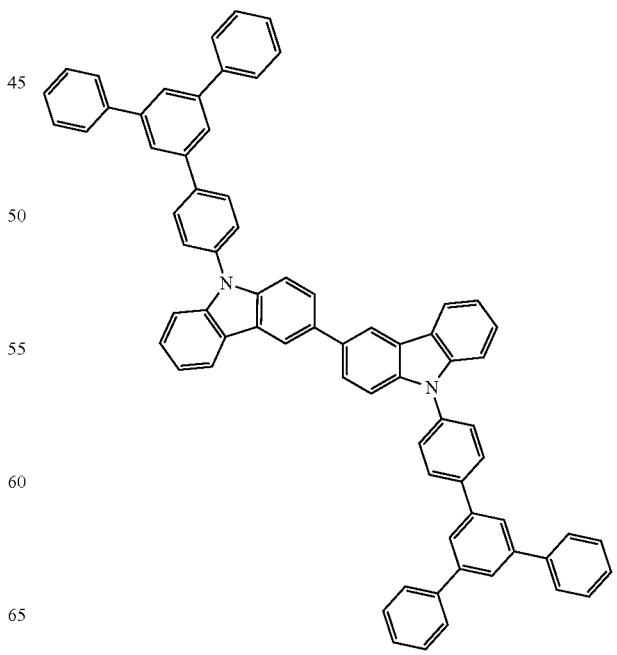

[B-126]
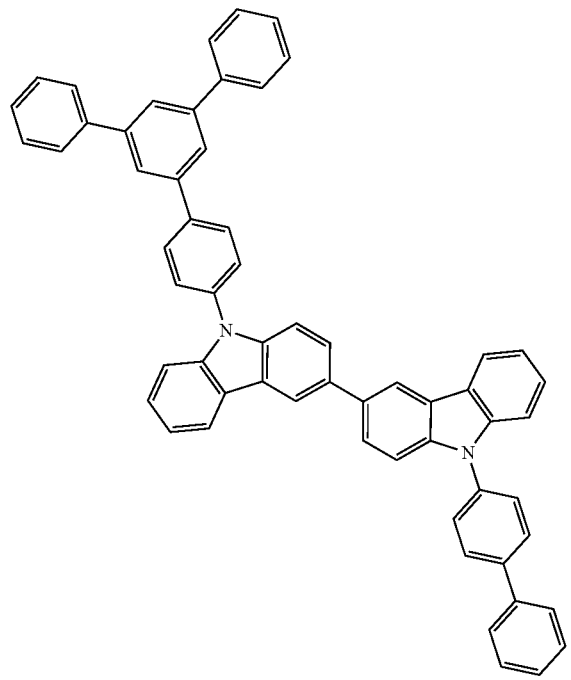
[B-127]
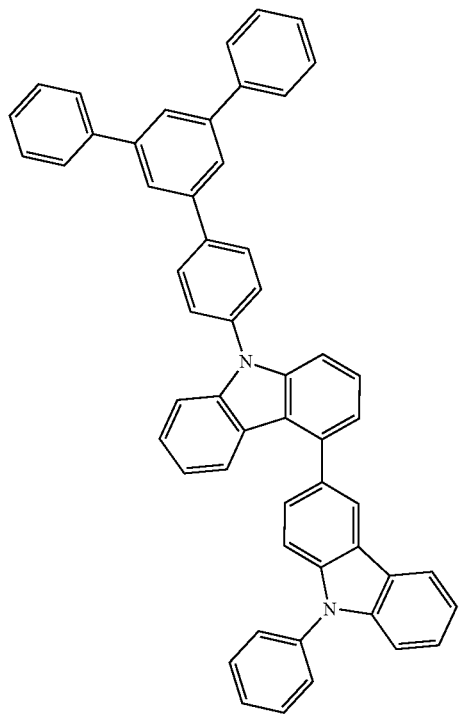
[B-128]
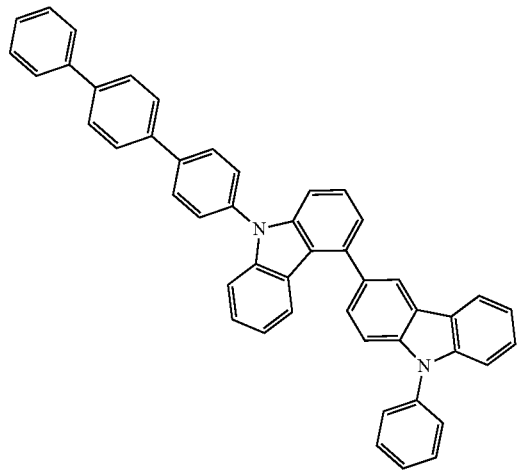
[B-129]
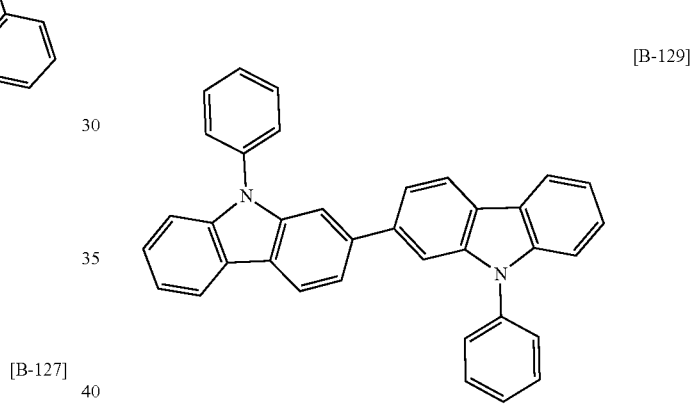
[B-130]
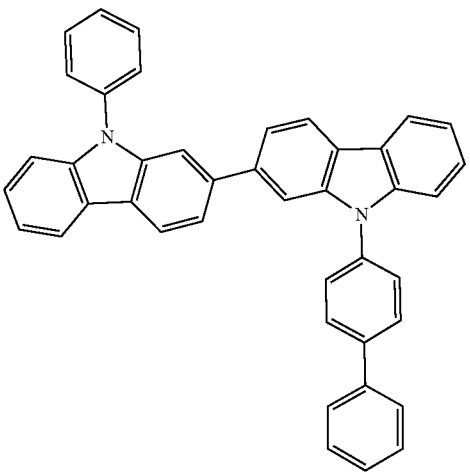

[B-131] 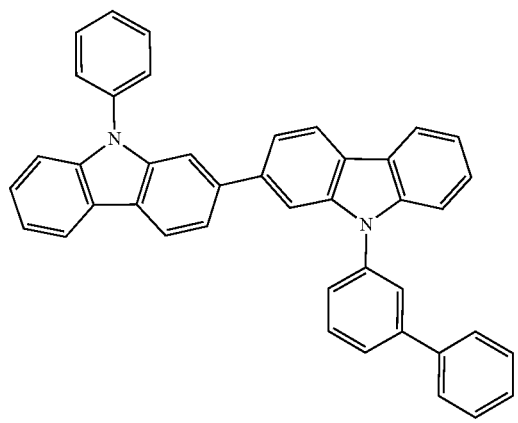
[B-132] 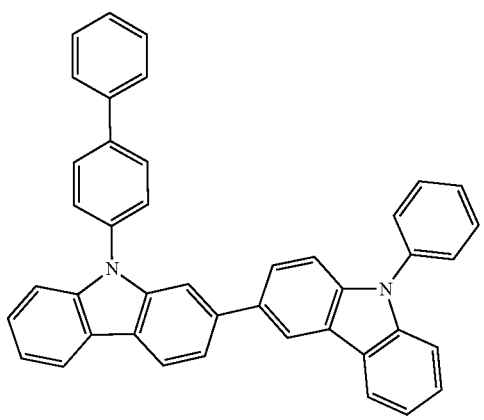
[B-133] 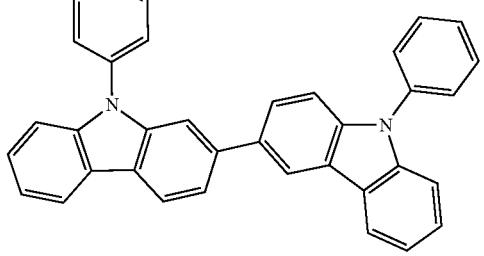
[B-134] 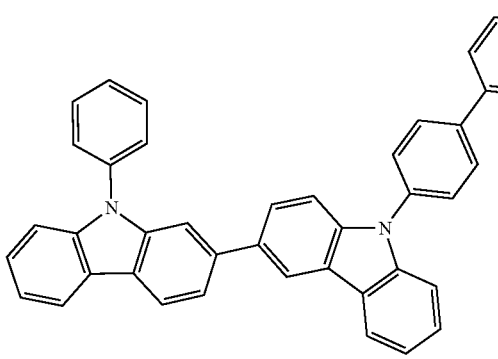
[B-135] 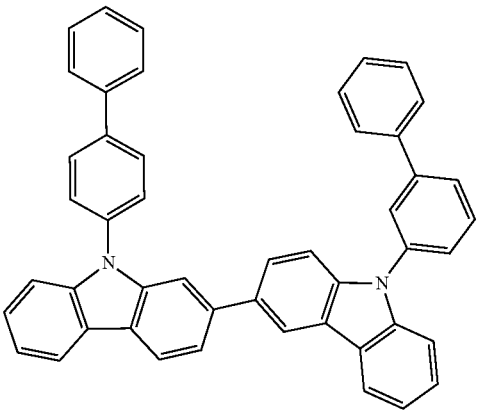
[B-136] 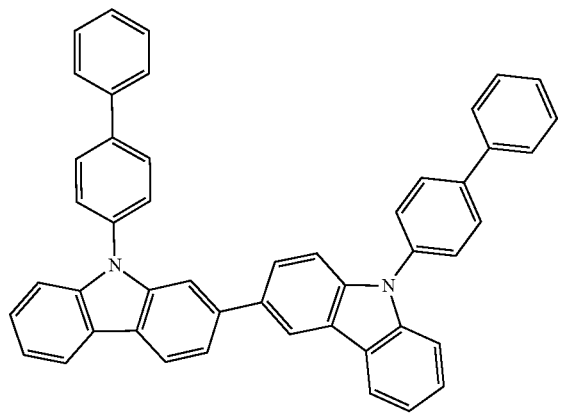
[B-137] 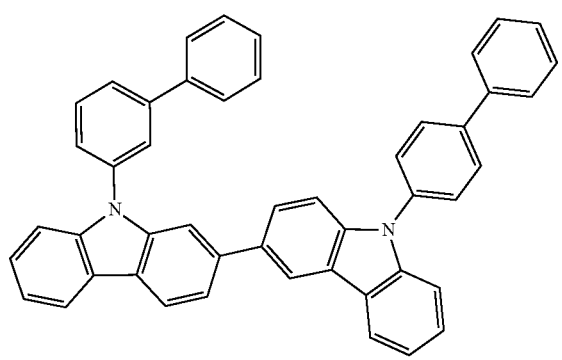

[B-138]
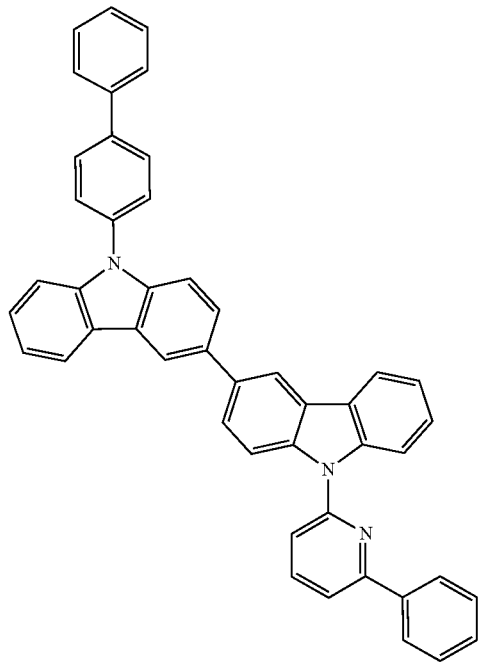
[B-139]
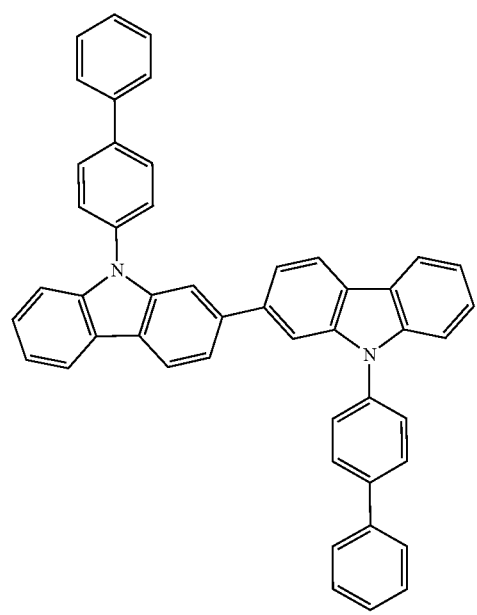
[B-140]
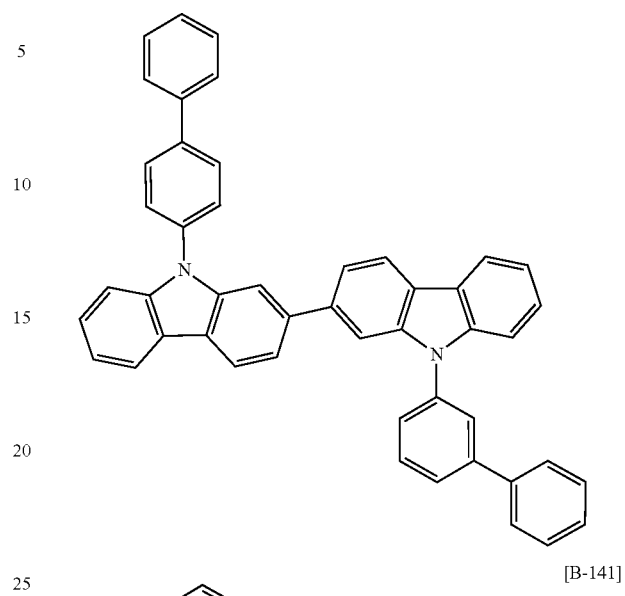
[B-141]
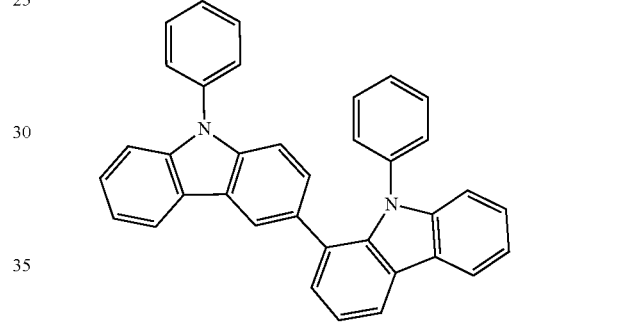
[B-142]
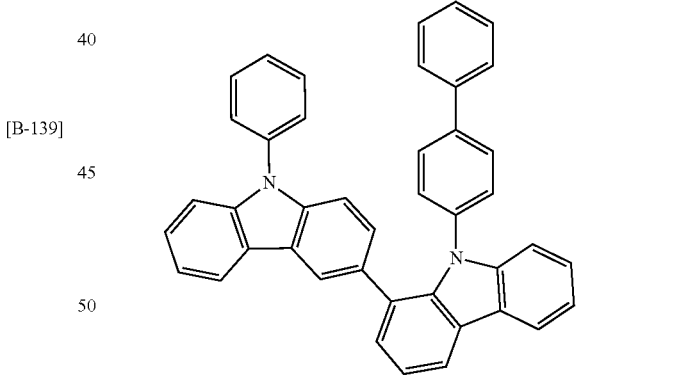
[B-143]
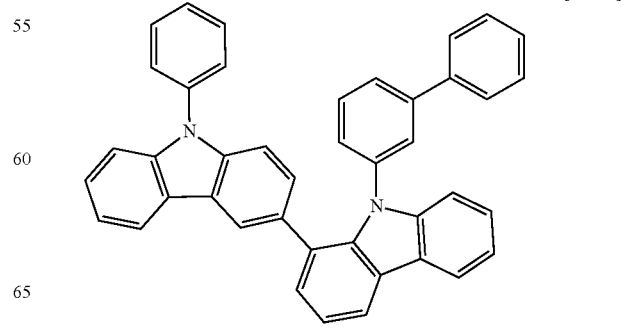

[B-144]
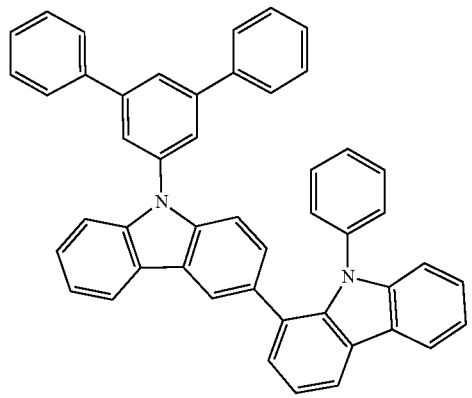
[B-145]
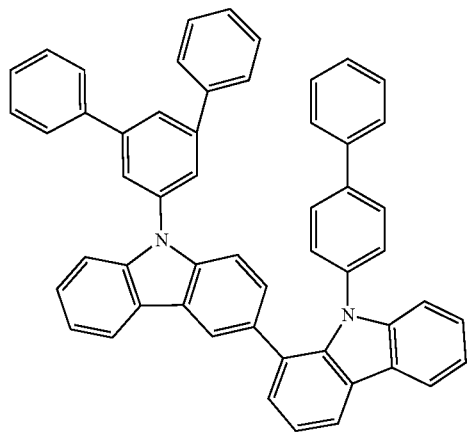
[B-146]
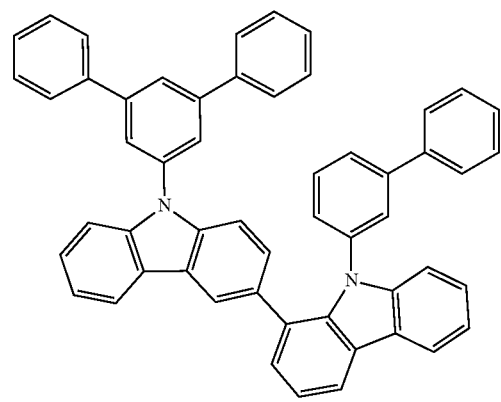
[B-147]
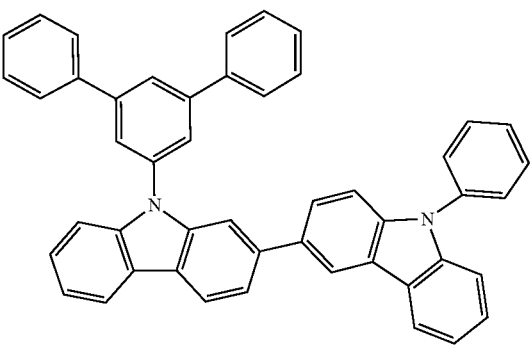
[B-148]
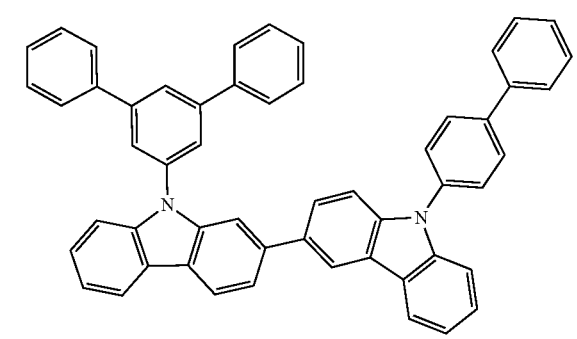
[B-149]
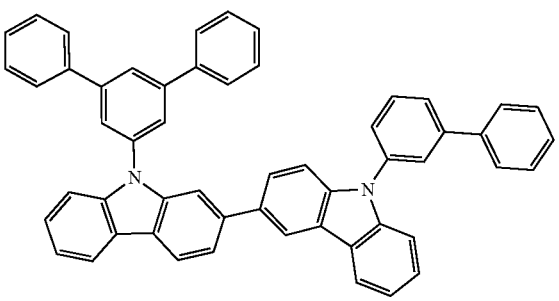
[B-150]
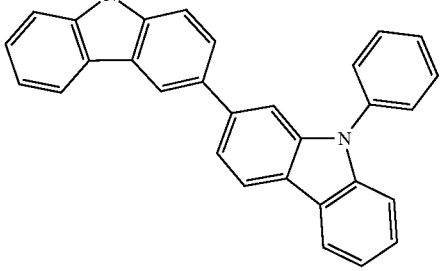

[B-151]
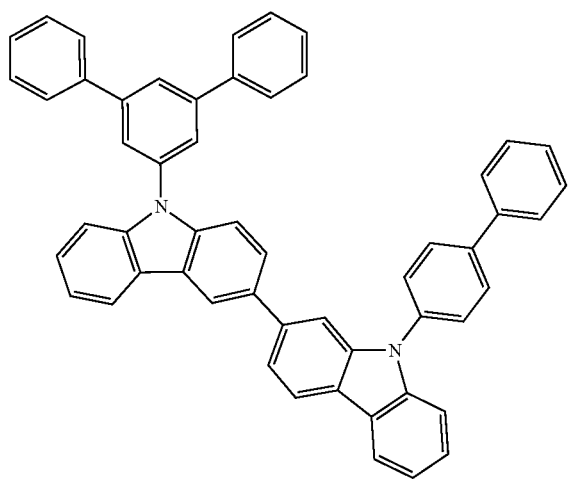
[B-152]
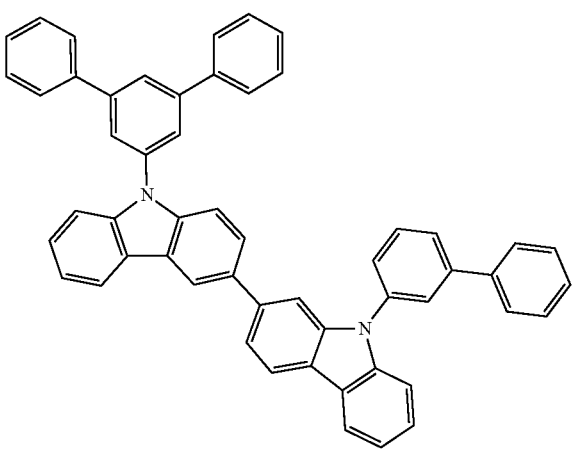
[B-153]
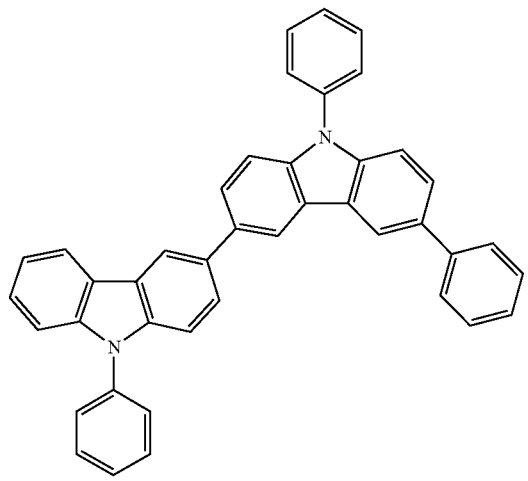
[B-154]
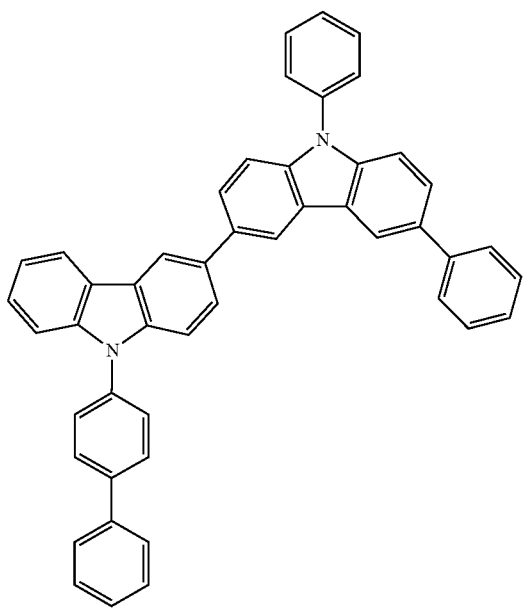
[B-155]
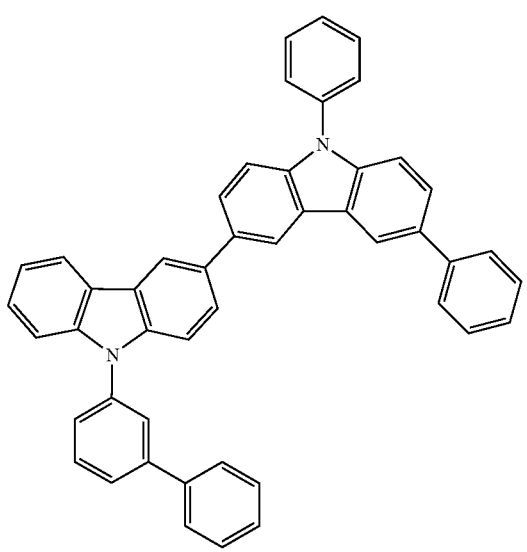

[B-156]
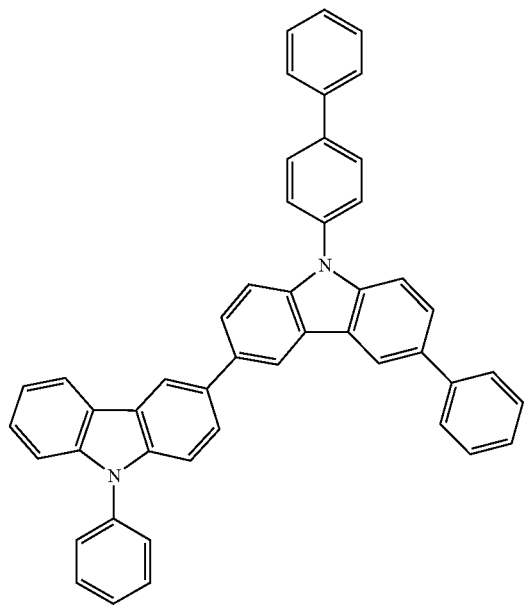
[B-159]
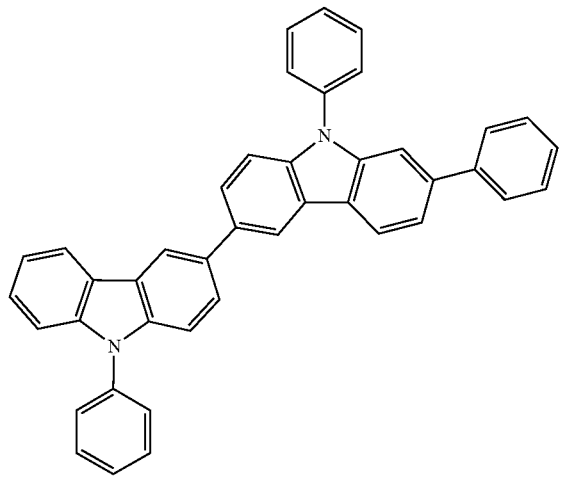
[B-157]
[B-158]
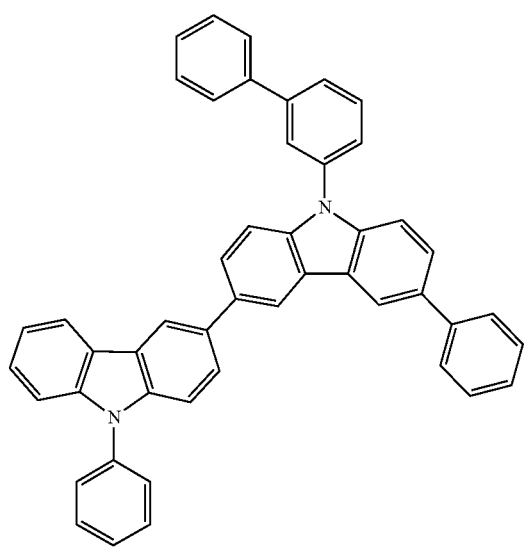
[B-160]
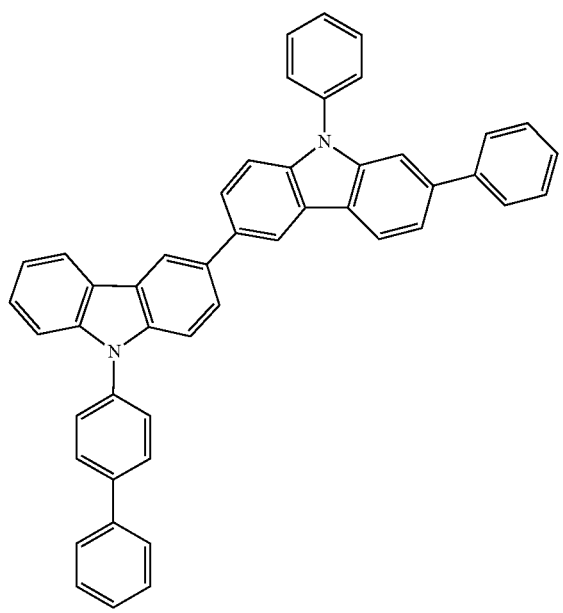

[B-161]
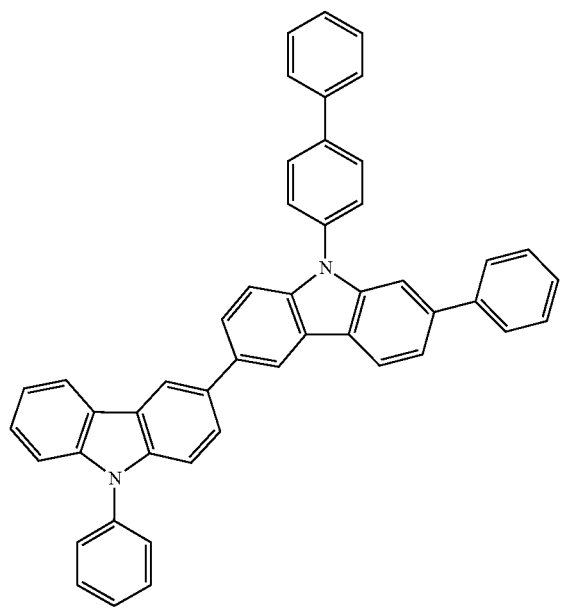
[B-163]
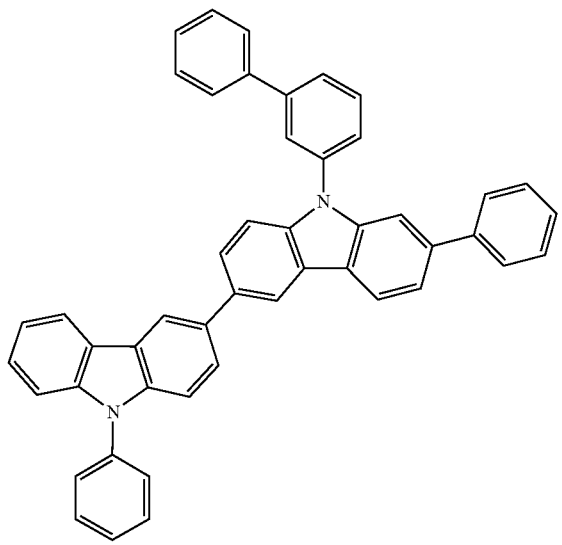
[B-162]
[B-164]
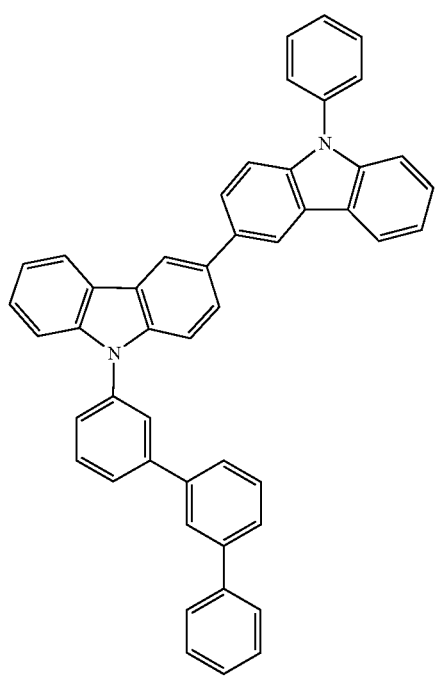

[B-165]
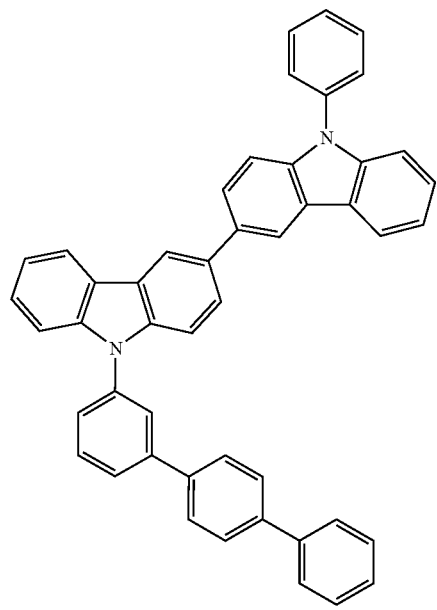
[group C]
[C-1]
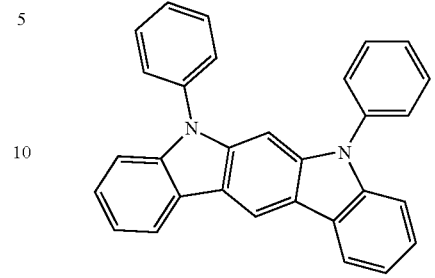
[C-2]
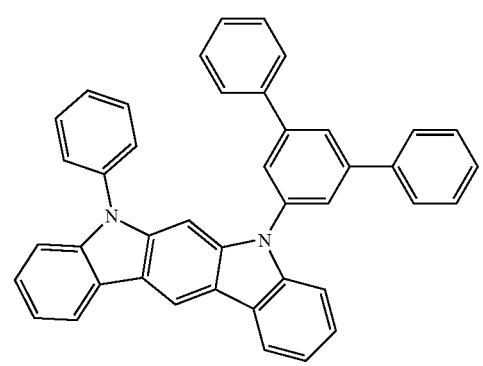
[B-166]
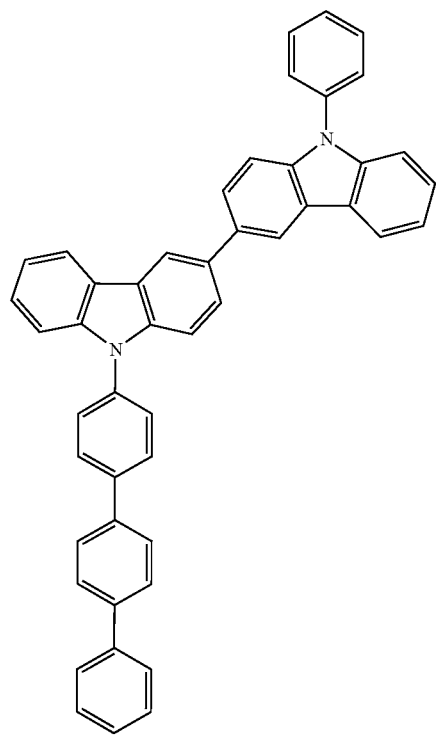
[C-3]
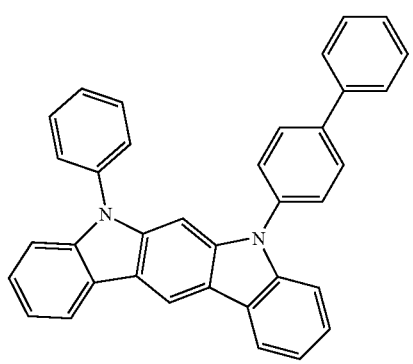
[C-4]
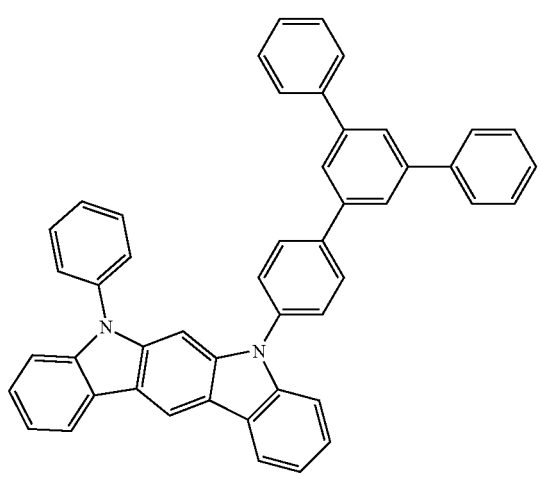

[C-5]
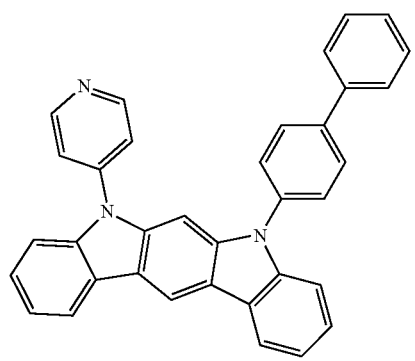
[C-6]
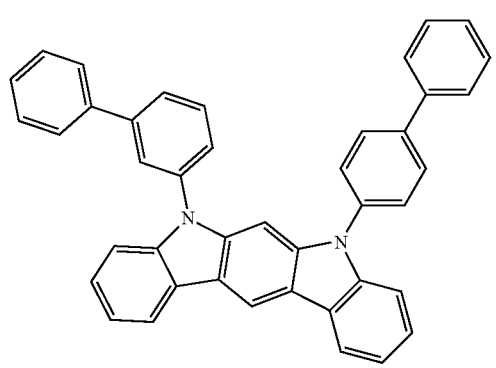
[C-7]
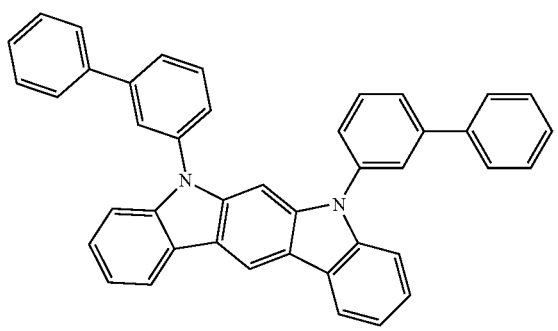
[C-8]
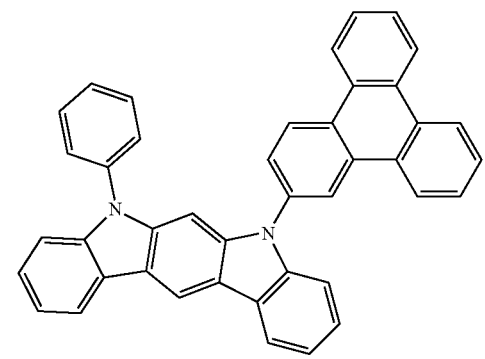
[C-9]
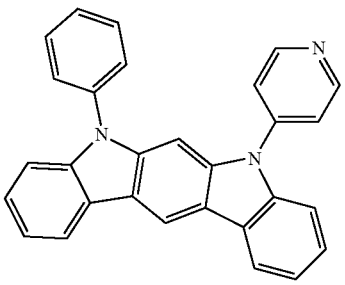
[C-10]
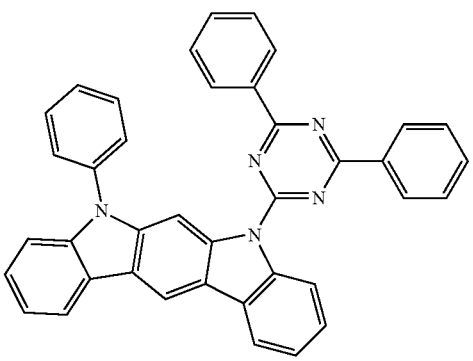
[C-11]
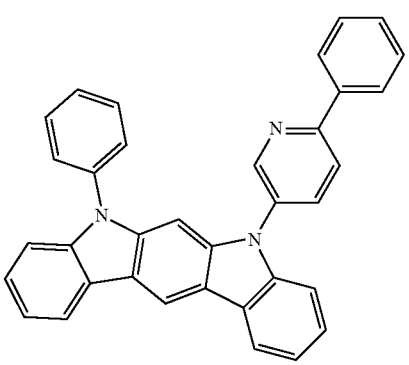
[C-12]
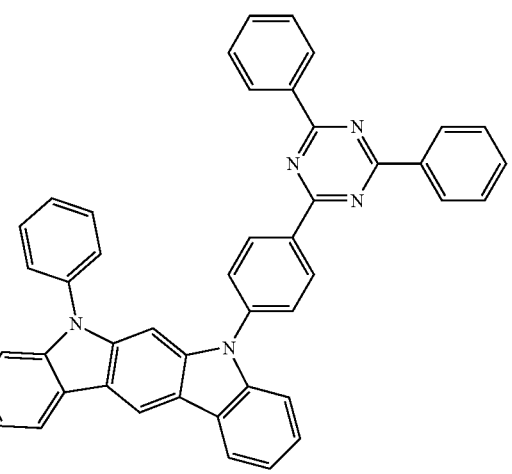

-continued
[C-13]
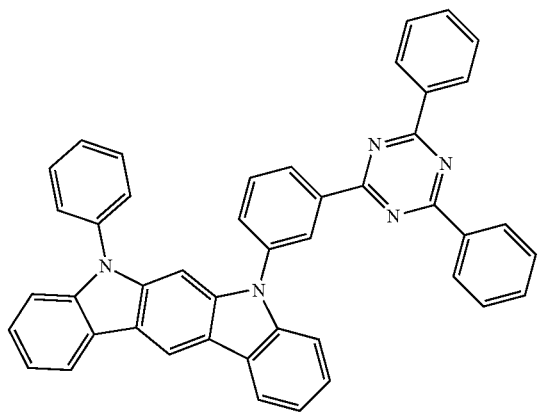
[C-14]
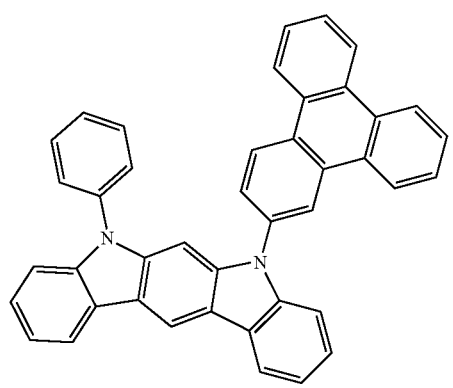
[C-15]
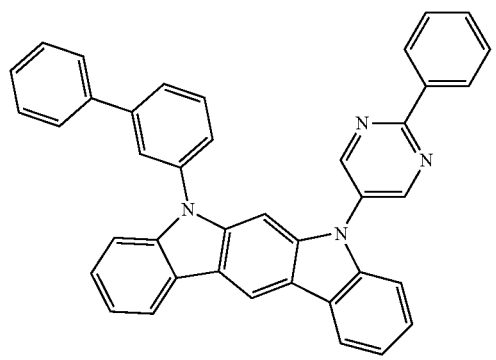
[C-16]
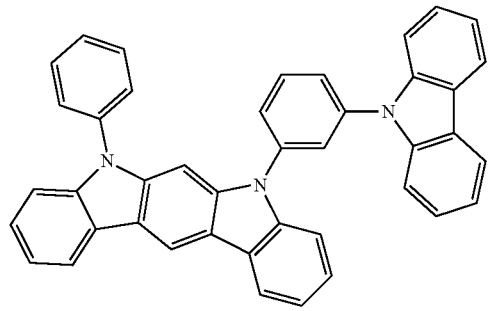
-continued
[C-17]
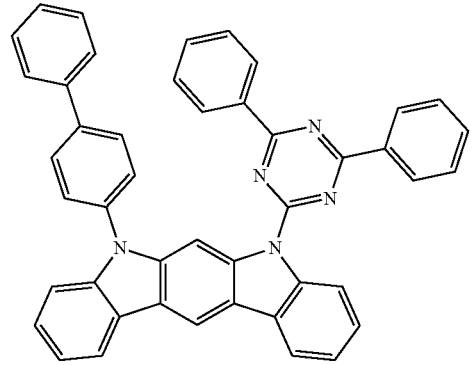
[C-18]
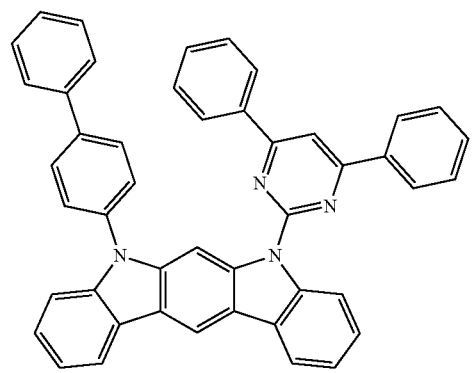
[C-19]
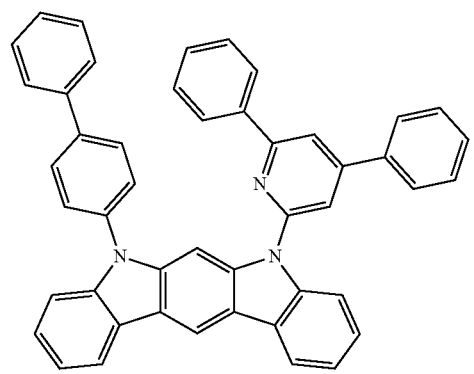
[C-20]
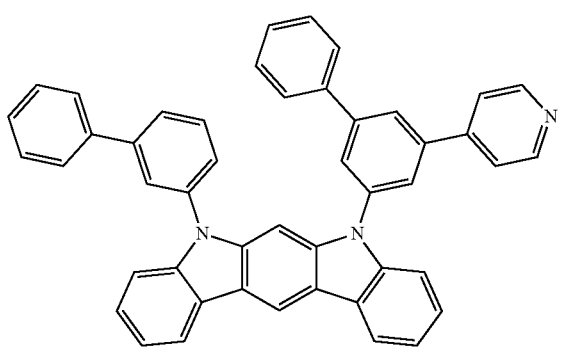

[C-21]
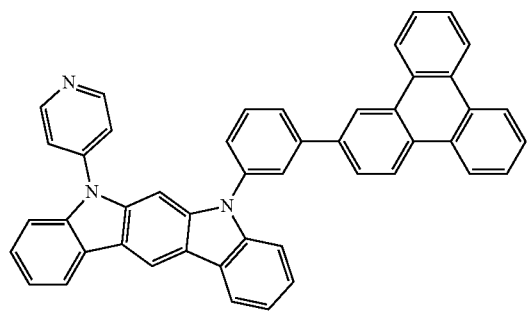
[C-22]
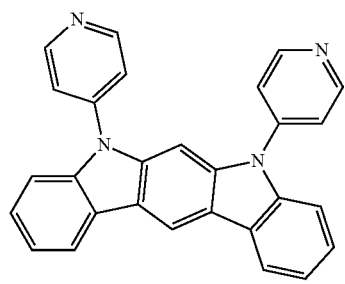
[C-23]
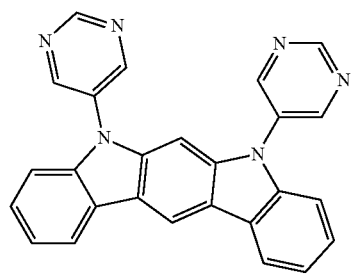
[C-24]
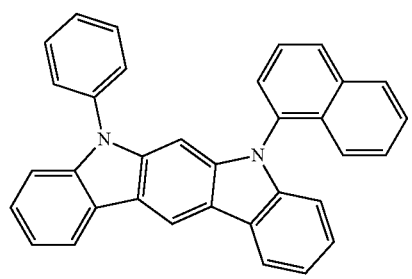
[C-25]
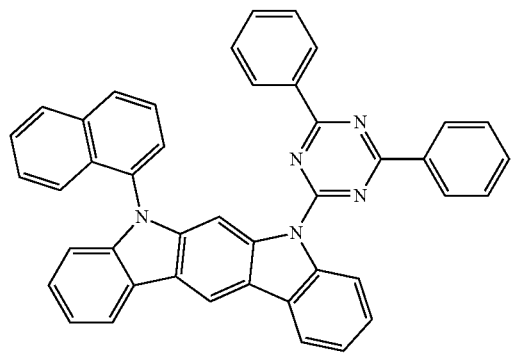
[C-26]
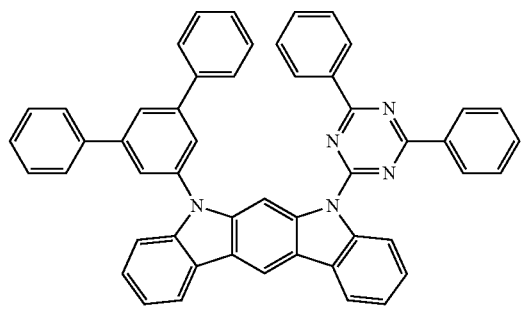
[C-27]
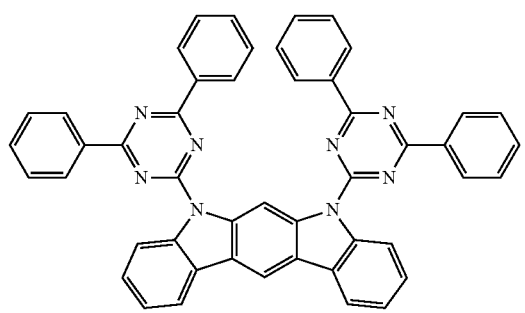
[C-28]
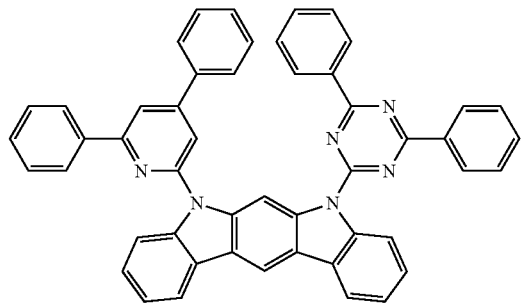
[C-29]
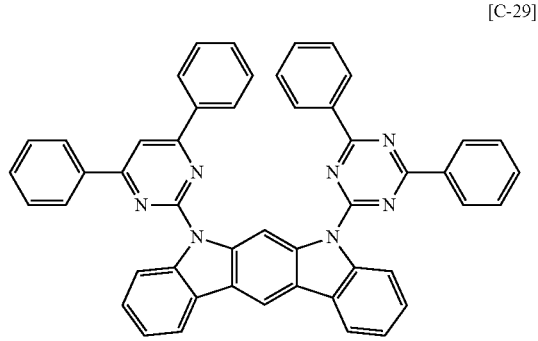

[C-30]
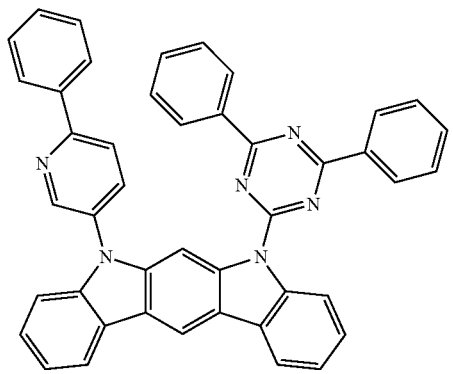
[C-34]
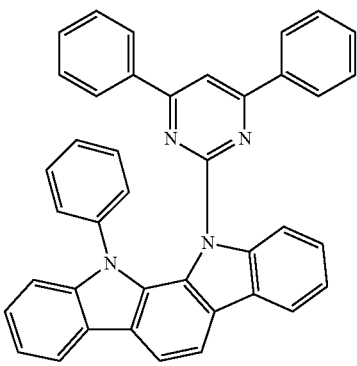
[C-31]
[C-35]
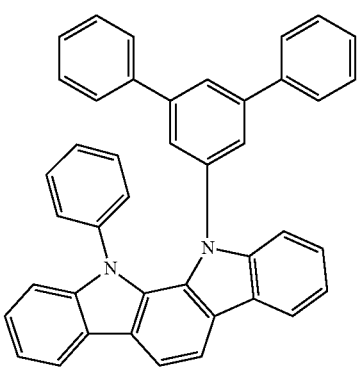
[C-32]
[C-36]
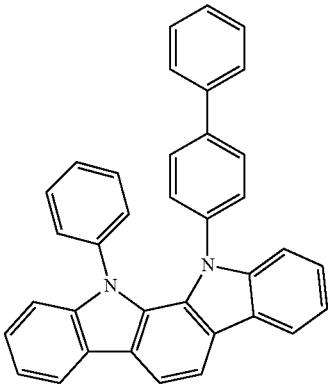
[C-33]
[C-37]
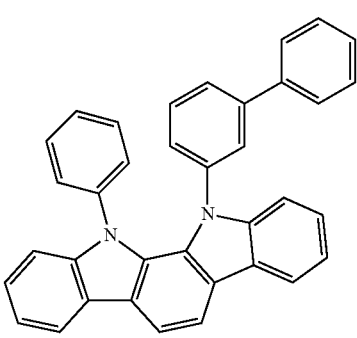

-continued

[C-38]
[C-39]
[C-40]

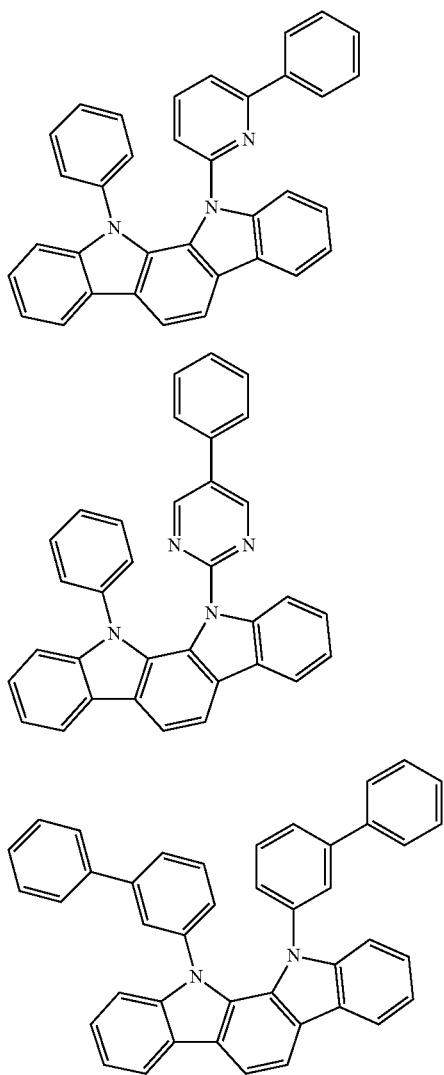

The aforementioned first and second hosts may be used in various ratios to prepare various compositions. For example, the first host and the second host may be used in a weight ratio ranging from about 1:99 to about 99:1, for example, about 10:90 to about 90:10. For example, the weight ratio may be about 2:8 to about 8:2, about 3:7 to about 7:3, about 4:6 to about 6:4, or about 5:5. When the first and second hosts satisfy the weight ratio ranges, electron transport characteristics by the first host and hole transport characteristics by the second host may be balanced and thus improve luminance efficiency and life-span of an organic light emitting diode.

For example, the compound may be used as a light-emitting material for an organic optoelectric device Herein, the light-emitting material may be the organic compound as a host, and may further include at least one dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

[Chemical Formula Z]

$L_2MX$

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd, or a combination thereof, and the L and X may be, for example a bidendate ligand.

A thickness of the emission layer may be about 100 Å to about 1000 Å, for example about 200 Å to about 600 Å. When the thickness of the emission layer is within these ranges, the emission layer may have improved emission characteristics without a substantial increase in a driving voltage.

Next, an electron transport region is disposed on the emission layer.

The electron transport region may include at least one of a hole blocking layer, an electron transport layer, and an electron injection layer.

For example, the electron transport region may have a structure of a hole blocking layer/electron transport layer/electron injection layer or electron transport layer/electron injection layer, but is not limited thereto. For example, an organic light emitting diode according to an embodiment of the present invention includes at least two electron transport layers in the electron transport region, and in this case, an electron transport layer contacting the emission layer is defined as an electron transport auxiliary layer.

The electron transport layer may have a monolayer or multi-layer structure including two or more different materials.

The electron transport region may include the compound for an organic optoelectric device represented by Chemical Formula 1. For example, the electron transport region may include an electron transport layer, and the electron transport layer may include the compound for an organic optoelectric device represented by Chemical Formula 1. More specifically, the electron transport auxiliary layer may include the compound for an organic optoelectric device represented by Chemical Formula 1.

The formation conditions of the hole blocking layer, electron transport layer, and electron injection layer of the electron transport region refers to the formation condition of the hole injection layer.

When the electron transport region includes the hole blocking layer, the hole blocking layer may include at least one of BCP, Bphen, and BAlq, but is not limited thereto.

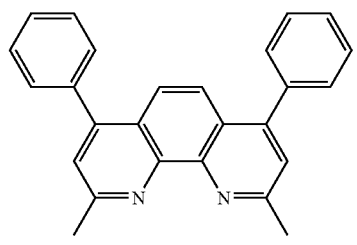

BCP

-continued

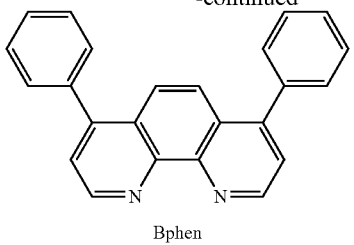

Bphen

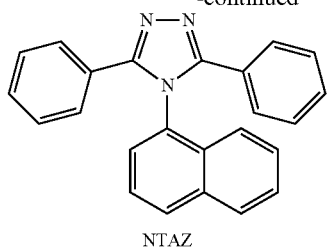

NTAZ

A thickness of the hole blocking layer may be from about 20 Å to about 1000 Å, for example about 30 Å to about 300 Å. When the thickness of the hole blocking layer is within these ranges, the hole blocking layer may have improved hole blocking ability without a substantial increase in a driving voltage.

The electron transport layer may further include at least one of the BCP, Bphen and the following Alq3, Balq, TAZ, and NTAZ.

Or, the electron transport layer may include at least one of Compounds ET1 and ET2, but is not limited thereto.

[Compound ET1]

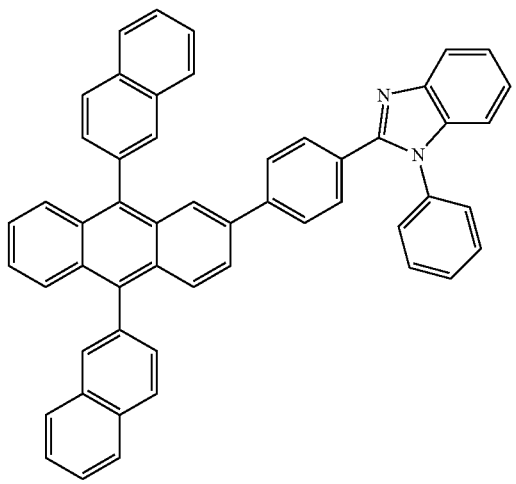

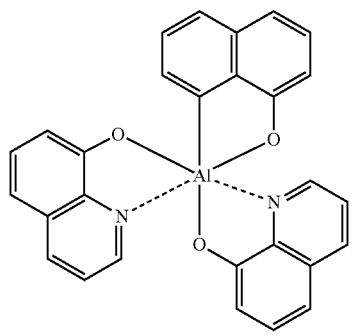

Alq₃

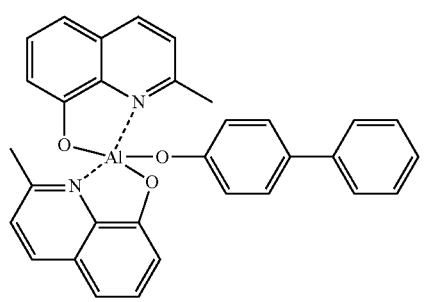

BAlq

[Compound ET2]

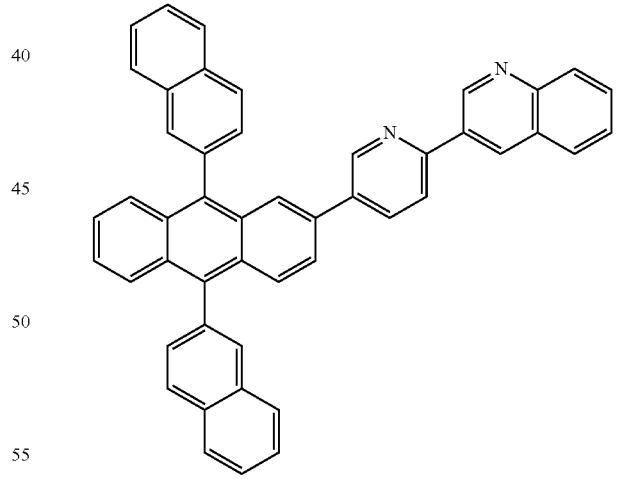

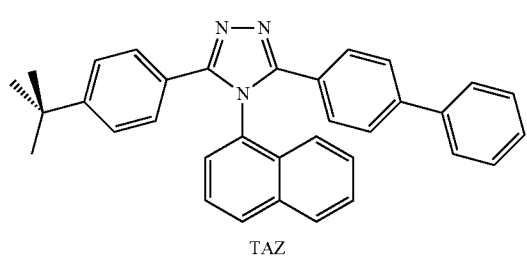

TAZ

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in a driving voltage.

The electron transport layer may further include a metal-containing material, in addition to the above-described materials.

The metal-containing material may include a lithium (Li) complex. The Li complex may include, for example, Compound ET-D1 (lithium quinolate, LiQ) or ET-D2.

[Compound ET-D1]

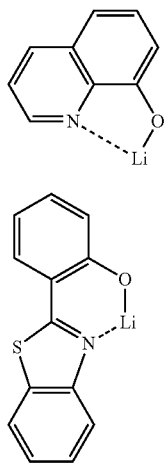

[Compound ET-D2]

In addition, the electron transport region may include an electron injection layer that may facilitate injection of electrons from the anode.

The electron injection layer is disposed on an electron transport layer and may play a role of facilitating an electron injection from a cathode and ultimately improving power efficiency and be formed by using any material used in a related art without a particular limit, for example, LiF, Liq, NaCl, CsF, Li2O, BaO, and the like.

The electron injection layer may include at least one selected from LiF, NaCl, CsF, $Li_2O$. and BaO.

A thickness of the electron injection layer may be from about 1 Å to about 100 Å, or about 3 Å to about 90 Å. When the thickness of the electron injection layer is within these ranges, the electron injection layer may have satisfactory electron injection ability without a substantial increase in driving voltage.

A cathode is disposed on the organic layer. A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al-Li), calcium (Ca), magnesium-indium (Mg-In), magnesium-silver (Mg-Ag), etc. In order to manufacture a top-emission light-emitting device, the anode 110 may be formed as a transmissive electrode from, for example, indium tin oxide (ITO) or indium zinc oxide (IZO).

Hereinafter, the embodiments are illustrated in more detail with reference to examples. These examples, however, are not in any sense to be interpreted as limiting the scope of the invention.

The organic light emitting diode may be applied to an organic light emitting diode (OLED) display.

Hereinafter, starting materials and reactants used in Examples and Synthesis

Examples were purchased from Sigma-Aldrich Co. Ltd. or TCI Inc. as far as there in no particular comment.

Synthesis of Intermediate 1-2

First Step: Synthesis of Intermediate 1-1

A 9-fluorene intermediate compound was synthesized through the following reaction process.

[Reaction Scheme 1]

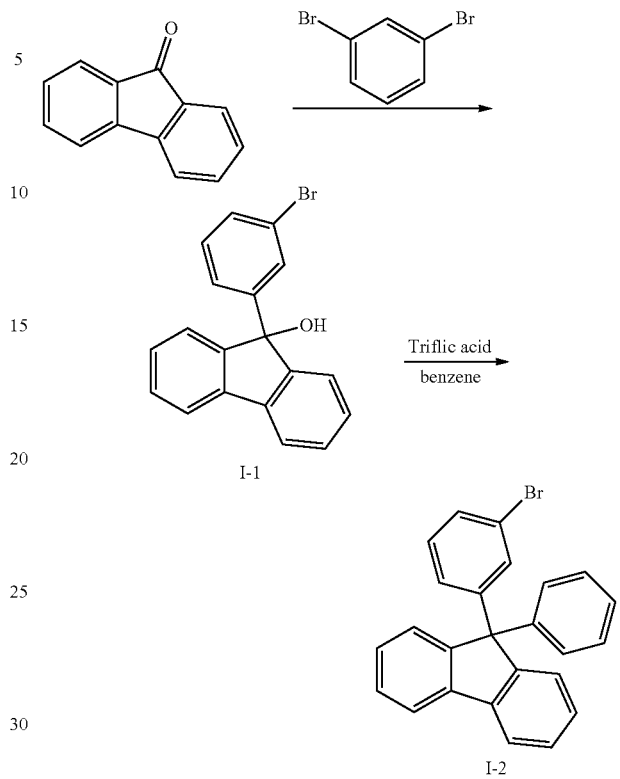

1,3-dibromobenzene (1.0 eq) was put in anhydrous THF (0.5 M) in a 1000 mL round flask and then, cooled down in a dry ice acetone bath, and butyllithium (1.0 eq, 2.5 M in hex) was slowly added thereto through a dropping funnel. After stirring the obtained mixture for 1 hour, fluorenone (1.0 eq) dissolved in anhydrous TI-IF (0.5 M) was slowly added thereto through the dropping funnel. Two hours later after slowly heating the reactant up to room temperature, the reaction was completed by adding a chloride ammonium aqueous solution thereto. Then, the THF was removed under a reduced pressure, and the reactant was dissolved in dichloromethane again and washed with water. After removing an appropriate amount of an organic solvent, the reactant was treated through column chromatography to obtain Compound I-1 (70% of a yield).

calcd. $C_{19}H_{13}BrO$: C, 67.67; H, 3.89; Br, 23.70; 0, 4.74; found: C, 67.67; H, 3.85; Br, 23.73; O, 4.76

Second Step: Synthesis of Intermediate 1-2

12.0 g (35.5 mmol) of the Intermediate I-1 was put in a 250 mL round flask and then, dissolved in an anhydrous benzene solution. After diluting trifluoromethanesulfonic acid (6.3 mL, 2 eq) in 30 mL of benzene. the diluted solution was slowly added to the reactant. The obtained reactant was heated and refluxed under a nitrogen current for 48 hours. The reactant was washed with a 0.5 N sodium hydroxide aqueous solution and water, methanol (5 times as much as benzene) was added thereto after appropriately removing the benzene under a reduced pressure to obtain a crystallized solid, and the crystallized solid was filtered to obtain Compound I-2 (8.5 g, 60% of a yield).

calcd. $C_{25}H_{17}Br$: C, 75.58; H, 4.31; Br, 20.11; found: C, 75.57; H, 4.30; Br, 20.13

Synthesis of Intermediate I-4

Intermediate I-4 was synthesized by using 1,2-dibromobenzene instead of the 1,3-dibromobenzene in the first step of synthesizing the Intermediate 1-2 as a starting material and sequentially applying the second step thereto.

[Reaction Scheme 2]

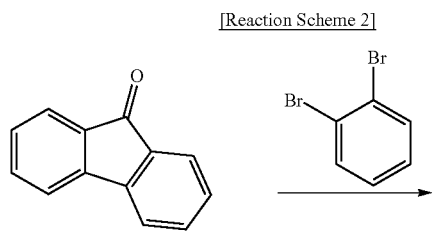

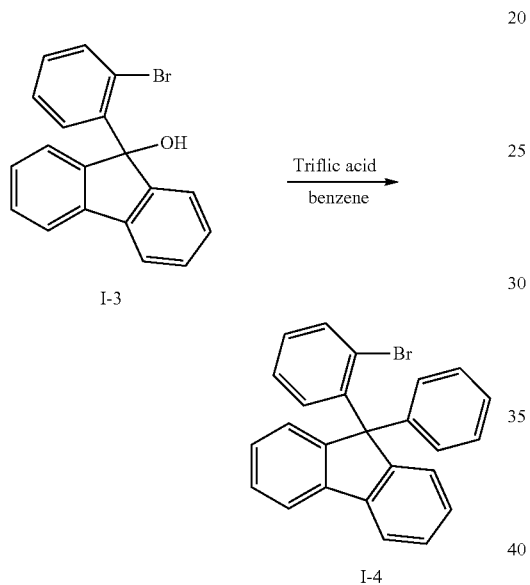

I-3: 65% of a yield calcd. C₁₉₁H₁₃BrO: C, 67.67; H, 3.89; Br, 23.70; O, 4.74; found: C, 67.67; H, 3.85; Br, 23.73; O, 4.75

I-4: 50% of a yield calcd. C₂₅H₁₇Br: C, 75.58; H, 4.31; Br, 20.11; found: C, 75.57; H, 4.31; Br, 20.12

Synthesis of Intermediate I-6

Intermediate I-6 was synthesized by using 1,4-dibromobenzene instead of the 1,3-dibromobenzene in the first step of synthesizing the Intermediate I-2 as a starting material and sequentially applying the second step thereto.

[Reaction Scheme 3]

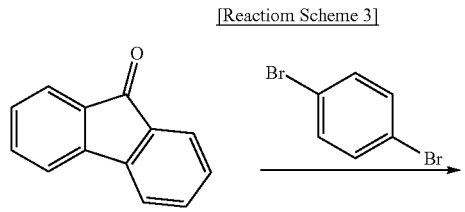

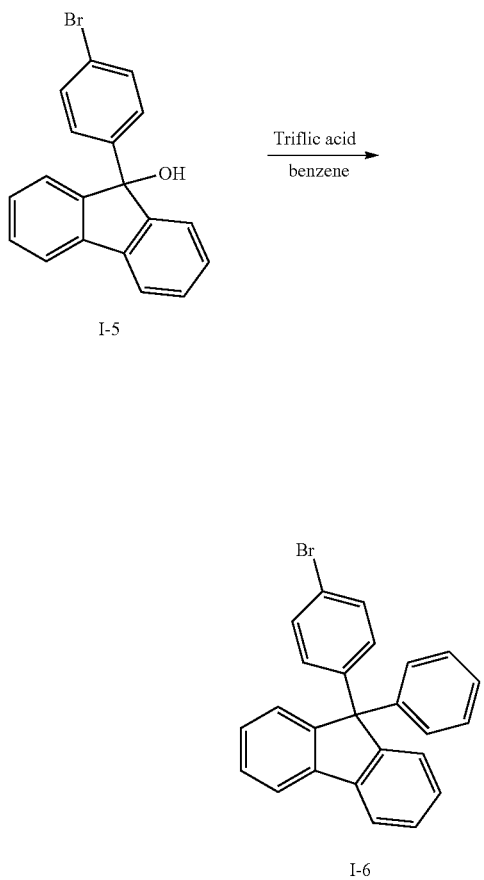

I-5: 80% of a yield calcd. C₁₉H₁₃BrO: C, 67.67; H, 3.89; Br, 23.70; O, 4.74; found: C, 67.67; H, 3.84; Br, 23.74; O, 4.75

I-6: 60% of a yield calcd. C₂₅H₁₇Br: C, 75.58; H, 4.31; Br, 20.11; found: C, 75.57; H, 4.31; Br, 20.13

Synthesis of Organic Compound

Synthesis Example 1: Synthesis of Compound 2-1

Compound 2-1 as one specific example of the present invention was synthesized through the following two steps.

[Reaction Scheme 4]

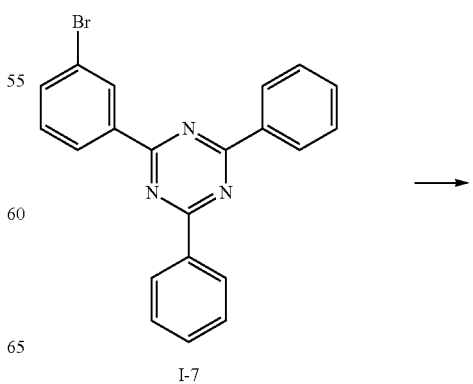

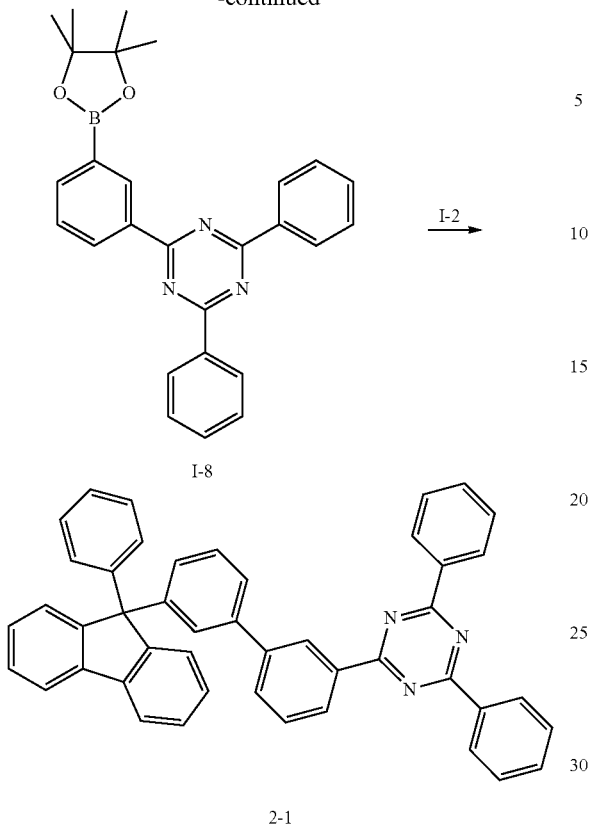

First Step: Synthesis of Intermediate I-8 (Boration Reaction)

50.0 g (129 mmol) of the intermediate I-7 (commercially available, TCI), 36 g (142 mmol) of 4,4,4',4',5,5,5',5'-octamethyl-2,2'-bi-1,3,2-dioxaborolane, 3.15 g (3.9 mmol) of [1,1¹-bis(diphenylphosphino)ferrocene]dichloropalladium (II) (Pd(dppf)Cl₂), and 38 g (387 mmol) of potassium acetate (KOAc) were put in 430 mL (0.3 M) of toluene in a 1000 mL flask and then, heated at 110 ° C. under a nitrogen current for 12 hours. The obtained mixture was added to 1000 mL of methanol, and a solid crystallized therein was filtered and treated through column chromatography to obtain Intermediate I-8 (47.7 g, 85% of a yield).

calcd. $C_{27}H_{26}BN_3O_2$: C, 74.49; H, 6.02; B, 2.48; N, 9.65; O, 7.35; found: C, 74.47; H, 6.03; B, 2.47; N, 9.67; O, 7.35

Second Step: Synthesis of Compound 2-1

11.9 g (34.8 mmol) of the Intermediate I-2, 13.6 g (30.0 mmol) of arylboronester I-8, 12.4 g (90.0 mmol) of potassium carbonate, and 1.7 g (1.5 mmol) of Pd(PPh₃)₄ (tetrakis-(triphenylphosphine) palladium (0)) were put in 50 mL of water and 100 mL of tetrahydrofuran in a 1000 mL flask and then, heated at 70 ° C. under a nitrogen current for 12 hours. The obtained mixture was added to 500 mL of methanol to crystallize a solid, and the solid was filtered, dissolved in dichlorobenzene, filtered with silica gel/Celite, and then, recrystalized with methanol after removing an appropriate amount of an organic solvent to obtain Compound 2-1 (15.0 g. 80% of a yield).

calcd. $C_{46}H_{31}N_3$: C, 88.29; H, 4.99; N, 6.72; found: C, 88.27; H, 4.98; N, 6.75

Synthesis Example 2: Synthesis of Compound 2-2

Compound 2-2 was synthesized as one specific example of the present invention through the following two steps.

[Reaction Scheme 5]

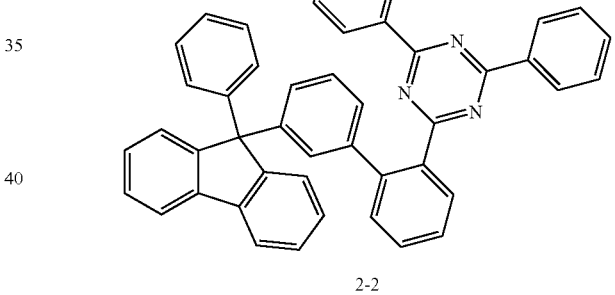

First Step: Synthesis of Intermediate I-10 (Boration Reaction)

Intermediate I-10 (60% of yield) was synthesized by using the intermediate I-9 (Ark Pharm, cas:77989-15-2) instead of the Intermediate I-7 according to the same method as the synthesis of the Intermediate I-8.

calcd. $C_{27}H_{26}BN_3O_2$: C, 74.49; H, 6.02; B, 2.48; N, 9.65; O, 7.35; found: C, 74.47; H, 6.03; B, 2.47; N, 9.68; O, 7.34

Second Step: Synthesis of Compound 2-2

Compound 2-2 (50% of a yield) was synthesized according to the same method as the synthesis of the Compound 2-1 by using the Intermediate I-10 instead of the Intermediate I-8.

calcd. $C_{46}H_{31}N_3$: C, 88.29; H, 4.99; N, 6.72; found: C, 88.27; H, 4.98; N, 6.75

Synthesis Example 3: Synthesis of Compound 2-4

Compound 2-4 was synthesized according to the same method as the synthesis of the Compound 2-1 by using the Intermediate 1-4.

calcd. $C_{46}H_{31}N_3$: C, 88.29; H, 4.99; N, 6.72; found: C, 88.27; H, 4.98; N, 6.75

Synthesis Example 4: Synthesis of Compound 2-5

Compound 2-5 was synthesized according to the same method as the synthesis of the Compound 2-1 by using the Intermediate I-6.

calcd. $C_{46}H_{31}N_3$: C, 88.29; H, 4.99; N, 6.72; found: C, 88.28; H, 4.98; N, 6.76

Synthesis Example 5: Synthesis of Compound 2-7

Compound 2-7 was synthesized as one specific example of the present invention through the following three steps.

[Reaction Scheme 6]

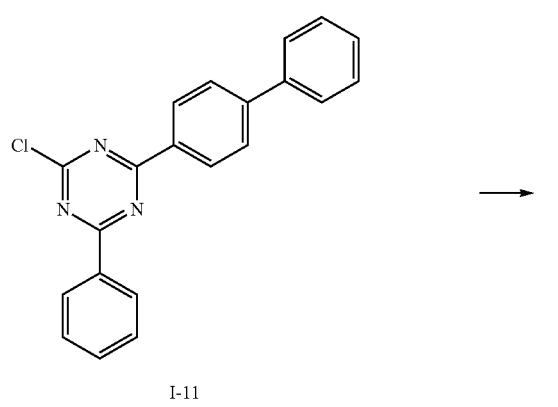

I-11

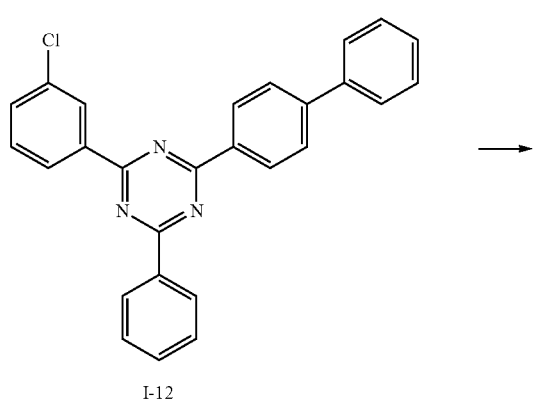

I-12

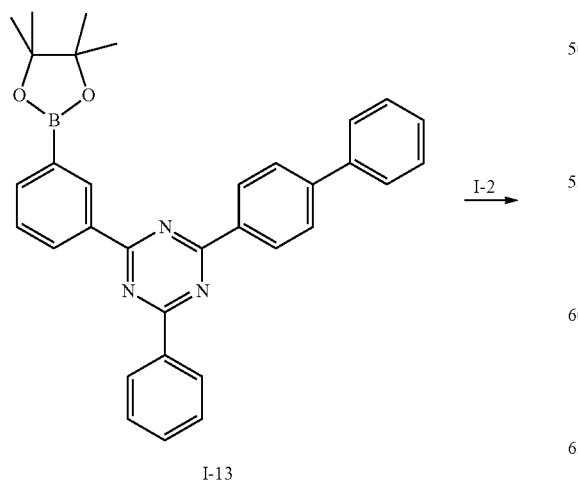

I-13

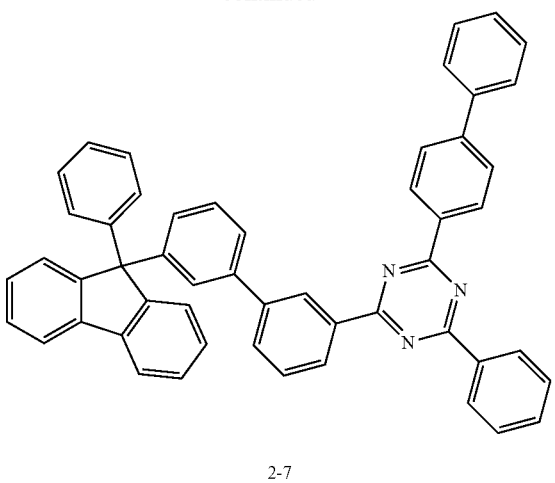

2-7

First Step: Synthesis of Intermediate I-12

Intermediate I-12 (90% of a yield) was synthesized according to the same method as the second step of synthesizing the Compound 2-1 by using the Intermediate I-11 (PharmaBlock, cas: 1472062-94-4) and 3-chlorophenyl boronic acid.

calcd. $C_{27}H_{18}ClN_3$: C, 77.23; H, 4.32; Cl, 8.44; N, 10.01; found: C, 77.23; H, 4.32; Cl, 8.44; N, 10.01

Second Step: Synthesis of Intermediate I-13

Intermediate I-13 (70% of a yield) was synthesized according to the same method as the first step of synthesizing the Compound 2-1 by using the Intermediate I-12.

calcd. $C_{33}H_{30}BN_3O_2$: C, 77.50: H, 5.91; B, 2.11; N, 8.22; O, 6.26; found: C. 77.52; H. 5.91: B, 2.10; N, 8.21; O, 6.26

Third Step: Synthesis of Compound 2-7

Compound 2-7 (80% of a yield) was synthesized according to the same method as the second step of synthesizing the Compound 2-1 by using the Intermediate I-13.

calcd. $C_{52}H_{35}N_3$: C, 88.99; H, 5.03; N, 5.99; found: C, 88.97; H, 5.06; N, 5.98

Synthesis Example 6: Synthesis of Compound 2-12

Compound 2-12 was synthesized as one specific example of the present invention through the following three steps.

[Reaction Scheme 7]

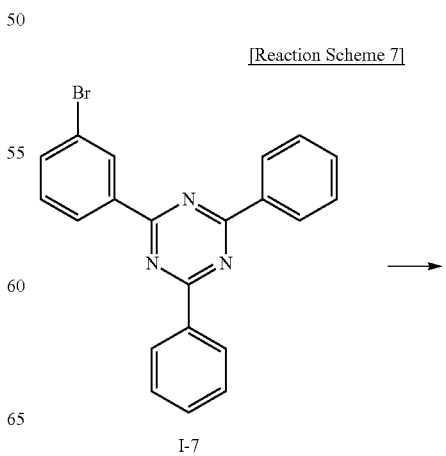

I-7

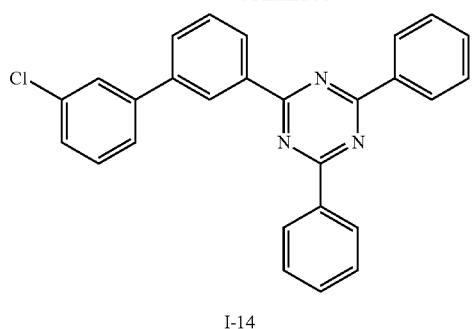

I-14

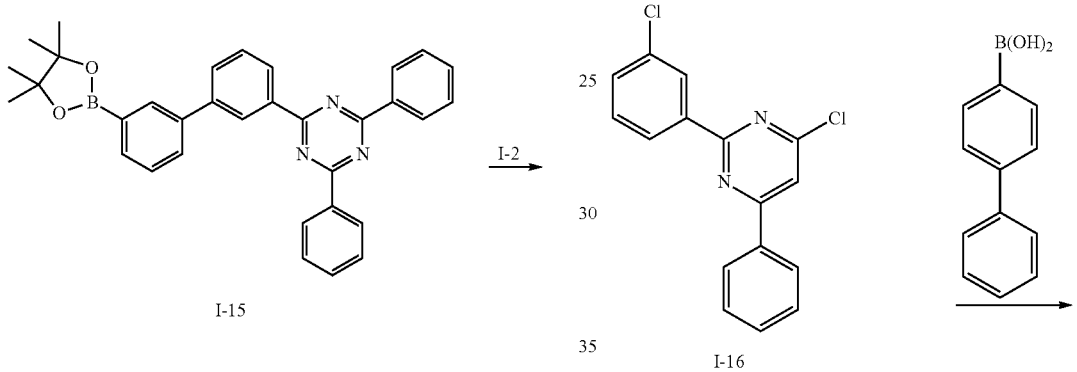

I-15

2-12

First Step: Synthesis of Intermediate I-14

Intermediate I-14 (80% of a yield) was synthesized by using the Intermediate I-7 and 3-chlorophenyl boronic acid according to the same method as the second step of synthesizing the Compound 2-1.

calcd. $C_{27}H_{18}ClN_3$: C, 77.23; H, 4.32; Cl, 8.44; N, 10.01; found: C, 77.23; H, 4.32; Cl. 8.44; N, 10.01

Second Step: Synthesis of Intermediate I-15

Intermediate I-15 (70% of a yield) was synthesized by using the Intermediate I-14 according to the same method as the first step of synthesizing the Compound 2-1.

calcd. $C_{33}H_{33}BN_3O_2$: C, 77.50; H, 5.91; B, 2.11; N, 8.22; O, 6.26; found: C, 77.50; H, 5.90; B, 2.11; N, 8.21; O, 6.26

Third Step: Synthesis of Compound 2-12

Compound 2-12 (80% of a yield) was synthesized by using the Intermediate I-15 according to the same method as the second step of synthesizing the Compound 2-1.

calcd. $C_{52}H_{35}N_3$: C, 88.99; H, 5.03; N, 5.99; found: C, 88.99; H, 5.03; N, 5.99

Synthesis Example 7: Synthesis of Compound 3-9

Compound 3-9 was synthesized as one specific example of the present invention through the following three steps.

[Reaction Scheme 8]

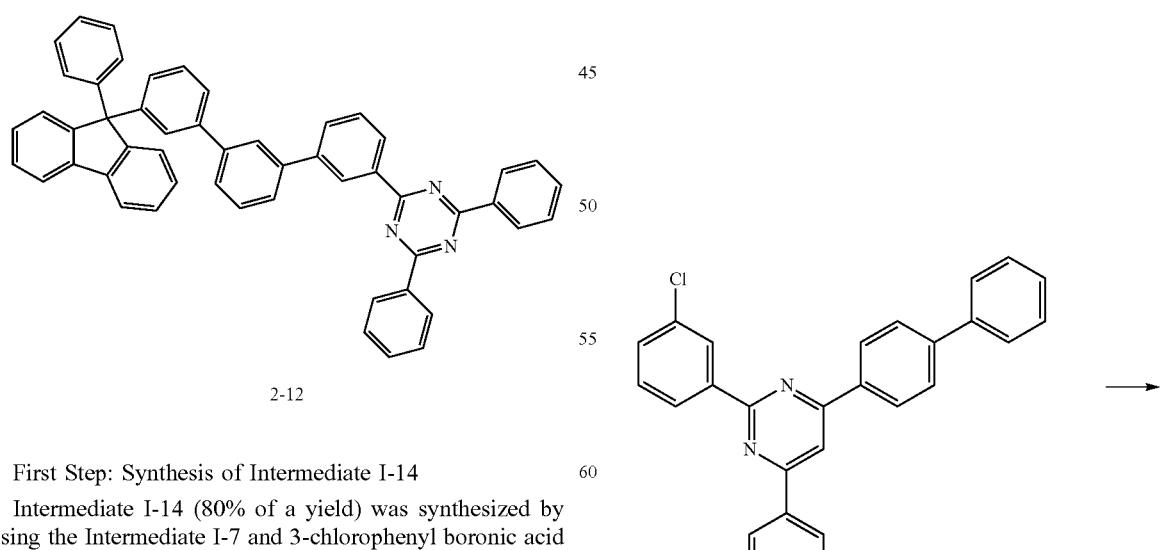

I-16

I-17

143

-continued

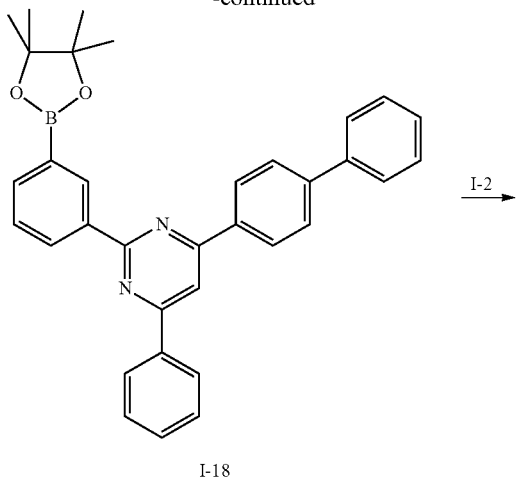

I-18

3-9

First Step: Synthesis of Intermediate I-17

30.1 g (100 mmol) of the intermediate I-16 (Aurora Building Blocks, cas: 1155152-53-6), 25.6 g (210 mmol) of phenylboronic acid, 41.5 g (300 mmol) of potassium carbonate, and 3.5 g (3.0 mmol) of Pd(PPh$_3$)$_4$ (tetrakis-(triphenylphosphine) palladium (0)) were put in 200 mL of tetrahydrofuran and 100 mL of water in a 1000 mL flask and then, heated at 70 ° C. under a nitrogen current for 12 hours. The obtained mixture was added to 600 mL of methanol to crystallize a solid, and the solid was filtered. dissolved in dichlorobenzene, filtered with silica gel/Celite, and then, recrystalized with methanol after removing an appropriate amount of an organic solvent to obtain Intermediate I-17 (27.4 g, 80% of a yield).

calcd. C$_{22}$H$_{15}$ClN$_2$: C, 77.08; H, 4.41; Cl, 10.34; N, 8.17; found: C, 77.06; H, 4.43; Cl, 10.34; N, 8.17

Second Step: Synthesis of Intermediate I-18

Intermediate I-18 (75% of a yield) was synthesized by using the Intermediate I-17 according to the same method as the first step of synthesizing the Compound 2-1.

calcd. C$_{28}$H$_{27}$BN$_2$O$_2$: C, 77.43; H, 6.27; B, 2.49; N, 6.45; O, 7.37; found: C, 77.44; H, 6.26; B, 2.48; N, 6.46; O, 7.37

Third Step: Synthesis of Compound 3-9

Compound 3-9 (80% of a yield) was synthesized by using the Intermediate I-18 according to the same method as the second step of synthesizing the Compound 2-1.

calcd. C$_{47}$H$_{32}$N$_2$: C, 90.35; H, 5.16; N, 4.48; found: C, 90.34; H, 5.17; N, 4.49

144

Synthesis Example 8: Synthesis of Compound 3-14

Compound 3-14 was synthesized as one specific example of the present invention through the following three steps.

[Reaction Scheme 9]

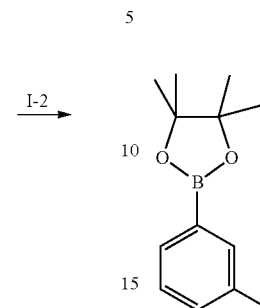

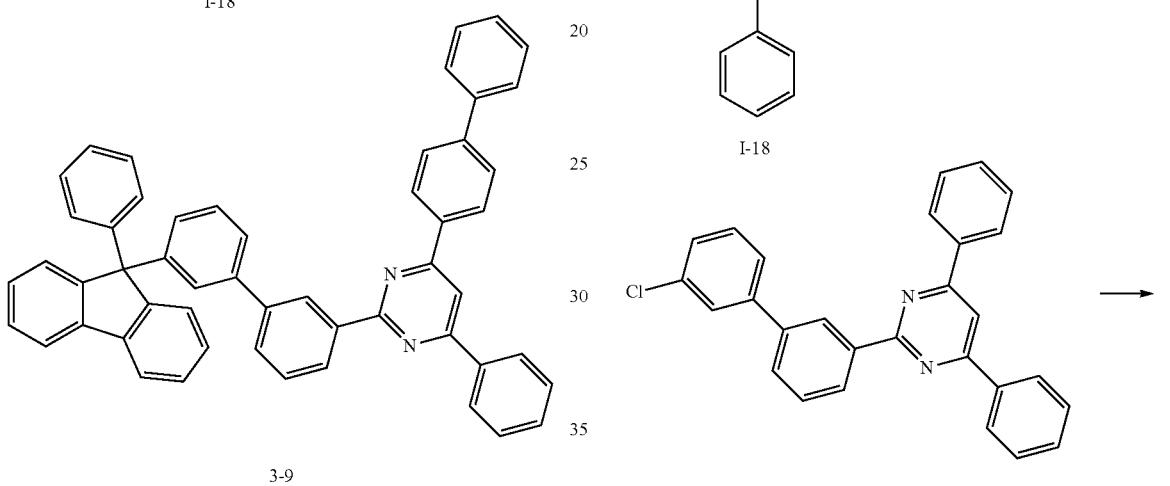

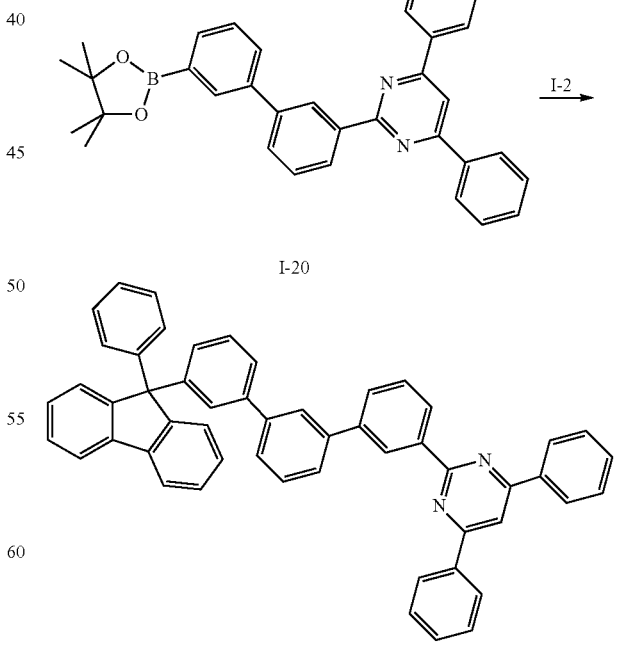

3-14

First Step: Synthesis of Intermediate I-19

8 g (30 mmol) of the Intermediate I-18, 4.2 mL (36 mmol) of 1-bromo-3- chlorobenzene, 13.7g (90 mmol) of potassium carbonate, and 1.15 g (1.0 mmol) of Pd(PPh$_3$)$_4$ (tetrakis-(triphenylphosphine) palladium (0)) were added to 100 mL of tetrahydrofuran and 50 mL of water in a 1000 mL flask and then, heated at 70 ° C. for 12 hours under a nitrogen current. The obtained mixture was added to 500 mL of methanol to crystallize a solid, and the solid was filtered, dissolved in dichlorobenzene, filtered with silica gel/Celite, and then, recrystalized with methanol after removing an amount remove of an organic solvent to obtain Intermediate I-19 (9.1 g, 70% of a yield).

Second Step: Synthesis of Intermediate I-20

Intermediate I-20 (75% of a yield) was synthesized according to the same method as the first step of synthesizing the Compound 2-1 by using the Intermediate I-19.

calcd. C$_{34}$H$_{31}$BN$_2$O$_2$: C, 80.00; H, 6.12; B, 2.12; N, 5.49; O, 6.27; found: C, 80.00; H, 6.13; B, 2.12; N, 5.49; O, 6.26

Third Step: Synthesis of Compound 3-14

Compound 3-14 (80% of a yield) was synthesized according to the same method of synthesizing the second step of the Compound 2-1 by using the Intermediate I-20.

calcd. C$_{53}$H$_{36}$N$_2$: C, 90.83; H, 5.18; N, 4.00; found: C, 90.84; H, 5.17; N, 4.00

Synthesis Example 9: Synthesis of Compound 4-9

Compound 4-9 was synthesized according to the same method as the synthesis of the Compound 3-9 of Synthesis Example 7 by using the Intermediate I-21 (Aurora Building Blocks, cas: 145903-35-1).

[Reaction Scheme 10]

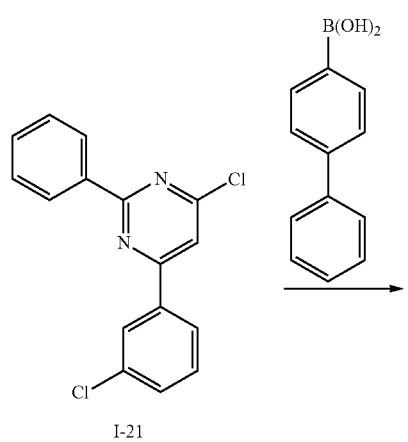

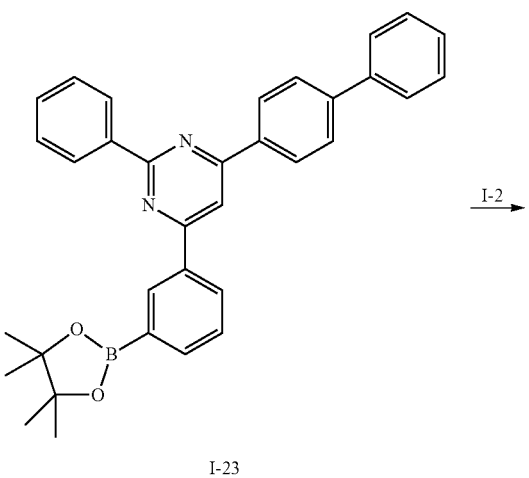

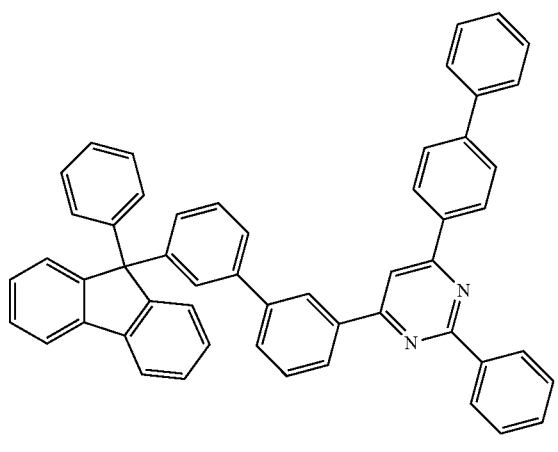

calcd. C$_{47}$H$_{32}$N$_2$: C, 90.35; H, 5.16; N, 4.48; found: C, 90.34; H, 5.17; N, 4.47

Synthesis Example 10: Synthesis of Compound 4-14

Compound 4-14 was synthesized according to the same method as the synthesis of the Compound 2-12 by using the Intermediate 1-24 (Apichemical, cas: 1262866-93- 2).

calcd. C$_{53}$H$_{36}$N$_2$: C, 90.83; H, 5.18; N, 4.00; found: C, 90.84; H, 5.17; N, 4.00

Synthesis Example 11: Synthesis of Compound 5-1

Compound 5-9 as one specific example of the present invention was synthesized through the following three steps.

[Reaction Scheme 11]

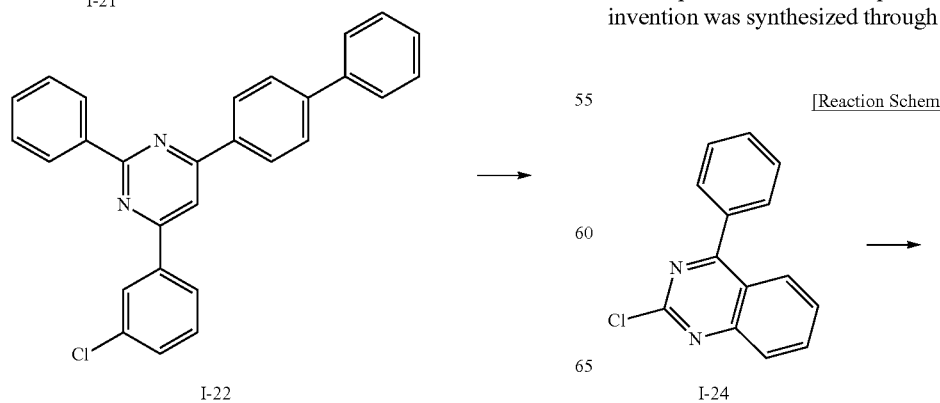

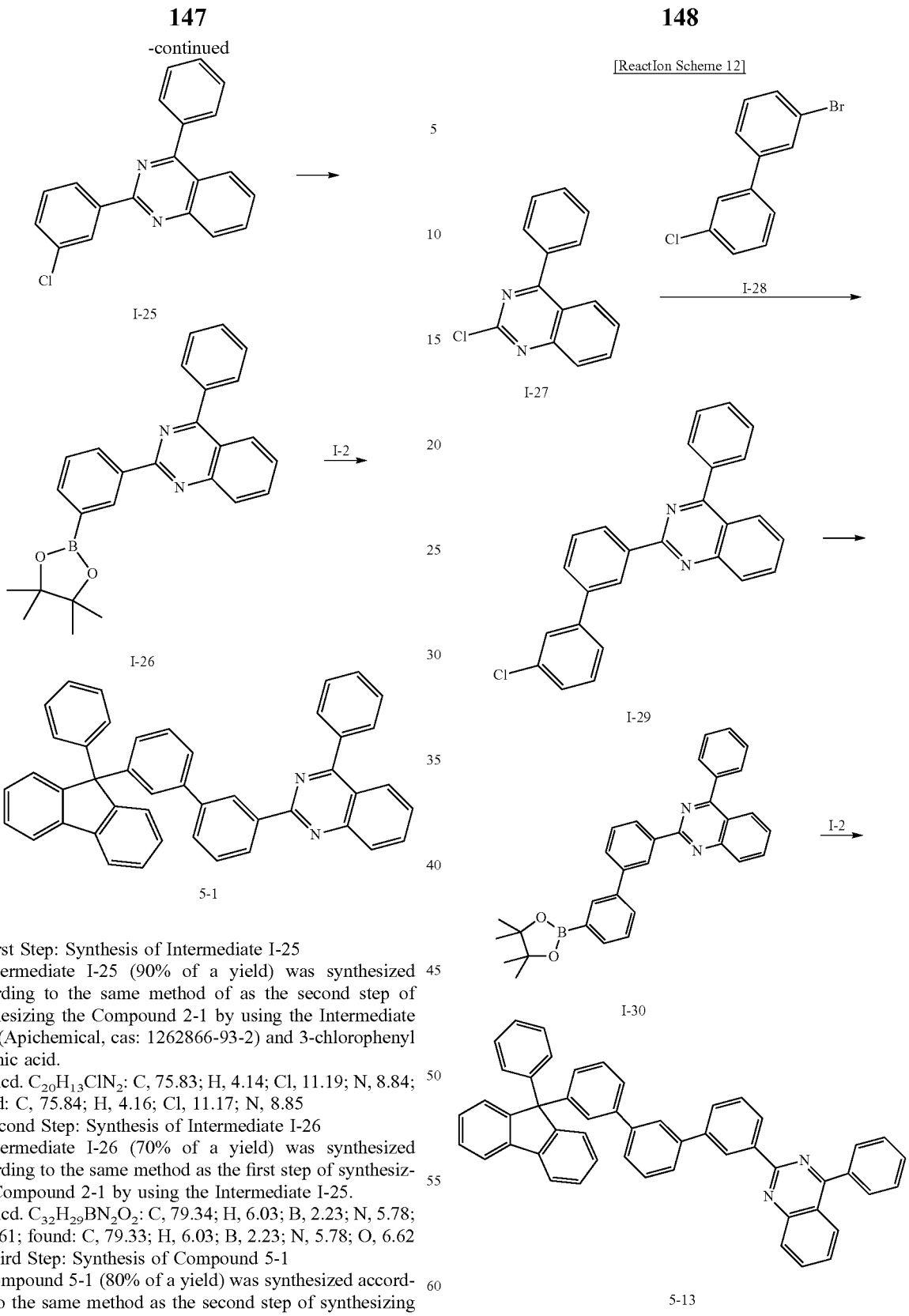

First Step: Synthesis of Intermediate I-25

Intermediate I-25 (90% of a yield) was synthesized according to the same method of as the second step of synthesizing the Compound 2-1 by using the Intermediate I-24 (Apichemical, cas: 1262866-93-2) and 3-chlorophenyl boronic acid.

calcd. $C_{20}H_{13}ClN_2$: C, 75.83; H, 4.14; Cl, 11.19; N, 8.84; found: C, 75.84; H, 4.16; Cl, 11.17; N, 8.85

Second Step: Synthesis of Intermediate I-26

Intermediate I-26 (70% of a yield) was synthesized according to the same method as the first step of synthesizing Compound 2-1 by using the Intermediate I-25.

calcd. $C_{32}H_{29}BN_2O_2$: C, 79.34; H, 6.03; B, 2.23; N, 5.78; O, 6.61; found: C, 79.33; H, 6.03; B, 2.23; N, 5.78; O, 6.62

Third Step: Synthesis of Compound 5-1

Compound 5-1 (80% of a yield) was synthesized according to the same method as the second step of synthesizing Compound 2-1 by using the Intermediate I-26.

calcd. $C_{51}H_{34}N_2$: C, 90.77; H, 5.08; N, 4.15; found: C, 90.77; H, 5.08; N, 4.14

Synthesis Example 12: Synthesis of Compound 5-13

Compound 5-9 was synthesized as one specific example of the present invention through the following three steps.

First Step: Synthesis of Intermediate I-29

Intermediate I-29 (80% of a yield) was synthesized according to the same method as the second step of synthesizing the Compound 2-1 by using the Intermediate I-27

(Apichemical, cas: 29874-83-7) and 3-bromo-3'-chlorobiphenyl of the Intermediate I-28 (Oakwood Chemical, cas: 844856-42-4).

calcd. $C_{26}H_{17}ClN_2$: C, 79.48; H, 4.36; Cl, 9.02; N, 7.13; found: C, 79.48; H, 4.35; CI, 9.02; N, 7.14

Second Step: Synthesis of Intermediate I-30

Intermediate I-30 (70% of a yield) was synthesized according to the same method as the first step of synthesizing Compound 2-1 by using the Intermediate I-29.

calcd. $C_{32}H_{29}BN_2O_2$: C, 79.34; H, 6.03; B, 2.23; N, 5.78; O, 6.61; found: C, 79.34; H, 6.03; B, 2.23; N, 5.77; O, 6.61

Third Step: Synthesis of Compound 5-13

Compound 5-13 (77% of a yield) was synthesized according to the same method of synthesizing the Compound 2-1 by using the Intermediate I-30.

calcd. $C_{51}H_{34}N_2$: C, 90.77; H, 5.08; N, 4.15; found: C, 90.77; H. 5.08; N, 4.14

Synthesis Example 13: Synthesis of Compound 6-9

Compound 6-9 was synthesized as one specific examples of the present invention through the following four steps.

[Reaction Scheme 13]

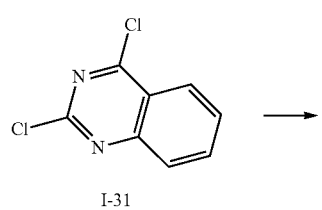

I-31

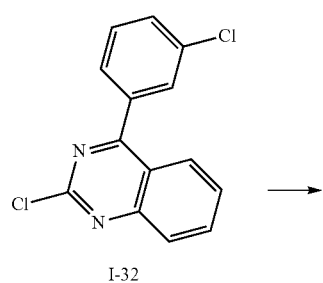

I-32

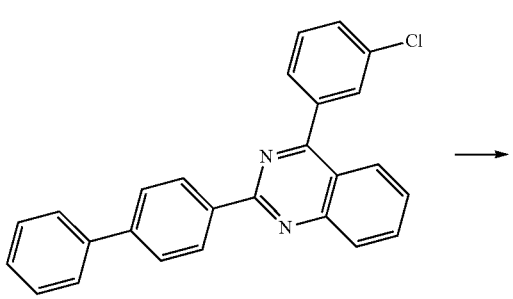

I-33

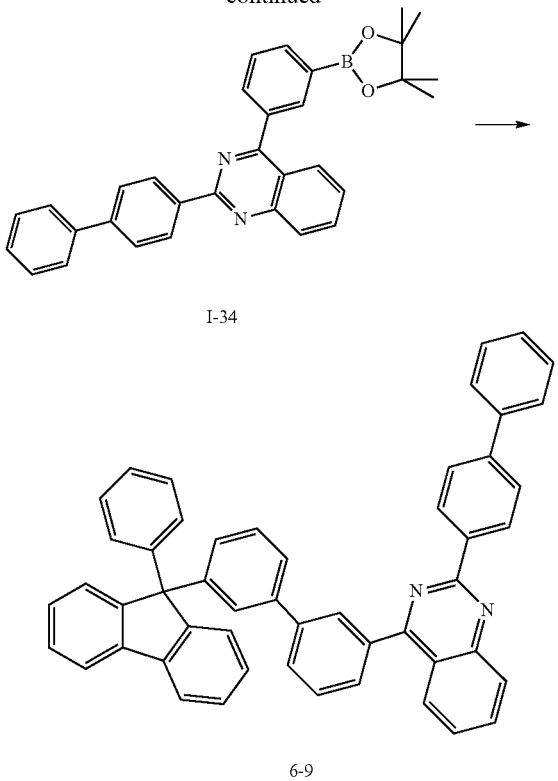

First Step: Synthesis of Intermediate I-32

Intermediate I-32 (80% of a yield) was synthesized according to the same method as the second step of synthesizing the Compound 2-1 by using the Intermediate I-31 (TCI) and 3-chlorophenyl boronic acid (1 eq). Herein, the reaction was performed under the same condition except for changing the temperature into 60 ° C.

calcd. $C_{14}H_8Cl_2N_2$: C, 61.12; H, 2.93; Cl, 25.77; N, 10.18; found: C, 61.12; H, 2.93; Cl, 25.77; N, 10.18

Second Step: Synthesis of Intermediate I-33

Intermediate I-33 (60% of a yield) was synthesized according to the same method as the second step of synthesizing the Compound 2-1 by using the Intermediate I-32 and 4-biphenylboronic acid.

calcd. $C_{26}H_{17}ClN_2$: C, 79.48; H, 4.36; Cl, 9.02; N, 7.13; found: C, 79.48; H, 4.36; Cl, 9.03; N, 7.13

Third Step: Synthesis of Intermediate I-34

Intermediate I-34 (80% of a yield) was synthesized according to the same method as the first step of synthesizing the Intermediate I-33.

calcd. $C_{32}H_{29}BN_2O_2$: C, 79.34; H, 6.03; B, 2.23; N, 5.78; O, 6.61; found: C, 79.34; H, 6.03; B, 2.23; N, 5.78; O, 6.61

Fourth Step: Synthesis of Compound 6-9

Compound 6-9 (75% of a yield) was synthesized according to the same method as the second step of synthesizing the Compound 2-1 by using the Intermediate I-34.

calcd. $C_{51}H_{34}N_2$: C, 90.77; H, 5.08; N, 4.15; found: C, 90.78; H, 5.07; N, 4.15

Synthesis of Reference Example Compound

Reference Compound 1 (an effect depending on a linking group or not)

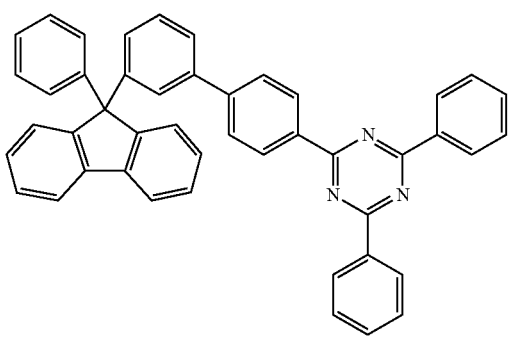 [SMILES: c1ccc(-c2nc(-c3ccccc3)nc(-c3ccc(-c4cccc(C5(c6ccccc6)c6ccccc6-c6ccccc65)c4)cc3)n2)cc1]
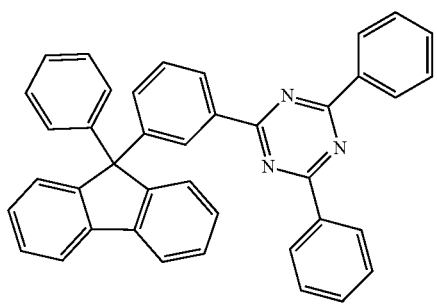
Reference Compound 1 (60% of a yield) was synthesized according to the same method as the Compound 2-1 of Synthesis Example 1.
calcd. $C_{40}H_{27}N_3$: C, 87.40; 4.95; N, 7.64; found: C, 87.41; H, 4.95; N, 7.64
Reference Compound 2 (an effect of substituting an alkyl group in 9,9-diphenylfluorene)
[Reaction Scheme 14]
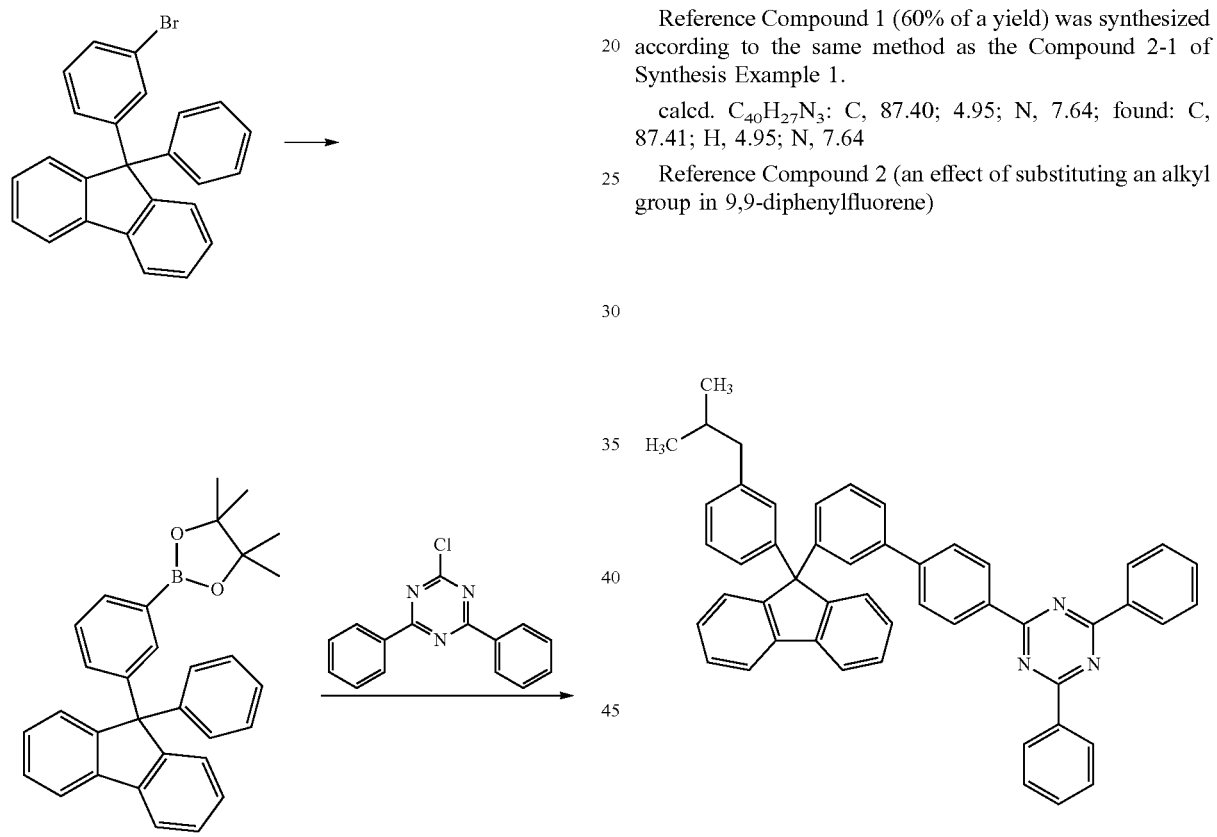
[Reaction Scheme 15]
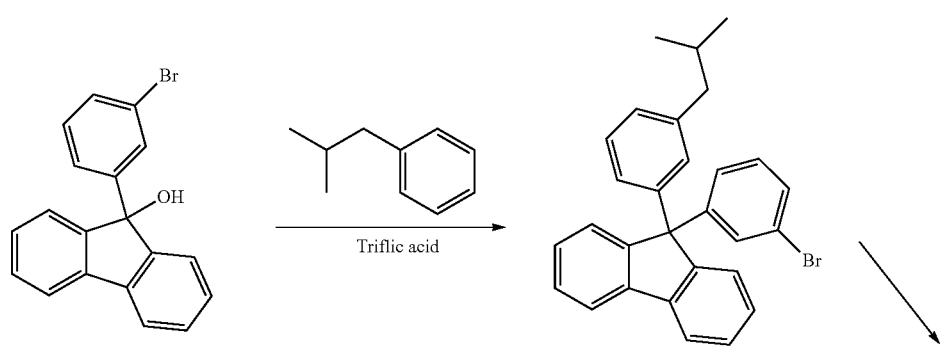

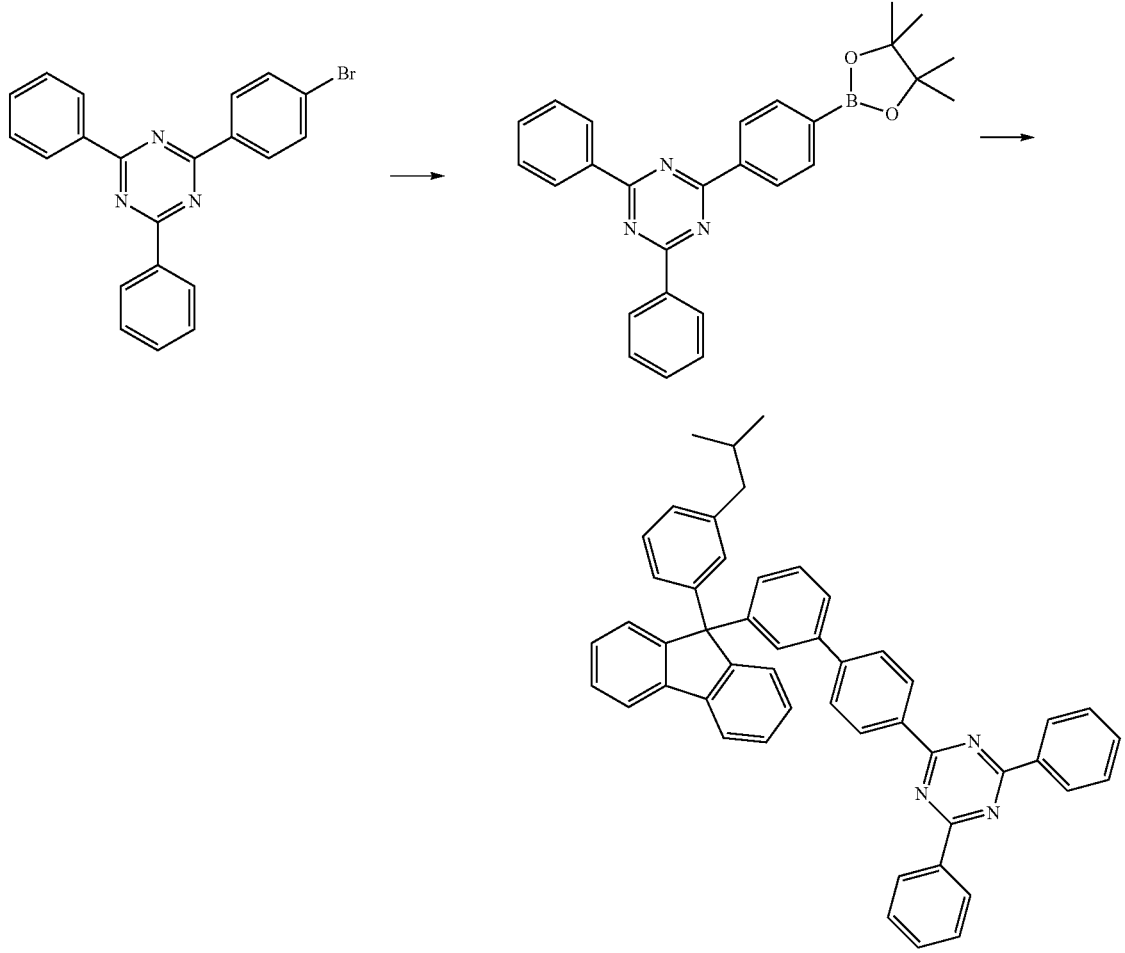
Reference Compound 2 (30% of a yield) was synthesized according to the same method as the Intermediate I-2 and the Compound 2-1 of Synthesis Example.
calcd. $C_{50}H_{39}N_3$: C, 88.07; H, 5.77; N, 6.16; found: C, 88.08; H, 5.76; N, 6.15
Reference Compound 3 (an effect of an $Ar^1$ substituent having electron characteristics and no additional substituent such as an aryl group and the like)
[Reaction Scheme 16]
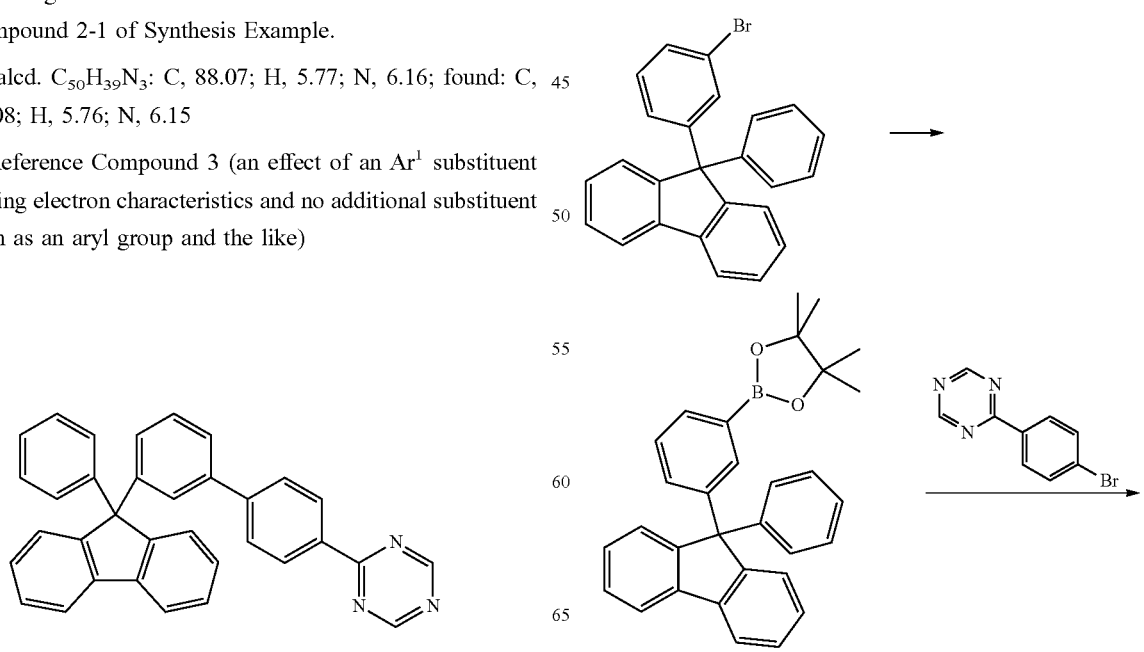

-continued

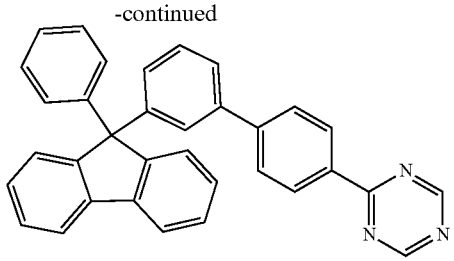

Reference Compound 3 (65% of a yield) was synthesized through a Suzuki reaction used for the synthesis of Compound 2-1 by using the Intermediate of Reference Compound 1 and 2-(4-bromophenyl)-1,3,5-triazine (Aurora Building Blocks, cas: 1369015-30-4).

calcd. $C_{34}H_{23}N_3$: C, 86.23; H, 4.90; N, 8.87; found: C, 86.24; H, 4.89; N, 8.87

Manufacture of Organic Light Emitting Diode 1: Host Alone

Example 1

An organic light emitting diode was manufactured by using the Compound 2-1 according to Synthesis Example 1 as a host and Ir(PPy)$_3$ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropyl alcohol, and pure water respectively for 15 minutes, and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick film as an emission layer was formed by using the Compound 2-1 according to Synthesis Example 1 under the same vacuum deposition condition as above, and herein, Ir(PPy)$_3$ as a phosphorescent dopant was simultaneously deposited. Herein, the phosphorescent dopant was deposited in an amount of 10 wt % based on 100 wt % of the total amount of the emission layer by adjusting a deposition rate.

On the emission layer, a 50 Å-thick film as a hole blocking layer was formed by depositing bis(2-methyl-8-quinolinolate)-4-(phenylphenolato)aluminum (BAlq) under the same vacuum deposition condition as above. Subsequently, a 200 Å-thick film as an electron transport layer was formed by depositing Alq3 under the same vacuum deposition condition as above. On the electron transport layer, LiF and Al were sequentially deposited as a cathode, manufacturing the organic photoelectric device.

The organic photoelectric device had a structure of ITO/ NPB (80 nm)/ EML (Compound 2-1 (90 wt %)+Ir(PPy)$_3$ (10 wt %), 30 nm)/ Balq (5 nm)/ Alq3 (20 nm)/ LiF (1 nm)/Al (100 nm).

Examples 2 to 8

Organic light emitting diodes according to Examples 2 to 8 were manufactured according to the same method as Example 1 by respectively using the Compounds 2-2, 2-4, 2-5, 2-7, 2-12, 3-9, and 4-9 of Synthesis Examples 2 to 7 and 9 instead of the Compound 2-1 of Synthesis Example 1.

Comparative Example 1

An organic light emitting diode was manufactured according to the same method as Example 1 except for using CBP having the following structure instead of the Compound 2-1 of Synthesis Example 1.

Reference Examples 1 to 3

Organic light emitting diodes according to Reference Examples 1 to 3 were manufactured according to the same method as Example 1 except for respectively using the Reference Compounds 1 to 3 according to Reference Examples instead of the Compound 2-1 according to Synthesis Example 1.

NPB, BAlq, CBP, and Ir(PPy)$_3$ used in the organic light emitting diodes respectively have the following structures.

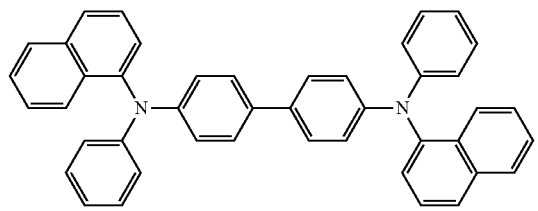

[NPB]

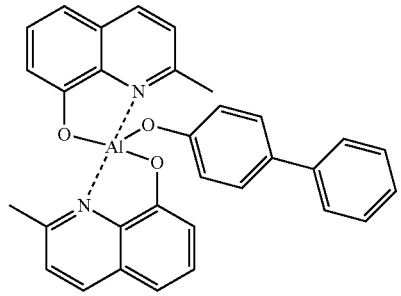

[BAlq]

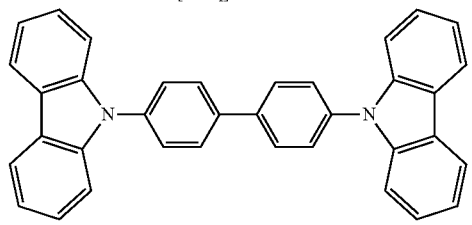

[CBP]

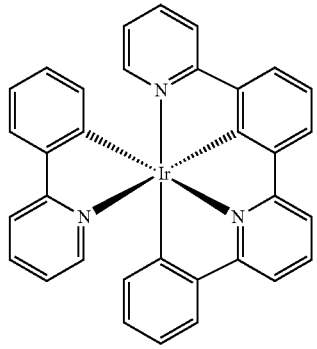

[Ir[PPy]$_3$]]

Evaluation

A current density change, a luminance change, and luminous efficiency of each organic light emitting diode according to Examples 1 to 8, Comparative Example 1, and Reference Examples 1 to 3 were measured.

Specific measurement methods are as follows, and the results are shown in Table 1.

(1) Measurement of Current Density Change Depending on Voltage Change

The obtained organic light emitting diodes were measured regarding a current value flowing in a unit device by using a current-voltage meter (Keithley 2400), while a voltage was increased from 0 V to 10 V, and the measured current value was divided by an area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) was calculated by using the luminance, current density, and voltages (V) from the items (1) and (2).

(4) Measurement of Life-span

A life span was obtained by measuring a time when current efficiency (cd/A) was decreased down to 90%, while luminance (cd/m$^2$) was maintained to be 5000 cd/m$^2$.

TABLE 1

| Nos. | Compound | Driving voltage (V) | Color (EL color) | Efficiency (cd/A) | 90% life-span (h) (@5000 cd/m$^2$) |
|---|---|---|---|---|---|
| Example 1 | Compound 2-1 | 4.01 | Green | 42.2 | 90 |
| Example 2 | Compound 2-2 | 4.10 | Green | 44.3 | 45 |
| Example 3 | compound 2-4 | 3.91 | Green | 38.7 | 85 |
| Example 4 | compound 2-5 | 4.08 | Green | 41.0 | 85 |
| Example 5 | Compound 2-7 | 3.84 | Green | 41.9 | 95 |
| Example 6 | Compound 2-12 | 4.12 | Green | 41.5 | 100 |
| Example 7 | compound 3-9 | 4.33 | Green | 43.2 | 46 |
| Example 8 | compound 4-9 | 4.42 | Green | 42.5 | 47 |
| Comparative Example 1 | CBP | 4.60 | Green | 31.7 | 25 |
| Reference Example 1 | Reference Compound 1 | 4.29 | Green | 35.6 | 40 |
| Reference Example 2 | Reference Compound 2 | 4.24 | Green | 41.1 | 5 |
| Reference Example 3 | Reference Compound 3 | 4.80 | Green | 26.6 | 3 |

Referring to Table 1, the organic light emitting diodes according to Examples 1 to 8 showed equivalent or excellent efficiency and improved life-span characteristics compared with the organic light emitting diodes according to Comparative Example 1 and Reference Examples 1 to 3. Particularly, the organic light emitting diodes according to Examples 2 to 6 showed an excellent driving voltage and simultaneously, excellent efficiency and life-span compared with the organic light emitting diode according to Reference Example 1, which is a positive effect of introduction of a linker.

As described above, when the linker was included in the substituent having a 9,9-diphenylfluorene structure and electron characteristics, the linking group may increase flexibility of a compound and thus apply much excellent morphology characteristics thereto, which may play a significant role of realizing high efficiency, a long life-span, and a low driving voltage of an organic optoelectric device.

Furthermore, the substituent having electron characteristics necessarily includes another substituent and thus may protect the weakest part of a heteroring and resultantly, obtain a heat resistance increase effect compared with a substituent having electron characteristics but being not substited. In addition, the substituent having electron characteristics and including another substituent shows excellent thermal resistant stability compared with an alkyl substitution and remarkably improves a life-span of a device in addition to the thermal and electronic stability. That is why Examples 1 to 8 are excellent compared with Reference Examples 2 and 3.

Manufacture of Organic Light Emitting Diode 2: Mixed Host

Example 9

A glass substrate coated with ITO (indium tin oxide) as a 1500 Å-thick thin film was ultrasonic wave-washed with distilled water. After washed with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing the compound A, and a hole transport layer was formed on the injection layer by depositing the compound B to be 50 Å thick and the compound C to be 1020 Å thick. On the hole transport layer, a 400 Å-thick emission layer was formed by vacuum-depositing both the Compound 2-1 according to Synthesis Example 1 and the Compound B-1 according to Synthesis Example 26 as a second host compound simultaneously as a host and tris(2- phenylpyridine)iridium (III) [Ir(ppy)$_3$]as a dopant in a doping amount of 10 wt %. Herein, the Compound 2-1 and the Compound B-1 were used in a 1:1 ratio.

Subsequently, an organic light emitting diode was manufactured by simultaneously vacuum-depositing the Compound D and Liq in a ratio of 1:1 to form a 300 Å-thick electron transport layer on the emission layer and sequentially vacuum- depositing Liq (15 Å) and Al (1200 Å) on the electron transport layer to form a cathode.

The organic light emitting diode had the following five organic thin film-layered structure, specifically, a structure of ITO/Compound A 700 Å/Compound B 50 Å/Compound C 1020 Å/EML[Compound 1: B-1:Ir(ppy)$_3$=45 wt %:45 wt%:10 wt %] 400 Å/Compound D:Liq 300 Å/Liq 15 Å/Al 1200 Å.

Compound A: N4,N4α-diphenyl-N4,N4'-bis(9-phenyl-9H-carbazol-3- yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3- yl)phenyl)-9H-fluoren-2-amine Compound D: 8-(4-(4,6-di(naphthalen-2-yl)-1,3,5-triazin-2-yl)phenyl)quinoline Example 10

An organic light emitting diode was manufactured according to the same method as Example 9 except for using Compound 2-1 and Compound B-31 in a weight ratio of 1:1.

Example 11

An organic light emitting diode was manufactured according to the same method as Example 9 except for using Compound 2-7 and Compound B-31 in a weight ratio of 1:1.

Example 12

An organic light emitting diode was manufactured according to the same method as Example 9 except for using Compound 2-12 and Compound B-31 in a weight ratio of 1:1.

Example 13

An organic light emitting diode was manufactured according to the same method as Example 9 except for using Compound 2-1 and Compound C-1 in a weight ratio of 1:1.

Example 14

An organic light emitting diode was manufactured according to the same method as Example 9 except for using Compound 3-9 and Compound B-31 in a weight ratio of 1:1.

Comparative Example 2

An organic light emitting diode was manufactured according to the same method as Example 9 except for using CBP as a single host.

Reference Examples 4 to 6

Each organic light emitting diode according to Reference Examples 4 to 6 was manufactured according to the same method as Example 9 except for using Reference Compounds 1 to 3 as a single host.

Evaluation

Luminous efficiency and life-span characteristics of each organic light emitting diode according to Examples 9 to 14, Comparative Example 2, and Reference Examples 4 to 6.

Specific measurement methods are as above except "(4) Measurement of Life- span," and the results are shown in Table 2.

(4) Measurement of Life-span

A life span was obtained by measuring a time when current efficiency (cd/A) was decreased down to 97%, while luminance (cd/m$^2$) was maintained to be 6000 cd/m$^2$.

TABLE 2

| | First host | Second host | First host: Second host | Luminous efficiency (cd/A) | Life-span T 97 (h) |
|---|---|---|---|---|---|
| Example 9 | Compound 2-1 | B-1 | 1:1 | 46.2 | 65 |
| Example 10 | Compound 2-1 | B-31 | 1:1 | 53.5 | 71 |
| Example 11 | Compound 2-7 | B-31 | 1:1 | 52.8 | 68 |
| Example 12 | Compound 2-12 | B-31 | 1:1 | 52.5 | 67 |
| Example 13 | Compound 2-1 | C-1 | 1:1 | 50.1 | 62 |
| Example 14 | Compound 3-9 | B-31 | 1:1 | 52.5 | 70 |
| Comparative Example 2 | CBP | | — | 31.7 | 25 |
| Reference Example 4 | Reference Compound 1 | | — | 44.3 | 45 |
| Reference Example 5 | Reference Compound 2 | | — | 45.1 | 15 |
| Reference Example 6 | Reference Compound 3 | | — | 22.1 | 3 |

Referring to Table 2, the organic light emitting diodes according to Examples 9 to 14 showed remarkably improved luminous efficiency and life-span characteristics compared with the organic light emitting diodes according to Comparative Example 2 and Reference Examples 4 to 6.

Manufacture of Organic Light Emitting Diode 3

Example 15

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, a 700 Å-thick hole injection layer was formed on the ITO substrate by vacuum-depositing the compound A, and a hole transport layer was formed on the injection layer by depositing the compound B to be 50 Å thick and the compound C to be 1020 Å thick. Then, a 200 Å-thick emission layer was formed thereon by vacuum-depositing BH113 and BD370 (Dealer: SFC Inc.) as a blue fluorescent luminescent host and a dopant in a dopant concentration of 5 wt%. On the emission layer, the Compound 2-1 was vacuum-deposited to form a 50 Å-thick electron transport auxiliary layer. The electron transport auxiliary layer may be formed by using a material represented by Chemical Formula I alone or mixing the material with the compounds of Groups B, C, D, and E. On the electron transport auxiliary layer, a 300 Å-thick electron transport layer was formed by vacuum-depositing Compound D and Liq simultaneously in a weight ratio of 1:1, and on the electron transport layer, a cathode was formed by sequentially vacuum-depositing Liq to be 15 Å thick and Al to be 1200 Å thick, manufacturing an organic light emitting diode. The organic light emitting diode had a structure of 5 organic thin film layers and specifically, ITO/Compound A 700 Å/Compound B 50 Å/Compound C 1020 Å/EML[BH113:BD370=95:5 (wt:wt)] 200 Å/Compound 2-1 50 Å/Compound D:Liq 300 Å=1:1/Liq 15 Å/Al 1200 Å.

(Compounds A, B, C and D are the same as used in the organic light emitting diode 2.)

Examples 16 to 23

Organic light emitting diodes of Examples 16 to 23 were manufactured according to the same method as Example 15 except for respectively using Compound 2-2, Compound 2-4, Compound 2-12, Compound 3-14, Compound 4-14, Compound 5- 1, Compound 5-13, and Compound 6-9 instead of the Compound 2-1.

Reference Example 7

The organic light emitting diode was manufactured according to the same method as Example 15 except for using Reference Compound 1 instead of the Compound 2-1.

Comparative Example 3

An organic light emitting diode was manufactured according to the same method as Example 15 except fof using no electron transport auxiliary layer.

Evaluation

A current density change, a luminance change, and luminous efficiency of each organic light emitting diode according to Examples 15 to 23, Reference Example 7, and Comparative Example 3 were measured.

Specific measurement methods are as above except "(4) Measurement of Life- span," and the results are shown in Table 3.

(4) Measurement of Life-span

T97 life-spans of the organic light emitting diodes according to Example 15 to Example 23, Reference Example 7, and Comparative Example 3 were measured as a time when their luminance decreased down to 97% relative to the initial luminance (cd/m$^2$) after emitting light with 750 cd/m$^2$ as the initial luminance (cd/m$^2$) and measuring their luminance decreases depending on a time with a Polanonix life-span measurement system.

TABLE 3

| Devices | Electron transport auxiliary layer (weight ratio) | Luminous efficiency (cd/A) | Color coordinate (x, y) | T97 (h) @750 nit |
|---|---|---|---|---|
| Example 15 | Compound 2-1 | 7.7 | (0.132, 0.149) | 66 |
| Example 16 | Compound 2-2 | 7.9 | (0.133, 0.148) | 49 |
| Example 17 | Compound 2-4 | 7.4 | (0.132, 0.149) | 80 |
| Example 18 | Compound 2-12 | 7.8 | (0.132, 0.150) | 65 |
| Example 19 | Compound 3-14 | 6.9 | (0.132, 0.149) | 90 |
| Example 20 | Compound 4-14 | 7.0 | (0.133, 0.148) | 70 |
| Example 21 | Compound 5-1 | 6.6 | (0.132, 0.149) | 85 |
| Example 22 | Compound 5-13 | 6.8 | (0.132, 0.159) | 95 |
| Example 23 | Compound 6-9 | 6.5 | (0.132, 0.159) | 65 |

TABLE 3-continued

| Devices | Electron transport auxiliary layer (weight ratio) | Luminous efficiency (cd/A) | Color coordinate (x, y) | T97 (h) @750 nit |
|---|---|---|---|---|
| Reference Example 7 | Reference Compound 1 | 6.9 | (0.132, 0.149) | 38 |
| Comparative Example 3 | Not used | 5.8 | (0.135, 0.147) | 40 |

Referring to Table 3, the organic light emitting diodes of Examples 15 to 23 showed improved luminous efficiency and life-span characteristics simultaneously, compared with the organic light emitting diode of Comparative Example 3. In addition, the organic light emitting diodes of Examples 15 to 23 showed much improved life-span characteristics compared with the organic light emitting diode of Reference Example 7.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200, 300, 400: organic light emitting diode
105: organic layer
110: cathode
120: anode
130: emission layer
140: hole transport layer
141: hole injection layer
150: electron transport layer
151: electron injection layer
152: hole blocking layer (electron transport auxiliary layer).

What is claimed is:

1. An organic compound represented by Chemical Formula 1:

[Chemical Formula 1]

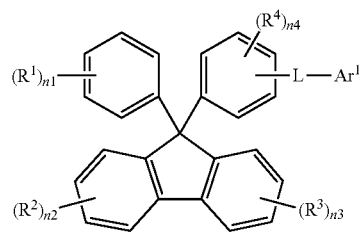

wherein, in Chemical Formula 1,
$R^1$ to $R^4$ are independently hydrogen or deuterium,
L is represented by one selected from Chemical Formula L-1 to Chemical Formula L-7:

[Chemical Formula L-1]

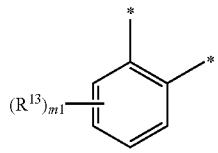

[Chemical Formula L-2]

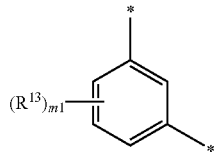

[Chemical Formula L-3]

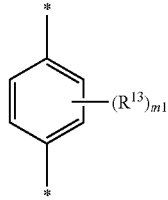

[Chemical Formula L-4]

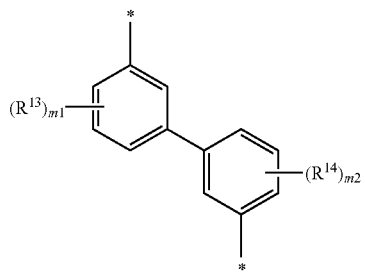

[Chemical Formula L-5]

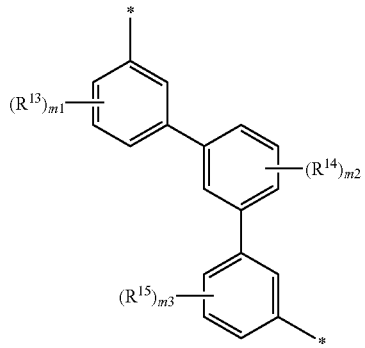

[Chemical Formula L-6]

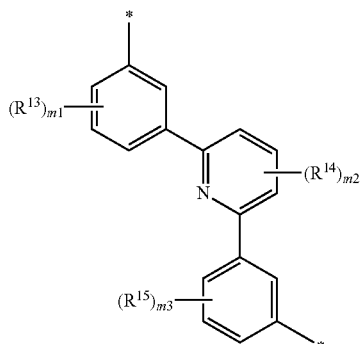

[Chemical Formula L-7]

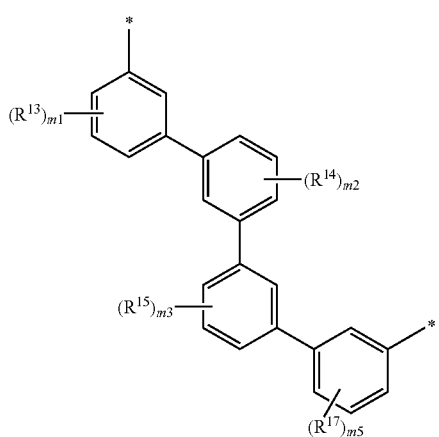

wherein, in Chemical Formula L-1 to Chemical Formula L-7, $R^{13}$ to $R^{17}$ are independently a substituted or unsubstituted C1 to C20 alkyl group or a substituted or unsubstituted C6 to C20 aryl group, m1 to m3 and m5 are independently an integer of 0 to 4, and m4 is an integer of 0 to 3

$Ar^1$ is represented by one selected from Chemical Formula 2 to Chemical Formula 6:

[Chemical Formula 2]

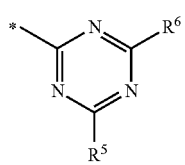

[Chemical Formula 3]

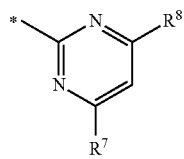

[Chemical Formula 4]

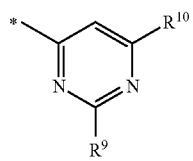

[Chemical Formula 5]

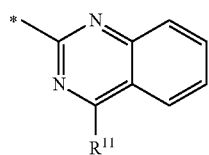

[Chemical Formula 6]

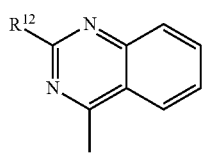

wherein, in Chemical Formula 2 to Chemical Formula 6, $R^5$ to $R^{12}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, or a substituted or unsubstituted pyrenyl group, and n1 is an integer of 5, and n2 to n4 are independently integers of 4.

2. An organic compound selected from Chemical Formula 2-1 to Chemical Formula 2-24, Chemical Formula 3-1 to Chemical Formula 3-24, Chemical Formula 4-1 to Chemical Formula 4-24, Chemical Formula 5-1 to Chemical Formula 5-23, and Chemical Formula 6-1 to Chemical Formula 6-23:

[Chemical Formula 2-1]
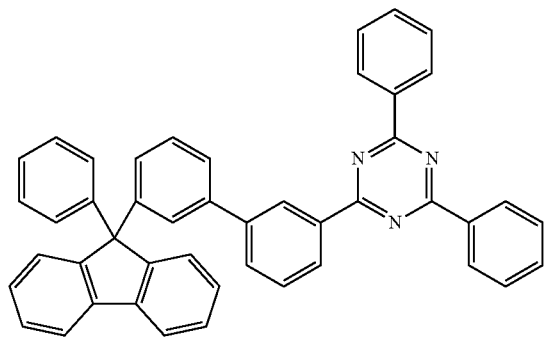
[Chemical Formula 2-2]
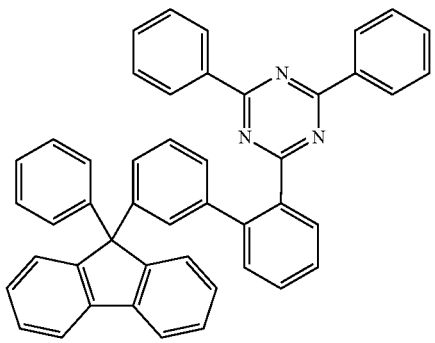
[Chemical Formula 2-3]
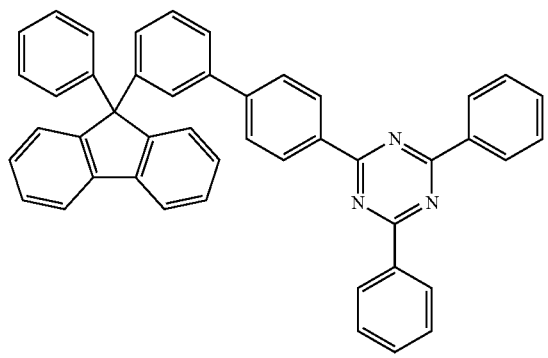
[Chemical Formula 2-4]
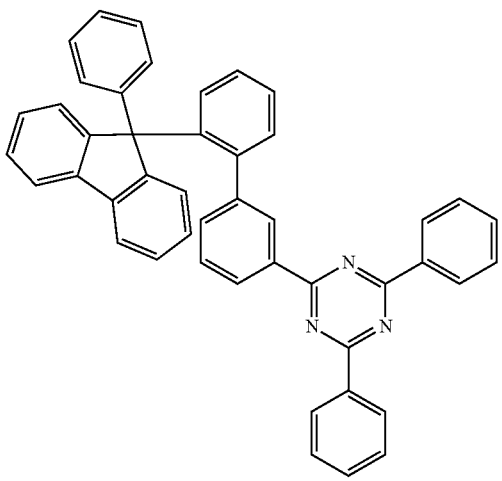
[Chemical Formula 2-5]
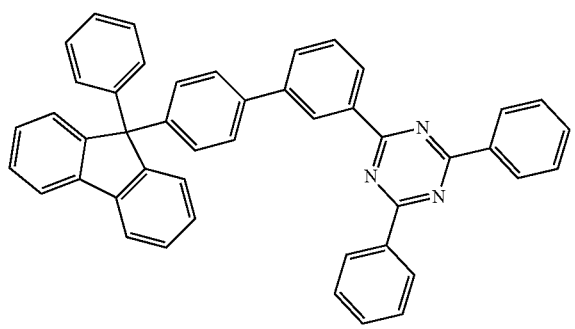
[Chemical Formula 2-6]
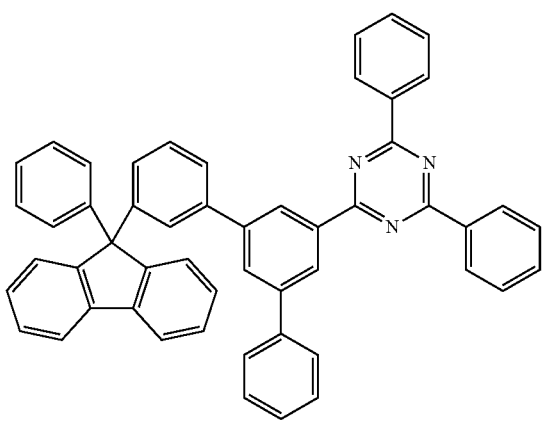

[Chemical Formula 2-7]
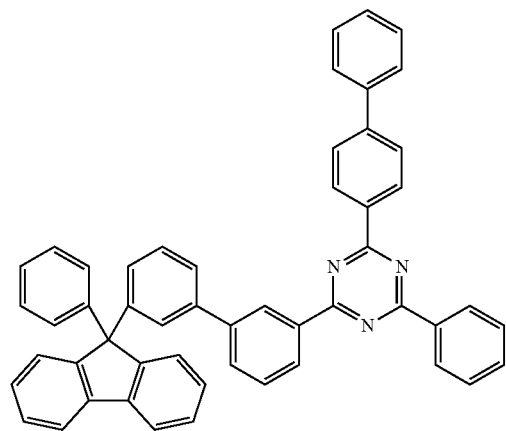
[Chemical Formula 2-8]
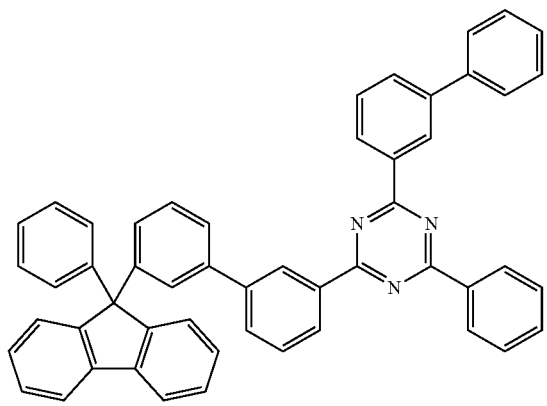
[Chemical Formula 2-9]
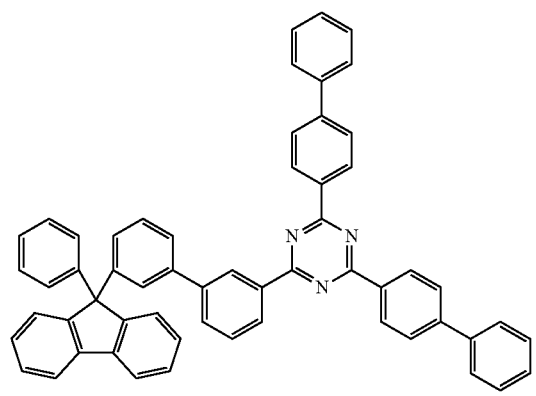
[Chemical Formula 2-10]
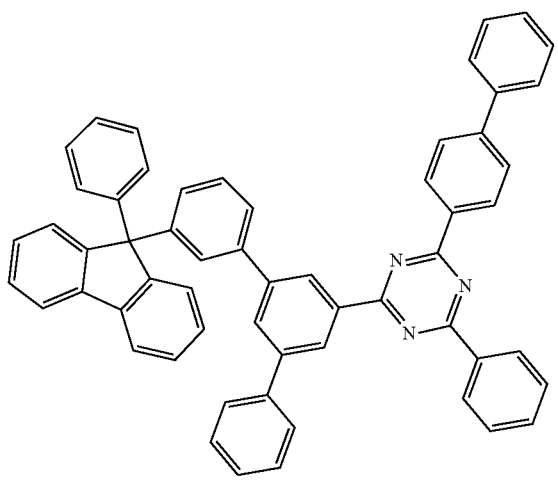
[Chemical Formula 2-11]
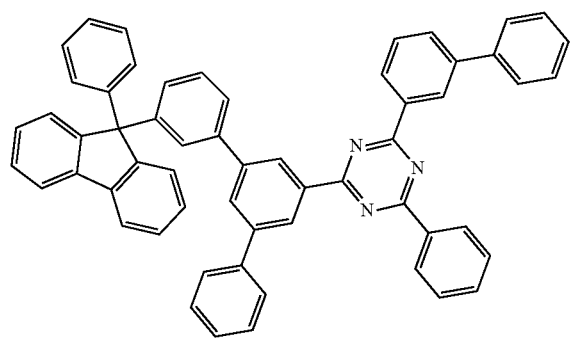
[Chemical Formula 2-12]
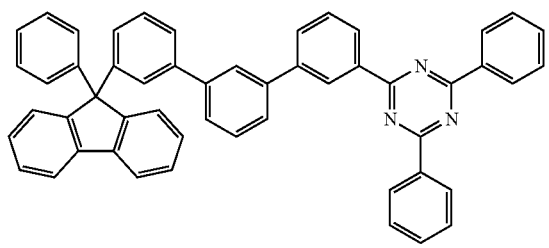

-continued
[Chemical Formula 2-13]
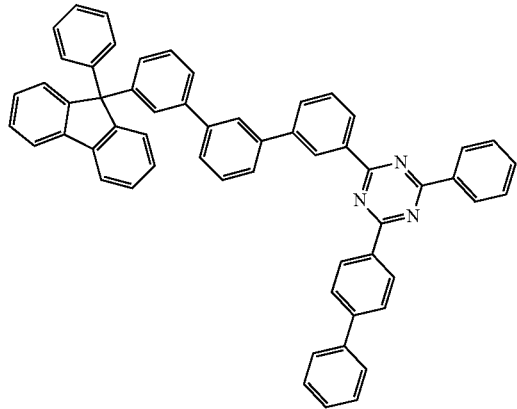
[Chemical Formula 2-14]
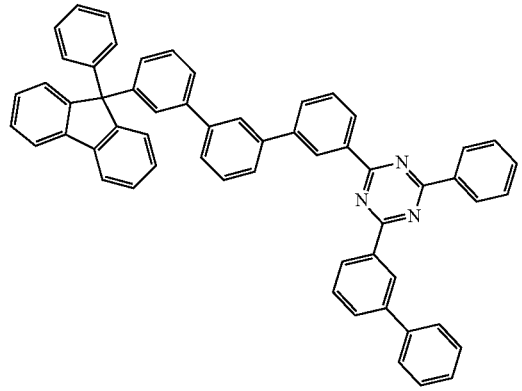
[Chemical Formula 2-15]
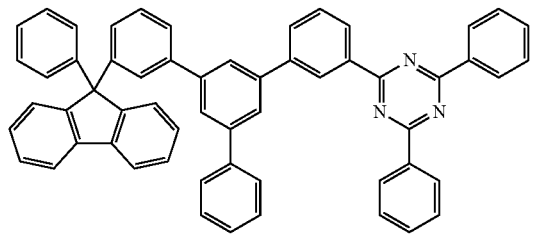
[Chemical Formula 2-16]
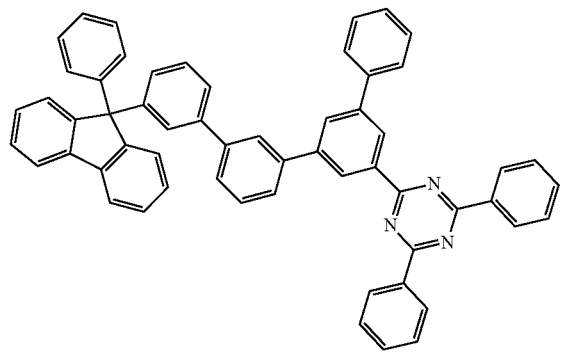
[Chemical Formula 2-17]
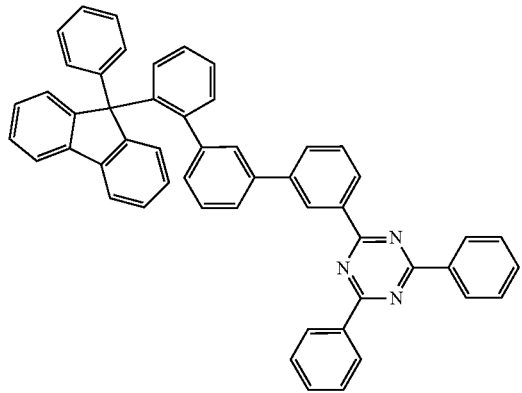
[Chemical Formula 2-18]
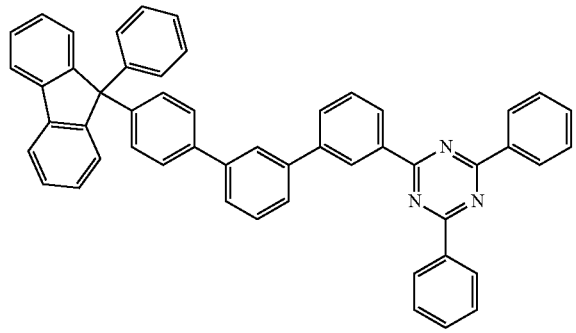

[Chemical Formula 2-19]
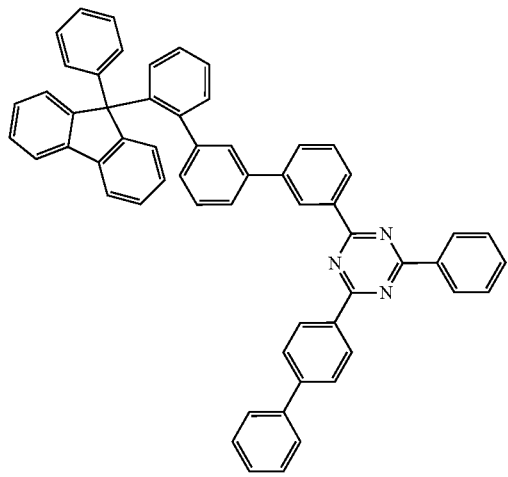
[Chemical Formula 2-20]
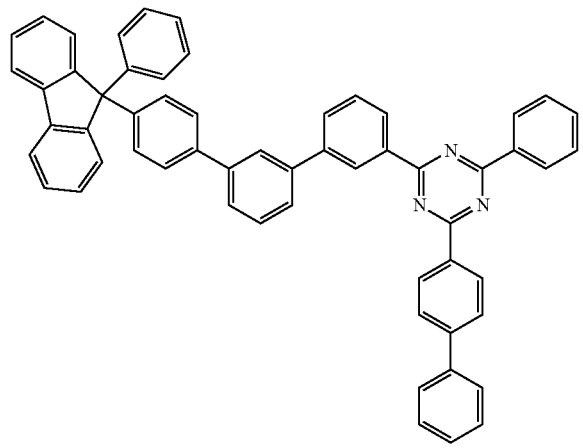
[Chemical Formula 2-21]
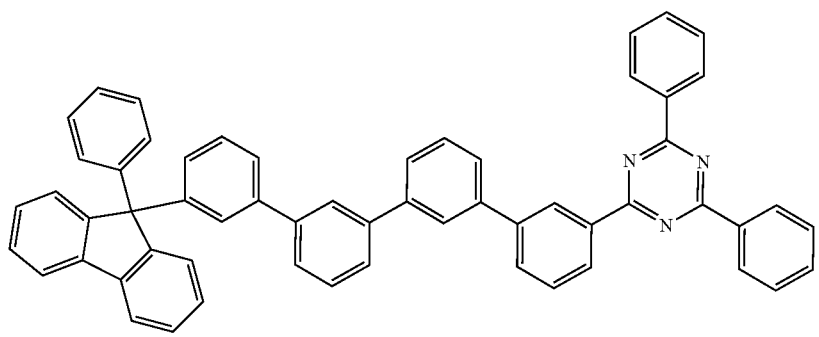
[Chemical Formula 2-22]
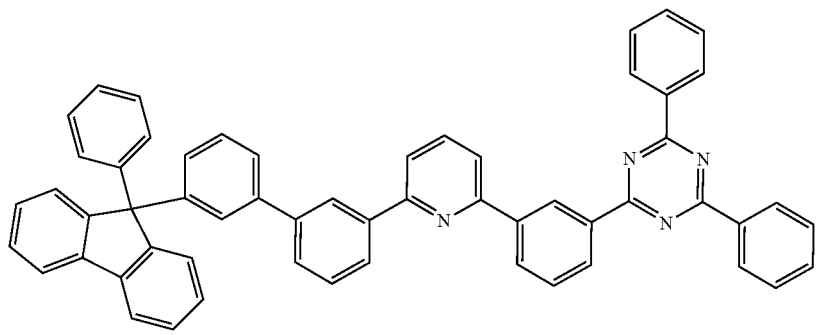
[Chemical Formula 2-23]
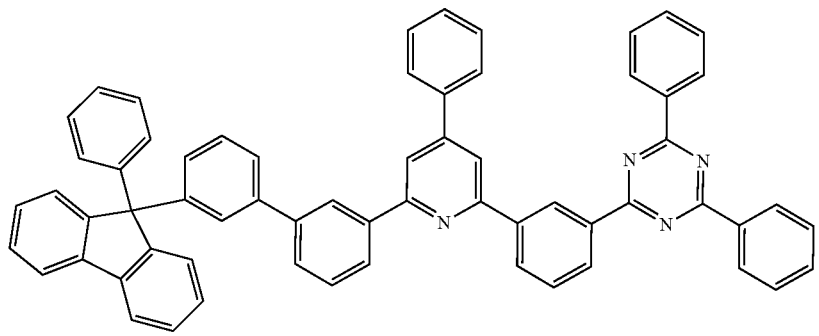

[Chemical Formula 2-24]
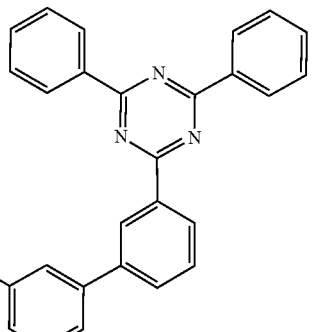
[Chemical Formula 3-1]
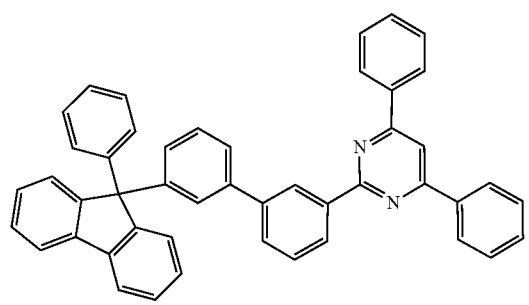
[Chemical Formula 3-2]
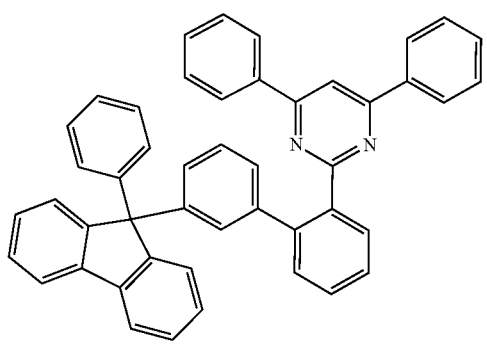
[Chemical Formula 3-3]
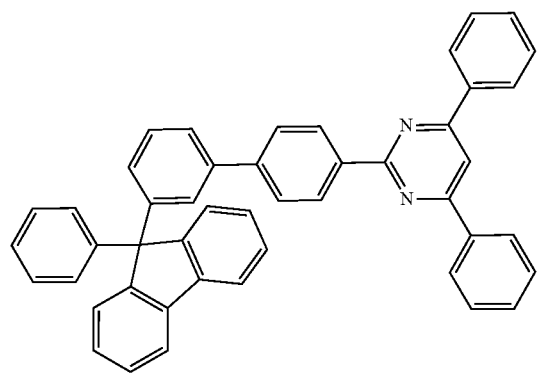
[Chemical Formula 3-4]
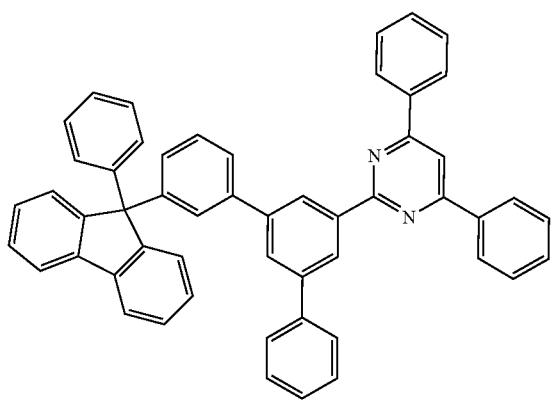

[Chemical Formula 3-5]
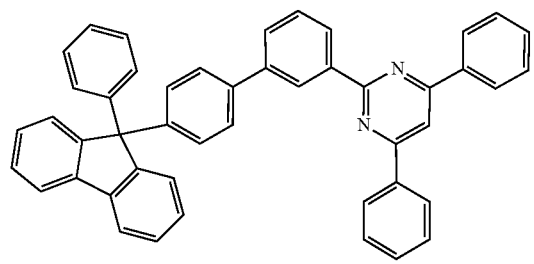
[Chemical Formula 3-6]
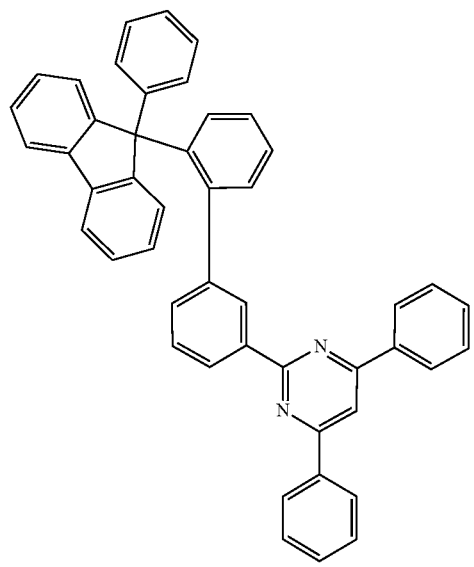
[Chemical Formula 3-7]
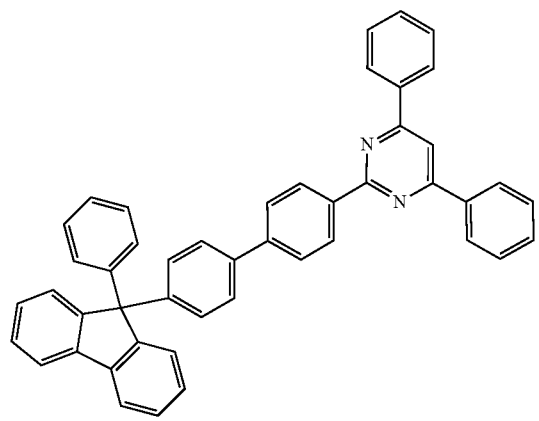
[Chemical Formula 3-8]
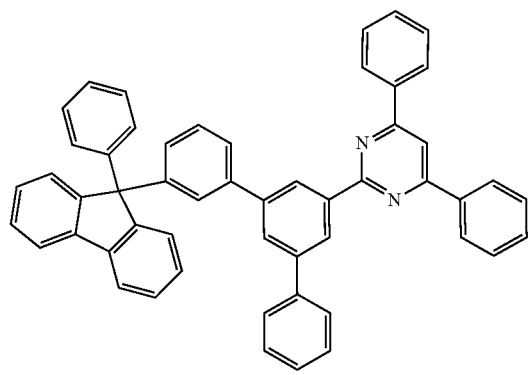
[Chemical Formula 3-9]
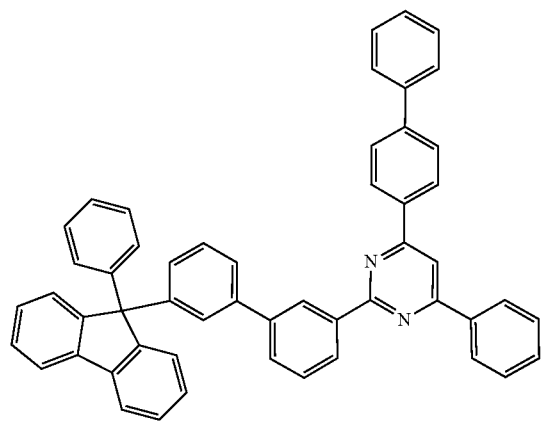
[Chemical Formula 3-10]
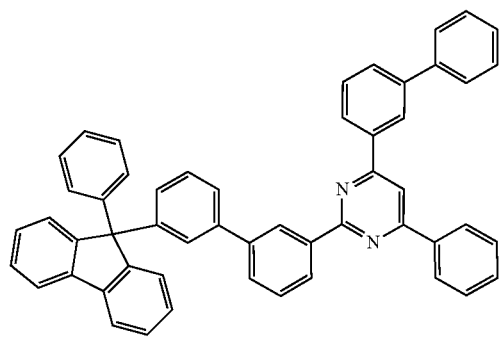

[Chemical Formula 3-11]
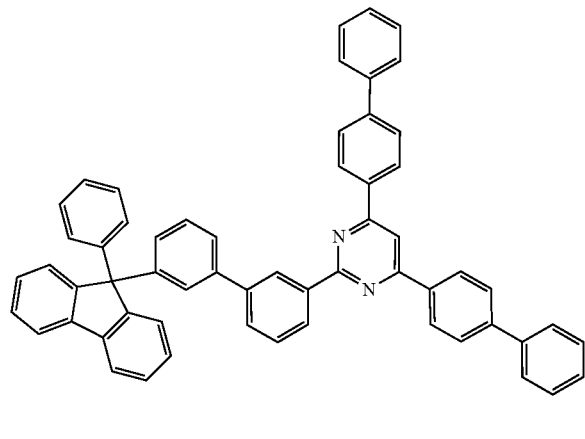
[Chemical Formula 3-12]
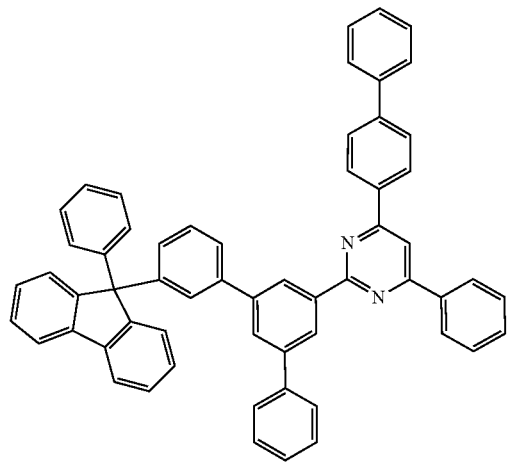
[Chemical Formula 3-13]
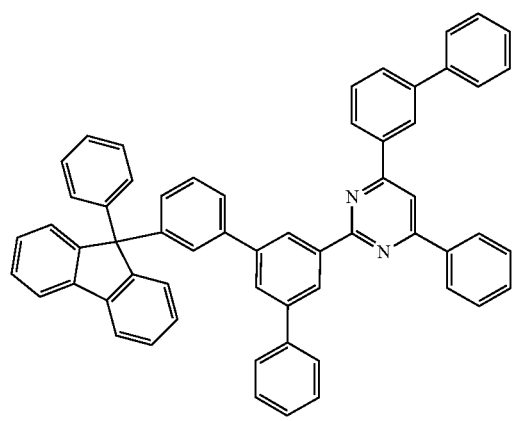
[Chemical Formula 3-14]
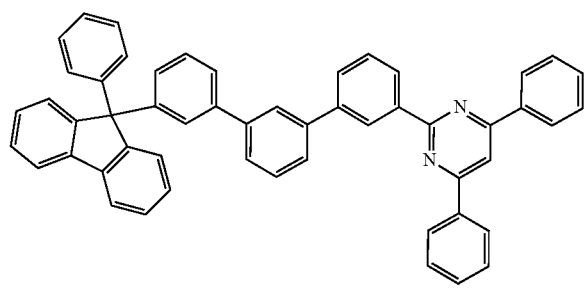
[Chemical Formula 3-15]
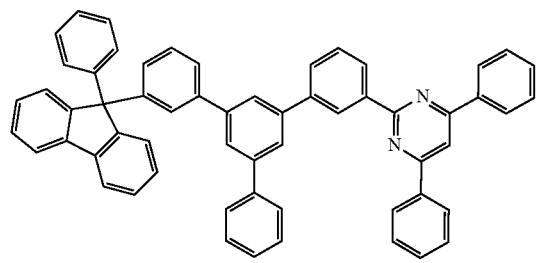
[Chemical Formula 3-16]
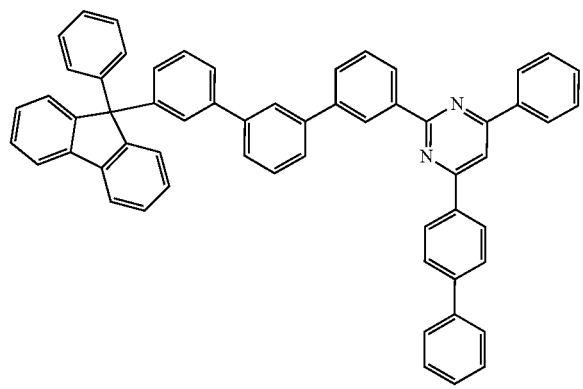

[Chemical Formula 3-17]
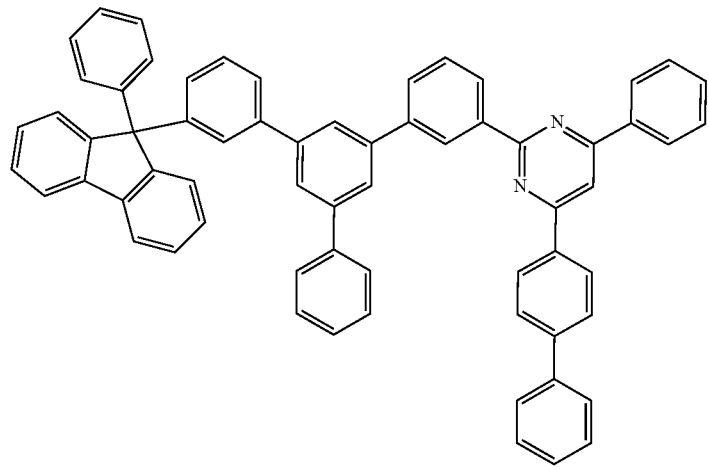
[Chemical Formula 3-18]
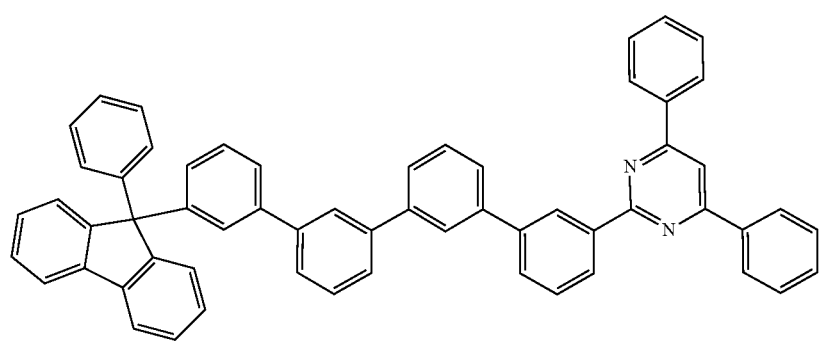
[Chemical Formula 3-19]
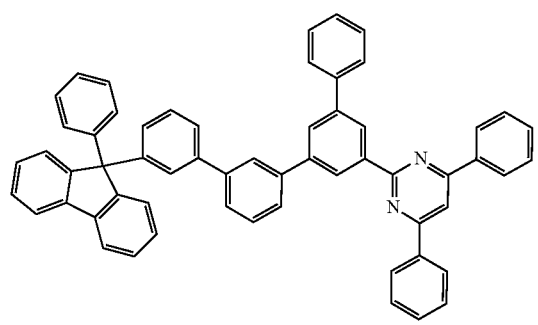
[Chemical Formula 3-20]
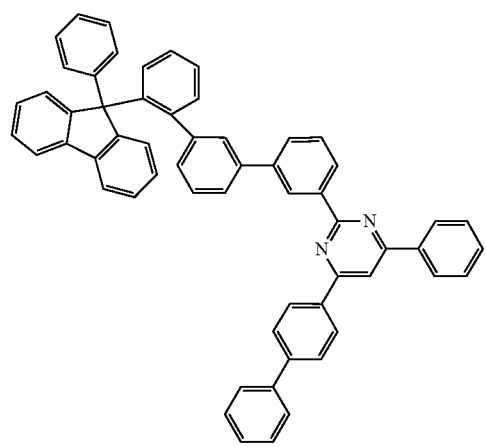

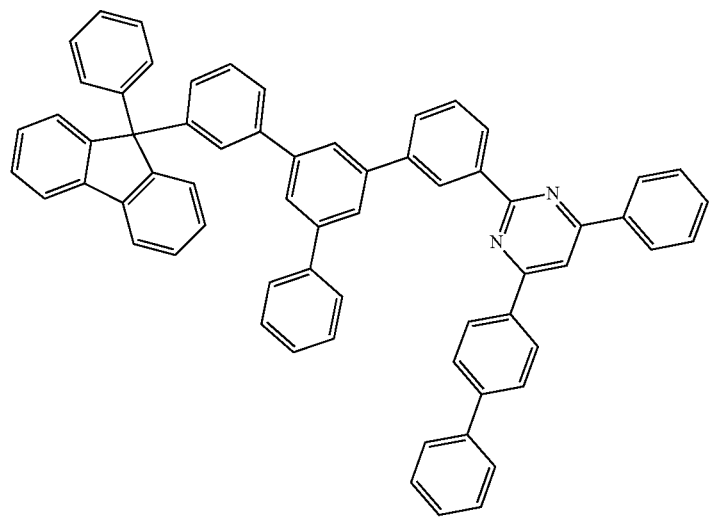
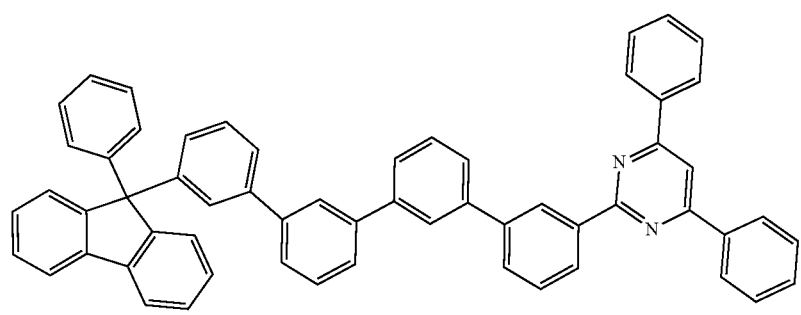
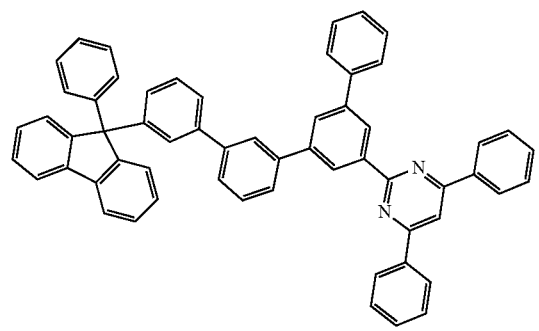
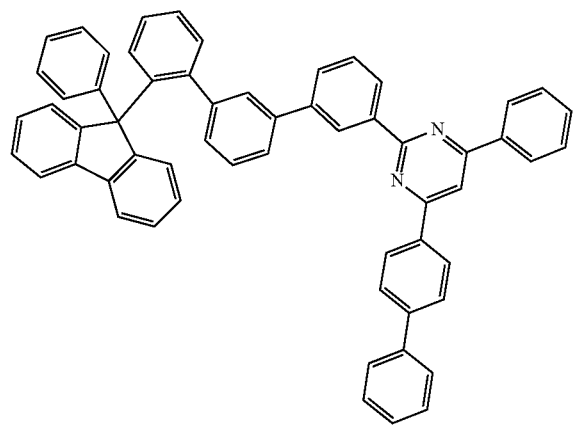

[Chemical Formula 3-21]
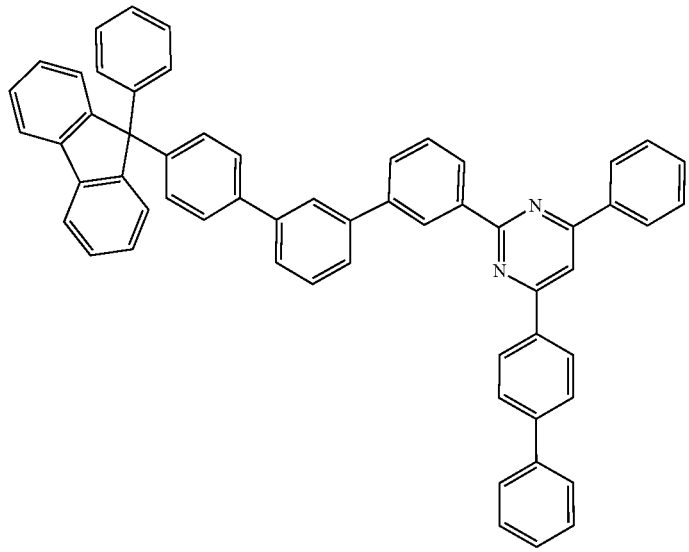
[Chemical Formula 3-22]
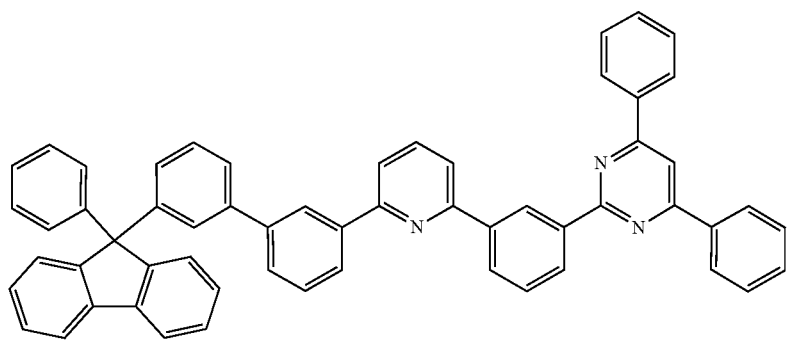
[Chemical Formula 3-23]
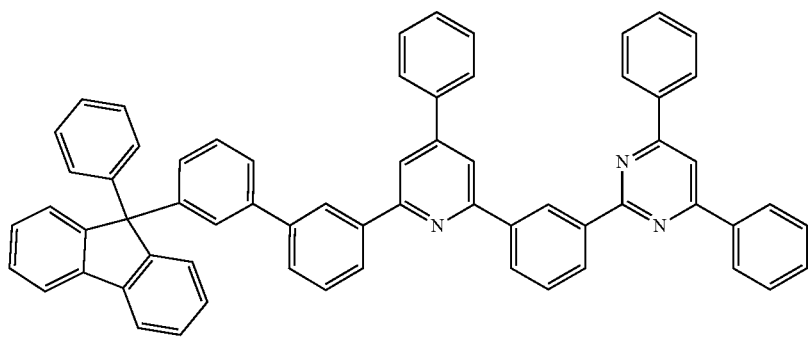
[Chemical Formula 3-24]
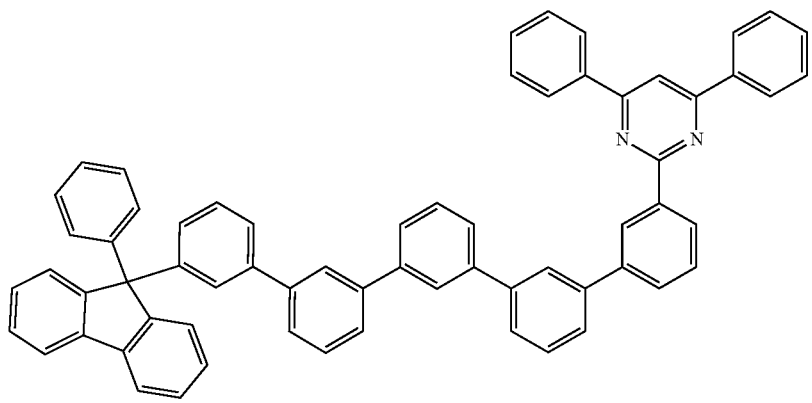

-continued
[Chemical Formula 4-1]
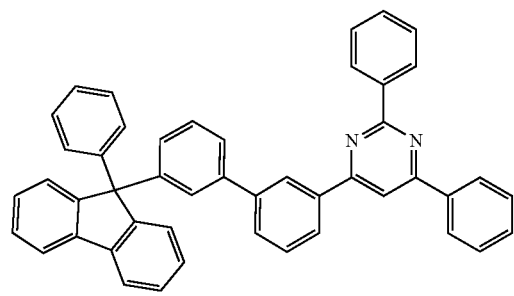
[Chemical Formula 4-2]
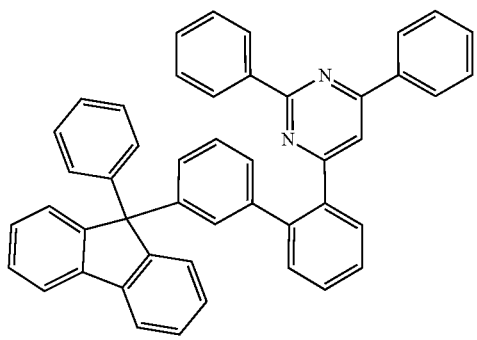
[Chemical Formula 4-3]
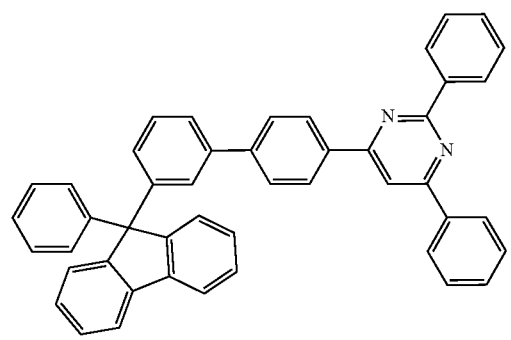
[Chemical Formula 4-4]
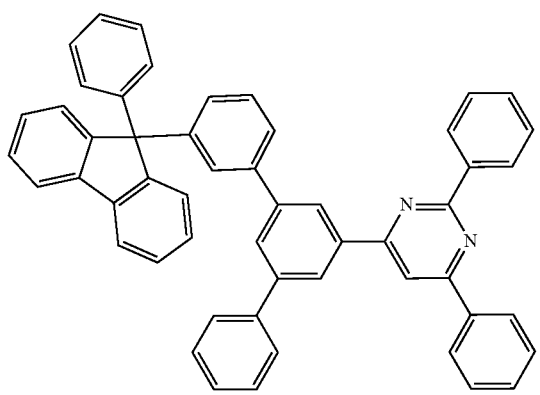
[Chemical Formula 4-5]
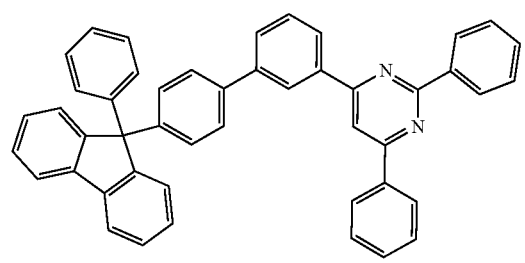
[Chemical Formula 4-6]
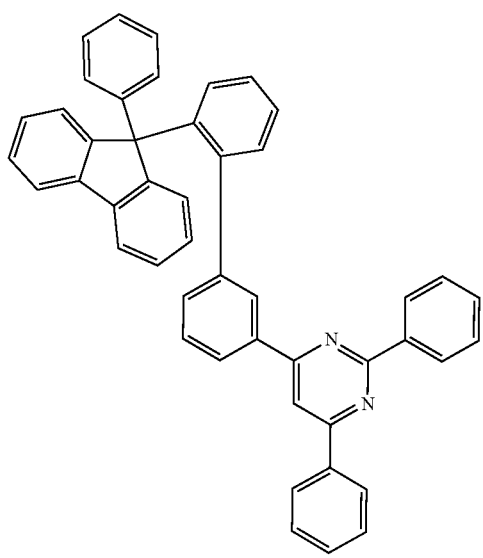

[Chemical Formula 4-7]
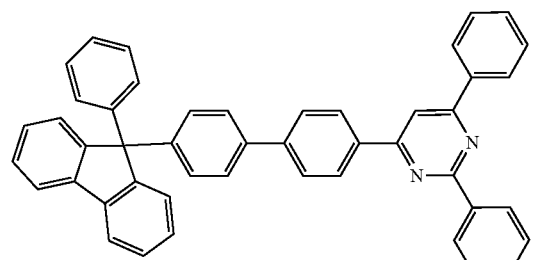
[Chemical Formula 4-8]
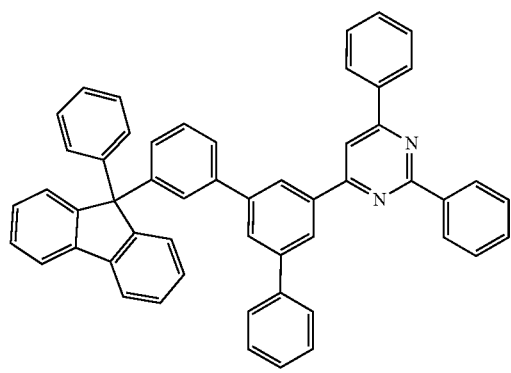
[Chemical Formula 4-9]
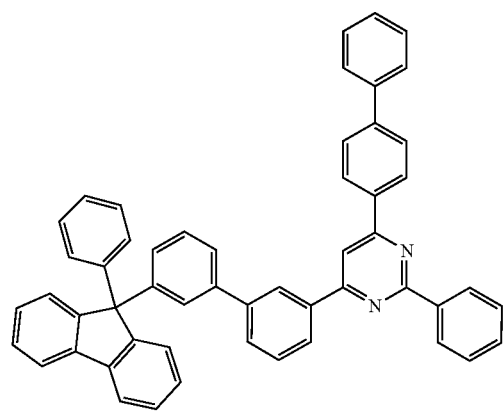
[Chemical Formula 4-10]
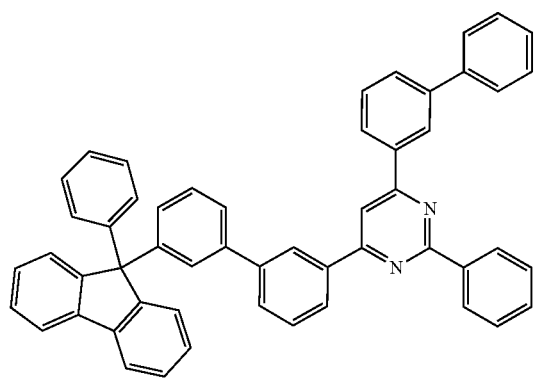
[Chemical Formula 4-11]
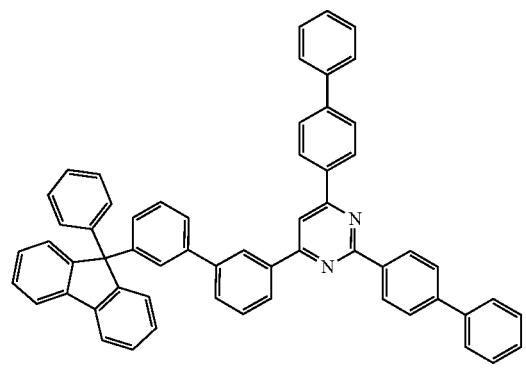
[Chemical Formula 4-12]
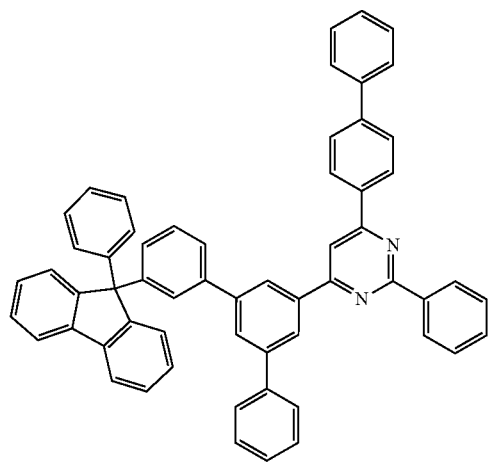

-continued
[Chemical Formula 4-13]
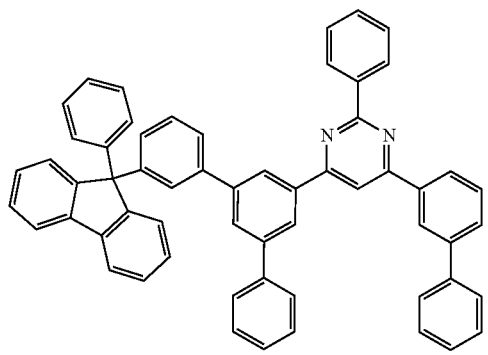
[Chemical Formula 4-14]
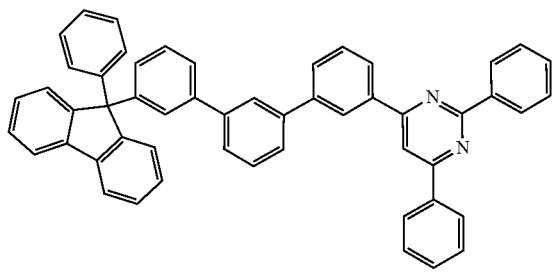
[Chemical Formula 4-15]
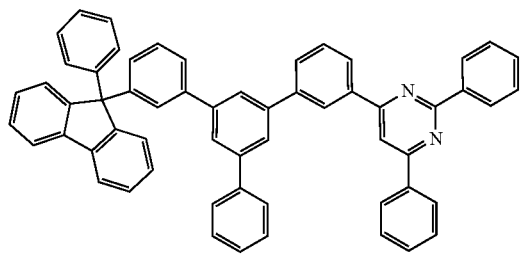
[Chemical Formula 4-16]
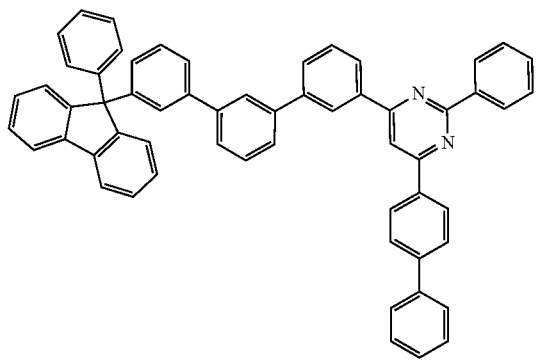
[Chemical Formula 4-17]
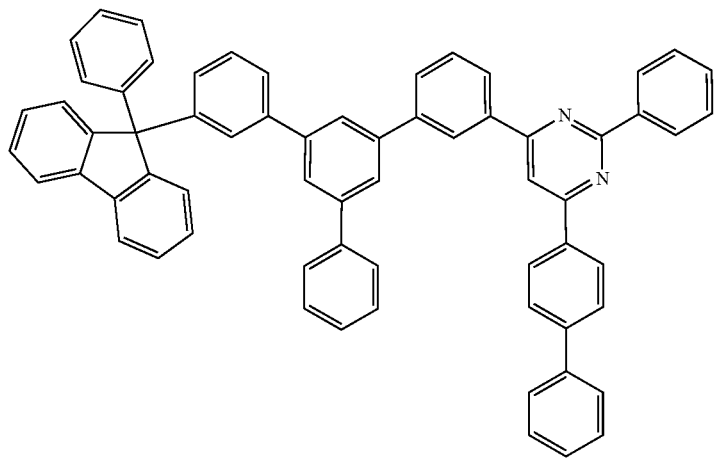
[Chemical Formula 4-18]
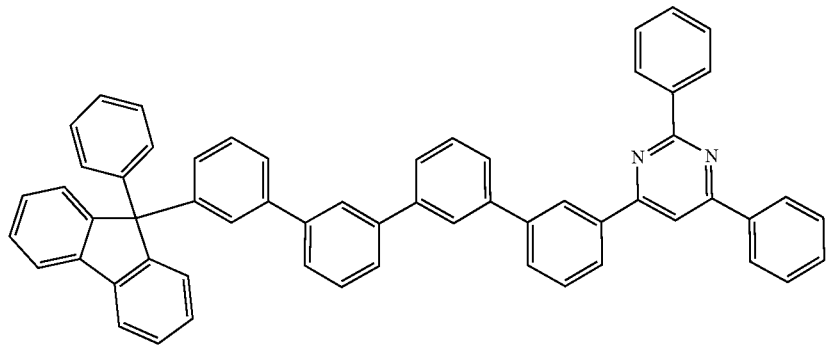

[Chemical Formula 4-19]
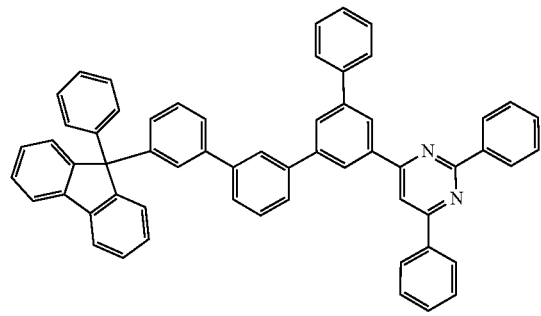
[Chemical Formula 4-20]
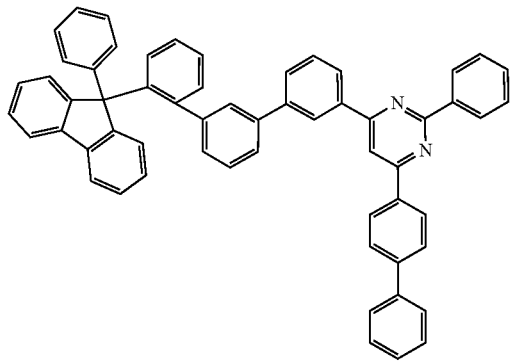
[Chemical Formula 4-21]
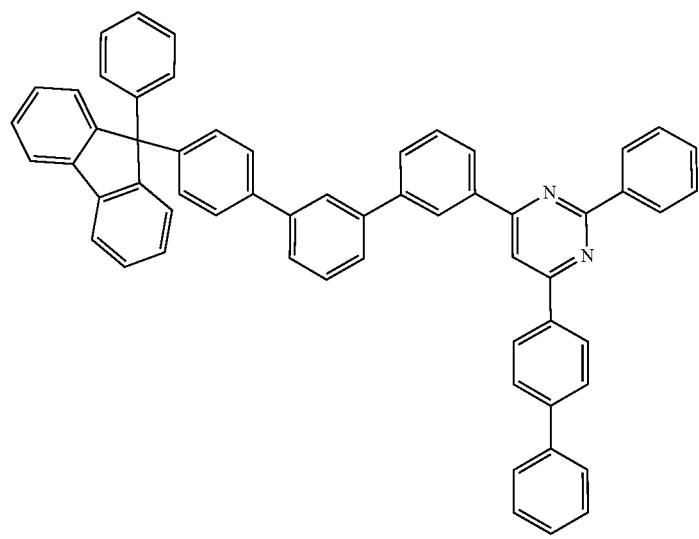
[Chemical Formula 4-22]
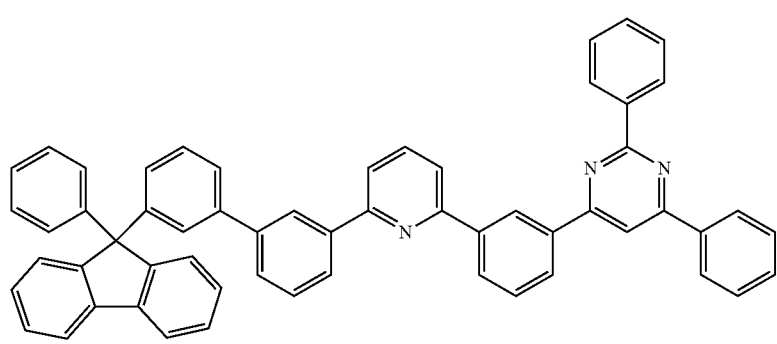
[Chemical Formula 4-23]
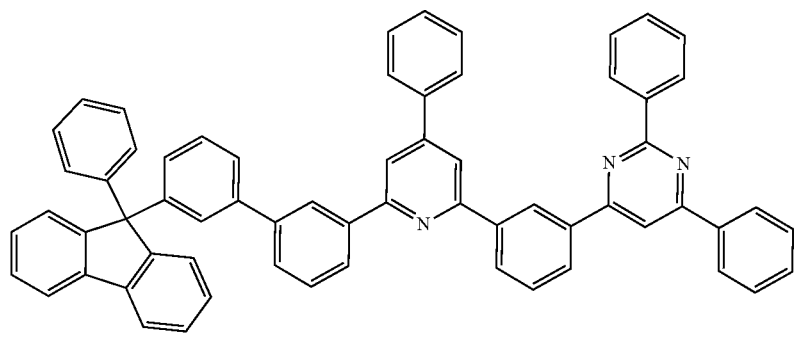

[Chemical Formula 4-24]
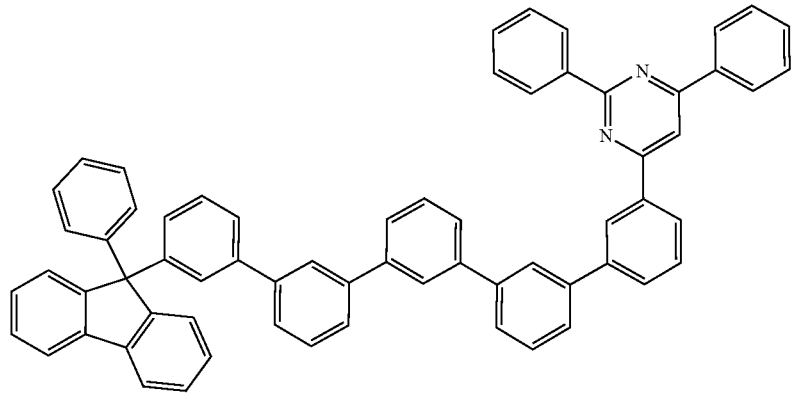
[Chemical Formula 5-1]
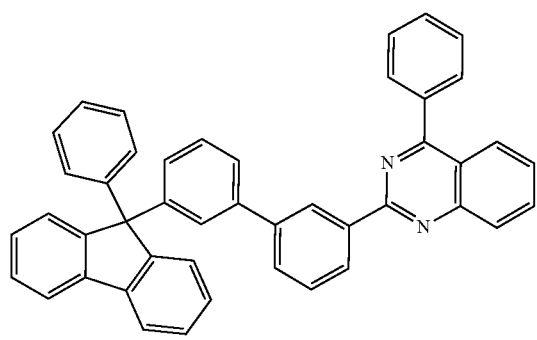
[Chemical Formula 5-2]
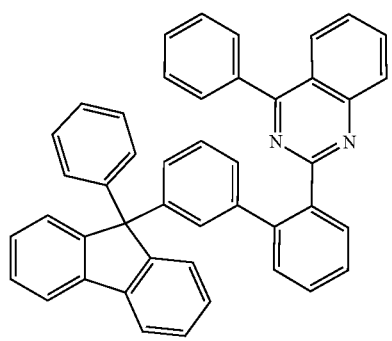
[Chemical Formula 5-3]
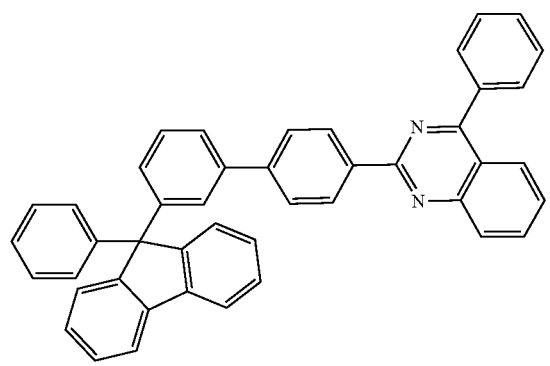
[Chemical Formula 5-4]
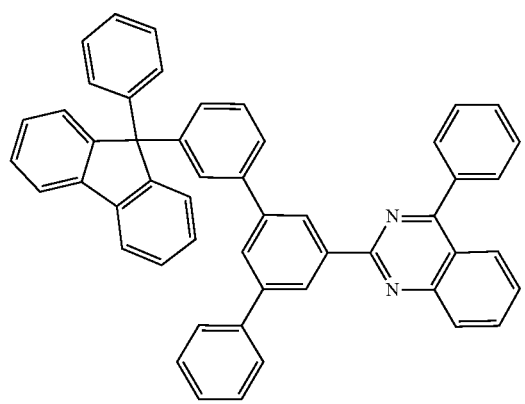

[Chemical Formula 5-5]
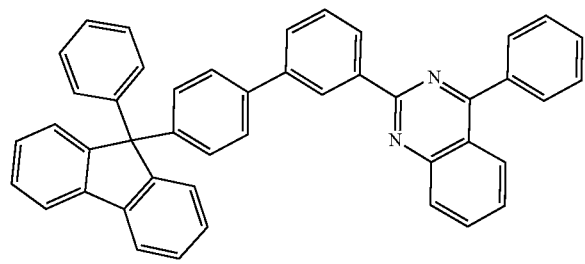
[Chemical Formula 5-6]
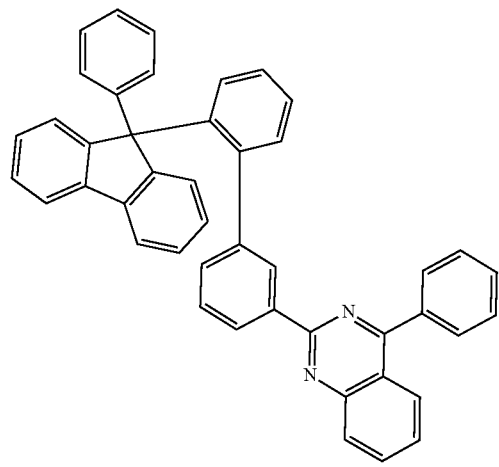
[Chemical Formula 5-7]
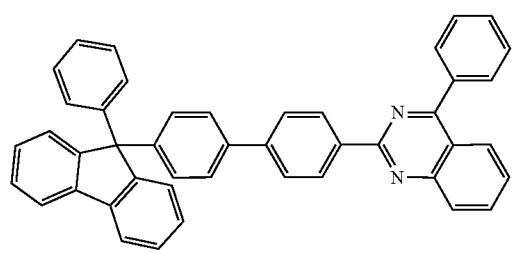
[Chemical Formula 5-8]
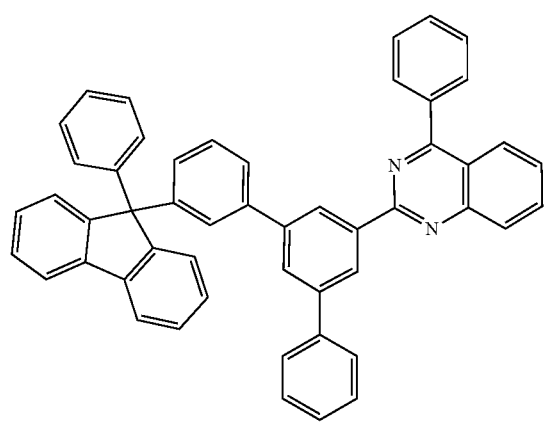
[Chemical Formula 5-9]
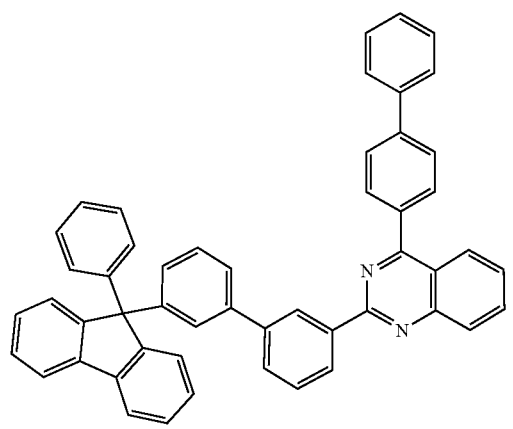
[Chemical Formula 5-10]
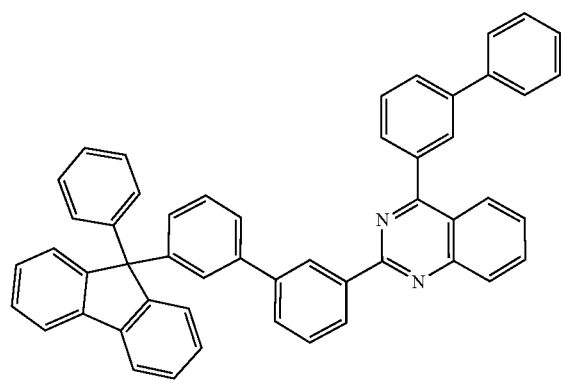

[Chemical Formula 5-11]
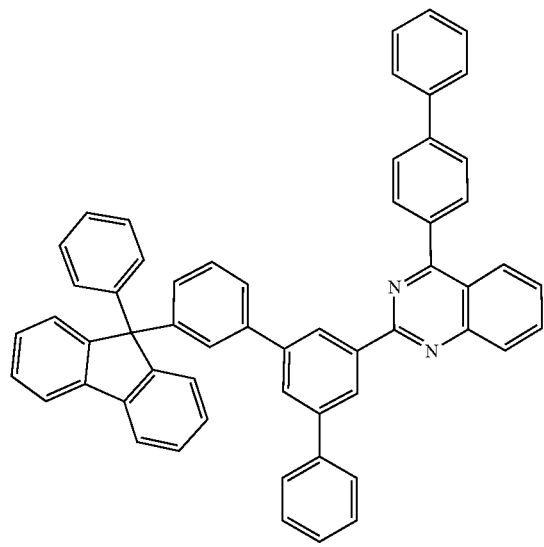
[Chemical Formula 5-12]
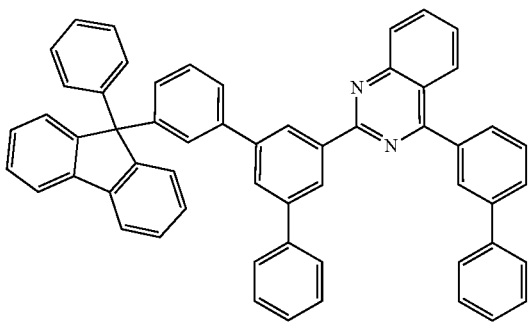
[Chemical Formula 5-13]
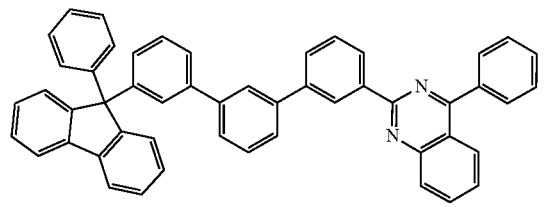
[Chemical Formula 5-14]
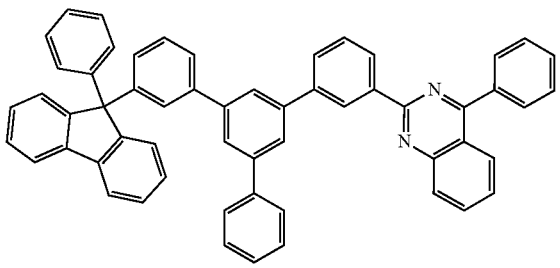
[Chemical Formula 5-15]
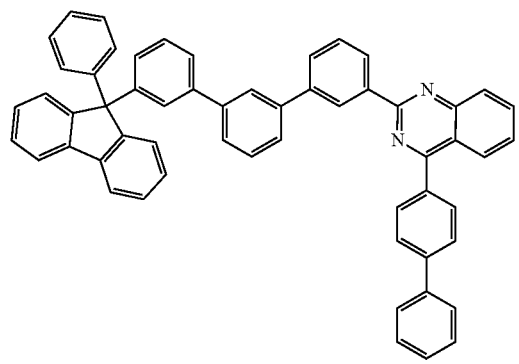
[Chemical Formula 5-16]
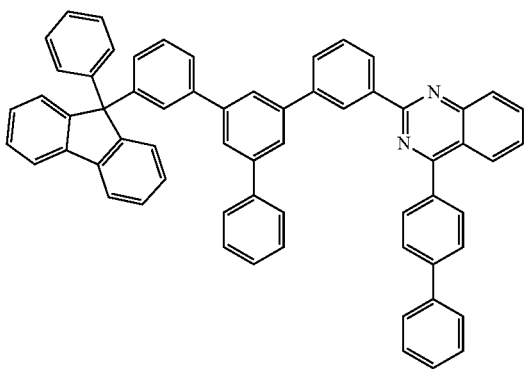
[Chemical Formula 5-17]
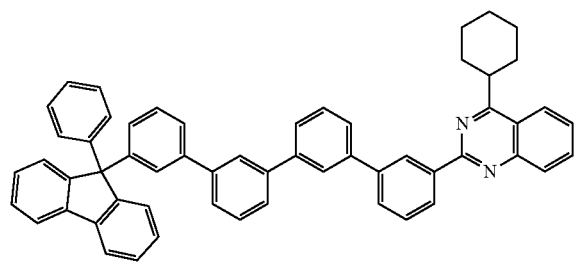
[Chemical Formula 5-18]
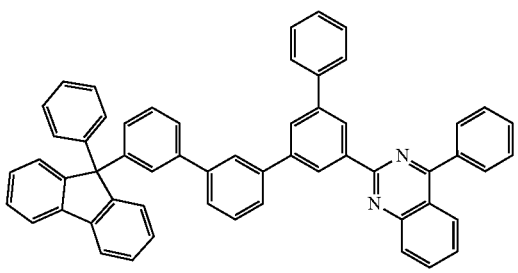

[Chemical Formula 5-19]
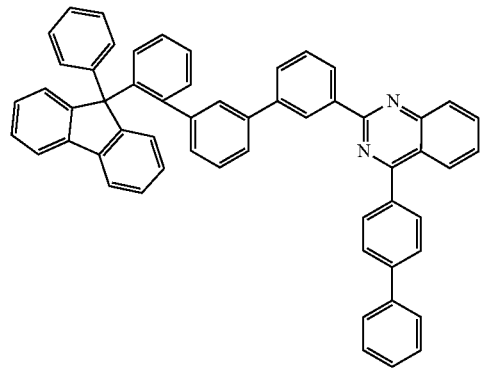
[Chemical Formula 5-20]
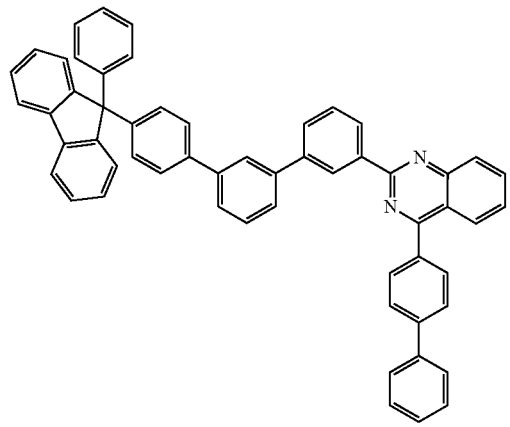
[Chemical Formula 5-21]
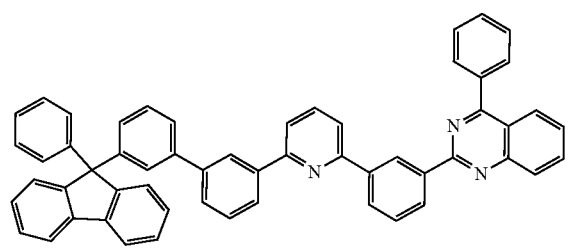
[Chemical Formula 5-22]
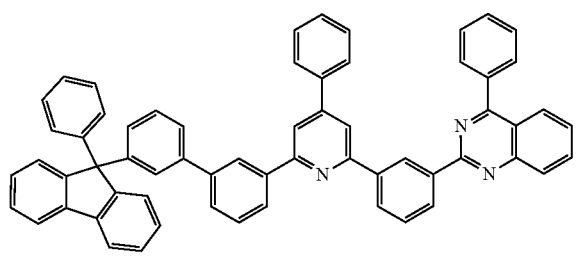
[Chemical Formula 5-23]
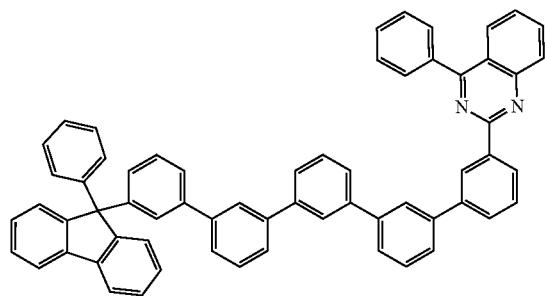
[Chemical Formula 6-1]
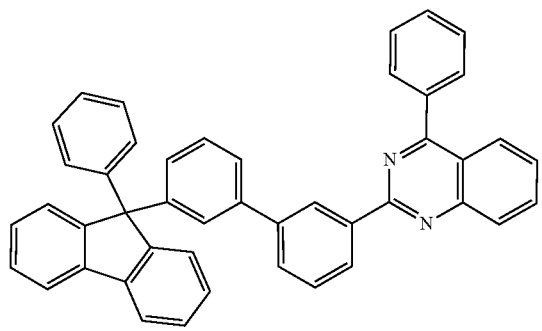
[Chemical Formula 6-2]
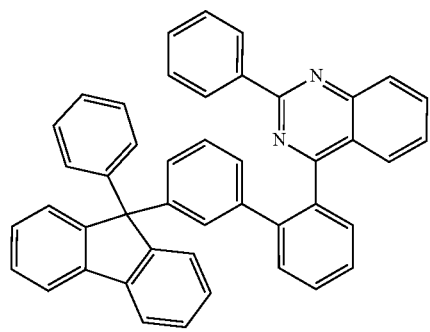
[Chemical Formula 6-3]
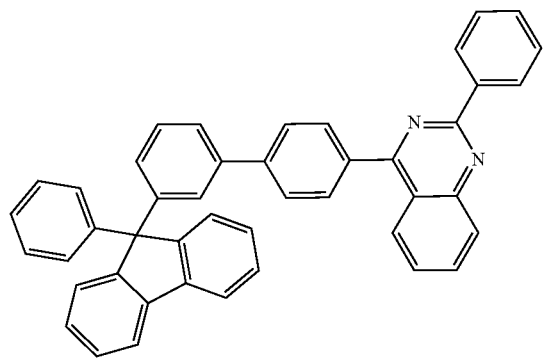

-continued
[Chemical Formula 6-4]
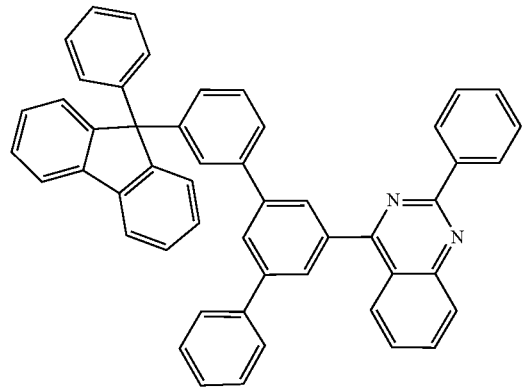
[Chemical Formula 6-5]
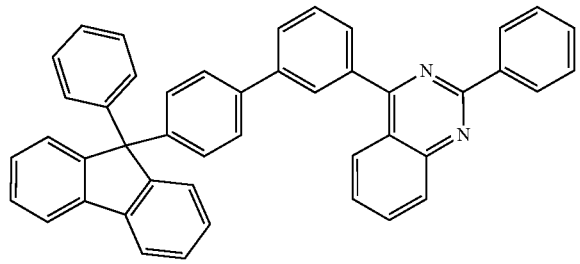
[Chemical Formula 6-6]
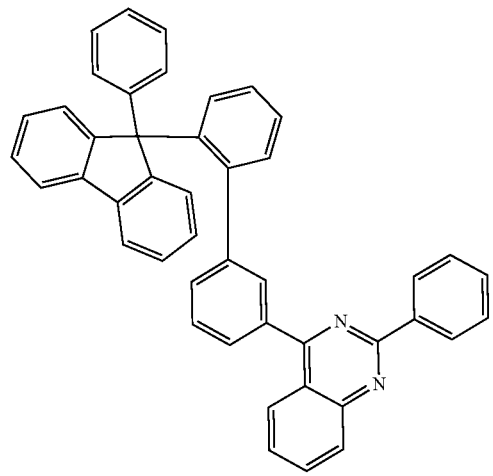
[Chemical Formula 6-7]
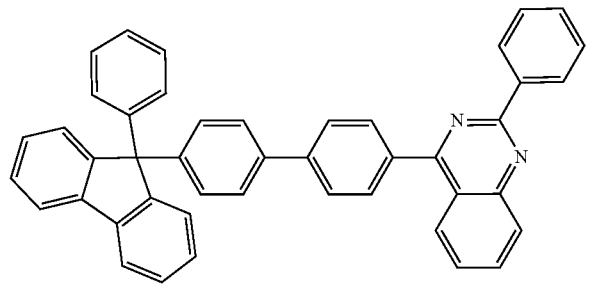
[Chemical Formula 6-8]
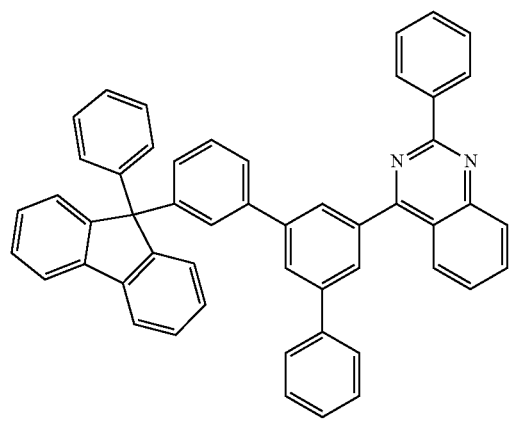
[Chemical Formula 6-9]
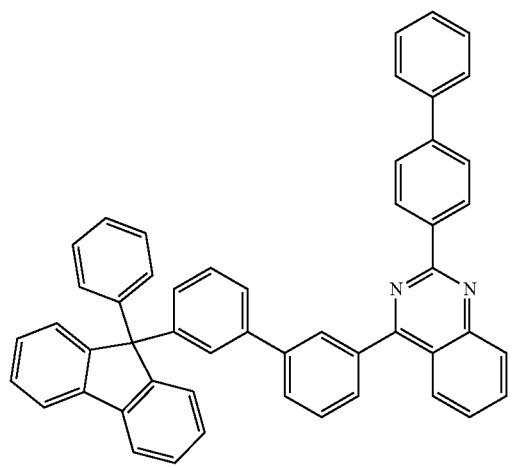

-continued
[Chemical Formula 6-10]
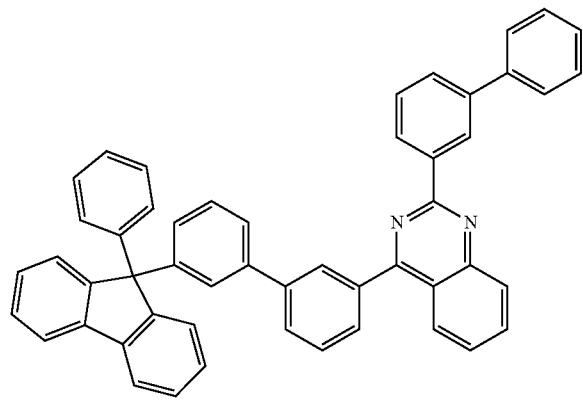
[Chemical Formula 6-11]
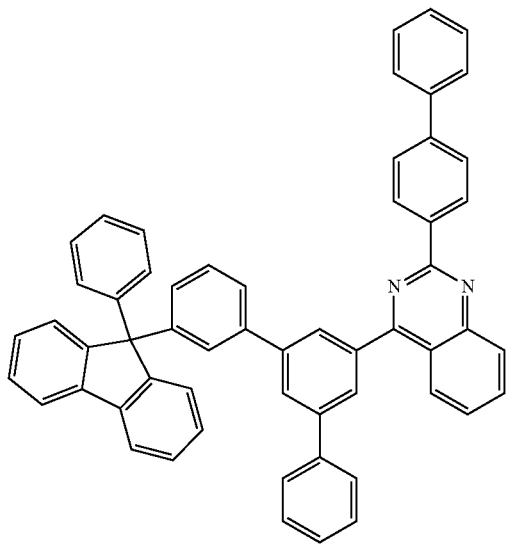
[Chemical Formula 6-12]
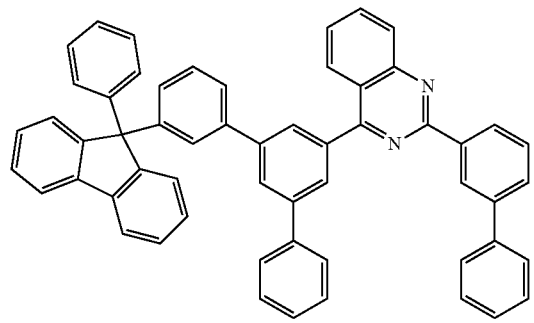
[Chemical Formula 6-13]
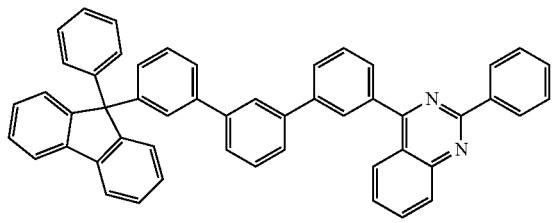
[Chemical Formula 6-14]
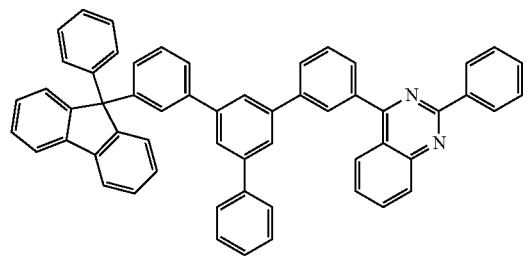
[Chemical Formula 6-15]
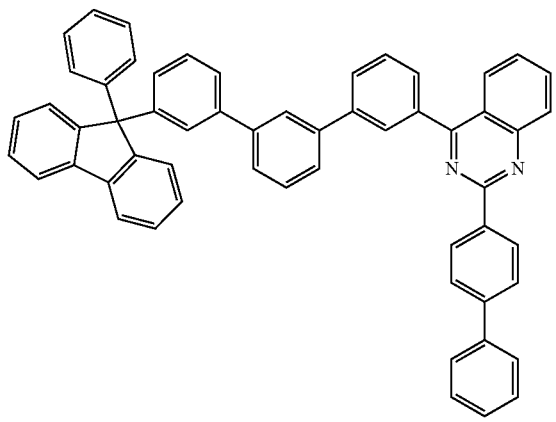

[Chemical Formula 6-16]
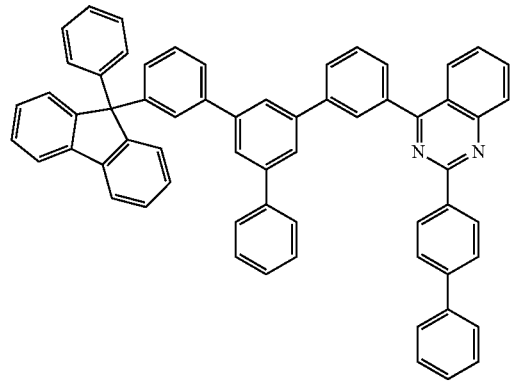
[Chemical Formula 6-17]
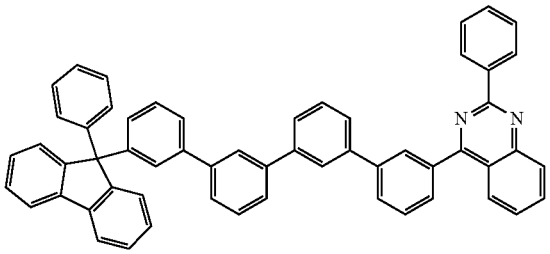
[Chemical Formula 6-18]
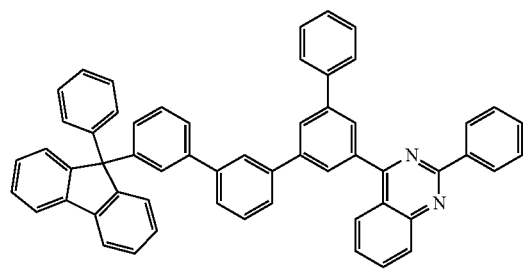
[Chemical Formula 6-19]
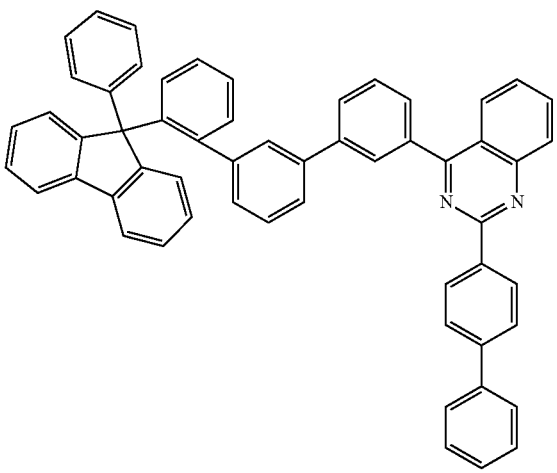
[Chemical Formula 6-20]
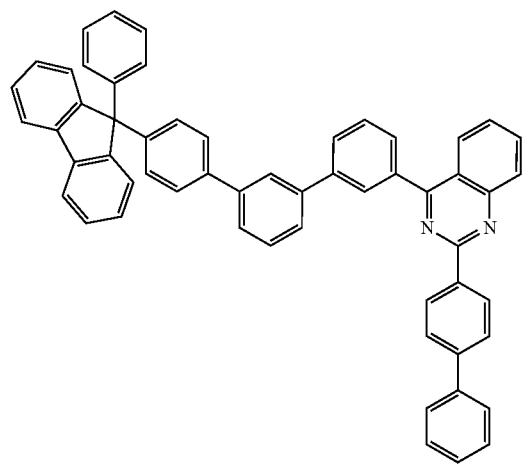
[Chemical Formula 6-21]
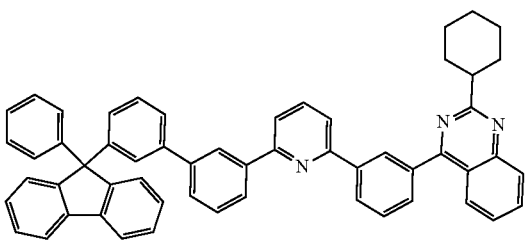

-continued

[Chemical Formula 6-22]

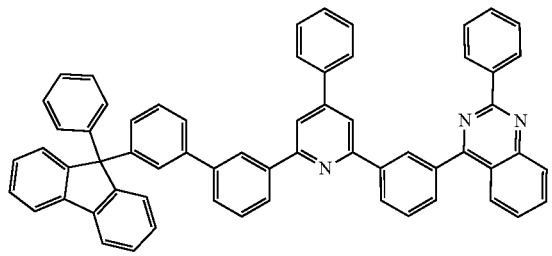

[Chemical Formula 6-23]

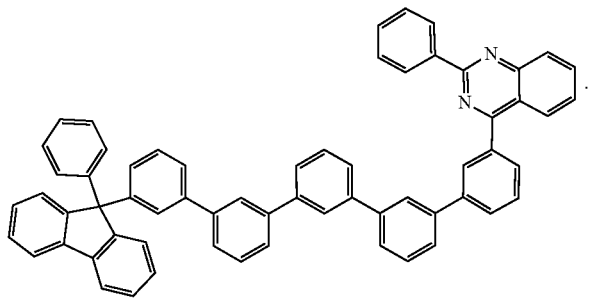

3. An organic optoelectric device comprising
an anode and a cathode facing each other, and
at least one organic layer between the anode and the cathode,
wherein the organic layer includes the organic compound of claim 1.

4. The organic optoelectric device of claim 3, wherein the organic layer includes
a hole transport layer, an electron transport layer, and
an emission layer between the hole transport layer and the electron transport layer, and
the organic compound is included in the electron transport layer.

5. The organic optoelectric device of claim 3, wherein the organic layer includes
a hole transport layer, an electron transport layer, and
an emission layer between the hole transport layer and the electron transport layer,
the organic compound is included in the emission layer.

6. The organic optoelectric device of claim 5, wherein the organic compound is used as a host material in the emission layer.

7. An organic optoelectric device comprising:
an anode and a cathode facing each other, and
at least one organic layer between the anode and the cathode, wherein the organic layer includes an organic compound, and a hole transport layer, an electron transport layer, and
an emission layer between the hole transport layer and the electron transport layer,
wherein the emission layer includes a first organic compound represented by Chemical Formula 1 and a second organic compound as a host material:

[Chemical Formula 1]

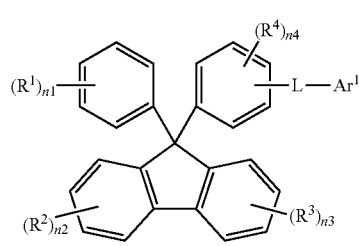

wherein, in Chemical Formula 1,
$R^1$ to $R^4$ are independently hydrogen or deuterium,
L is represented by *-$L^1$-$L^2$-$L^3$-$L^4$-*,
$L^1$ to $L^4$ are independently a single bond, a substituted or unsubstituted C6 to C20 arylene group, or a substituted or unsubstituted C2 to C20 heteroarylene group, provided that at least one of $L^1$ to $L^4$ is a substituted or unsubstituted C6 to C20 arylene group.
$Ar^1$ is a substituted C2 to C20 heteroaryl group,
n1 is an integer of 5, and
n2 to n4 are independently integers of 4,
wherein the second organic compound includes at least one of 'a compound represented by Chemical Formula A' and 'a compound consisting of a combination of a moiety represented by Chemical Formula B and a moiety represented by Chemical Formula C:

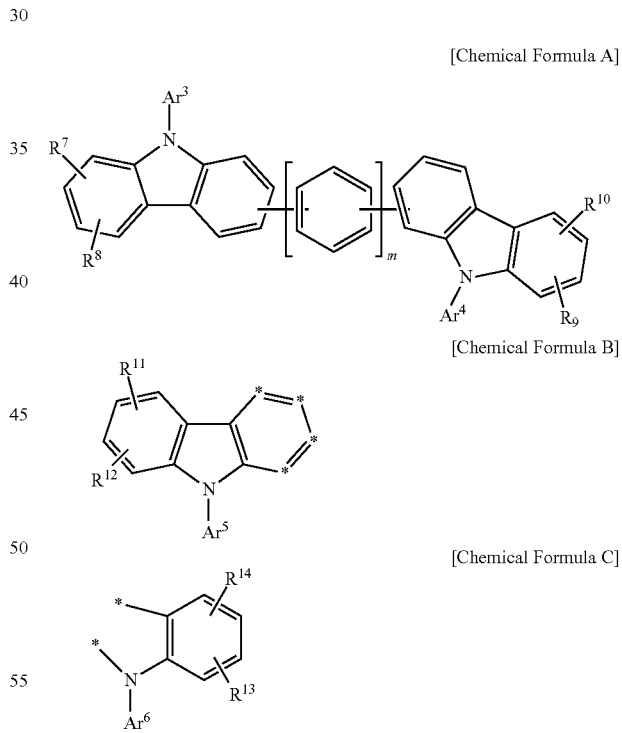

wherein, in Chemical Formulae A to C,
$Ar^3$ to $Ar^6$ are independently a substituted or unsubstituted C6 to C30 aryl group, or a substituted or unsubstituted C2 to C30 heteroaryl group,
m is an integer of 0 or 1,
adjacent two *'s of Chemical Formula B are combined with two *'s of Chemical Formula C to form a fused ring and * that does not form the fused ring of Chemical Formula B is independently $CR^b$, and $R^b$ and $R^7$ to $R^{14}$ are independently hydrogen, deuterium, a substituted or unsubstituted C1 to C10 alkyl group, a substituted or unsubstituted C6 to C30 aryl group or a substituted or unsubstituted C2 to C30 heteroaryl group.

8. The organic optoelectric device of claim 3, wherein the organic layer includes a hole transport layer, an electron transport layer, an emission layer between the hole transport layer and the electron transport layer, and an electron transport auxiliary layer (hole blocking layer) between the emission layer and the electron transport layer, and the organic compound is included in the electron transport auxiliary layer.

9. A display device comprising the organic optoelectric device of claim 3.

\* \* \* \* \*